(12) United States Patent
Ozpolat et al.

(10) Patent No.: US 9,073,851 B2
(45) Date of Patent: Jul. 7, 2015

(54) COMPOSITIONS AND METHODS FOR TREATING CANCER

(71) Applicant: Board of Regents, The University of Texas System, Austin, TX (US)

(72) Inventors: Bulent Ozpolat, Houston, TX (US); Gabriel Lopez-Berestein, Bellaire, TX (US); Kevin N. Dalby, Cedar Park, TX (US); Jiney Jose, Austin, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 0 days.

(21) Appl. No.: 13/662,135

(22) Filed: Oct. 26, 2012

(65) Prior Publication Data

US 2013/0129812 A1    May 23, 2013

Related U.S. Application Data

(60) Provisional application No. 61/553,051, filed on Oct. 28, 2011.

(51) Int. Cl.
| | |
|---|---|
| *A61K 9/127* | (2006.01) |
| *A01N 43/42* | (2006.01) |
| *A61K 31/44* | (2006.01) |
| *C07D 209/14* | (2006.01) |
| *C07D 471/04* | (2006.01) |
| *C07D 403/12* | (2006.01) |
| *C07D 209/18* | (2006.01) |
| *C07D 471/14* | (2006.01) |
| *C07D 209/20* | (2006.01) |

(52) U.S. Cl.
CPC ............ *C07D 209/14* (2013.01); *C07D 471/04* (2013.01); *C07D 403/12* (2013.01); *C07D 209/18* (2013.01); *C07D 471/14* (2013.01); *C07D 209/20* (2013.01)

(58) Field of Classification Search
None
See application file for complete search history.

(56) References Cited

U.S. PATENT DOCUMENTS

| | | | |
|---|---|---|---|
| 4,861,760 A | 8/1989 | Mazuel et al. | |
| 4,911,920 A | 3/1990 | Jani et al. | |
| 5,010,175 A | 4/1991 | Rutter et al. | |
| 5,034,506 A | 7/1991 | Summerton et al. | |
| 5,212,162 A | 5/1993 | Missel et al. | |
| 5,235,033 A | 8/1993 | Summerton et al. | |
| 5,403,841 A | 4/1995 | Lang et al. | |
| 5,496,957 A | 3/1996 | Glennon | |
| 7,482,465 B2 * | 1/2009 | Holzemann et al. | 548/126 |
| 2007/0218023 A1 | 9/2007 | Slominski et al. | |
| 2009/0264496 A1 | 10/2009 | Vafai et al. | |
| 2010/0063125 A1 * | 3/2010 | Anderson et al. | 514/406 |

FOREIGN PATENT DOCUMENTS

| | | | |
|---|---|---|---|
| EP | 1656939 | A1 | 5/2006 |
| WO | 91/19735 | A1 | 12/1991 |
| WO | 93/20242 | A1 | 10/1993 |
| WO | 96/05309 | A2 | 2/1996 |
| WO | 9626923 | A1 | 9/1996 |
| WO | 00/34242 | A1 | 6/2000 |
| WO | 0228347 | A2 | 4/2002 |
| WO | 0276970 | A2 | 10/2002 |
| WO | 2005018569 | A2 | 3/2005 |
| WO | 2005048986 | A1 | 6/2005 |
| WO | 2007133772 | A2 | 11/2007 |
| WO | 2008/049116 | A2 | 4/2008 |
| WO | 2009037308 | A1 | 3/2009 |
| WO | 2009037343 | A1 | 3/2009 |
| WO | 2009073620 | A2 | 6/2009 |
| WO | 2010001391 | A1 | 1/2010 |
| WO | 2010089327 | A2 | 8/2010 |
| WO | 2012022780 | A1 | 2/2012 |
| WO | 2012127032 | A1 | 9/2012 |
| WO | 2013063216 | A1 | 5/2013 |

OTHER PUBLICATIONS

Slikker et al. (Journal of Pharmacology and Experimental Therapeutics, 1984, 228, 43-52).*
Medina et al. (Current Pharmaceutical Design, 2004, 10, 2981-2989).*
CAS registry No. 1026399-71-2, 2-[4-[[3-[2-(dimethylamino)ethyl]-1H-indol-4-yl]oxy]butyl]-butanedioic acid (Entered STN Jun. 8, 2008) (See attached STN registry clip).*
Stoll et al. (Helvetica Chimica Acta, 1955, 38, 1452-1472) (English Abstract included).*
International Search Report and Written Opinion mailed Oct. 26, 2012 for PCT Patent Application No. PCT/US2012/062256, 13 pages.
Abramczyk et al., "Purification and characterization of tagless recombinant human elongation factor 2 kinase (eEF-2k) expressed in *Escherichia coli*", Protein Expression and Purification, ELSEVIER, 79:237-244 (2011).
Abukhdeir and Park, "p21 and p27: roles in carcinogenesis and drug resistance", *Expert Reviews in Molecular Medicine*, 10:e19, 18 pages (2008).
Alessi et al., "Mechanism of activation of protein kinase B by insulin and IGF-1", *The EMBO Journal*, 15(23):6541-6551 (1996).
Alkarain et al., "p27 Deregulation in Breast Cancer: Prognostic Significance and Implications for Therapy", *Journal of Mammary Gland Biology Neoplasia*, 9(1):67-80 (2004).
Al-Muhammed et al., "In-vivo studies on dexamethasone sodium phosphate liposomes", *J. Microencapsulation*, 13:293-306 (1996).
Arora et al., "Identification and Characterization of an Inhibitor of Eukaryotic Elongation Factor 2 Kinase against Human Cancer Cell Lines", Cancer Research, 63:6894-6899 (2003).
Bagaglio and Hait, "Role of Calmodulin-dependent Phosphorylation of Elongation Factor 2 in the Proliferation of Rat Glial Cells", *Cell Growth & Differentiation* 5:1403-1408 (1994).

(Continued)

*Primary Examiner* — Dennis Heyer
*Assistant Examiner* — Daniel M Podgorski
(74) *Attorney, Agent, or Firm* — Mintz Levin Cohn Ferris Glovsky and Popeo PC

(57) ABSTRACT

Provided herein are methods and compositions inter alia for treating diseases, including hyperproliferative diseases, migraine headaches, and depression.

27 Claims, 39 Drawing Sheets

(56) References Cited

OTHER PUBLICATIONS

Browne et al., "Stimulation of the AMP-activated Protein Kinase Leads to Activation of Eukaryotic Elongation Factor 2 Kinase and to Its Phosphorylation at a Novel Site, Serine 398", *The Journal of Biological Chemistry*, 279:12220-12231 (2004).
Browne and Proud, "A Novel mTOR-Regulated Phosphorylation Site in Elongation Factor 2 Kinase Modulates the Activity of the Kinase and It's Binding to Calmodulin",*Molecular and Cellular Biology*, 24:2986-2997 (2004).
Carlberg et al., "Functional properties of phosphorylated elongation factor 2", *European Journal of Biochemistry* 191:639-645 (1990).
Castaneda et al., "The phosphatidyl inositol 3-kinase/AKT signaling pathway in breast cancer", *Cancer Metastasis Reviews*, 29:751-959 (2010).
Cattaneo et al., "Mitogenic effect of serotonin in human small cell lung carcinoma cells via both $5-HT_{1A}$ and $5-HT_{1D}$ receptors", *European Journal of Pharmacology*, 291:209-211 (1995).
Celts et al., "Increased phosphorylation of elongation factor 2 during mitosis in transformed human amnion cells correlates with a decreased rate of protein synthesis", *Proceedings of the National Academy of Sciences USA*, 87:4231-5 (1990).
Chafouleas et al., "Regulation of intracellular levels of calmodulin and tubulin in normal and transformed cells", *Proceedings of the National Academy of Sciences USA*, 78:996-1000 (1981).
Chin and Means, "Calmodulin: a prototypical calcium sensor", *Cell Biology*, 10:322-328 (2000).
Chonn and Cullis, "Recent advances in liposomal drug-delivery systems", *Current Opinion in Biotechnology*, 6:698-708 (1995).
Dalby et al., "Targeting the prodeath and prosurvival functions of autophagy as novel therapeutic strategies in cancer", *Autophagy*, 6:322-329 (2010).
Diggle et al., "Phosphorylation of elongation factor-2 kinase on serine 499 by cAMP-dependent protein kinase induced $Ca^{2+}$/calmodulin-independnent activity," *Biochemical Journal*, 353:621-626 (2001).
Diggle et al., "Regulation of protein-synthesis elongation-factor-2 kinase by cAMP in adipocytes", *Biochemical Journal*, 336:525-529 (1998).
Eyles et al., "Oral Delivery and Fate of Poly(lactic acid) Mircrosphere-encapsulated Interferon in Rats", *Journal of Pharmacy and Pharmacology*, 49:669-674 (1997).
Esteva et al., "Phase II Study of Weekly Docetaxel and Trastuzumab for Patients With HER-2-Overexpressing Metastatic Breast Cancer", *Journal of Clinical Oncology*, 20(7):1800-1808 (2002).
Finn, R.S., "Targeting Src in breast cancer", *Annals of Oncology*, 19:1379-1386 (2008).
Franken et al., "Clonogenic assay of cells in vitro", *Nature Protocols*, 1:2315-2319 (2006).
Gao et al., "Controlled Release of Contraceptive Steroids from Biodegradable and Injectable Gel Formulations: In Vivo Evaluation", *Pharmaceutical Research*, 12:864-868 (1995).
Glennon et al., "Bidning of O-Alkyl Derivatives of Serotonin at Human 5-HT1Dβ Receptors", *Journal of Medicinal Chemistry*, 39:314-322 (1996).
Gillett et al., "Amplification and Overexpression of Cyclin D1 in Breast Cancer Detected by Immunohistochemical Staining", *Cancer Research*, 54:1812-1817 (1994).
Gross and Yee, "The type-1 insulin-like growth factor receptor tyrosine kinase and breast cancer: Biology and therapeutic relevance", *Cancer and Metastasis Reviews*, 22:327-336 (2003).
Hait et al., "Elongation Factor-2 Kinase", *Autophagy*, 2(4):294-296 (2006).
Halazy et al., "Serotonin Dimers: Application of the Bivalent Ligand Approach to the Design of New Potent and Selective $5-HT_{1B/1D}$ Agonists", *Journal of Medicinal Chemistry*, 39(25):4920-4927 (1996).
Hershey, J. W. B., "Translational Control in Mammalian Cells", *Annual Review of Biochemistry*, 60:717-755 (1991).

Ishizuka et al., "Receptor-Mediated Autocrine Growth-Simulatory Effect of 5-Hydroxytryptamine on Cultured Human Pancreatic Carcinoid Cells", *Journal of Cellular Physiology*, 150:1-7 (1992).
Kanzawa et al., "Induction of Autophagic Cell Death in Malignant Glioma Cells by Arsenic Trioxide", *Cancer Research*, 63:2103-2108 (2003).
Knebel et al., "Stress-induced regulation of eukaryotic elongation factor 2 kinase by SB 203580-sensitive and—insensitive pathways", *Biochemical Journal*, 367:525-532 (2002).
Knebel et al., "A novel method to identify protein kinase substrates: eEF2 kinase is phosphorylated and inhibited by SAPK4/p38δ", *The EMBO Journal*, 20:4360-4369 (2001).
Kroemer and Levine, "Autophagic cell death: the story of a misnomer", *Nature Reviews: Molecular Cell Biology*, 9:1004-1010 (2008).
Liao and Dickson, "c-*Myc* in breast cancer", *Endocrine Related Cancer*, 7:143-164 (2000).
Lu and Means, "Regulation of the Cell Cycle by Calcium and Calmodulin", *Endocrine Reviews* 14(1):40-58 (1993).
Mitsui et al., "Purification and Characterization of Calmodulin-dependent Protein Kinase III from Rabbit Reticulocytes and Rat Pacreas", *The Journal of Biological Chemistry*, 268(18):13422-13433 (1993).
Moazed and Noller, "Intermediate states in the movement of transfer RNA in the ribosome", *Nature*, 342:142-148 (1989).
Moldave, K., "Eukaryotic Protein Synthesis", *Annual Review of Biochemistry*, 54:1109-1149 (1985).
Morley and Thomas, "Intracellular Messengers and the Control of Protein Synthesis", *Pharmacology & Therapeutics*, 50:291-319 (1991).
Musgrove, E.A., "Cyclins: Roles in mitogenic signaling and oncogenic transformation", *Growth Factors*, 24(1):13-19 (2006).
Nairn et al., "Identification of calmodulin-dependent protein kinase III and its major $M_r$ 100,000 substrate in mammalian tissues", *Proceedings of the National Academy of Sciences USA*, 82:7939-7943 (1985).
Nairn and Palfrey, "Identification of the Major $M_r$ 100,000 Substrate for Calmodulin-dependnent Protein Kinase III in Mammalian Cells as Elongation Factor-2" *The Journal of Biological Chemistry*, 262(36):17299-17303 (1987).
Nemecek et al., "Stimulation of aortic smooth muscle cell mitogenesis by serotonin", *Proceedings of the National Academy of Sciences USA*, 83:674-678 (1986).
Nicolaou et al., "An Expedient Strategy for the Synthesis of Tryptamines and Other Heterocycles", *Angewandte Chemie International Edition*, 47:4217-4220 (2008).
Nilsson and Nygard, "Phosphorylation of eukaryotic elongation factor 2 in differentiating and proliferating HL-60 cells", *Biochmica et Biophysica Acta*, 1268:263-268 (1995).
Oltersdorf et al., "An inhibitor of Bcl-2 family proteins induces regression of solid tumours", *Nature*, 435:677-681 (2005).
Ostro and Cullis, "Use of liposomes as injectable-drug delivery systems", *American Journal of Hospital Pharmacy*, 46:1576-1587 (1989).
Pai et al., "Altered serotonin physiology in human breast cancers favors paradoxical growth and cell survival", *Breast Cancer Research*, 11(6):R81, 17 pages (2009).
Parmer et al., "Activity and regulation by growth factors of calmodulin-dependent protein kinase III (elongation factor 2-kinase) in human breast cancer", *British Journal of Cancer*, 79(1):59-64 (1999).
Parmer et al., "Effects of Rottlerin, a Inhibitor of Calmodulin-dependent Protein Kinase III, on Cellular Proliferation, Viability, and Cell Cycle Distribution in Malignant Glioma Cells[1] ", *Cell Growth & Differentiation*, 8:327-334 (1997).
Peterson et al., "Src Phosphorylates the Insulin-like Growth Factor Type I Receptor on the Autophosphorylation Sites", *The Journal of Biological Chemistry*, 271(49):31562-31571 (1996).
"Polychemotherapy for early breast cancer: an overview of the randomised trials", *Early Breast Cancer Trialists' Collaborative Group, The Lancet*, 352:930-942 (1998).
Proud, C.G., "Signalling to translation: how signal transduction pathways control the protein synthetic machinery", *Biochemical Journal*, 403:217-234 (2007).

(56) References Cited

OTHER PUBLICATIONS

Proud C.G., "Protein Phosphorylation in Translational Control", *Current Topics in Cellular Regulation*, Academic Press, Inc., 32:243-369 (1992).
Proud, C.G., "Peptide-chain elongation in eukaryotes", *Molecular Biology Reports*, 19:161-170 (1994).
Qu et al., "Tryptamine derivatives as novel non-nucleosidic inhibitors against hepatitis B virus", *Bioorganic & Medicinal Chemistry*, 19(10):3120-3127 (2011).
Rao, K.P., "Recent developments on collagen-based materials for medical applications and drug delivery systems", *Journal of Biomaterials Science Polymer Edition*, 7(7):623-645 (1995).
Redpath and Proud, "Cyclic AMP-dependent protein kinase phosphorylates rabbit reticulocyte elongation factor-2 kinase and induces calcium-independent activity", *Biochemical Journal*, 293:31-34 (1993).
Redpath and Proud, "Purification and phosphorylation of elongation factor-2 kinase from rabbit reticulocytes", *European Journal of Biochemistry*, 212:511-520 (1993).
Ren et al., "Farnesyltransferase Inhibitor SCH66336 Induces Rapid Phosphorylation of Eukaryotic Translation Elongation Factor 2 in Head and Neck Squamous Cell Carcinoma Cells", *Cancer Research*, 65:5841-5847 (2005).
Revial et al., "Aromatization of 1,6,7,7a-Tetrahydro-2H-indo-2-ones by a Novel Process. Preparation of Key-Intermediate Methyl 1-Benzyl-5-methoxy-1H-indole-3-acetate and the Syntheses of Serotonin, Melatonin, and Bufotenin", *Journal of Organic Chemistry*, 67:2252-2256 (2002).
Rhoads, R. E., "Signal Transduction Pathways That Regulate Eukaryotic Protein Synthesis", *Journal of Biological Chemistry*, 274, 30337-30340 (1999).
Rosenzweig and Atreya, "Defining the pathway to insulin-like growth factor system targeting in cancer", *Biochemical Pharmacology*, 80:1115-1124 (2010).
Ryazanov et al., "Regulation of protein synthesis at the elongation stage: New insights in the control of gene expression in eukaryotes", *Federation of European Biochemical Societies*, 285:170-175 (1991).
Ryazanov, A.G., "$Ca^{2+}$/calmodulin-dependent phosphorylation of elongation factor 2", *Federation of European Biochemical Societies*, 214:331-334 (1987).
Ryazanov et al., "Phosphorylation of the elongation factor 2: the fifth $Ca^{2+}$/calmodulin-dependent system of protein phosphorylation", *Biochimie*, 70:619-626 (1988).
Schmidt et al., "Tryptamine-derived alkaloids from Annonaceae exerting neurotrophin-like properties on primary dopaminergic neurons", *Bioorganic & Medicinal Chemistry, ELSEVIER*, 18:5103-5113 (2010).
Seuwen and Pouysségur, "Serotonin as a growth factor", *Biochemical Pharmacology*, 39:985-990 (1990).
Shaw, L.M. "Tumor Cell Invasion Assays", *Methods in Molecular Biology*, 294:97-105 (2005).
Shibata et al., "Inhibition of NF-kB Activity decreases the VEGF mRNA expression in MDA-MB-231 breast cancer cells", *Breast Cancer Research and Treatment*, 73:237-243 (2002).
Siddiqui et al., "The effect of serotonin and serotonin antagonists on bladder cancer cell proliferation", *BJU International*, 97:634-639 (2006).
Smith and Proud, "cdc2-cyclin B regulates eEF2 kinase activity in a cell cycle- and amino acid-dependent manner", *The European Molecular Biology Organization Journal*, 27:1005-1016 (2008).
Soll et al., "Serotonin Promotes Tumor Growth in Human Hepatocellular Cancer", *Hepatology* 51(4):1244-1254 (2010).
Song et al., "Synthesis of Chiral 3-Substituted Hexahydropyrroloindoline via Intermolecular Cyclopropanation", Organic Letters, 8(26): 6011-6014 (2006).
Sun et al., "AKT1/PKBα Kinase is Frequently Elevated in Human Cancers and Its Constitutive Activation is Required for Oncgenic Transformation in NIH3T3 Cells", *American Journal of Pathology*, 159:431-437 (2001).
Swulius and Waxham, "$CA^{2+}$/Calmodulin-dependnent Protein Kinases", *Cellular and Molecular Life Sciences*, 65:2637-2657 (2008).
Takuwa et al., "Studies of the mitogenic effect of serotonin in rat renal mesangial cells", *The American Journal of Physiology*, 257:F431-F439 (1989).
Tekedereli et al, "Targeting Silencing of Elongation Factor 2 Kinase Suppresses Growth and Sensitizes Tumors to Doxorubicin in an Orthotopic Model of Breast Cancer", *PLos One, Targeting eEF-2K in Breast Cancer Cells*, 7(7):e41171 (Jul. 2012).
Tsujimoto and Shimizu, "Another way to die: autophagic programmed cell death", *Cell Death and Differentiation*, 12:1528-1534 (2005).
Tuynder et al., "Translationally controlled tumor protein is a target of tumor reversion", Proceedings of the National Academy of Sciences USA, 101(43):15364-15369 (2004).
Wang et al. "Regulation of elongation factor 2 kinase by $p90^{RSK1}$ and P70 S6 kinase", *The European Molecular Biology Organization Journal*, 20(16):4370-4379 (2001).
Weatherill et al., "Compartment-specific, differential regulation of eukaryotic elongation factor 2 and its kinase within *Aplysia* sensory neurons", *Journal of Neurochemistry* 117:841-855 (2011).
White et al., "Doxorubicin generates a proapoptotic phenotype by phosphorylation of elongation factor 2", *Free Radical Biology & Medicine, ELSEVIER*, 43:1313-1321 (2007).
Wilson et al., "Activated c-SRC in ductal carcinoma in situ correlates with high tumour grade, high proliferation and HER2 positivity", *British Journal of Cancer*, 95:1410-1414 (2006).
Wu et al., "A Versatile Linkage Strategy for Solid-Phase Synthesis of N, N-Dimethyltryptamines and β-Carbolines", *Organic Letters*, 4(23):4033-4036 (2002).
Wu et al., "Elongation Factor-2 Kinase Regulates Autophagy in Human Glioblastoma Cells", *Cancer Research*, 66:3015-3023 (2006).
Wu et al., "Silencing of Elongation Factor-2 Kinase Potentiates the Effect of 2-Deoxy-d-Glucose against Human Glioma Cells through Blunting of Autophagy", *Cancer Research*, 69(6):2453-2460 (2009).
Jeanty et al., "Synthesis of 4- and 6-Azaindoles via the Fischer Reaction", *Organic Letters* (2009), 11(22):5142-5145.
International Preliminary Report on Patentability and Written Opinion dated Apr. 29, 2014 for International Application No. PCT/US2012/062256, 7 pages.
Arutyunyan, G.S. et al., "Relations between chemical structure and pharmacological activity of 5-alkoxytryptamines," Farmakologiya i Toksikologiya, vol. 27(6):681-686 (1964).
Chernov, V.A. et al., "Antitumor activity of some amines and amino acids of the indole series," Voprosy Onkologii, vol. 10(8):76-81 (1964).
El-Salhy, M. et al., "Effects of triple treatment with octreotide, galanin and serotonin on a human pancreas cancer cell line in xenografts," Histology and Histopathology, vol. 20:745-752 (2005).
Gopal, Vijaya et al., "Targeted liposomes to deliver DNA to cells expressing 5-HT receptors," International Journal of Pharmaceutics, vol. 419:347-354 (2011).
Shoeb, Mohammad et al., "Montamine, a unique dimeric indole alkaloid, from the seeds of Centaurea montana (Asteraceae), and its in vitro cytotoxic activity against the CaCo2 colon cancer cells," Tetrahedron, vol. 62:11172-11177 (2006).
Shultz, Michael D. et al., "Optimization of the in Vitro Cardiac Safety of Hydroxamate-Based Histone Deacetylase Inhibitors," Journal of Medicinal Chemistry, vol. 54:4752-4772 (2011).
Van Waarde, Aren et al., "Sigma Receptors in Oncology: Therapeutic and Diagnostic Applications of Sigma Ligands," Current Pharmaceutical Design, vol. 16:3519-3537 (2010).
Supplementary European Search Report for Application No. 12844554.1, 15 pages, dated Apr. 8, 2015.

\* cited by examiner

A.

B.

C.

SEQUENCE LISTING

<160> NUMBER OF SEQ ID NOS: 6

<210> SEQ ID NO 1
<211> LENGTH: 30
<212> TYPE: DNA
<213> ORGANISM: Artificial sequence
<220> FEATURE:
<223> OTHER INFORMATION: Synthetic polynucleotide primer

```
<400> SEQUENCE: 1
tttggtacca tggcagacga agatctcatc                                    30

<210> SEQ ID NO 2
<211> LENGTH: 33
<212> TYPE: DNA
<213> ORGANISM: Artificial sequence
<220> FEATURE:
<223> OTHER INFORMATION: Synthetic polynucleotide primer

<400> SEQUENCE: 2
aaatgcggcc gcttactcct ccatctgggc cca                                33

<210> SEQ ID NO 3
<211> LENGTH: 19
<212> TYPE: RNA
<213> ORGANISM: Artificial sequence
<220> FEATURE:
<223> OTHER INFORMATION: Synthetic polynucleotide

<400> SEQUENCE: 3
gccaaccagu acuaccaaa                                                19

<210> SEQ ID NO 4
<211> LENGTH: 19
<212> TYPE: RNA
<213> ORGANISM: Artificial sequence
<220> FEATURE:
<223> OTHER INFORMATION: Synthetic polynucleotide

<400> SEQUENCE: 4
aagcucgaac cagaauguc                                                19

<210> SEQ ID NO 5
<211> LENGTH: 21
<212> TYPE: RNA
<213> ORGANISM: Artificial sequence
<220> FEATURE:
<223> OTHER INFORMATION: Synthetic polynucleotide

<400> SEQUENCE: 5
aauucuccga acgugucacg u                                             21

<210> SEQ ID NO 6
<211> LENGTH: 16
<212> TYPE: PRT
<213> ORGANISM: Artificial sequence
<220> FEATURE:
<223> OTHER INFORMATION: Synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (16)..(16)
<223> OTHER INFORMATION: AMIDATION

<400> SEQUENCE: 6

Arg Lys Lys Tyr Lys Phe Asn Glu Asp Thr Glu Arg Arg Arg Phe Leu
1               5                   10                  15
```

COMPOSITIONS AND METHODS FOR TREATING CANCER

CROSS-REFERENCES TO RELATED APPLICATIONS

This application claims the benefit of U.S. Provisional Patent Application No. 61/553,051, filed Oct. 28, 2011, which is incorporated herein by reference in its entirety and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 93331-853706_ST25.TXT, created on Oct. 26, 2012, 1,755 bytes, machine format IBM-PC, MS-Windows operating system, is hereby incorporated by reference.

BACKGROUND OF THE INVENTION

Breast Cancer is the most common malignancy in women in the Western world and every year about 200,000 women are diagnosed with breast cancer in the US and more than 40,000 die from this disease (www.cdc.gov). Despite the fact that combination chemotherapy regimens elicit a 50-70% objective response rate in patients with metastatic breast carcinoma less than 20% of patients achieve durable complete remission (Esteva F J, et al. J Clin Oncol 2002: 20:1800-8). The major reason for patient death is due to metastasis and resistance to current therapies including chemotherapy, hormonal therapy and radiation (Polychemotherapy for early breast cancer: an overview of the randomised trials. Early Breast Cancer Trialists' Collaborative Group. Lancet 1998: 352:930-42.). Thus, the development of novel targeted therapeutic strategies is urgently needed to enhance the efficacy of current therapies and prolong patient survival.

Calmodulin-dependent protein Kinase-III (CaMK-III) a.k.a. Eukaryotic elongation factor 2 kinase (eEF-2K) is an unusual calcium/calmodulin (Ca/CaM)-dependent Ser/Thr-kinase that is activated by mitotic agents involved in cell proliferation and viability (Parmer T G, et al. Br J Cancer 1999: 79:59-64). CaMK-III was originally identified as a $Ca^{2+}$/CaM dependent protein kinase (Nairn A C, et al. Proc Natl Acad Sci USA 1985: 82:7939-43). It is highly regulated by second messengers (e.g. $Ca^{2+}$, $PIP_3$), as well as by a number of different protein kinases. Upon mitogenic stimulation there is a rapid activation of CaMK-III, which leads to the subsequent phosphorylation of elongation factor 2 (eEF2), which regulates elongation of protein synthesis (Parmer T G, et al. Cell Growth Differ 1997: 8:327-34).

CaMK-III activity has been found to be significantly increased in breast cancer specimens but absent in normal tissue adjacent to breast cancer (Chafouleas J G, et al. Proc Natl Acad Sci USA 1981: 78:996-1000). Increased activity of this kinase has been reported in proliferating cells (e.g. malignant glioma cells (Bagaglio D M, Hait W N. Cell Growth Differ 1994: 5:1403-8), and HL60 leukemia cells (Nilsson A, Nygard O. Biochim Biophys Acta 1995: 1268:263-8)), but is reported to be absent in nonproliferating cells (Parmer T G, et al. Cell Growth Differ 1997: 8:327-34). In breast cancer cells, the activity of CaMK-III is stimulated by mitogens and growth factors (Parmer T G, et al. Activity and regulation by growth factors of calmodulin-dependent protein kinase III (elongation factor 2-kinase) in human breast cancer. Br J Cancer 1999: 79:59-64). Progression through the G1-phase of the cell cycle and entry into the S phase (the G1/S transition) requires the activity of CaMK-III, which is mediated by a rise in intracellular calcium ($Ca^{2+}$), and/or the up-regulation of c-AMP (Proud C G. Biochem J2007: 403:217-34). Hypoxia, nutrient deprivation and metabolic stress stimulate CaMK-III through activation of AMPK, leading to the phosphorylation of eEF2 and the inhibition of protein synthesis (Browne G J, et al. J Biol Chem 2004: 279:12220-31).

Serotonin (5-hydroxytryptamine, 5-HT), a monoamine neurotransmitter, is a critical local regulator of epithelial homeostasis in the breast and other organs. Serotonin exerts its actions through a repertoire of 15 or more receptor proteins, belonging to seven discreet families. Six of the families of 5-HT receptors are G-protein-coupled, including $G_i$: $5-HT_1$, Gs: $5-HT_{4,6,7}$, and $G_{q/11}$: $5-HT_{2,5}$. $5-HT_3$ is uniquely a ligand-gated cation channel, related to the nicotinic acetylcholine receptor. Previous studies suggest that serotonin, plays a mitogenic role in cancer cells including bladder, pancreatic, prostate hepatocellular cancers, small cell lung carcinoma cells [Parmer T G, et al. Br J Cancer 1999: 79:59-64, Nairn A C, et al. Proc Natl Acad Sci USA 1985: 82:7939-43, Parmer T G, et al. Cell Growth Differ 1997: 8:327-34, Chafouleas J G, et al. Proc Natl Acad Sci USA 1981: 78:996-1000, Bagaglio D M, Hait W N. Cell Growth Differ 1994: 5:1403-8, Nilsson A, Nygard O. Biochim Biophys Acta 1995: 1268:263-8] and breast cancer (Sonier et al., 2006). Among the 5-HT receptors, the 5-HTR2B has been described to mediate proliferation [Proud C G. Biochem J2007: 403:217-34, Browne G J, et al. J Biol Chem 2004: 279:12220-31, Franken N A, et al. Nat Protoc 2006: 1:2315-9] and recently, 5-HTR2A signaling has been shown to promote mitogenic signal in MCF7 breast cancer cells [Lu K P, Means A R. Endocr Rev 1993: 14:40-58]. It has been reported that complex alterations in the intrinsic mammary gland serotonin system of human breast cancers exist [Liao D J, Dickson R B. Endocr Relat Cancer 2000: 7:143-64]. Pai et al. demonstrated that in the normal mammary gland, 5-HT acts as a physiological regulator of lactation and involution, in part by favoring growth arrest and cell death. This tightly regulated 5-HT system is dysregulated in multiple ways in human breast cancers. Specifically, tyrosine hydroxylase, TPH1, (an enzyme found in peripheral tissues leads to production of serotonin and expressed in non neuronal tissues) expression increases during malignant progression. 5-HT receptor expression is dysregulated in human breast cancer cells, with increased expression of some isoforms and suppression of others. The receptor expression change is accompanied by altered downstream signaling of 5-HT receptors in human breast cancer cells, resulting in resistance to 5-HT-induced apoptosis, and stimulated proliferation. Pai et al found that HT1D, 1F, 2C and 3A are expressed in some breast cancer cells compared to MCF10A normal breast epithelium [Liao D J, Dickson R B. Endocr Relat Cancer 2000: 7:143-64].

Apoptosis (programmed cell death type I) and autophagic cell death (programmed cell death type II) are crucial physiological mechanisms that control the development, homeostasis, and elimination of unwanted and malignant cells [Musgrove E A. Growth Factors 2006: 24:13-9]. It is now evident that elimination of cancer cells following chemotherapy treatment occurs, in part, via the induction of autophagic cell death [Abukhdeir A M, Park B H. Expert Rev Mol Med 2008; 10:e19, Ozpolat B, Mol Cancer Res 2007: 5:95-108, Shaw L M. Methods Mol Biol 2005: 294:97-105], Autophagic cell death or type II programmed cell death is a form of non-apoptotic cell death that can be induced by different conditions including serum starvation, gamma-radiation, toxic stimuli, and chemotherapy [Musgrove E A. Growth Factors 2006: 24:13-9].

Autophagy is characterized by an increase in the number of autophagosomes, vesicles that surround such cellular organelles as Golgi complexes, polyribosomes, and the endoplasmic reticulum [Finn R S. Ann Oncol 2008: 19:1379-86]. Subsequently, autophagosomes merge with lysosomes and digest the organelles, leading to cell death. In contrast to apoptosis, autophagic cell death does not involve classic DNA laddering. A growing body of evidence suggests that alterations in the pathways regulating autophagic cell death may result in cancer development. Provided herein are methods and compositions addressing these and other needs in the art.

BRIEF SUMMARY OF THE INVENTION

In a first aspect, a compound is provided having the formula:

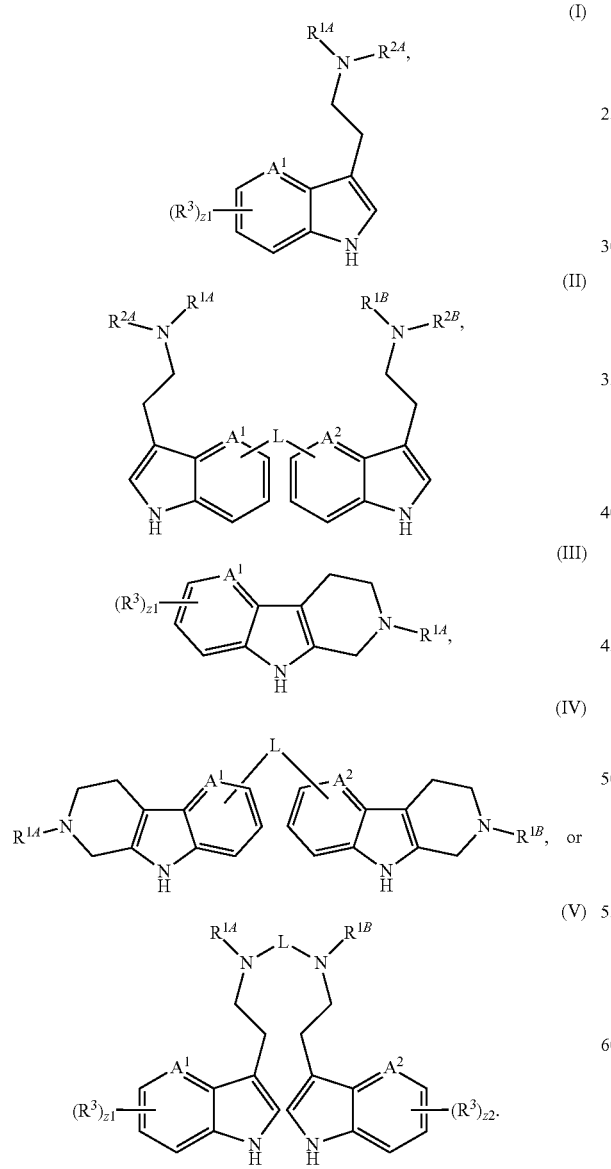

$R^{1A}$ is independently hydrogen, halogen, $—CX^{1A}_3$, $—C(O)R^{7A}$, $—C(O)—OR^{7A}$, $—C(O)NR^{7A}R^{8A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1B}$ is independently hydrogen, halogen, $—CX^{1B}_3$, $—C(O)R^{7B}$, $—C(O)—OR^{7B}$, $—C(O)NR^{7B}R^{8B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{2A}$ is independently hydrogen, halogen, $—CX^{2A}_3$, $—C(O)R^{9A}$, $—C(O)—OR^{9A}$, $—C(O)NR^{9A}R^{10A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{2B}$ is independently hydrogen, halogen, $—CX^{2B}_3$, $—C(O)R^{9B}$, $—C(O)—OR^{9B}$, $—C(O)NR^{9B}R^{10B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$ and $R^{2A}$ are optionally joined to form a substituted or unsubstituted heterocycloalkyl or substituted or unsubstituted heteroaryl. $R^{1B}$ and $R^{2B}$ are optionally joined to form a substituted or unsubstituted heterocycloalkyl or substituted or unsubstituted heteroaryl. $R^3$ is independently hydrogen, halogen, $—CX^3_3$, $—CN$, $—SO_2Cl$, $—SO_nR^{14}$, $—SO_kNR^{11}R^{12}$, $—NHNH_2$, $—ONR^{11}R^{12}$, $—NHC=(O)NHNH_2$, $—NHC=(O)NR^{11}R^{12}$, $—N(O)_m$, $—NR^{11}R^{12}$, $—C(O)R^{13}$, $—C(O)—OR^{13}$, $—O—C(O)—R^{13}$, $—C(O)NR^{11}R^{12}$, $—NR^{11}C(O)R^{13}$, $—OR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{7A}$, $R^{7B}$, $R^{8A}$, $R^{8B}$, $R^{9A}$, $R^{9B}$, $R^{10A}$, $R^{10B}$, $R^{11}$, $R^{12}$, $R^{13}$, and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols $A^1$ and $A^2$ are independently $=N—$ or $=CR^3—$. The symbol L is independently a bond, $—O—$, $—NH—$, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene,

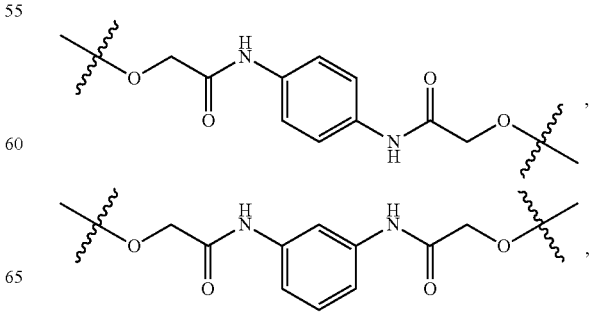

-continued

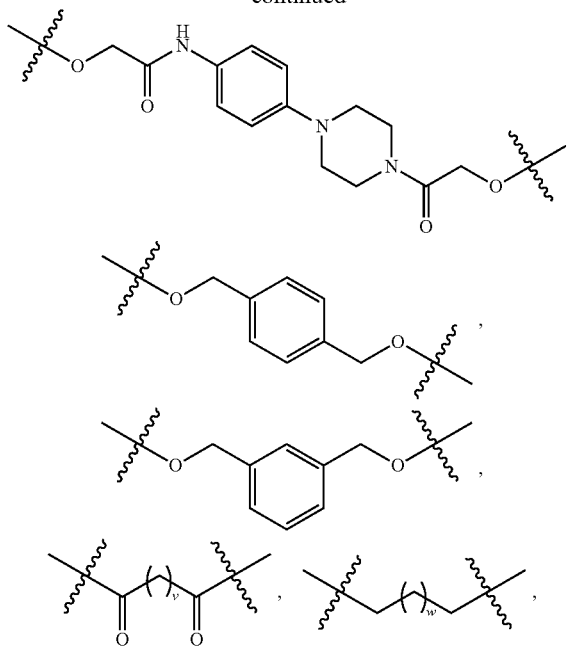

or —O—(CH$_2$)$_p$—O—. The symbols k and m are independently 1 or 2. The symbol n is independently an integer from 0 to 4. The symbols p, v, and w are independently an integer from 1 to 20. The symbols z1 and z2 are independently an integer from 0 to 3. The symbols $X^{1A}$, $X^{1B}$, $X^{2A}$, $X^{2B}$, and $X^3$ are independently —Cl, —Br, —I, or —F.

In a second aspect, a pharmaceutical composition is provided that includes a pharmaceutically acceptable excipient and a compound as described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih) or (IIIh), including embodiments, or any compound described in the Examples section herein).

In a third aspect, a method of treating a disease in a patient in need of such treatment is provided. The method includes administering a therapeutically effective amount of a compound as described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih) or (IIIh), including embodiments, or any compound described in the Examples section herein).

In another aspect, a pharmaceutical composition is provided that includes a pharmaceutically acceptable excipient and an anti-eEF-2K inhibitory nucleic acid, anti-5-HTR$_{1B}$ inhibitory nucleic acid, anti-5-HTR$_{1D}$ inhibitory nucleic acid, or an anti-5-HTR inhibitory nucleic acid.

In another aspect, a method of treating a disease in a patient in need of such treatment is provided. The method includes administering a therapeutically effective amount of an anti-eEF-2K inhibitory nucleic acid, anti-5-HTR$_{1B}$ inhibitory nucleic acid, anti-5-HTR$_{1D}$ inhibitory nucleic acid, or an anti-5-HTR inhibitory nucleic acid.

In another aspect, a method of treating a disease in a patient in need of such treatment is provided. The method includes administering a therapeutically effective amount of a pharmaceutical composition as described herein (e.g. including a compound of Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih) or (IIIh), including embodiments, or any compound described in the Examples section herein).

DETAILED DESCRIPTION OF THE INVENTION

Definitions

Figure 1:
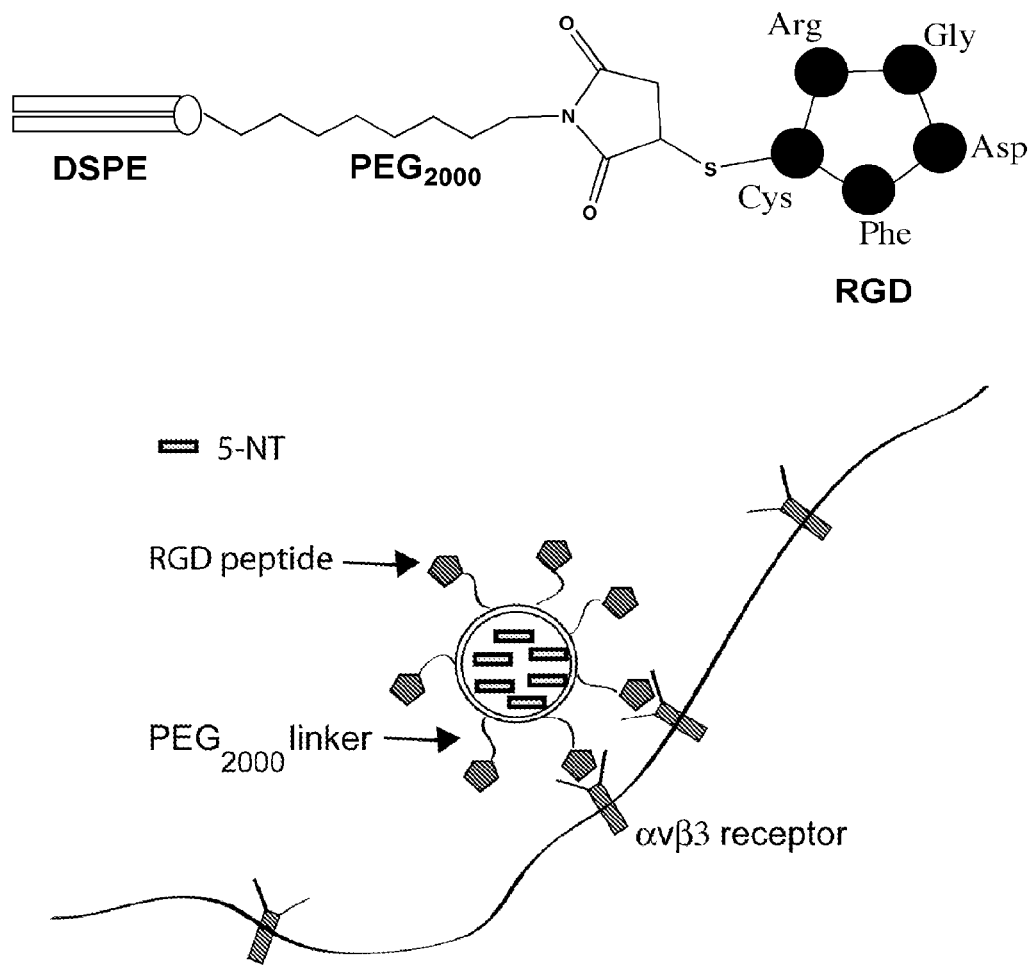
FIG. 1. An example of a targeted long circulating liposome. RGD-modified (αVβ3 integrin receptor targeted) long circulating liposomes for tumor-specific compound (e.g. triptan) delivery.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R'', —OR', —SR', and/or —SO$_2$R'. Where "heteroalkyl" is recited, followed by recitations of specific heteroalkyl groups, such as —NR'R'' or the like, it will be understood that the terms heteroalkyl and —NR'R'' are not redundant or mutually exclusive. Rather, the specific heteroalkyl groups are recited to add clarity. Thus, the term "heteroalkyl" should not be interpreted herein as excluding specific heteroalkyl groups, such as —NR'R'' or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —NR'NR"R"', —ONR'R", —NR'C=(O)NR"NR"'R"", —CN, —$NO_2$, in a number ranging from zero to (2 m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', NR'NR"R"', —ONR'R", —NR'C=(O)NR"NR"'R"", —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R"', and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R"' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, —COOH, —CONH$_2$, —SO$_2$Cl, —SO$_3$H, —SO$_4$H, —SO$_2$NH$_2$, —NHNH$_2$, —ONH$_2$, —NHC=(O)NHNH$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:
  (i) oxo, —OH, —NH$_2$, —SH, —CN, —CF$_3$, —NO$_2$, halogen, —COOH, —CONH$_2$, —SO$_2$Cl, —SO$_3$H, —SO$_4$H, —SO$_2$NH$_2$, —NHNH$_2$, —ONH$_2$, —NHC=(O)NHNH$_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo, —OH, —NH$_2$, —SH, —CN, —CF$_3$, —NO$_2$, halogen, —COOH, —CONH$_2$, —SO$_2$Cl, —SO$_3$H, —SO$_4$H, —SO$_2$NH$_2$, —NHNH$_2$, —ONH$_2$, —NHC=(O)NHNH$_2$, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, —COOH, —CONH$_2$, —SO$_2$Cl, —SO$_3$H, —SO$_4$H, —SO$_2$NH$_2$, —NHNH$_2$, —ONH$_2$, —NHC=(O)NHNH$_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 9 membered heteroarylene. In some embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present invention, whether radioactive or not, are encompassed within the scope of the present invention.

The symbol ⟿ denotes the point of attachment of a chemical moiety to the remainder of a molecule or chemical formula.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka,

*Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science,* 274:1520-1522 (1996) and U.S. Pat. No. 5,593,853). The methods above may be used to synthesize single molecular species.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer and or causing remission of cancer. The term "treating," and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, reduce one or more symptoms of a disease or condition, reduce the level of a kinase activity in a cell, reduce the level of activity of eEF-2K, reduce the level of activity of a serotonin receptor in a cell, reduce the level of activity of a 5-$HTR_{1B}$ in a cell, reduce the level of activity of a 5-$HTR_{1D}$ in a cell, reduce the level of activity of mTOR, c-myc, cyclin-D1. Bcl-2, VEGF, HIF1alpha, c-SRC, Fak, Paxillin, IGR-1R, and/or AKT in a cell, increase the level of activity of a serotonin receptor in a cell, increase the level of activity of a 5-$HTR_{1B}$ in a cell, or increase the level of activity of a 5-$HTR_{1D}$ in a cell). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist (inhibitor) required to decrease the activity of an enzyme relative to the absence of the antagonist. An "activity increasing amount," as used herein, refers to an amount of agonist (activator) required to increase the activity of an enzyme relative to the absence of the agonist. A "function disrupting amount," as used herein, refers to the amount of antagonist (inhibitor) required to disrupt the function of an enzyme or protein relative to the absence of the antagonist. A "function increasing amount," as used herein, refers to the amount of agonist (activator) required to increase the function of an enzyme or protein relative to the absence of the agonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, German), Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme (e.g. kinase, eEF-2K, receptor, 5-HTR$_{1B}$, or 5-HTR$_{1D}$). In some embodiments, the protein may be a 5-HTR. In some embodiments, the protein may be 5-HTR$_{1B}$. In some embodiments, the protein may be 5-HTR$_{1D}$. In some embodiments, the protein may be eEF-2K. In some embodiments contacting includes allowing a compound described herein to interact with a protein or enzyme that is involved in a signaling pathway.

As defined herein, the term "inhibition", "inhibit", "inhibiting" and the like in reference to a protein-inhibitor (e.g. antagonist) interaction means negatively affecting (e.g. decreasing) the activity or function of the protein (e.g. decreasing the phosphorylation of another protein by a kinase) relative to the activity or function of the protein (e.g. kinase) in the absence of the inhibitor (e.g. kinase inhibitor or kinase inhibitor compound). In some embodiments inhibition refers to reduction of a disease or symptoms of disease. In some embodiments, inhibition refers to a reduction in the activity of a signal transduction pathway or signaling pathway (e.g. reduction of a pathway involving a 5-HTR, 5-HTR$_{1B}$, 5-HTR$_{1D}$, or eEF-2K). Thus, inhibition includes, at least in part, partially or totally blocking stimulation, decreasing, preventing, or delaying activation, or inactivating, desensitizing, or down-regulating signal transduction or enzymatic activity or the amount of a protein (e.g. a 5-HTR, 5-HTR$_{1B}$, 5-HTR$_{1D}$, eEF-2K, or phosphorylated eEF-2). In some embodiments, inhibition refers to inhibition of a protein, such as 5-HTR$_{1B}$, 5-HTR$_{1D}$, eEF-2K, or eEF-2. In some embodiments, the 5-HTR, 5-HTR$_{1B}$, 5-HTR$_{1D}$, eEF-2K, or phosphorylated eEF-2 is a human protein.

As defined herein, the term "activation", "activate", "activating" and the like in reference to a protein-activator (e.g. agonist) interaction means positively affecting (e.g. increasing) the activity or function of the protein (e.g. increasing the phosphorylation of another protein by a kinase) relative to the activity or function of the protein (e.g. kinase) in the absence of the activator (e.g. kinase activator or kinase activator compound or kinase agonist, 5-HTR agonist or activator, 5-HTR$_{1B}$ agonist or activator, or 5-HTR$_{1D}$ agonist or activator). In some embodiments, activation refers to an increase in the activity of a signal transduction pathway or signaling pathway (e.g. activation of a pathway involving a 5-HTR, 5-HTR$_{1B}$, 5-HTR$_{1D}$, or eEF-2K). Thus, activation includes, at least in part, partially or totally increasing stimulation, increasing or enabling activation, or activating, sensitizing, or up-regulating signal transduction or enzymatic activity or the amount of a protein (e.g. a 5-HTR, 5-HTR$_{1B}$, 5-HTR$_{1D}$, eEF-2K, or de-phosphorylated eEF-2). In some embodiments, activation refers to activation of a protein, such as 5-HTR$_{1B}$, 5-HTR$_{1D}$, eEF-2K, or eEF-2. In some embodiments, the 5-HTR, 5-HTR$_{1B}$, 5-HTR$_{1D}$, eEF-2K, or de-phosphorylated eEF-2 is a human protein.

The term "modulator" refers to a composition that increases or decreases the level of a target molecule or the function of a target molecule (e.g. a target may be a kinase (e.g. eEF-2K) and the function may be to phosphorylate a molecule (e.g. eEF-2) or the target may be a 5-HTR and the function may be the downstream signaling pathway or phosphorylation of eEF-2 or the target may be eEF-2 and the function may be the ribosomal translocation of the nascent peptide chain from the A-site to the P-site during translation). In some embodiments, a kinase modulator is a compound that reduces the activity of a kinase in a cell. A kinase modulator may reduce the activity of one kinase but cause an increase in enzyme activity of another kinase that results in a reduction or increase, respectively, of cell growth and proliferation. In some embodiments, a kinase disease modulator is a compound that reduces the severity of one or more symptoms of a disease associated with the kinase (e.g. cancer). A 5-HTR modulator is a compound that increases or decreases the activity or level of one or more 5-HTRs. A 5-HTR$_{1B}$ modulator is a compound that increases or decreases the activity or level of 5-HTR$_{1B}$. A 5-HTR$_{1D}$ modulator is a compound that increases or decreases the activity or level of 5-HTR$_{1D}$. An eEF-2K modulator is a compound that increases or decreases the activity or level of eEF-2K. An eEF-2 modulator is a compound that increases or decreases the activity or level of eEF-2K.

"Patient" or "subject in need thereof" refers to a living organism suffering from or prone to a disease or condition that can be treated by administration of a compound, inhibitory nucleic acid, or pharmaceutical composition, all as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with a compound, inhibitory nucleic acid, pharmaceutical composition, or method provided herein. In some embodiments, the disease is a disease related to (e.g. caused by) an activated or overactive kinase or aberrant kinase activity (e.g. cancer with increased level of eEF-2K activity or increased signal transduction activity in pathways involving 5-HTR$_{1B}$ or 5-HTR$_{1D}$). In some embodiments, the disease is a disease related to (e.g. caused by) an inhibited kinase or reduced kinase activity (e.g. cancer with decreased level of eEF-2 activity or decreased signal transduction activity in pathways involving 5-HTR$_{1B}$ or 5-HTR$_{1D}$). Examples of diseases, disorders, or conditions include, but are not limited to, cancer, melanoma, breast cancer, ovarian cancer, pancreatic cancer, liver cancer, metastatic cancer, lung cancer, glioblastoma, glioma, prostate cancer, leukemia, sarcoma, carcinoma, lymphoma, neuroblastoma, depression, major depression, chronic depression, atypical depression, bipolar depression, seasonal depression, anxiety, compulsive behavior, addiction, post-traumatic stress syndrome, major psychotic depression, stress disorders, cognitive impairment in depressed patients, chronic pain, postpartum psychosis, postpartum depression, neurological disorders in premature infants, migraine headaches, or psychotic depression. In some instances, "disease" or "condition" refer to cancer. In some further instances, "cancer" refers to human cancers and carcinomas, sarcomas, adenocarcinomas, lymphomas, leukemias, melanomas, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "cancer" refers to all types of cancer, neoplasm or malignant tumors found in mammals, including leukemia, carcinomas and sarcomas. Exemplary cancers that may be treated with a compound, inhibitory nucleic acid, pharmaceutical composition, or method provided herein include breast cancer (e.g. ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, or melanoma. Additional examples include, cancer of the thyroid, endocrine system, brain, breast, cervix, colon, head & neck, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, inhibitory nucleic acid, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, inhibitory nucleic acid, pharmaceutical composition, or method provided herein include a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, inhibitory nucleic acid, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, inhibitory nucleic acid, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniformi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

A "cancer associated with aberrant 5-HTR$_{1B}$ activity" (also referred to herein as "5-HTR$_{1B}$ related cancer") is a cancer caused by aberrant 5-HTR$_{1B}$ activity (e.g. increased or decreased level of activity of 5-HTR$_{1B}$). A "cancer associated with aberrant 5-HTR$_{1D}$ activity" (also referred to herein as "5-HTR$_{1D}$ related cancer") is a cancer caused by aberrant 5-HTR$_{1D}$ activity (e.g. an increased or decreased level of activity of 5-HTR$_{1D}$). A "cancer associated with aberrant eEF-2K activity" (also referred to herein as "eEF-2K related cancer") is a cancer caused by aberrant eEF-2K activity (e.g. a mutated eEF-2K gene or abnormal (increased or decreased) level of activity of eEF-2K).

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound or inhibitory nucleic acid with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compound or inhibitory nucleic acid of the invention can be administered alone or can be coadministered to the patient. Coadministration is meant to include simultaneous or sequential administration of the compound or inhibitory nucleic acid individually or in combination (more than one compound or inhibitory nucleic acid). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The term "administer (or administering) a 5-HTR inhibitor" means administering a compound or inhibitory nucleic acid that inhibits the activity or reduces the level (e.g. amount) of one or more 5-HTR(s) (e.g. a 5-HTR$_{1B}$ inhibitor, HTR$_{1D}$ inhibitor, HTR$_{1B/1D}$ inhibitor, a pan 5-HTR inhibitor) to a subject and, without being limited by mechanism, allowing sufficient time for the 5-HTR inhibitor to reduce the activity of one or more 5-HTR(s), for the 5-HTR inhibitor to reduce the level (e.g. amount) of one or more 5-HTR(s), or for the 5-HTR inhibitor to reduce one or more symptoms of a disease (e.g. cancer, wherein the 5-HTR inhibitor may arrest the cell cycle, slow the cell cycle, reduce DNA replication, reduce cell replication, reduce cell growth, reduce metastasis, reduce proliferation of cancer cells, reduce migration, reduce angiogenesis, or cause cell death).

The term "administer (or administering) a 5-HTR activator" means administering a compound or inhibitory nucleic acid that increases the activity or level (e.g. amount) of one or more 5-HTR(s) (e.g. a 5-HTR$_{1B}$ activator, HTR$_{1D}$ activator, HTR$_{1B/1D}$ activator, a pan 5-HTR activator) to a subject and, without being limited by mechanism, allowing sufficient time for the 5-HTR activator to increase the activity of one or more 5-HTR(s), to increase the level (e.g. amount) of one or more 5-HTR(s), or for the 5-HTR activator to reduce one or more symptoms of a disease (e.g. cancer, wherein the 5-HTR activator may arrest the cell cycle, slow the cell cycle, reduce DNA replication, reduce cell replication, reduce cell growth, reduce metastasis, reduce proliferation of cancer cells, reduce migration, reduce angiogenesis, or cause cell death).

The term "administer (or administering) an eEF-2K inhibitor" means administering a compound or inhibitory nucleic acid that inhibits the activity or reduces the level (e.g. amount) of eEF-2K to a subject and, without being limited by mechanism, allowing sufficient time for the eEF-2K inhibitor to reduce the activity of eEF-2K, for the eEF-2K inhibitor to reduce the level (e.g. amount) of eEF-2K, or for the eEF-2K inhibitor to reduce one or more symptoms of a disease (e.g. cancer, wherein the eEF-2K inhibitor may arrest the cell cycle, slow the cell cycle, reduce DNA replication, reduce cell replication, reduce cell growth, reduce metastasis, reduce proliferation of cancer cells, reduce migration, reduce angiogenesis, or cause cell death).

The term "associated" or "associated with" as used herein to describe a disease (e.g. a protein associated disease, a cancer associated with aberrant 5-HTR activity, a cancer associated with aberrant 5-HTR$_{1B}$ activity, a cancer associated with aberrant 5-HTR$_{1D}$ activity, a cancer associated with aberrant eEF-2K activity, 5-HTR$_{1B}$ associated cancer, 5-HTR$_{1D}$ associated cancer, 5-HTR associated cancer, eEF-2K associated cancer, depression or migraine pain or pain associated with 5-HTR activity, 5-HTR$_{1B}$ activity, 5-HTR$_{1D}$ activity, or eEF-2K activity) means that the disease (e.g. cancer, depression, migraine pain, pain) is caused by, or a symptom of the disease is caused by, what is described as disease associated or what is described as associated with the disease. For example, a cancer associated with aberrant 5-HTR$_{1B}$ activity may be a cancer that results (entirely or partially) from aberrant 5-HTR$_{1B}$ activity or a cancer wherein a particular symptom of the disease is caused (entirely or partially) by aberrant 5-HTR$_{1B}$ activity. As used herein, what is described as being associated with a disease, if a causative agent, could be a target for treatment of the disease. For example, a cancer associated with aberrant 5-HTR$_{1B}$ activity or a 5-HTR$_{1B}$ associated cancer, may be treated with a 5-HTR$_{1B}$ modulator or 5-HTR$_{1B}$ inhibitor, in the instance where increased 5-HTR$_{1B}$ activity causes the cancer or 5-HTR$_{1B}$ activator, in the instance where decreased 5-HTR$_{1B}$ activity causes the cancer.

The term "aberrant" as used herein refers to different from normal. When used to described enzymatic or signal transduction activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or inhibitory nucleic acid or using a method as described herein), results in reduction of the disease or one or more disease symptoms.

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. In certain embodiments. the nucleic acids herein contain phosphodiester bonds. In other embodiments, nucleic acid analogs are included that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

A particular nucleic acid sequence also encompasses "splice variants." Similarly, a particular protein encoded by a nucleic acid encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The terms "identical" or percent sequence "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site at ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. Employed algorithms can account for gaps and the like.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 600, usually about 20 to about 200, more usually about 50 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively.

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA).

The phrase "stringent hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent hybridization conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent hybridization conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

Nucleic acids may be substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

An "inhibitory nucleic acid" is a nucleic acid (e.g. DNA, RNA, polymer of nucleotide analogs) that is capable of binding to a target nucleic acid (e.g. an mRNA translatable into an eEF-2K, 5-HTR, 5-HTR$_{1B}$, or 5-HTR$_{1D}$) and reducing transcription of the target nucleic acid (e.g. mRNA from DNA) or reducing the translation of the target nucleic acid (e.g. mRNA) or altering transcript splicing. In some embodiments, the "inhibitory nucleic acid" is a nucleic acid that is capable of binding (e.g. hybridizing) to a target nucleic acid (e.g. an mRNA translatable into an eEF-2K, 5-HTR, 5-HTR$_{1B}$, or 5-HTR$_{1D}$) and reducing translation of the target nucleic acid. The target nucleic acid is or includes one or more target nucleic acid sequences to which the inhibitory nucleic acid binds (e.g. hybridizes). Thus, an inhibitory nucleic acid typically is or includes a sequence (also referred to herein as an "antisense nucleic acid sequence") that is capable of hybridizing to at least a portion of a target nucleic acid at a target nucleic acid sequence. An example of an inhibitory nucleic acid is an antisense nucleic acid. Another example of an inhibitory nucleic acid is siRNA or RNAi (including their derivatives or pre-cursors, such as nucleotide analogs). Further examples include shRNA, miRNA, shmiRNA, or certain of their derivatives or pre-cursors. In some embodiments, the inhibitory nucleic acid is single stranded. In other embodiments, the inhibitory nucleic acid is double stranded. An "anti-eEF-2K inhibitory nucleic acid" is an inhibitory nucleic acid that is capable of binding to a nucleic acid that codes for at least a portion of eEF-2K and reducing transcription or translation of the target nucleic acid or altering transcript splicing. An "anti-5-HTR$_{1B}$ inhibitory nucleic acid" is an inhibitory nucleic acid that is capable of binding to a nucleic acid that codes for at least a portion of 5-HTR$_{1B}$ and reducing transcription or translation of the target nucleic acid or altering transcript splicing. An "anti-5-HTR$_{1D}$ inhibitory nucleic acid" is an inhibitory nucleic acid that is capable of binding to a nucleic acid that codes for at least a portion of 5-HTR$_{1D}$ and reducing transcription or translation of the target nucleic acid or altering transcript splicing. An "anti-5-HTR inhibitory nucleic acid" is an inhibitory nucleic acid that is capable of binding to a nucleic acid that codes for at least a portion of a 5-HTR and reducing transcription or translation of the target nucleic acid or altering transcript splicing.

An "antisense nucleic acid" is a nucleic acid (e.g. DNA, RNA or analogs thereof) that is at least partially complementary to at least a portion of a specific target nucleic acid (e.g. a target nucleic acid sequence), such as an mRNA molecule (e.g. a target mRNA molecule) (see, e.g., Weintraub, *Scientific American*, 262:40 (1990)), for example antisense, siRNA, shRNA, shmiRNA, miRNA (microRNA). Thus, antisense nucleic acids are capable of hybridizing to (e.g. selectively hybridizing to) a target nucleic acid (e.g. target mRNA). In some embodiments, the antisense nucleic acid hybridizes to the target nucleic acid sequence (e.g. mRNA) under stringent hybridization conditions. In some embodiments, the antisense nucleic acid hybridizes to the target nucleic acid (e.g. mRNA) under moderately stringent hybridization conditions. Antisense nucleic acids may comprise naturally occurring nucleotides or modified nucleotides such as, e.g., phosphorothioate, methylphosphonate, and -anomeric sugar-phosphate, backbone-modified nucleotides. An "anti-eEF-2K antisense nucleic acid" is an antisense nucleic acid that is at least partially complementary to at least a portion of a target nucleic acid sequence, such as an mRNA molecule, that codes for at least a portion of eEF-2K. An "anti-5-HTR$_{1B}$ antisense nucleic acid" is an antisense nucleic acid that is at least partially complementary to at least a portion of a target nucleic acid sequence, such as an mRNA molecule, that codes for at least a portion of the 5-HTR$_{1B}$. An "anti-5-HTR$_{1D}$ antisense nucleic acid" is an antisense nucleic acid that is at least partially complementary to at least a portion of a target nucleic acid sequence, such as an mRNA molecule, that codes for at least a portion of the 5-HTR$_{1D}$. An "anti-5-HTR antisense nucleic acid" is an antisense nucleic acid that is at least partially complementary to at least a portion of a target nucleic acid sequence, such as an mRNA molecule, that codes for at least a portion of a 5-HTR. Antisense nucleic acids may be single or double stranded nucleic acids.

In the cell, the antisense nucleic acids may hybridize to the target mRNA, forming a double-stranded molecule. The antisense nucleic acids, interfere with the translation of the mRNA, since the cell will not translate a mRNA that is double-stranded. The use of antisense methods to inhibit the in vitro translation of genes is well known in the art (Marcus-Sakura, *Anal. Biochem.*, 172:289, (1988)). Antisense molecules which bind directly to the DNA may be used.

Inhibitory nucleic acids can be delivered to the subject using any appropriate means known in the art, including by injection, inhalation, or oral ingestion. Another suitable delivery system is a colloidal dispersion system such as, for example, macromolecule complexes, nanocapsules, microspheres, beads, and lipid-based systems including oil-in-water emulsions, micelles, mixed micelles, and liposomes. An example of a colloidal system of this invention is a liposome (e.g. dioleoyl-sn-glycero-3-phosphocholine containing or dimyristoyl-phosphatidylcholine containing). Liposomes are artificial membrane vesicles which are useful as delivery vehicles in vitro and in vivo. Nucleic acids, including RNA and DNA within liposomes can be delivered to cells in a biologically active form (Fraley, et al., *Trends Biochem. Sci.*, 6:77, 1981). The compounds described herein (e.g. Formula (I), (II), (III), or (IV), including embodiments) may also be delivered to cells by liposomes. Liposomes can be targeted to specific cell types or tissues using any means known in the art (e.g. by modifying the liposome with RGD or folate). Inhibitory nucleic acids (e.g. antisense nucleic acids, siRNAs) may be delivered to a cell using cell permeable delivery systems (e.g. cell permeable peptides). In some embodiments, inhibitory nucleic acids are delivered to specific cells or tissues using viral vectors or viruses.

An "siRNA" refers to a nucleic acid that forms a double stranded RNA, which double stranded RNA has the ability to reduce or inhibit expression of a gene or target gene when the siRNA is present (e.g. expressed) in the same cell as the gene or target gene. The siRNA is typically about 5 to about 100 nucleotides in length, more typically about 10 to about 50 nucleotides in length, more typically about 15 to about 30 nucleotides in length, most typically about 20-30 base nucleotides, or about 20-25 or about 24-29 nucleotides in length, e.g., 20, 21, 22, 23, 24, 25, 26, 27, 28, 29, or 30 nucleotides in length. siRNA molecules and methods of generating them are described in, e.g., Bass, 2001, *Nature,* 411, 428-429; Elbashir et al., 2001, *Nature,* 411, 494-498; WO 00/44895; WO 01/36646; WO 99/32619; WO 00/01846; WO 01/29058; WO 99/07409; and WO 00/44914. A DNA molecule that transcribes dsRNA or siRNA (for instance, as a hairpin duplex) also provides RNAi. DNA molecules for transcribing dsRNA are disclosed in U.S. Pat. No. 6,573,099, and in U.S. Patent Application Publication Nos. 2002/0160393 and 2003/0027783, and Tuschl and Borkhardt, *Molecular Interventions,* 2:158 (2002). An "anti-eEF-2K siRNA" is an siRNA that is at least partially complementary to at least a portion of a target nucleic acid sequence, such as an mRNA molecule, that codes for at least a portion of eEF-2K. An "anti-5-HTR$_{1B}$ siRNA" is an siRNA that is at least partially complementary to at least a portion of a target nucleic acid sequence, such as an mRNA molecule, that codes for at least a portion of the 5-HTR$_{1B}$. An "anti-5-HTR$_{1D}$ siRNA" is an siRNA that is at least partially complementary to at least a portion of a target nucleic acid sequence, such as an mRNA molecule, that codes for at least a portion of the 5-HTR$_{1D}$. An "anti-5-HTR siRNA" is an siRNA that is at least partially complementary to at least a portion of a target nucleic acid sequence, such as an mRNA molecule, that codes for at least a portion of a 5-HTR.

The siRNA can be administered directly or siRNA expression vectors can be used to induce RNAi that have different design criteria. A vector can have inserted two inverted repeats separated by a short spacer sequence and ending with a string of T's which serve to terminate transcription.

Construction of suitable vectors containing the desired therapeutic gene coding and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and re-ligated in the form desired.

The term "eEF-2" refers to the eukaryotic (translation) elongation factor 2 (e.g. *Homo sapien* accession no. NM_0001961). eEF-2 may refer to the protein, DNA, or mRNA.

The term "eEF-2K" refers to the eukaryotic elongation factor 2 kinase (e.g. *Homo sapien* accession no. NM_013302). eEF-2K may refer to the protein, DNA, or mRNA. eEF-2K is also called "CaMK-III" and is also known as Calmodulin-dependent protein kinase-III, and these terms may be used interchangeably.

The term "5-HTR$_{1B}$" refers to the 5-hydroxytryptamine (serotonin) receptor 1B (e.g. *Homo sapien* accession no. NM_000863). 5-HTR$_{1B}$ may refer to the protein, DNA, or mRNA.

The term "5-HTR$_{1D}$" refers to the 5-hydroxytryptamine (serotonin) receptor 1D (e.g. *Homo sapien* accession no. NM_000864). 5-HTR$_{1D}$ may refer to the protein, DNA, or mRNA.

The term "5-HTR" refers to a 5-hydroxytryptamine (serotonin) receptor (e.g. selected from 5-HTR$_1$ through 5-HTR$_7$, including subtypes). 5-HTR may refer to the protein, DNA, or mRNA.

Compounds

In a first aspect, a compound is provided having the formula:

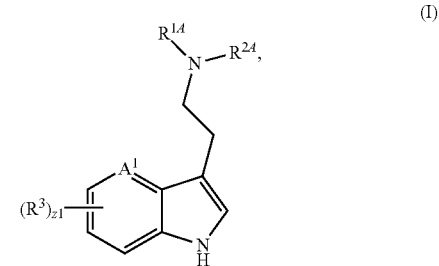

(I)

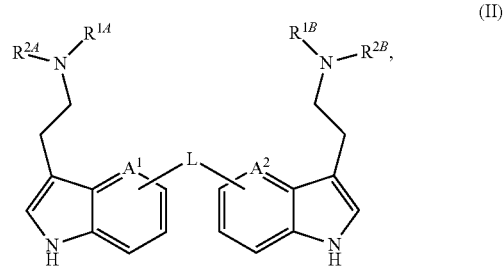

(II)

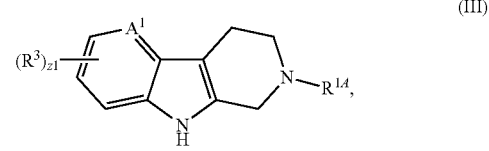

(III)

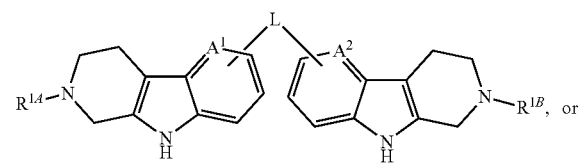

(IV)

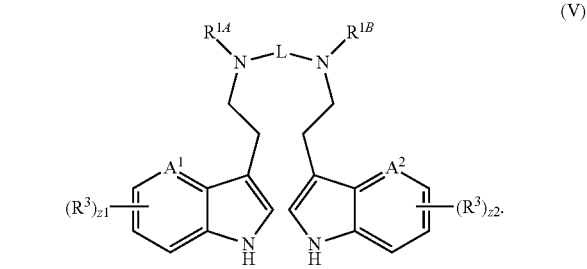

(V)

$R^{1A}$ is independently hydrogen, halogen, —CX$^{1A}_3$, —C(O)R$^{7A}$, —C(O)—OR$^{7A}$, —C(O)NR$^{7A}$R$^{8A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted membered heteroaryl. $R^{1B}$ is independently hydrogen, halogen, $-CX^{1B}{}_3$, $-C(O)R^{7B}$, $-C(O)-OR^{7B}$, $-C(O)NR^{7B}R^{8B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{2A}$ is independently hydrogen, halogen, $-CX^{2A}{}_3$, $-C(O)R^{9A}$, $-C(O)-OR^{9A}$, $-C(O)NR^{9A}R^{10A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{2B}$ is independently hydrogen, halogen, $-CX^{2B}{}_3$, $-C(O)R^{9B}$, $-C(O)-OR^{9B}$, $-C(O)NR^{9B}R^{10B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$ and $R^{2A}$ are optionally joined to form a substituted or unsubstituted heterocycloalkyl or substituted or unsubstituted heteroaryl. $R^{1B}$ and $R^{2B}$ are optionally joined to form a substituted or unsubstituted heterocycloalkyl or substituted or unsubstituted heteroaryl. $R^3$ is independently hydrogen, halogen, $-CX^3{}_3$, $-CN$, $-SO_2Cl$, $-SO_nR^{14}$, $-SO_kNR^{11}R^{12}$, $-NHNH_2$, $-ONR^{11}R^{12}$, $-NHC=(O)NHNH_2$, $-NHC=(O)NR^{11}R^{12}$, $-N(O)_m$, $-NR^{11}R^{12}$, $-C(O)R^{13}$, $-C(O)-OR^{13}$, $-O-C(O)-R^{13}$, $-C(O)NR^{11}R^{12}$, $-NR^{11}C(O)R^{13}$, $-OR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{7A}$, $R^{7B}$, $R^{8A}$, $R^{9A}$, $R^{9B}$, $R^{10A}$, $R^{10B}$, $R^{11}$, $R^{12}$, $R^{13}$, an $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols $A^1$ and $A^2$ are independently $=N-$ or $=CR^3-$. The symbol L is independently a bond, $-O-$, $-NH-$, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene,

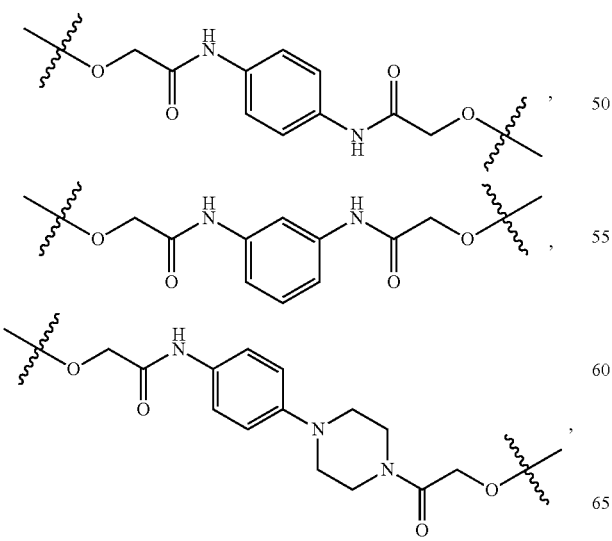

-continued

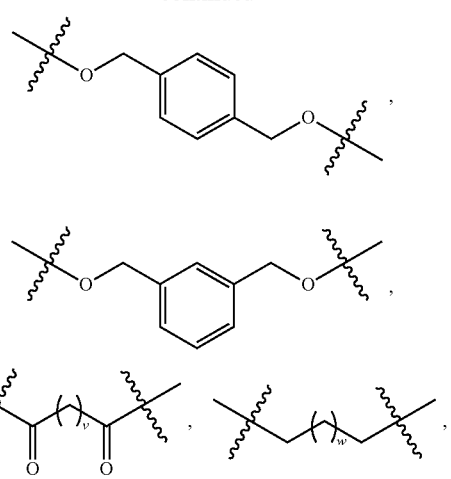

or $-O-(CH_2)_p-O-$. The symbols k and m are independently 1 or 2. The symbol n is independently an integer from 0 to 4. The symbol p is independently an integer from 1 to 20. The symbol v is independently an integer from 1 to 20. The symbol w is independently an integer from 1 to 20. The symbols z1 and z2 are independently an integer from 0 to 3. The symbols $X^{1A}$, $X^{1B}$, $X^{2A}$, $X^{2B}$, and $X^3$ are independently $-Cl$, $-Br$, $-I$, or $-F$.

In some embodiments, the compound has the formula:

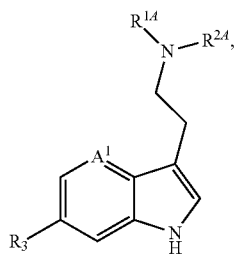
(Ia)

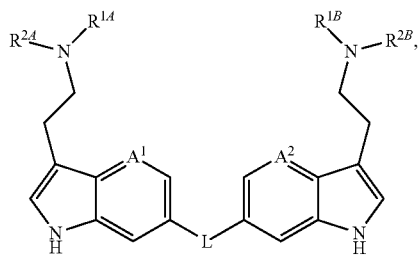
(IIa)

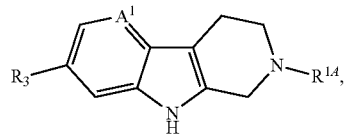
(IIIa)

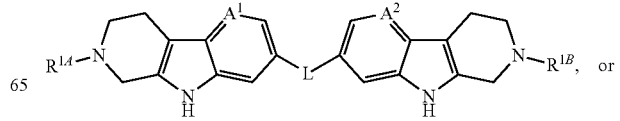
(IVa) or

-continued

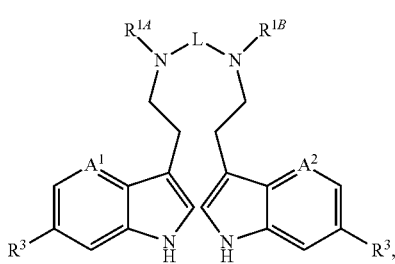
(Va)

wherein the variables (e.g. $R^{1A}, R^{1B}, R^{2A}, R^{2B}, R^3, A^1, A^2, L$) are as defined above.

In some embodiments, the compound has the formula:

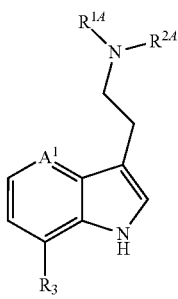
(Ib)

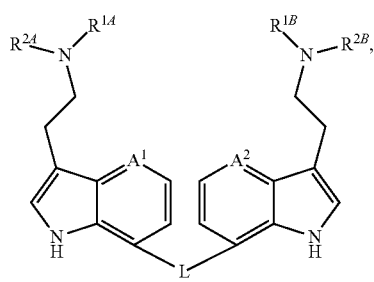
(IIb)

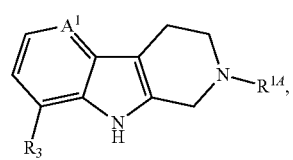
(IIIb)

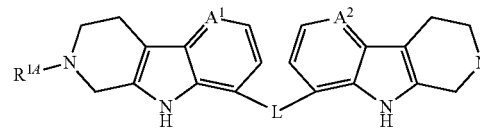
(IVb)

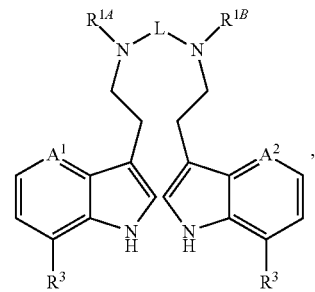
(Vb)

wherein the variables (e.g. $R^{1A}, R^{1B}, R^{2A}, R^{2B}, R^3, A^1, A^2, L$) are as defined above.

In some embodiments, the compound has the formula:

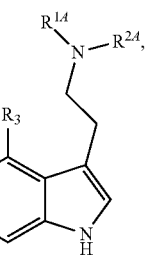
(Ic)

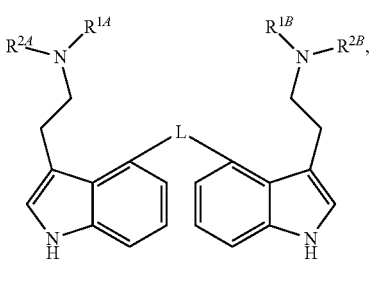
(IIc)

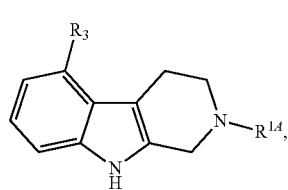
(IIIc)

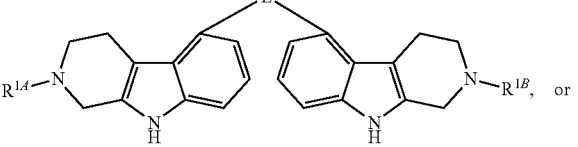
(IVc)

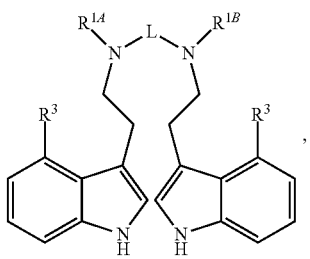
(Vc)

wherein the variables (e.g. $R^{1A}, R^{1B}, R^{2A}, R^{2B}, R^3, A^1, A^2, L$) are as defined above.

In some embodiments, the compound has the formula:

(Id)

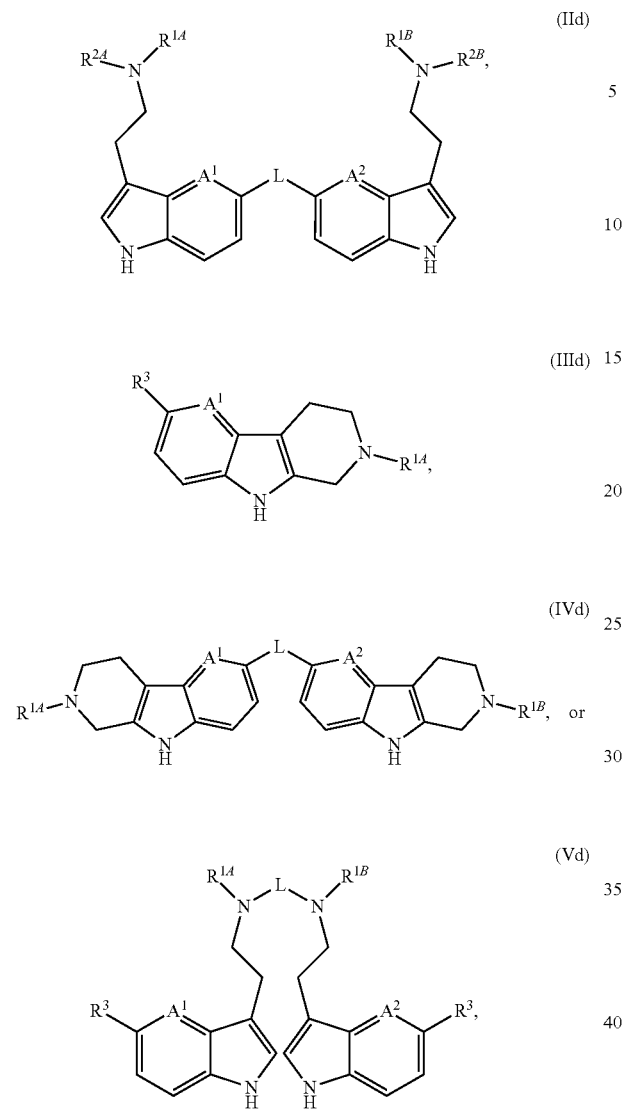

wherein the variables (e.g. $R^{1A}, R^{1B}, R^{2A}, R^{2B}, R^3, A^1, A^2, L$) are as defined above.

In some embodiments, the compound has the formula:

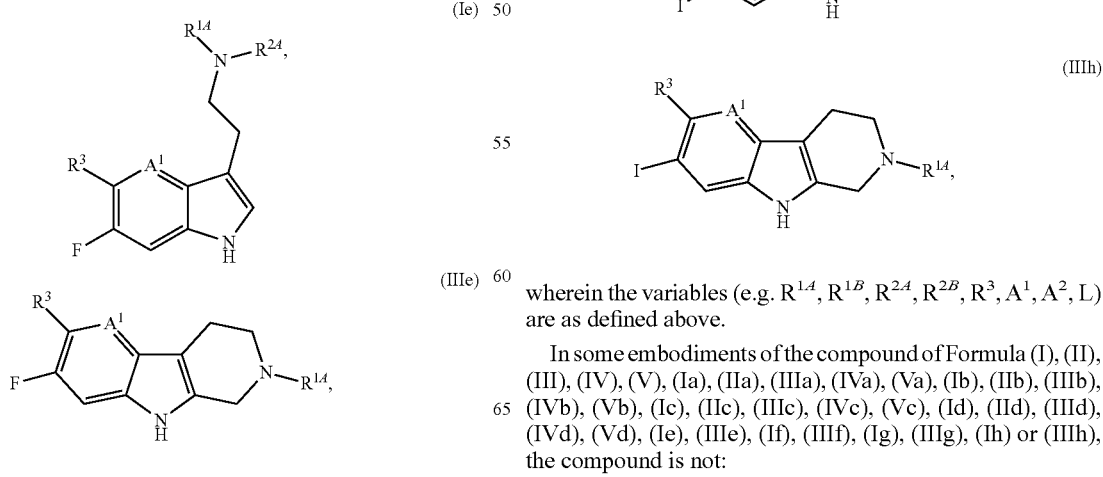

wherein the variables (e.g. $R^{1A}, R^{1B}, R^{2A}, R^{2B}, R^3, A^1, A^2, L$) are as defined above.

In some embodiments of the compound of Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih) or (IIIh), the compound is not:

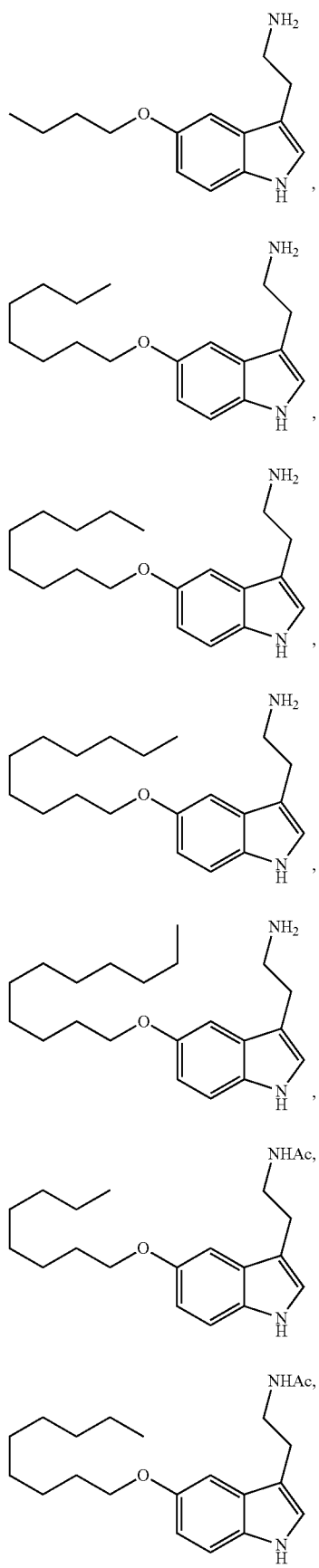
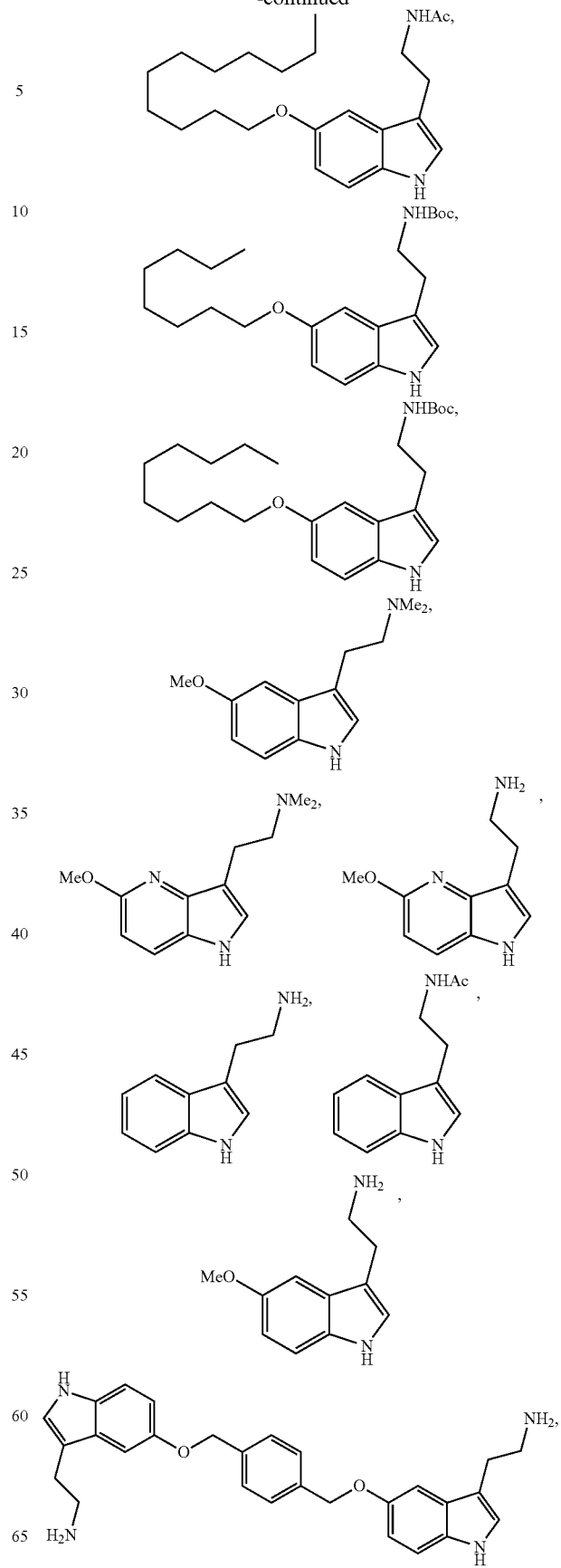

-continued
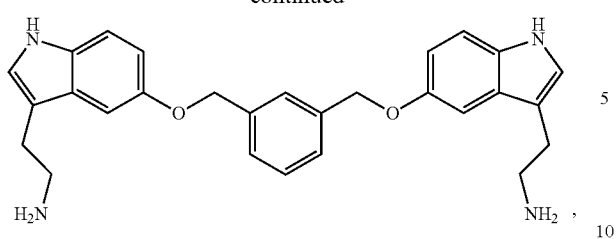
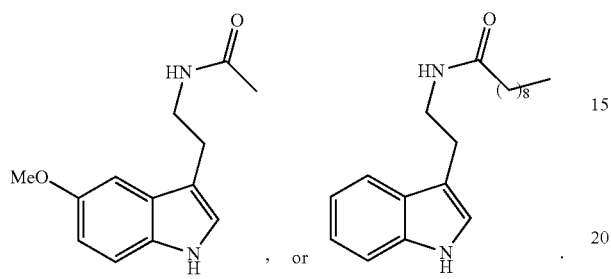
In some embodiments of the compound of Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih) or (IIIh), the compound is selected from:
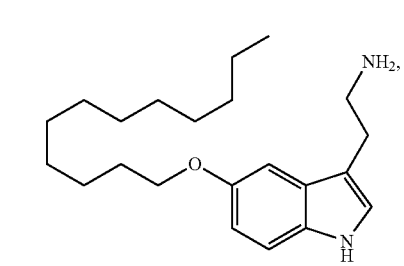
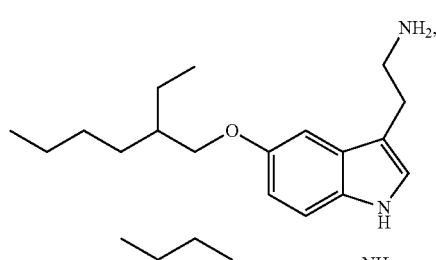
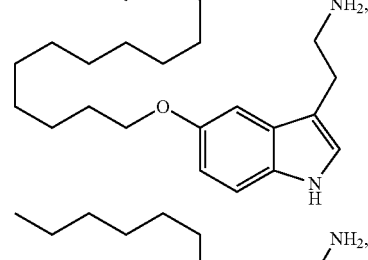
-continued
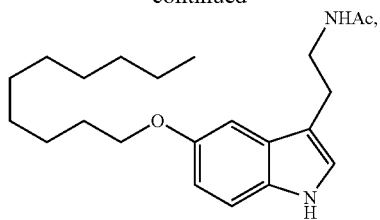
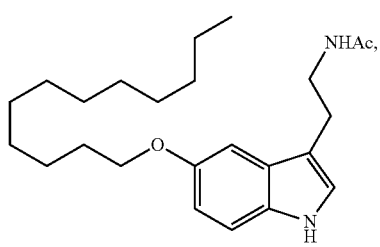
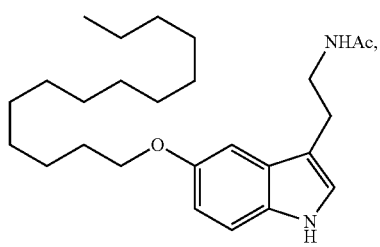
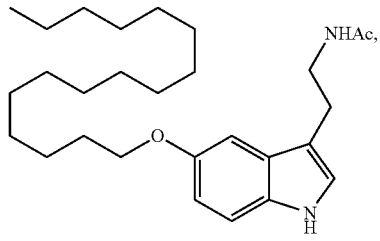
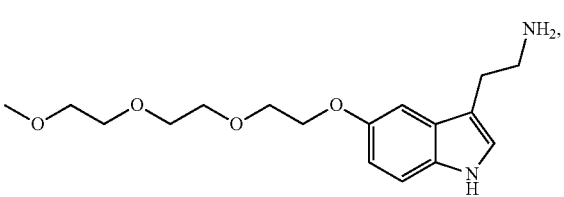
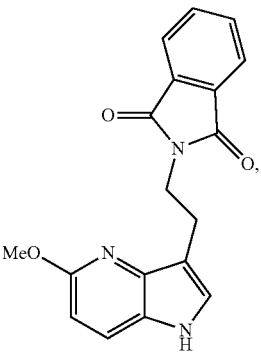

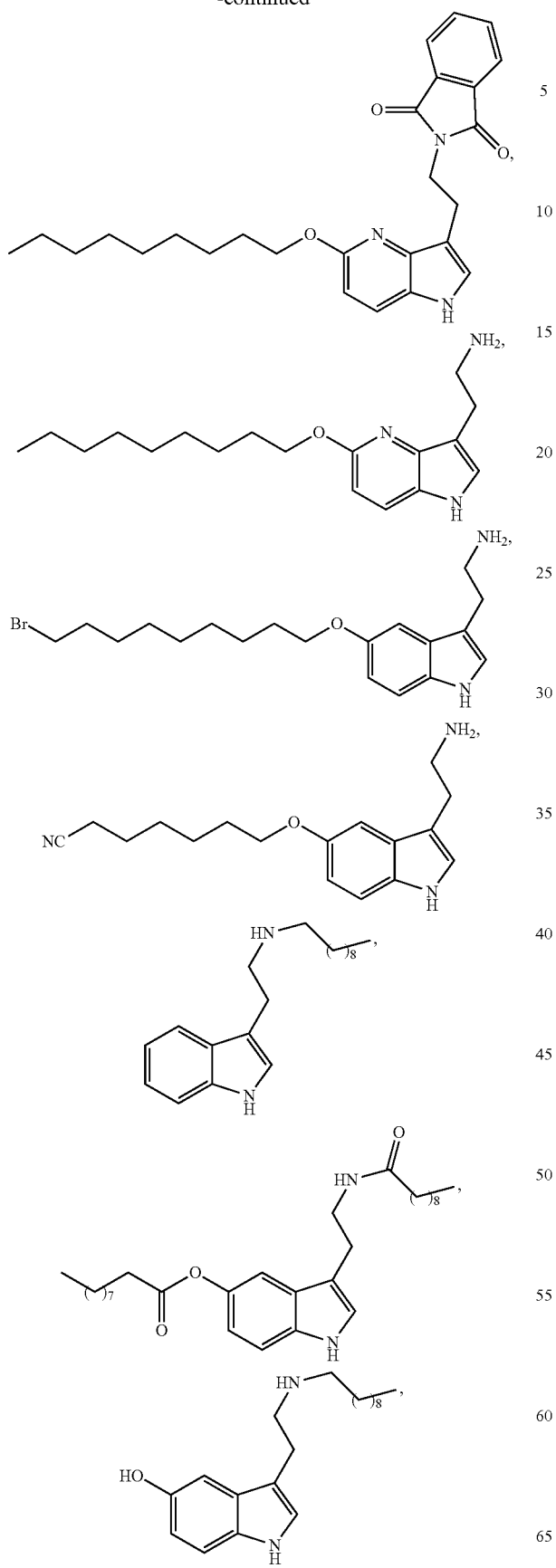
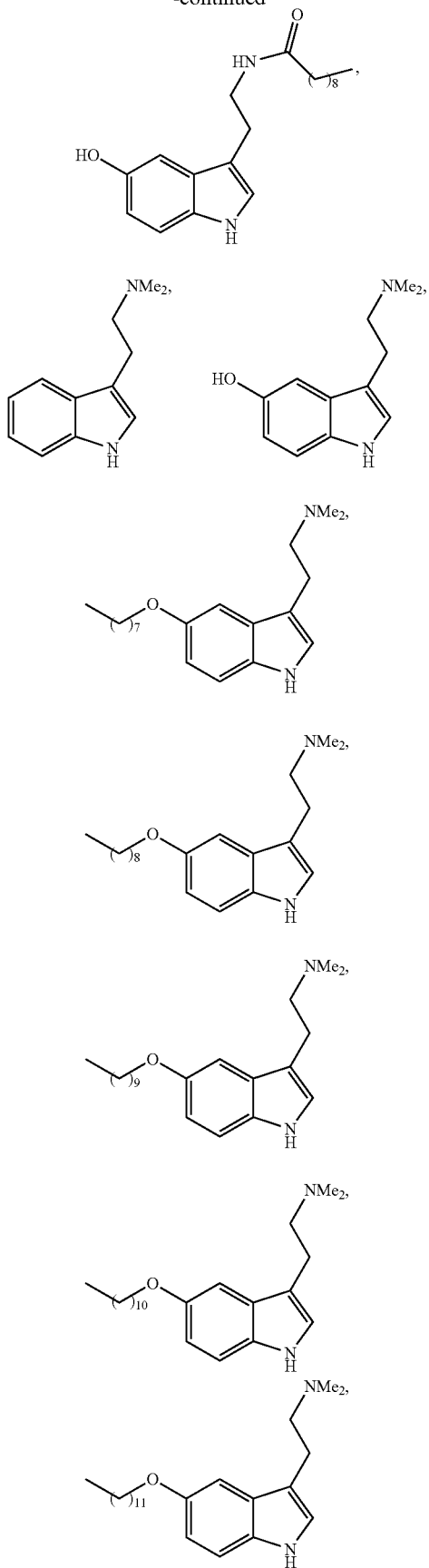

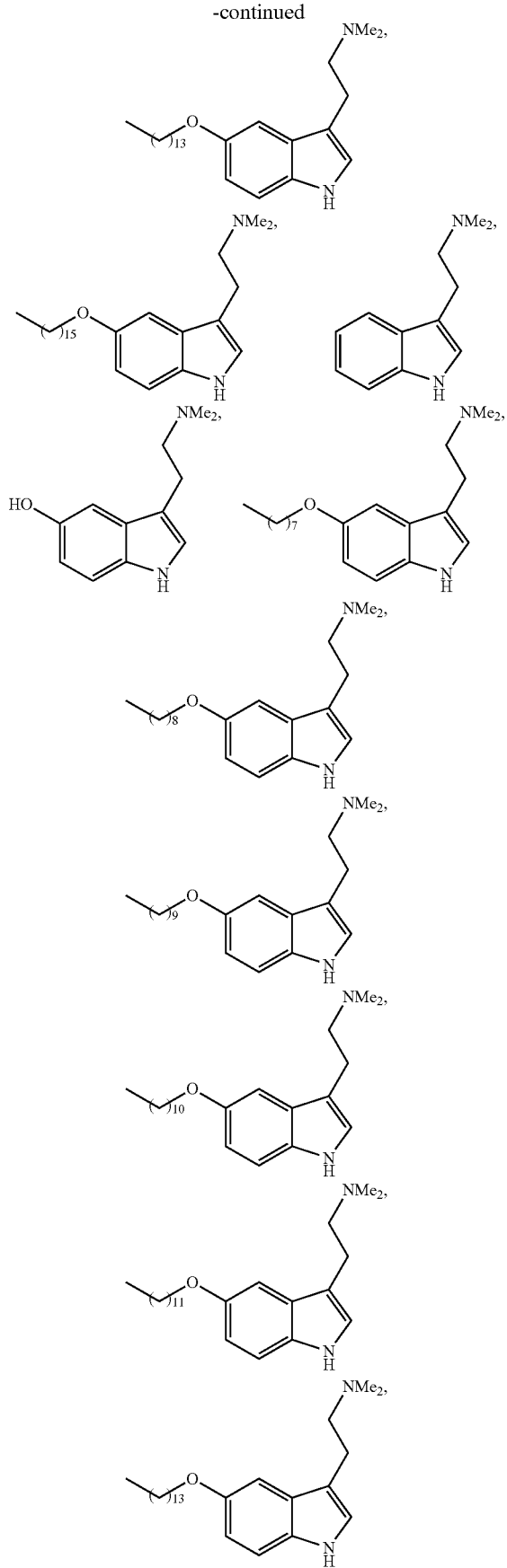
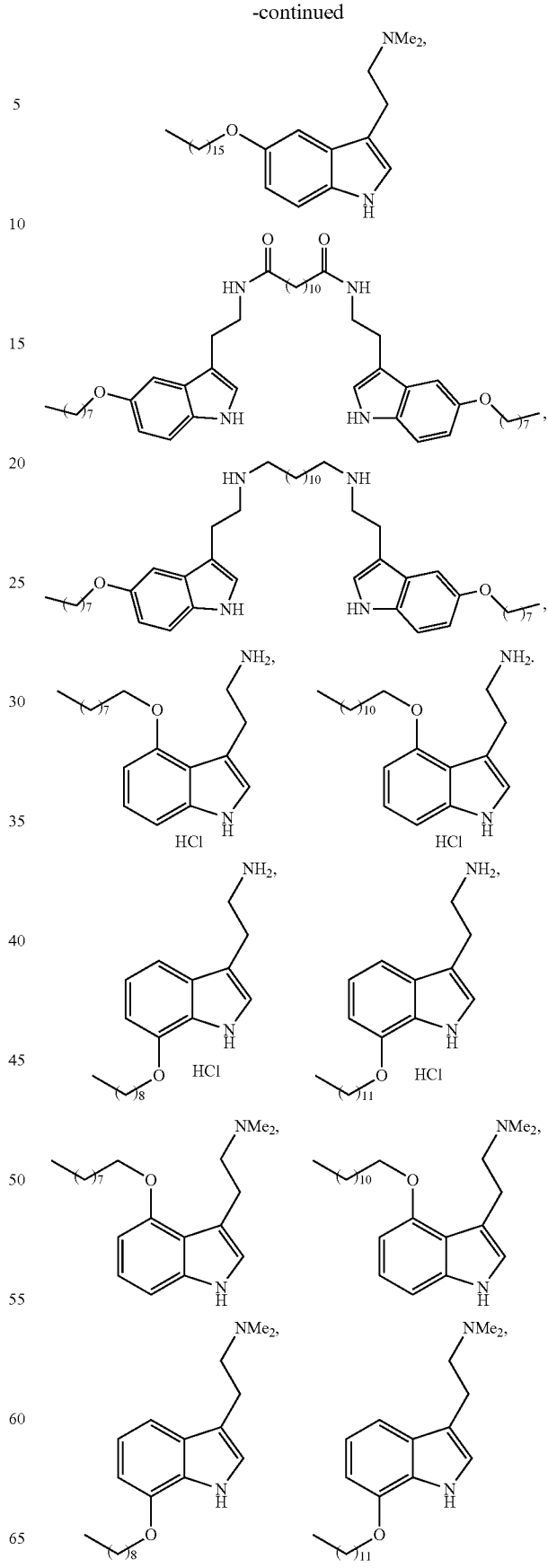

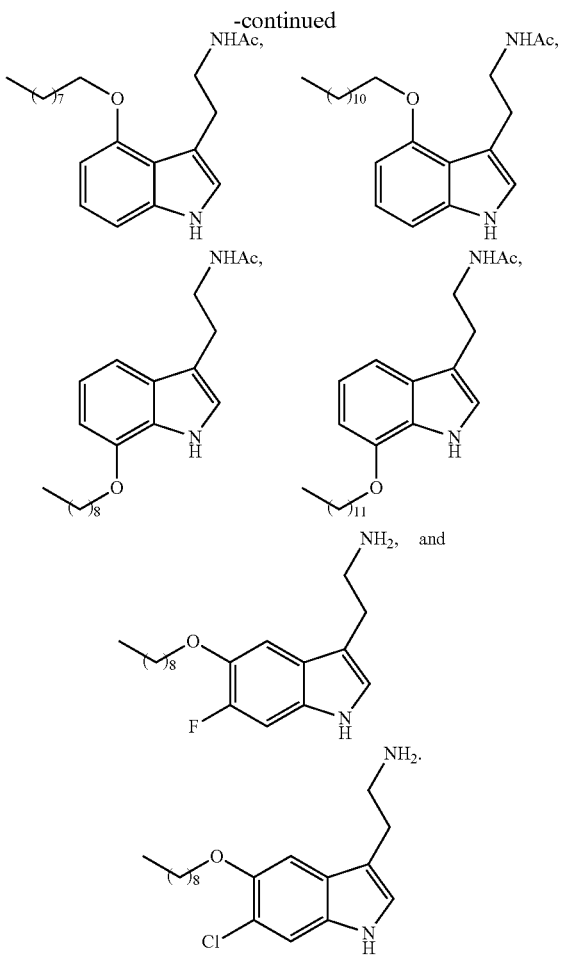

In some embodiments of the compounds, $R^{1A}$ is —C(O)$R^{7A}$ or —C(O)—OR$^{7A}$. In some embodiments, $R^{1A}$ is —C(O)$R^{7A}$. In some embodiments, $R^{1A}$ is —C(O)—OR$^{7A}$. In some embodiments, $R^{2A}$ is —C(O)$R^{9A}$ or —C(O)—OR$^{9A}$. In some embodiments, $R^{2A}$ is —C(O)$R^{9A}$. In some embodiments, $R^{2A}$ is —C(O)—OR$^{9A}$. In some embodiments, $R^{1A}$ is hydrogen. In some embodiments, $R^{2A}$ is hydrogen. In some embodiments, $R^{1A}$ and $R^{2A}$ are joined to form a substituted or unsubstituted heterocycloalkyl or substituted or unsubstituted heteroaryl. In some embodiments, $R^{1A}$ and $R^{2A}$ are joined to form a substituted or unsubstituted heterocycloalkyl. In some embodiments, $R^{1A}$ and $R^{2A}$ are joined to form a heterocycloalkyl fused to an aryl. In some embodiments, $R^{1A}$ and $R^{2A}$ are joined to form a substituted or unsubstituted isoindolin-2-yl-1,3-dione.

In some embodiments of the compounds, $R^{1B}$ is —C(O)$R^{7B}$ or —C(O)—OR$^{7B}$. In some embodiments, $R^{1B}$ is —C(O)$R^{7B}$. In some embodiments, $R^{1B}$ is —C(O)—OR$^{7B}$. In some embodiments, $R^{2B}$ is —C(O)$R^{9B}$ or —C(O)—OR$^{9B}$. In some embodiments, $R^{2B}$ is —C(O)$R^{9B}$. In some embodiments, $R^{2B}$ is —C(O)—OR$^{9B}$. In some embodiments, $R^{1B}$ is hydrogen. In some embodiments, $R^{2B}$ is hydrogen. In some embodiments, $R^{1B}$ and $R^{2B}$ are joined to form a substituted or unsubstituted heterocycloalkyl or substituted or unsubstituted heteroaryl. In some embodiments, $R^{1B}$ and $R^{2B}$ are joined to form a substituted or unsubstituted heterocycloalkyl. In some embodiments, $R^{1B}$ and $R^{2B}$ are joined to form a heterocycloalkyl fused to an aryl. In some embodiments, $R^{1B}$ and $R^{2B}$ are joined to form a substituted or unsubstituted isoindolin-2-yl-1,3-dione.

In some embodiments, $R^{1A}$ is substituted or unsubstituted $C_1$-$C_{20}$ alkyl. In some embodiments, $R^{1A}$ is substituted $C_1$-$C_{20}$ alkyl. In some embodiments, $R^{1A}$ is unsubstituted $C_1$-$C_{20}$ alkyl. In some embodiments, $R^{1A}$ is substituted or unsubstituted $C_1$-$C_{12}$ alkyl. In some embodiments, $R^{1A}$ is substituted $C_1$-$C_{12}$ alkyl. In some embodiments, $R^{1A}$ is unsubstituted $C_1$-$C_{12}$ alkyl. In some embodiments, $R^{1A}$ is substituted or unsubstituted $C_1$-$C_5$ alkyl. In some embodiments, $R^{1A}$ is substituted $C_1$-$C_5$ alkyl. In some embodiments, $R^{1A}$ is unsubstituted $C_1$-$C_5$ alkyl. In some embodiments, $R^{1A}$ is unsubstituted methyl. In some embodiments, $R^{1A}$ is unsubstituted ethyl. In some embodiments, $R^{1A}$ is unsubstituted propyl. In some embodiments, $R^{1A}$ is tert-butyloxycarbonyl.

In some embodiments, $R^{2A}$ is substituted or unsubstituted $C_1$-$C_{20}$ alkyl. In some embodiments, $R^{2A}$ is substituted $C_1$-$C_{20}$ alkyl. In some embodiments, $R^{2A}$ is unsubstituted $C_1$-$C_{20}$ alkyl. In some embodiments, $R^{2A}$ is substituted or unsubstituted $C_1$-$C_{12}$ alkyl. In some embodiments, $R^{2A}$ is substituted $C_1$-$C_{12}$ alkyl. In some embodiments, $R^{2A}$ is unsubstituted $C_1$-$C_{12}$ alkyl. In some embodiments, $R^{2A}$ is substituted or unsubstituted $C_1$-$C_5$ alkyl. In some embodiments, $R^{2A}$ is substituted $C_1$-$C_5$ alkyl. In some embodiments, $R^{2A}$ is unsubstituted $C_1$-$C_5$ alkyl. In some embodiments, $R^{2A}$ is unsubstituted methyl. In some embodiments, $R^{2A}$ is unsubstituted ethyl. In some embodiments, $R^{2A}$ is unsubstituted propyl. In some embodiments, $R^{2A}$ is tert-butyloxycarbonyl.

In some embodiments, $R^{1B}$ is substituted or unsubstituted $C_1$-$C_{20}$ alkyl. In some embodiments, $R^{1B}$ is substituted $C_1$-$C_{20}$ alkyl. In some embodiments, $R^{1B}$ is unsubstituted $C_1$-$C_{20}$ alkyl. In some embodiments, $R^{1B}$ is substituted or unsubstituted $C_1$-$C_{12}$ alkyl. In some embodiments, $R^{1B}$ is substituted $C_1$-$C_{12}$ alkyl. In some embodiments, $R^{1B}$ is unsubstituted $C_1$-$C_{12}$ alkyl. In some embodiments, $R^{1B}$ is substituted or unsubstituted $C_1$-$C_5$ alkyl. In some embodiments, $R^{1B}$ is substituted $C_1$-$C_5$ alkyl. In some embodiments, $R^{1B}$ is unsubstituted $C_1$-$C_5$ alkyl. In some embodiments, $R^{1B}$ is unsubstituted methyl. In some embodiments, $R^{1B}$ is unsubstituted ethyl. In some embodiments, $R^{1B}$ is unsubstituted propyl. In some embodiments, $R^{1B}$ is tert-butyloxycarbonyl.

In some embodiments, $R^{2B}$ is substituted or unsubstituted $C_1$-$C_{20}$ alkyl. In some embodiments, $R^{2B}$ is substituted $C_1$-$C_{20}$ alkyl. In some embodiments, $R^{2B}$ is unsubstituted $C_1$-$C_{20}$ alkyl. In some embodiments, $R^{2B}$ is substituted or unsubstituted $C_1$-$C_{12}$ alkyl. In some embodiments, $R^{2B}$ is substituted $C_1$-$C_{12}$ alkyl. In some embodiments, $R^{2B}$ is unsubstituted $C_1$-$C_{12}$ alkyl. In some embodiments, $R^{2B}$ is substituted or unsubstituted $C_1$-$C_5$ alkyl. In some embodiments, $R^{2B}$ is substituted $C_1$-$C_5$ alkyl. In some embodiments, $R^{2B}$ is unsubstituted $C_1$-$C_5$ alkyl. In some embodiments, $R^{2B}$ is unsubstituted methyl. In some embodiments, $R^{2B}$ is unsubstituted ethyl. In some embodiments, $R^{2B}$ is unsubstituted propyl. In some embodiments, $R^{2B}$ is tert-butyloxycarbonyl.

In some embodiments of the compounds, $R^3$ is independently hydrogen, —C(O)$R^{13}$, —O—C(O)—$R^{13}$, —C(O)—OR$^{13}$, —OR$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^3$ is independently hydrogen, —C(O)$R^{13}$, —O—C(O)—$R^{13}$, —C(O)—OR$^{13}$, or —OR$^{14}$. In some embodiments, $R^3$ is independently halogen. In some embodiments, $R^3$ is independently hydrogen. In some embodiments, $R^3$ is independently —C(O)$R^{13}$. In some embodiments, $R^3$ is independently —C(O)—OR$^{13}$. In some embodiments, $R^3$ is independently —O—C(O)—$R^{13}$. In some embodiments, $R^3$ is independently —OR$^{14}$. In some embodiments, $R^3$ is independently —F. In some embodiments, $R^3$ is independently —Cl. In some embodiments, $R^3$ is independently —Br. In some embodiments, $R^3$ is independently —I.

In some embodiments of the compounds, $R^{7A}$ is hydrogen, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In some embodiments, $R^{7A}$ is hydrogen, substituted or unsubstituted $C_1$-$C_{10}$ alkyl or substituted or unsubstituted 2 to 10 membered heteroalkyl. In some embodiments, $R^{7A}$ is hydrogen or substituted or unsubstituted 2 to 10 membered heteroalkyl. In some embodiments, $R^{7A}$ is hydrogen or substituted or unsubstituted $C_1$-$C_{10}$ alkyl. In some embodiments, $R^{7A}$ is substituted or unsubstituted $C_1$-$C_{10}$ alkyl. In some embodiments, $R^{7A}$ is unsubstituted methyl. In some embodiments, $R^{7A}$ is hydrogen.

In some embodiments of the compounds, $R^{8A}$ is hydrogen, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In some embodiments, $R^{8A}$ is hydrogen, substituted or unsubstituted $C_1$-$C_{10}$ alkyl or substituted or unsubstituted 2 to 10 membered heteroalkyl. In some embodiments, $R^{8A}$ is hydrogen or substituted or unsubstituted 2 to 10 membered heteroalkyl. In some embodiments, $R^{8A}$ is hydrogen or substituted or unsubstituted $C_1$-$C_{10}$ alkyl. In some embodiments, $R^{8A}$ is substituted or unsubstituted $C_1$-$C_{10}$ alkyl. In some embodiments, $R^{8A}$ is unsubstituted methyl. In some embodiments, $R^{8A}$ is hydrogen.

In some embodiments of the compounds, $R^{9A}$ is hydrogen, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In some embodiments, $R^{9A}$ is hydrogen, substituted or unsubstituted $C_1$-$C_{10}$ alkyl or substituted or unsubstituted 2 to 10 membered heteroalkyl. In some embodiments, $R^{9A}$ is hydrogen or substituted or unsubstituted 2 to 10 membered heteroalkyl. In some embodiments, $R^{9A}$ is hydrogen or substituted or unsubstituted $C_1$-$C_{10}$ alkyl. In some embodiments, $R^{9A}$ is substituted or unsubstituted $C_1$-$C_{10}$ alkyl. In some embodiments, $R^{9A}$ is unsubstituted methyl. In some embodiments, $R^{9A}$ is hydrogen.

In some embodiments of the compounds, $R^{10A}$ is hydrogen, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In some embodiments, $R^{10A}$ is hydrogen, substituted or unsubstituted $C_1$-$C_{10}$ alkyl or substituted or unsubstituted 2 to 10 membered heteroalkyl. In some embodiments, $R^{10A}$ is hydrogen or substituted or unsubstituted 2 to 10 membered heteroalkyl. In some embodiments, $R^{10A}$ is hydrogen or substituted or unsubstituted $C_1$-$C_{10}$ alkyl. In some embodiments, $R^{10A}$ is substituted or unsubstituted $C_1$-$C_{10}$ alkyl. In some embodiments, $R^{10A}$ is unsubstituted methyl. In some embodiments, $R^{10A}$ is hydrogen.

In some embodiments of the compounds, $R^{7B}$ is hydrogen, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In some embodiments, $R^{7B}$ is hydrogen, substituted or unsubstituted $C_1$-$C_{10}$ alkyl or substituted or unsubstituted 2 to 10 membered heteroalkyl. In some embodiments, $R^{7B}$ is hydrogen or substituted or unsubstituted 2 to 10 membered heteroalkyl. In some embodiments, $R^{7B}$ is hydrogen or substituted or unsubstituted $C_1$-$C_{10}$ alkyl. In some embodiments, $R^{7B}$ is substituted or unsubstituted $C_1$-$C_{10}$ alkyl. In some embodiments, $R^{7B}$ is unsubstituted methyl. In some embodiments, $R^{7B}$ is hydrogen.

In some embodiments of the compounds, $R^{8B}$ is hydrogen, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In some embodiments, $R^{8B}$ is hydrogen, substituted or unsubstituted $C_1$-$C_{10}$ alkyl or substituted or unsubstituted 2 to 10 membered heteroalkyl. In some embodiments, $R^{8B}$ is hydrogen or substituted or unsubstituted 2 to 10 membered heteroalkyl. In some embodiments, $R^{8B}$ is hydrogen or substituted or unsubstituted $C_1$-$C_{10}$ alkyl. In some embodiments, $R^{8B}$ is substituted or unsubstituted $C_1$-$C_{10}$ alkyl. In some embodiments, $R^{8B}$ is unsubstituted methyl. In some embodiments, $R^{8B}$ is hydrogen.

In some embodiments of the compounds, $R^{9B}$ is hydrogen, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In some embodiments, $R^{9B}$ is hydrogen, substituted or unsubstituted $C_1$-$C_{10}$ alkyl or substituted or unsubstituted 2 to 10 membered heteroalkyl. In some embodiments, $R^{9B}$ is hydrogen or substituted or unsubstituted 2 to 10 membered heteroalkyl. In some embodiments, $R^{9B}$ is hydrogen or substituted or unsubstituted $C_1$-$C_{10}$ alkyl. In some embodiments, $R^{9B}$ is substituted or unsubstituted $C_1$-$C_{10}$ alkyl. In some embodiments, $R^{9B}$ is unsubstituted methyl. In some embodiments, $R^{9B}$ is hydrogen.

In some embodiments of the compounds, $R^{10B}$ is hydrogen, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In some embodiments, $R^{10B}$ is hydrogen, substituted or unsubstituted $C_1$-$C_{10}$ alkyl or substituted or unsubstituted 2 to 10 membered heteroalkyl. In some embodiments, $R^{10B}$ is hydrogen or substituted or unsubstituted 2 to 10 membered heteroalkyl. In some embodiments, $R^{10B}$ is hydrogen or substituted or unsubstituted $C_1$-$C_{10}$ alkyl. In some embodiments, $R^{10B}$ is substituted or unsubstituted $C_1$-$C_{10}$ alkyl. In some embodiments, $R^{10B}$ is unsubstituted methyl. In some embodiments, $R^{10B}$ is hydrogen.

In some embodiments of the compounds, $R^{13}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^{13}$ is independently hydrogen, substituted or unsubstituted alkyl, or substituted or unsubstituted heteroalkyl. In some embodiments, $R^{13}$ is independently hydrogen. In some embodiments, $R^{13}$ is independently substituted or unsubstituted alkyl. In some embodiments, $R^{13}$ is independently substituted or unsubstituted $C_1$-$C_{20}$ alkyl. In some embodiments, $R^{13}$ is independently substituted or unsubstituted $C_6$-$C_{16}$ alkyl. In some embodiments, $R^{13}$ is independently $C_6$-$C_{16}$ alkyl. In some embodiments, $R^{13}$ is independently substituted $C_6$-$C_{16}$ alkyl. In some embodiments, $R^{13}$ is independently substituted or unsubstituted heteroalkyl. In some embodiments, $R^{13}$ is independently substituted or unsubstituted 2 to 20 membered heteroalkyl. In some embodiments, $R^{13}$ is independently substituted or unsubstituted 6 to 16 membered heteroalkyl. In some embodiments, $R^{13}$ is independently substituted 6 to 16 membered heteroalkyl. In some embodiments, $R^{13}$ is independently unsubstituted 6 to 16 membered heteroalkyl. In some embodiments, $R^{13}$ is:

In some embodiments, $R^{13}$ is:

and $R^3$ is independently —C(O)$R^{13}$ or —O—C(O)—$R^{13}$. In some embodiments, $R^{13}$ is independently substituted or unsubstituted $C_{12}$-$C_{16}$ alkyl. In some embodiments, $R^{13}$ is independently unsubstituted $C_{12}$-$C_{16}$ alkyl. In some embodiments, $R^{13}$ is independently substituted $C_{12}$-$C_{16}$ alkyl. In some embodiments, $R^{13}$ is independently substituted or unsubstituted $C_{13}$-$C_{16}$ alkyl. In some embodiments, $R^{13}$ is independently unsubstituted $C_{13}$-$C_{16}$ alkyl. In some embodiments, $R^{13}$ is independently substituted $C_{13}$-$C_{16}$ alkyl. In some embodiments, $R^{13}$ is independently substituted or unsubstituted $C_{14}$-$C_{16}$ alkyl. In some embodiments, $R^{13}$ is independently unsubstituted $C_{14}$-$C_{16}$ alkyl. In some embodiments, $R^{13}$ is independently substituted $C_{14}$-$C_{16}$ alkyl. In some embodiments, $R^{13}$ is independently substituted or unsubstituted $C_{15}$-$C_{16}$ alkyl. In some embodiments, $R^{13}$ is independently unsubstituted $C_{15}$-$C_{16}$ alkyl. In some embodiments, $R^{13}$ is independently substituted $C_{15}$-$C_{16}$ alkyl. In some embodiments, $R^{13}$ is independently substituted or unsubstituted $C_8$-$C_{14}$ alkyl. In some embodiments, $R^{13}$ is independently unsubstituted $C_8$-$C_{14}$ alkyl. In some embodiments, $R^{13}$ is independently substituted $C_8$-$C_{14}$ alkyl. In some embodiments, $R^{13}$ is independently substituted or unsubstituted $C_6$-$C_9$ alkyl. In some embodiments, $R^{13}$ is independently unsubstituted $C_6$-$C_9$ alkyl. In some embodiments, $R^{13}$ is independently substituted $C_6$-$C_9$ alkyl. In some embodiments, $R^{13}$ is independently substituted or unsubstituted $C_9$ alkyl. In some embodiments, $R^{13}$ is independently unsubstituted $C_9$ alkyl. In some embodiments, $R^{13}$ is independently substituted $C_9$ alkyl. In some embodiments, $R^{13}$ is independently substituted or unsubstituted $C_3$-$C_{20}$ branched alkyl. In some embodiments, $R^{13}$ is independently unsubstituted $C_3$-$C_{20}$ branched alkyl. In some embodiments, $R^{13}$ is independently substituted $C_3$-$C_{20}$ branched alkyl. In some embodiments, $R^{13}$ is independently substituted or unsubstituted $C_6$-$C_{16}$ branched alkyl. In some embodiments, $R^{13}$ is independently unsubstituted $C_6$-$C_{16}$ branched alkyl. In some embodiments, $R^{13}$ is independently substituted $C_6$-$C_{16}$ branched alkyl. In some embodiments, $R^{13}$ is independently substituted or unsubstituted $C_6$-$C_{12}$ branched alkyl. In some embodiments, $R^{13}$ is independently unsubstituted $C_6$-$C_{12}$ branched alkyl. In some embodiments, $R^{13}$ is independently substituted $C_6$-$C_{12}$ branched alkyl. In some embodiments, $R^{13}$ is independently substituted or unsubstituted $C_9$-$C_{16}$ branched alkyl. In some embodiments, $R^{13}$ is independently unsubstituted $C_9$-$C_{16}$ branched alkyl. In some embodiments, $R^{13}$ is independently substituted $C_9$-$C_{16}$ branched alkyl. In some embodiments, $R^{13}$ is independently substituted or unsubstituted $C_9$-$C_{12}$ branched alkyl. In some embodiments, $R^{13}$ is independently unsubstituted $C_9$-$C_{12}$ branched alkyl. In some embodiments, $R^{13}$ is independently substituted $C_9$-$C_{12}$ branched alkyl. In some embodiments, $R^{13}$ is independently substituted or unsubstituted 12 to 20 membered heteroalkyl. In some embodiments, $R^{13}$ is independently substituted 12 to 20 membered heteroalkyl. In some embodiments, $R^{13}$ is independently unsubstituted 12 to 20 membered heteroalkyl. In some embodiments, $R^{13}$ is independently substituted or unsubstituted 13 to 20 membered heteroalkyl. In some embodiments, $R^{13}$ is independently substituted 13 to 20 membered heteroalkyl. In some embodiments, $R^{13}$ is independently unsubstituted 13 to 20 membered heteroalkyl. In some embodiments, $R^{13}$ is independently substituted or unsubstituted 14 to 20 membered heteroalkyl. In some embodiments, $R^{13}$ is independently substituted 14 to 20 membered heteroalkyl. In some embodiments, $R^{13}$ is independently unsubstituted 14 to 20 membered heteroalkyl. In some embodiments, $R^{13}$ is independently substituted or unsubstituted 15 to 20 membered heteroalkyl. In some embodiments, $R^{13}$ is independently substituted 15 to 20 membered heteroalkyl. In some embodiments, $R^{13}$ is independently unsubstituted 15 to 20 membered heteroalkyl. In some embodiments, $R^{13}$ is substituted or unsubstituted $C_3$-$C_8$ cycloalkyl. In some embodiments, $R^{13}$ is substituted or unsubstituted 3 to 8 membered heterocycloalkyl. In some embodiments, $R^{13}$ is substituted or unsubstituted $C_6$-$C_{10}$ aryl. In some embodiments, $R^{13}$ is substituted or unsubstituted 5 to 10 membered heteroaryl. In some embodiments, $R^{13}$ is substituted or unsubstituted 5 to 6 membered heteroaryl. In some embodiments, $R^{13}$ is unsubstituted ethyl. In some embodiments, $R^{13}$ is unsubstituted propyl. In some embodiments, $R^{13}$ is unsubstituted methyl.

In some embodiments of the compounds, $R^{14}$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^{14}$ is independently hydrogen, substituted or unsubstituted alkyl, or substituted or unsubstituted heteroalkyl. In some embodiments, $R^{14}$ is independently hydrogen. In some embodiments, $R^{14}$ is independently substituted or unsubstituted alkyl. In some embodiments, $R^{14}$ is independently substituted or unsubstituted $C_1$-$C_{20}$ alkyl. In some embodiments, $R^{14}$ is independently substituted or unsubstituted $C_6$-$C_{16}$ alkyl. In some embodiments, $R^{14}$ is independently unsubstituted $C_6$-$C_{16}$ alkyl. In some embodiments, $R^{14}$ is independently substituted $C_6$-$C_{16}$ alkyl. In some embodiments, $R^{14}$ is independently substituted or unsubstituted heteroalkyl. In some embodiments, $R^{14}$ is independently substituted or unsubstituted 2 to 20 membered heteroalkyl. In some embodiments, $R^{14}$ is independently substituted or unsubstituted 6 to 16 membered heteroalkyl. In some embodiments, $R^{14}$ is independently substituted 6 to 16 membered heteroalkyl. In some embodiments, $R^{14}$ is independently unsubstituted 6 to 16 membered heteroalkyl. In some embodiments, $R^{14}$ is:

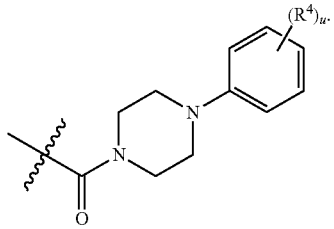

In some embodiments, $R^{14}$ is independently substituted or unsubstituted $C_{12}$-$C_{16}$ alkyl. In some embodiments, $R^{14}$ is independently unsubstituted $C_{12}$-$C_{16}$ alkyl. In some embodiments, $R^{14}$ is independently substituted $C_{12}$-$C_{16}$ alkyl. In some embodiments, $R^{14}$ is independently substituted or unsubstituted $C_{13}$-$C_{16}$ alkyl. In some embodiments, $R^{14}$ is independently unsubstituted $C_{13}$-$C_{16}$ alkyl. In some embodiments, $R^{14}$ is independently substituted $C_{13}$-$C_{16}$ alkyl. In some embodiments, $R^{14}$ is independently substituted or unsubstituted $C_{14}$-$C_{16}$ alkyl. In some embodiments, $R^{14}$ is independently unsubstituted $C_{14}$-$C_{16}$ alkyl. In some embodiments, $R^{14}$ is independently substituted $C_{14}$-$C_{16}$ alkyl. In some embodiments, $R^{14}$ is independently substituted or unsubstituted $C_{15}$-$C_{16}$ alkyl. In some embodiments, $R^{14}$ is independently unsubstituted $C_{15}$-$C_{16}$ alkyl. In some embodiments, $R^{14}$ is independently substituted $C_{15}$-$C_{16}$ alkyl. In some embodiments, $R^{14}$ is independently substituted or unsubstituted $C_8$-$C_{14}$ alkyl. In some embodiments, $R^{14}$ is independently unsubstituted $C_8$-$C_{14}$ alkyl. In some embodiments, $R^{14}$ is independently substituted $C_8$-$C_{14}$ alkyl. In some embodiments, $R^{14}$ is independently substituted or unsubstituted $C_6$-$C_9$ alkyl. In some embodiments, $R^{14}$ is independently unsubstituted $C_6$-$C_9$ alkyl. In some embodiments, $R^{14}$ is independently substituted $C_6$-$C_9$ alkyl. In some embodiments, $R^{14}$ is independently substituted or unsubstituted $C_9$ alkyl. In some embodiments, $R^{14}$ is independently unsubstituted $C_9$ alkyl. In some embodiments, $R^{14}$ is independently substituted $C_9$ alkyl. In some embodiments, $R^{14}$ is independently substituted or unsubstituted $C_3$-$C_{20}$ branched alkyl. In some embodiments, $R^{14}$ is independently unsubstituted $C_3$-$C_{20}$ branched alkyl. In some embodiments, $R^{14}$ is independently substituted $C_3$-$C_{20}$ branched alkyl. In some embodiments, $R^{14}$ is independently substituted or unsubstituted $C_6$-$C_{16}$ branched alkyl. In some embodiments, $R^{14}$ is independently unsubstituted $C_6$-$C_{16}$ branched alkyl. In some embodiments, $R^{14}$ is independently substituted $C_6$-$C_{16}$ branched alkyl. In some embodiments, $R^{14}$ is independently substituted or unsubstituted $C_6$-$C_{12}$ branched alkyl. In some embodiments, $R^{14}$ is independently unsubstituted $C_6$-$C_{12}$ branched alkyl. In some embodiments, $R^{14}$ is independently substituted $C_6$-$C_{12}$ branched alkyl. In some embodiments, $R^{14}$ is independently substituted or unsubstituted $C_9$-$C_{16}$ branched alkyl. In some embodiments, $R^{14}$ is independently unsubstituted $C_9$-$C_{16}$ branched alkyl. In some embodiments, $R^{14}$ is independently substituted $C_9$-$C_{16}$ branched alkyl. In some embodiments, $R^{14}$ is independently substituted or unsubstituted $C_9$-$C_{12}$ branched alkyl. In some embodiments, $R^{14}$ is independently unsubstituted $C_9$-$C_{12}$ branched alkyl. In some embodiments, $R^{14}$ is independently substituted $C_9$-$C_{12}$ branched alkyl. In some embodiments, $R^{14}$ is independently substituted or unsubstituted $C_8$-$C_{12}$ alkyl. In some embodiments, $R^{14}$ is independently substituted $C_8$-$C_{12}$ alkyl. In some embodiments, $R^{14}$ is independently unsubstituted $C_8$-$C_{12}$ alkyl. In some embodiments, $R^{14}$ is independently substituted or unsubstituted 12 to 20 membered heteroalkyl. In some embodiments, $R^{14}$ is independently substituted 12 to 20 membered heteroalkyl. In some embodiments, $R^{14}$ is independently unsubstituted 12 to 20 membered heteroalkyl. In some embodiments, $R^{14}$ is independently substituted or unsubstituted 13 to 20 membered heteroalkyl. In some embodiments, $R^{14}$ is independently substituted 13 to 20 membered heteroalkyl. In some embodiments, $R^{14}$ is independently unsubstituted 13 to 20 membered heteroalkyl. In some embodiments, $R^{14}$ is independently substituted or unsubstituted 14 to 20 membered heteroalkyl. In some embodiments, $R^{14}$ is independently substituted 14 to 20 membered heteroalkyl. In some embodiments, $R^{14}$ is independently unsubstituted 14 to 20 membered heteroalkyl. In some embodiments, $R^{14}$ is independently substituted or unsubstituted 15 to 20 membered heteroalkyl. In some embodiments, $R^{14}$ is independently substituted 15 to 20 membered heteroalkyl. In some embodiments, $R^{14}$ is independently unsubstituted 15 to 20 membered heteroalkyl. In some embodiments, $R^{14}$ is substituted or unsubstituted $C_3$-$C_8$ cycloalkyl. In some embodiments, $R^{14}$ is unsubstituted $C_3$-$C_8$ cycloalkyl. In some embodiments, $R^{14}$ is substituted $C_3$-$C_8$ cycloalkyl. In some embodiments, $R^{14}$ is substituted or unsubstituted 3 to 8 membered heterocycloalkyl. In some embodiments, $R^{14}$ is unsubstituted 3 to 8 membered heterocycloalkyl. In some embodiments, $R^{14}$ is substituted 3 to 8 membered heterocycloalkyl. In some embodiments, $R^{14}$ is substituted or unsubstituted $C_6$-$C_{10}$ aryl. In some embodiments, $R^{14}$ is unsubstituted $C_6$-$C_{10}$ aryl. In some embodiments, $R^{14}$ is substituted $C_6$-$C_{10}$ aryl. In some embodiments, $R^{14}$ is substituted or unsubstituted 5 to 10 membered heteroaryl. In some embodiments, $R^{14}$ is unsubstituted 5 to 10 membered heteroaryl. In some embodiments, $R^{14}$ is substituted 5 to 10 membered heteroaryl. In some embodiments, $R^{14}$ is substituted or unsubstituted 5 to 6 membered heteroaryl. In some embodiments, $R^{14}$ is unsubstituted 5 to 6 membered heteroaryl. In some embodiments, $R^{14}$ is substituted 5 to 6 membered heteroaryl. In some embodiments, $R^{14}$ is unsubstituted ethyl. In some embodiments, $R^{14}$ is unsubstituted propyl. In some embodiments, $R^{14}$ is unsubstituted methyl.

$R^4$ is independently hydrogen, halogen, —$CX^4_3$, —CN, —$SO_2Cl$, —$SO_qR^{18}$, —$SO_rNR^{15}R^{16}$, —$NHNH_2$, —$ONR^{15}R^{16}$, —$NHC=(O)NHNH_2$, —$NHC=(O)NR^{15}R^{16}$, —$N(O)_t$, —$NR^{15}R^{16}$, —$C(O)R^{17}$, —$C(O)$—$OR^{17}$, —$C(O)NR^{15}R^{16}$, —$OR^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted membered heteroaryl. $R^{15}$, $R^{16}$, $R^{17}$, and $R^{18}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols r and t are independently 1 or 2. The symbol q is independently an integer from 0 to 4. The symbol u is independently an integer from 0 to 5. The symbol $X^4$ is independently —Cl, —Br, —I, or —F.

In some embodiments of the compounds, the symbol L is

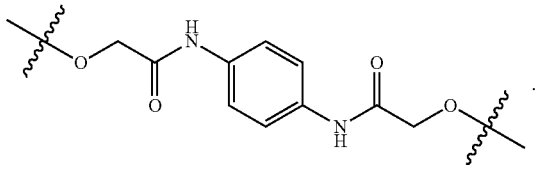 [SMILES: *OCC(=O)Nc1ccc(NC(=O)CO*)cc1]

In some embodiments of the compounds, the symbol L is

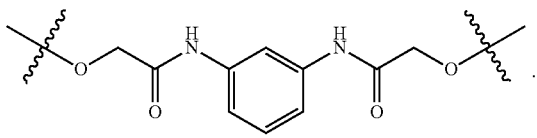 [SMILES: *OCC(=O)Nc1cccc(NC(=O)CO*)c1]

In some embodiments of the compounds, the symbol L is

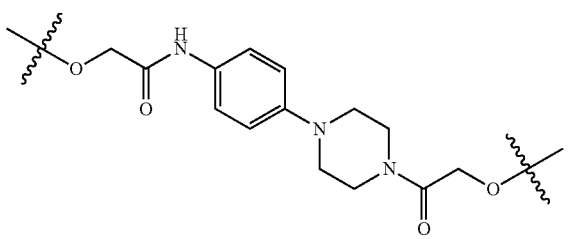

In some embodiments of the compounds, the symbol L is

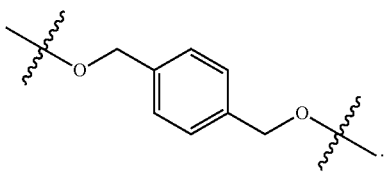 [SMILES: *OCc1ccc(CO*)cc1]

In some embodiments of the compounds, the symbol L is

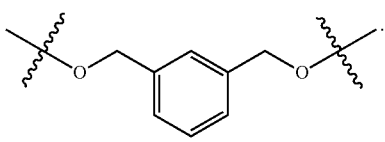 [SMILES: *OCc1cccc(CO*)c1]

In some embodiments of the compounds, the symbol L is —O—$(CH_2)_p$—O—. In some embodiments of the compounds, the symbol L is

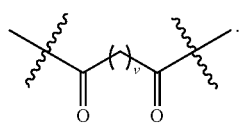

In some embodiments of the compounds, the symbol L is

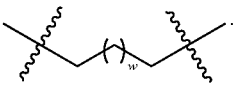

In some embodiments of the compounds, the symbol L is a bond. In some embodiments of the compounds, the symbol L is —O—. In some embodiments of the compounds, the symbol L is —NH—. In some embodiments of the compounds, the symbol L is substituted or unsubstituted alkylene. In some embodiments of the compounds, the symbol L is substituted or unsubstituted heteroalkylene. In some embodiments of the compounds, the symbol L is substituted or unsubstituted cycloalkylene. In some embodiments of the compounds, the symbol L is substituted or unsubstituted heterocycloalkylene. In some embodiments of the compounds, the symbol L is substituted or unsubstituted arylene. In some embodiments of the compounds, the symbol L is substituted or unsubstituted heteroarylene. In some embodiments of the compounds, the symbol L is unsubstituted alkylene. In some embodiments of the compounds, the symbol L is unsubstituted heteroalkylene. In some embodiments of the compounds, the symbol L is unsubstituted cycloalkylene. In some embodiments of the compounds, the symbol L is unsubstituted heterocycloalkylene. In some embodiments of the compounds, the symbol L is unsubstituted arylene. In some embodiments of the compounds, the symbol L is unsubstituted heteroarylene. In some embodiments of the compounds, the symbol L is substituted or unsubstituted $C_1$-$C_{20}$ alkylene. In some embodiments of the compounds, the symbol L is substituted or unsubstituted $C_8$-$C_{16}$ alkylene. In some embodiments of the compounds, the symbol L is substituted or unsubstituted $C_{10}$-$C_{14}$ alkylene. In some embodiments of the compounds, the symbol L is substituted $C_{10}$-$C_{14}$ alkylene. In some embodiments of the compounds, the symbol L is unsubstituted $C_{10}$-$C_{14}$ alkylene. In some embodiments of the compounds, the symbol L is unsubstituted $C_{12}$ alkylene. In some embodiments of the compounds, the symbol L is a substituted or unsubstituted 2 to 20 membered heteroalkylene. In some embodiments of the compounds, the symbol L is a substituted or unsubstituted $C_3$-$C_8$ cycloalkylene. In some embodiments of the compounds, the symbol L is a substituted or unsubstituted 3 to 8 membered heterocycloalkylene. In some embodiments of the compounds, the symbol L is substituted or unsubstituted $C_6$-$C_{10}$ arylene. In some embodiments of the compounds, the symbol L is a substituted or unsubstituted 5 to 10 membered heteroarylene. In some embodiments of the compounds, the symbol L is substituted or unsubstituted $C_1$-$C_8$ alkylene. In some embodiments of the compounds, the symbol L is a substituted or unsubstituted 2 to 8 membered heteroalkylene. In some embodiments of the compounds, the symbol L is a substituted or unsubstituted $C_3$-$C_7$ cycloalkylene. In some embodiments of the compounds, the symbol L is a substituted or unsubstituted 3 to 7 membered heterocycloalkylene. In some embodiments of the compounds, the symbol L is a substituted or unsubstituted 5 to 9 membered heteroarylene.

In some embodiments of the compounds, the symbol $A^1$ is =CH—. In some embodiments of the compounds, the symbol $A^1$ is =N—. In some embodiments of the compounds, the symbol $A^2$ is =CH—. In some embodiments of the compounds, the symbol $A^2$ is =N—. In some embodiments of the compounds, the symbol $A^2$ is =CR$^3$—. In some embodiments of the compounds, the symbol $A^1$ is =CR$^3$—.

In some embodiments, k is independently 1. In some embodiments, k is independently 2. In some embodiments, m is independently 1. In some embodiments, m is independently 2. In some embodiments, n is independently 0. In some embodiments, n is independently 1. In some embodiments, n is independently 2. In some embodiments, n is independently 3. In some embodiments, n is independently 4. In some embodiments, the symbol $X^{1A}$ is independently —Cl. In some embodiments, the symbol $X^{1A}$ is independently —Br. In some embodiments, the symbol $X^{1A}$ is independently —I. In some embodiments, the symbol $X^{1A}$ is independently —F. In some embodiments, the symbol $X^{2A}$ is independently —Cl. In some embodiments, the symbol $X^{2A}$ is independently —Br. In some embodiments, the symbol $X^{2A}$ is independently —I. In some embodiments, the symbol $X^{2A}$ is independently —F. In some embodiments, the symbol $X^{1B}$ is independently —Cl. In some embodiments, the symbol $X^{1B}$ is independently —Br. In some embodiments, the symbol $X^{1B}$ is independently —I. In some embodiments, the symbol $X^{1B}$ is independently —F. In some embodiments, the symbol $X^{2B}$ is independently —Cl. In some embodiments, the symbol $X^{2B}$ is independently —Br. In some embodiments, the symbol $X^{2B}$ is independently —I. In some embodiments, the symbol $X^{2B}$ is independently —F. In some embodiments, the symbol $X^3$ is independently —Cl. In some embodiments, the symbol $X^3$ is independently —Br. In some embodiments, the symbol $X^3$ is independently —I. In some embodiments, the symbol $X^3$ is independently —F. In some embodiments, r is independently 1. In some embodiments, r is independently 2. In some embodiments, t is independently 1. In some embodiments, t is independently 2. In some embodiments, q is independently 0. In some embodiments, q is independently 1. In some embodiments, q is independently 2. In some embodiments, q is independently 3. In some embodiments, q is independently 4. In some embodiments, the symbol $X^4$ is independently —Cl. In some embodiments, the symbol $X^4$ is independently —Br. In some embodiments, the symbol $X^4$ is independently —I. In some embodiments, the symbol $X^4$ is independently —F. In some embodiments, u is independently 0. In some embodiments, u is independently 1. In some embodiments, u is independently 2. In some embodiments, u is independently 3. In some embodiments, u is independently 4. In some embodiments, u is independently 5. In some embodiments, the symbol p is independently 1. In some embodiments, the symbol p is independently 2. In some embodiments, the symbol p is independently 3. In some embodiments, the symbol p is independently 4. In some embodiments, the symbol p is independently 5. In some embodiments, the symbol p is independently 6. In some embodiments, the symbol p is independently 7. In some embodiments, the symbol p is independently 8. In some embodiments, the symbol p is independently 9. In some embodiments, the symbol p is independently 10. In some embodiments, the symbol p is independently 11. In some embodiments, the symbol p is independently 12. In some embodiments, the symbol p is independently 13. In some embodiments, the symbol p is independently 14. In some embodiments, the symbol p is independently 15. In some embodiments, the symbol p is independently 16. In some embodiments, the symbol p is independently 17. In some embodiments, the symbol p is independently 18. In some embodiments, the symbol p is independently 19. In some embodiments, the symbol p is independently 20. In some embodiments, the symbol v is independently 1. In some embodiments, the symbol v is independently 2. In some embodiments, the symbol v is independently 3. In some embodiments, the symbol v is independently 4. In some embodiments, the symbol v is independently 5. In some embodiments, the symbol v is independently 6. In some embodiments, the symbol v is independently 7. In some embodiments, the symbol v is independently 8. In some embodiments, the symbol v is independently 9. In some embodiments, the symbol v is independently 10. In some embodiments, the symbol v is independently 11. In some embodiments, the symbol v is independently 12. In some embodiments, the symbol v is independently 13. In some embodiments, the symbol v is independently 14. In some embodiments, the symbol v is independently 15. In some embodiments, the symbol v is independently 16. In some embodiments, the symbol v is independently 17. In some embodiments, the symbol v is independently 18. In some embodiments, the symbol v is independently 19. In some embodiments, the symbol v is independently 20. In some embodiments, the symbol w is independently 1. In some embodiments, the symbol w is independently 2. In some embodiments, the symbol w is independently 3. In some embodiments, the symbol w is independently 4. In some embodiments, the symbol w is independently 5. In some embodiments, the symbol w is independently 6. In some embodiments, the symbol w is independently 7. In some embodiments, the symbol w is independently 8. In some embodiments, the symbol w is independently 9. In some embodiments, the symbol w is independently 10. In some embodiments, the symbol w is independently 11. In some embodiments, the symbol w is independently 12. In some embodiments, the symbol w is independently 13. In some embodiments, the symbol w is independently 14. In some embodiments, the symbol w is independently 15. In some embodiments, the symbol w is independently 16. In some embodiments, the symbol w is independently 17. In some embodiments, the symbol w is independently 18. In some embodiments, the symbol w is independently 19. In some embodiments, the symbol w is independently 20. In some embodiments, z1 is independently 0. In some embodiments, z1 is independently 1. In some embodiments, z1 is independently 2. In some embodiments, z1 is independently 3. In some embodiments, z2 is independently 0. In some embodiments, z2 is independently 1. In some embodiments, z2 is independently 2. In some embodiments, z2 is independently 3.

In some embodiments of the compounds, the symbol $A^1$ is =CH—, $R^{2A}$ is hydrogen, $R^{1A}$ is hydrogen, $R^3$ is —$OR^{14}$, and $R^{14}$ is unsubstituted $C_{12}$-$C_{20}$ alkyl. In some embodiments, the symbol $A^1$ is =CH—, $R^{2A}$ is hydrogen, $R^{1A}$ is hydrogen, $R^3$ is —$OR^{14}$, and $R^{14}$ is unsubstituted $C_{13}$-$C_{20}$ alkyl. In some embodiments, the symbol $A^1$ is =CH—, $R^{2A}$ is hydrogen, $R^{1A}$ is hydrogen, $R^3$ is —$OR^{14}$, and $R^{14}$ is unsubstituted $C_{14}$-$C_{20}$ alkyl. In some embodiments, the symbol $A^1$ is =CH—, $R^{2A}$ is hydrogen, $R^{1A}$ is hydrogen, $R^3$ is —$OR^{14}$, and $R^{14}$ is unsubstituted $C_{15}$-$C_{20}$ alkyl. In some embodiments, the symbol $A^1$ is =CH—, $R^{2A}$ is hydrogen, $R^{1A}$ is hydrogen, $R^3$ is —$OR^{14}$, and $R^{14}$ is unsubstituted $C_{16}$-$C_{20}$ alkyl. In some embodiments, the symbol $A^1$ is =CH—, $R^{2A}$ is hydrogen, $R^{1A}$ is hydrogen, $R^3$ is —$OR^{14}$, and $R^{14}$ is halogen substituted $C_1$-$C_{20}$ alkyl. In some embodiments, the symbol $A^1$ is =CH—, $R^{2A}$ is hydrogen, $R^{1A}$ is hydrogen, $R^3$ is —$OR^{14}$, and $R^{14}$ is halogen substituted $C_3$-$C_{16}$ alkyl. In some embodiments, the symbol $A^1$ is =CH—, $R^{2A}$ is hydrogen, $R^{1A}$ is hydrogen, $R^3$ is —$OR^{14}$, and $R^{14}$ is halogen substituted $C_6$-$C_{12}$ alkyl. In some embodiments, the symbol $A^1$ is =CH—, $R^{2A}$ is hydrogen, $R^{1A}$ is hydrogen, $R^3$ is —$OR^{14}$, and $R^{14}$ is halogen substituted $C_6$-$C_9$ alkyl. In some embodiments, the symbol $A^1$ is =CH—, $R^{2A}$ is hydrogen, $R^{1A}$ is hydrogen, $R^3$ is —$OR^{14}$, and $R^{14}$ is —CN substituted $C_1$-$C_{20}$ alkyl. In some embodiments, the symbol $A^1$ is =CH—, $R^{2A}$ is hydrogen, $R^{1A}$ is hydrogen, $R^3$ is —$OR^{14}$, and $R^{14}$ is —CN substituted $C_3$-$C_{16}$ alkyl. In some embodiments, the symbol $A^1$ is =CH—, $R^{2A}$ is hydrogen, $R^{1A}$ is hydrogen, $R^3$ is —$OR^{14}$, and $R^{14}$ is —CN substituted $C_6$-$C_{12}$ alkyl. In some embodiments, the symbol $A^1$ is =CH—, $R^{2A}$ is hydrogen, $R^{1A}$ is hydrogen, $R^3$ is —$OR^{14}$, and $R^{14}$ is —CN substituted $C_6$-$C_9$ alkyl. In some embodiments, the symbol $A^1$ is =CH—, $R^{2A}$ is hydrogen, $R^{1A}$ is hydrogen, $R^3$ is —$OR^{14}$, and $R^{14}$ is unsubstituted branched $C_1$-$C_{20}$ alkyl. In some embodiments, the symbol $A^1$ is =CH—, $R^{2A}$ is hydrogen, $R^{1A}$ is hydrogen, $R^3$ is —$OR^{14}$, and $R^{14}$ is unsubstituted branched $C_3$-$C_{16}$ alkyl. In some embodiments, the symbol $A^1$ is =CH—, $R^{2A}$ is hydrogen, $R^{1A}$ is hydrogen, $R^3$ is —$OR^{14}$, and $R^{14}$ is unsubstituted branched $C_6$-$C_{12}$ alkyl. In some embodiments, the symbol $A^1$ is =CH—, $R^{2A}$ is hydrogen, $R^{1A}$ is hydrogen, $R^3$ is —$OR^{14}$, and $R^{14}$ is unsubstituted branched $C_6$-$C_9$ alkyl. In some embodiments, the symbol $A^1$ is =CH—, $R^{2A}$ is hydrogen, $R^{1A}$ is hydrogen, $R^3$ is —$OR^{14}$, and $R^{14}$ is unsubstituted branched $C_7$-$C_8$ alkyl. In some embodiments, the symbol $A^1$ is =CH—, $R^{2A}$ is hydrogen, $R^{1A}$ is hydrogen, $R^3$ is —$OR^{14}$, and $R^{14}$ is —$(CH_2CH_2O)_{1-10}CH_3$. In some embodiments, the symbol $A^1$ is =CH—, $R^{2A}$ is hydrogen, $R^{1A}$ is hydrogen, $R^3$ is —$OR^{14}$, and $R^{14}$ is —$(CH_2CH_2O)_{1-8}CH_3$. In some embodiments, the symbol $A^1$ is =CH—, $R^{2A}$ is hydrogen, $R^{1A}$ is hydrogen, $R^3$ is —$OR^{14}$, and $R^{14}$ is —$(CH_2CH_2O)_{1-6}CH_3$. In some embodiments, the symbol $A^1$ is =CH—, $R^{2A}$ is hydrogen, $R^{1A}$ is hydrogen, $R^3$ is —$OR^{14}$, and $R^{14}$ is —$(CH_2CH_2O)_{1-4}CH_3$. In some embodiments, the symbol $A^1$ is =CH—, $R^{2A}$ is hydrogen, $R^{1A}$ is hydrogen, $R^3$ is —$OR^{14}$, and $R^{14}$ is —$(CH_2CH_2O)_{1-8}CH_3$. In some embodiments, the symbol $A^1$ is =CH—, $R^{2A}$ is hydrogen, $R^{1A}$ is hydrogen, $R^3$ is —$OR^{14}$, and $R^{14}$ is —$(CH_2CH_2O)_{3-10}CH_3$. In some embodiments, the symbol $A^1$ is =CH—, $R^{2A}$ is hydrogen, $R^{1A}$ is hydrogen, $R^3$ is —$OR^{14}$, and $R^{14}$ is —$(CH_2CH_2O)_{3-8}CH_3$. In some embodiments, the symbol $A^1$ is =CH—, $R^{2A}$ is hydrogen, $R^{1A}$ is hydrogen, $R^3$ is —$OR^{14}$, and $R^{14}$ is —$(CH_2CH_2O)_{3-6}CH_3$.

In some embodiments of the compounds, the symbol $A^1$ is =N—, $R^{2A}$ is hydrogen, $R^{1A}$ is hydrogen, $R^3$ is —$OR^{14}$, and $R^{14}$ is unsubstituted $C_{12}$-$C_{20}$ alkyl. In some embodiments, the symbol $A^1$ is =N—, $R^{2A}$ is hydrogen, $R^{1A}$ is hydrogen, $R^3$ is —$OR^{14}$, and $R^{14}$ is unsubstituted $C_{13}$-$C_{20}$ alkyl. In some embodiments, the symbol $A^1$ is =N—, $R^{2A}$ is hydrogen, $R^{1A}$ is hydrogen, $R^3$ is —$OR^{14}$, and $R^{14}$ is unsubstituted $C_{14}$-$C_{20}$ alkyl. In some embodiments, the symbol $A^1$ is =N—, $R^{2A}$ is hydrogen, $R^{1A}$ is hydrogen, $R^3$ is —$OR^{14}$, and $R^{14}$ is unsubstituted $C_{15}$-$C_{20}$ alkyl. In some embodiments, the symbol $A^1$ is =N—, $R^{2A}$ is hydrogen, $R^{1A}$ is hydrogen, $R^3$ is —$OR^{14}$, and $R^{14}$ is unsubstituted $C_{16}$-$C_{20}$ alkyl. In some embodiments, the symbol $A^1$ is =N—, $R^{2A}$ is hydrogen, $R^{1A}$ is hydrogen, $R^3$ is —$OR^{14}$, and $R^{14}$ is unsubstituted $C_2$-$C_{20}$ alkyl. In some embodiments, the symbol $A^1$ is =N—, $R^{2A}$ is hydrogen, $R^{1A}$ is hydrogen, $R^3$ is —$OR^{14}$, and $R^{14}$ is unsubstituted $C_2$-$C_{16}$ alkyl. In some embodiments, the symbol $A^1$ is =N—, $R^{2A}$ is hydrogen, $R^{1A}$ is hydrogen, $R^3$ is —$OR^{14}$, and $R^{14}$ is unsubstituted $C_2$-$C_{12}$ alkyl. In some embodiments, the symbol $A^1$ is =N—, $R^{2A}$ is hydrogen, $R^{1A}$ is hydrogen, $R^3$ is —$OR^{14}$, and $R^{14}$ is unsubstituted $C_2$-$C_9$ alkyl. In some embodiments, the symbol $A^1$ is =N—, $R^{2A}$ is hydrogen, $R^{1A}$ is hydrogen, $R^3$ is —$OR^{14}$, and $R^{14}$ is unsubstituted $C_3$-$C_{12}$ alkyl. In some embodiments, the symbol $A^1$ is =N—, $R^{2A}$ is hydrogen, $R^{1A}$ is hydrogen, $R^3$ is —$OR^{14}$, and $R^{14}$ is unsubstituted $C_6$-$C_{12}$ alkyl.

In some embodiments of the compounds, the symbol $A^1$ is =CH—, $R^{2A}$ is hydrogen, $R^{1A}$ is —$C(O)CH_3$, $R^3$ is —$OR^{14}$, and $R^{14}$ is unsubstituted $C_{12}$-$C_{20}$ alkyl. In some embodiments, the symbol $A^1$ is =CH—, $R^{2A}$ is hydrogen, $R^{1A}$ is —$C(O)CH_3$, $R^3$ is —$OR^{14}$, and $R^{14}$ is unsubstituted $C_{13}$-$C_{20}$ alkyl. In some embodiments, the symbol $A^1$ is =CH—, $R^{2A}$ is hydrogen, $R^{1A}$ is —$C(O)CH_3$, $R^3$ is —$OR^{14}$, and $R^{14}$ is unsubstituted $C_{14}$-$C_{20}$ alkyl. In some embodiments, the symbol $A^1$ is =CH—, $R^{2A}$ is hydrogen, $R^{1A}$ is —$C(O)CH_3$, $R^3$ is —$OR^{14}$, and $R^{14}$ is unsubstituted $C_{15}$-$C_{20}$ alkyl. In some embodiments, the symbol $A^1$ is =CH—, $R^{2A}$ is hydrogen, $R^{1A}$ is —$C(O)CH_3$, $R^3$ is —$OR^{14}$, and $R^{14}$ is unsubstituted $C_{16}$-$C_{20}$ alkyl. In some embodiments, the symbol $A^1$ is =CH—, $R^{2A}$ is hydrogen, $R^{1A}$ is —$C(O)CH_3$, $R^3$ is —$OR^{14}$, and $R^{14}$ is substituted $C_{12}$-$C_{20}$ alkyl. In some embodiments, the symbol $A^1$ is =CH—, $R^{2A}$ is hydrogen, $R^{1A}$ is —$C(O)CH_3$, $R^3$ is —$OR^{14}$, and $R^{14}$ is substituted $C_{13}$-$C_{20}$ alkyl. In some embodiments, the symbol $A^1$ is =CH—, $R^{2A}$ is hydrogen, $R^{1A}$ is —$C(O)CH_3$, $R^3$ is —$OR^{14}$, and $R^{14}$ is substituted $C_{14}$-$C_{20}$ alkyl. In some embodiments, the symbol $A^1$ is =CH—, $R^{2A}$ is hydrogen, $R^{1A}$ is —$C(O)CH_3$, $R^3$ is —$OR^{14}$, and $R^{14}$ is substituted $C_{15}$-$C_{20}$ alkyl. In some embodiments, the symbol $A^1$ is =CH—, $R^{2A}$ is hydrogen, $R^{1A}$ is —$C(O)CH_3$, $R^3$ is —$OR^{14}$, and $R^{14}$ is substituted $C_{16}$-$C_{20}$ alkyl.

In some embodiments of the compounds, the symbol $A^1$ is =CH—, $R^{2A}$ is unsubstituted methyl, $R^{1A}$ is unsubstituted methyl, $R^3$ is —$OR^{14}$, and $R^{14}$ is hydrogen. In some embodiments, the symbol $A^1$ is =CH—, $R^{2A}$ is unsubstituted methyl, $R^{1A}$ is unsubstituted methyl, $R^3$ is —$OR^{14}$, and $R^{14}$ is unsubstituted $C_2$-$C_{20}$ alkyl. In some embodiments, the symbol $A^1$ is =CH—, $R^{2A}$ is unsubstituted methyl, $R^{1A}$ is unsubstituted methyl, $R^3$ is —$OR^{14}$, and $R^{14}$ is unsubstituted $C_2$-$C_{16}$ alkyl. In some embodiments, the symbol $A^1$ is =CH—, $R^{2A}$ is unsubstituted methyl, $R^{1A}$ is unsubstituted methyl, $R^3$ is —$OR^{14}$, and $R^{14}$ is unsubstituted $C_2$-$C_{12}$ alkyl. In some embodiments, the symbol $A^1$ is =CH—, $R^{2A}$ is unsubstituted methyl, $R^{1A}$ is unsubstituted methyl, $R^3$ is —$OR^{14}$, and $R^{14}$ is unsubstituted $C_2$-$C_8$ alkyl. In some embodiments, the symbol $A^1$ is =CH—, $R^{2A}$ is unsubstituted methyl, $R^{1A}$ is unsubstituted methyl, $R^3$ is —$OR^{14}$, and $R^{14}$ is unsubstituted $C_2$-$C_6$ alkyl. In some embodiments, the symbol $A^1$ is =CH—, $R^{2A}$ is unsubstituted methyl, $R^{1A}$ is unsubstituted methyl, $R^3$ is —$OR^{14}$, and $R^{14}$ is unsubstituted $C_4$-$C_{20}$ alkyl. In some embodiments, the symbol $A^1$ is =CH—, $R^{2A}$ is unsubstituted methyl, $R^{1A}$ is unsubstituted methyl, $R^3$ is —$OR^{14}$, and $R^{14}$ is unsubstituted $C_6$-$C_{20}$ alkyl. In some embodiments, the symbol $A^1$ is =CH—, $R^{2A}$ is unsubstituted methyl, $R^{1A}$ is unsubstituted methyl, $R^3$ is —$OR^{14}$, and $R^{14}$ is unsubstituted $C_8$-$C_{20}$ alkyl. In some embodiments, the symbol $A^1$ is =CH—, $R^{2A}$ is unsubstituted methyl, $R^{1A}$ is unsubstituted methyl, $R^3$ is —$OR^{14}$, and $R^{14}$ is unsubstituted $C_{10}$-$C_{20}$ alkyl. In some embodiments, the symbol $A^1$ is =CH—, $R^{2A}$ is unsubstituted methyl, $R^{1A}$ is unsubstituted methyl, $R^3$ is —$OR^{14}$, and $R^{14}$ is unsubstituted $C_{12}$-$C_{20}$ alkyl. In some embodiments, the symbol $A^1$ is =CH—, $R^{2A}$ is unsubstituted methyl, $R^{1A}$ is unsubstituted methyl, $R^3$ is —$OR^{14}$, and $R^{14}$ is unsubstituted $C_{14}$-$C_{20}$ alkyl. In some embodiments, the symbol $A^1$ is =CH—, $R^{2A}$ is unsubstituted methyl, $R^{1A}$ is unsubstituted methyl, $R^3$ is —$OR^{14}$, and $R^{14}$ is unsubstituted $C_{16}$-$C_{20}$ alkyl.

In some embodiments of the compounds, the symbol $A^1$ is =CH—, $R^{2A}$ is hydrogen, $R^{1A}$ is —$C(O)R^{7A}$, $R^{7A}$ is unsubstituted $C_8$-$C_{10}$ alkyl, $R^3$ is —$OC(O)R^{13}$, and $R^{13}$ is unsubstituted $C_1$-$C_{20}$ alkyl. In some embodiments, the symbol $A^1$ is =CH—, $R^{2A}$ is hydrogen, $R^{1A}$ is —$C(O)R^{7A}$, $R^{7A}$ is unsubstituted $C_8$-$C_{10}$ alkyl, $R^3$ is —$OC(O)R^{13}$, and $R^{13}$ is unsubstituted $C_1$-$C_{10}$ alkyl. In some embodiments, the symbol $A^1$ is =CH—, $R^{2A}$ is hydrogen, $R^{1A}$ is —$C(O)R^{7A}$, $R^{7A}$ is unsubstituted $C_8$-$C_{10}$ alkyl, $R^3$ is —$OC(O)R^{13}$, and $R^{13}$ is unsubstituted $C_1$-$C_{12}$ alkyl. In some embodiments, the symbol $A^1$ is =CH—, $R^{2A}$ is hydrogen, $R^{1A}$ is —$C(O)R^{7A}$, $R^{7A}$ is unsubstituted $C_8$-$C_{10}$ alkyl, $R^3$ is —$OC(O)R^{13}$, and $R^{13}$ is unsubstituted $C_1$-$C_9$ alkyl. In some embodiments, the symbol $A^1$ is =CH—, $R^{2A}$ is hydrogen, $R^{1A}$ is —C(O)$R^{7A}$, $R^{7A}$ is unsubstituted $C_8$-$C_{10}$ alkyl, $R^3$ is —OC(O)$R^{13}$, and $R^{13}$ is unsubstituted $C_4$-$C_{20}$ alkyl. In some embodiments, the symbol $A^1$ is =CH—, $R^{2A}$ is hydrogen, $R^{1A}$ is —C(O)$R^{7A}$, $R^{7A}$ is unsubstituted $C_8$-$C_{10}$ alkyl, $R^3$ is —OC(O)$R^{13}$, and $R^{13}$ is unsubstituted $C_8$-$C_{20}$ alkyl. In some embodiments, the symbol $A^1$ is =CH—, $R^{2A}$ is hydrogen, $R^{1A}$ is —C(O)$R^{7A}$, $R^{7A}$ is unsubstituted $C_8$-$C_{10}$ alkyl, $R^3$ is —OC(O)$R^{13}$, and $R^{13}$ is unsubstituted $C_8$-$C_{16}$ alkyl. In some embodiments, the symbol $A^1$ is =CH—, $R^{2A}$ is hydrogen, $R^{1A}$ is —C(O)$R^{7A}$, $R^{7A}$ is unsubstituted $C_8$-$C_{10}$ alkyl, $R^3$ is —OC(O)$R^{13}$, and $R^{13}$ is unsubstituted $C_8$-$C_{12}$ alkyl. In some embodiments, the symbol $A^1$ is =CH—, $R^{2A}$ is hydrogen, $R^{1A}$ is —C(O)$R^{7A}$, $R^{7A}$ is unsubstituted $C_8$-$C_{10}$ alkyl, and $R^3$ hydrogen.

In some embodiments of the compounds, the symbol $A^1$ is =CH—, $R^{2A}$ is hydrogen, $R^{1A}$ is unsubstituted $C_9$-$C_{12}$ alkyl, $R^3$ is —O$R^{14}$, and $R^{14}$ is unsubstituted $C_1$-$C_{20}$ alkyl. In some embodiments, the symbol $A^1$ is =CH—, $R^{2A}$ is hydrogen, $R^{1A}$ is unsubstituted $C_9$-$C_{12}$ alkyl, $R^3$ is —O$R^{14}$, and $R^{14}$ is unsubstituted $C_1$-$C_{14}$ alkyl. In some embodiments, the symbol $A^1$ is =CH—, $R^{2A}$ is hydrogen, $R^{1A}$ is unsubstituted $C_9$-$C_{12}$ alkyl, $R^3$ is —O$R^{14}$, and $R^{14}$ is unsubstituted $C_1$-$C_{12}$ alkyl. In some embodiments, the symbol $A^1$ is =CH—, $R^{2A}$ is hydrogen, $R^{1A}$ is unsubstituted $C_9$-$C_{12}$ alkyl, $R^3$ is —O$R^{14}$, and $R^{14}$ is unsubstituted $C_1$-$C_9$ alkyl. In some embodiments, the symbol $A^1$ is =CH—, $R^{2A}$ is hydrogen, $R^{1A}$ is unsubstituted $C_9$-$C_{12}$ alkyl, $R^3$ is —O$R^{14}$, and $R^{14}$ is unsubstituted $C_1$-$C_6$ alkyl. In some embodiments, the symbol $A^1$ is =CH—, $R^{2A}$ is hydrogen, $R^{1A}$ is unsubstituted $C_9$-$C_{12}$ alkyl, $R^3$ is —O$R^{14}$, and $R^{14}$ is unsubstituted $C_4$-$C_{20}$ alkyl. In some embodiments, the symbol $A^1$ is =CH—, $R^{2A}$ is hydrogen, $R^{1A}$ is unsubstituted $C_9$-$C_{12}$ alkyl, $R^3$ is —O$R^{14}$, and $R^{14}$ is unsubstituted $C_8$-$C_{20}$ alkyl. In some embodiments, the symbol $A^1$ is =CH—, $R^{2A}$ is hydrogen, $R^{1A}$ is unsubstituted $C_9$-$C_{12}$ alkyl, $R^3$ is —O$R^{14}$, and $R^{14}$ is unsubstituted $C_8$-$C_{16}$ alkyl. In some embodiments, the symbol $A^1$ is =CH—, $R^{2A}$ is hydrogen, $R^{1A}$ is unsubstituted $C_9$-$C_{12}$ alkyl, $R^3$ is —O$R^{14}$, and $R^{14}$ is unsubstituted $C_8$-$C_{12}$ alkyl. In some embodiments, the symbol $A^1$ is =CH—, $R^{2A}$ is hydrogen, $R^{1A}$ is unsubstituted $C_9$-$C_{12}$ alkyl, and $R^3$ is —OH. In some embodiments, the symbol $A^1$ is =CH—, $R^{2A}$ is hydrogen, $R^{1A}$ is unsubstituted $C_9$-$C_{12}$ alkyl, and $R^3$ is hydrogen.

In some embodiments of the compounds, the symbol $A^1$ is =N—, $R^{1A}$ and $R^{2A}$ are joined to form an unsubstituted isoindolin-2-yl-1,3-dione, $R^3$ is —O$R^{14}$, and $R^{14}$ is unsubstituted $C_1$-$C_{20}$ alkyl. In some embodiments, the symbol $A^1$ is =N—, $R^{1A}$ and $R^{2A}$ are joined to form an unsubstituted isoindolin-2-yl-1,3-dione, $R^3$ is —O$R^{14}$, and $R^{14}$ is unsubstituted $C_3$-$C_{20}$ alkyl. In some embodiments, the symbol $A^1$ is =N—, $R^{1A}$ and $R^{2A}$ are joined to form an unsubstituted isoindolin-2-yl-1,3-dione, $R^3$ is —O$R^{14}$, and $R^{14}$ is unsubstituted $C_6$-$C_{20}$ alkyl. In some embodiments, the symbol $A^1$ is =N—, $R^{1A}$ and $R^{2A}$ are joined to form an unsubstituted isoindolin-2-yl-1,3-dione, $R^3$ is —O$R^{14}$, and $R^{14}$ is unsubstituted $C_9$-$C_{20}$ alkyl. In some embodiments, the symbol $A^1$ is =N—, $R^{1A}$ and $R^{2A}$ are joined to form an unsubstituted isoindolin-2-yl-1,3-dione, $R^3$ is —O$R^{14}$, and $R^{14}$ is unsubstituted $C_1$-$C_{16}$ alkyl. In some embodiments, the symbol $A^1$ is =N—, $R^{1A}$ and $R^{2A}$ are joined to form an unsubstituted isoindolin-2-yl-1,3-dione, $R^3$ is —O$R^{14}$, and $R^{14}$ is unsubstituted $C_1$-$C_{12}$ alkyl. In some embodiments, the symbol $A^1$ is =N—, $R^{1A}$ and $R^{2A}$ are joined to form an unsubstituted isoindolin-2-yl-1,3-dione, $R^3$ is —O$R^{14}$, and $R^{14}$ is unsubstituted $C_1$-$C_9$ alkyl. In some embodiments, the symbol $A^1$ is =N—, $R^{1A}$ and $R^{2A}$ are joined to form an unsubstituted isoindolin-2-yl-1,3-dione, $R^3$ is —O$R^{14}$, and $R^{14}$ is unsubstituted $C_6$-$C_{12}$ alkyl. In some embodiments, the symbol $A^1$ is =N—, $R^{1A}$ and $R^{2A}$ are joined to form an unsubstituted isoindolin-2-yl-1,3-dione, $R^3$ is —O$R^{14}$, and $R^{14}$ is unsubstituted $C_8$-$C_{30}$ alkyl. In some embodiments, the symbol $A^1$ is =N—, $R^{1A}$ and $R^{2A}$ are joined to form an unsubstituted isoindolin-2-yl-1,3-dione, $R^3$ is —O$R^{14}$, and $R^{14}$ is substituted $C_1$-$C_{20}$ alkyl. In some embodiments, the symbol $A^1$ is =N—, $R^{1A}$ and $R^{2A}$ are joined to form an unsubstituted isoindolin-2-yl-1,3-dione, $R^3$ is —O$R^{14}$, and $R^{14}$ is substituted $C_3$-$C_{20}$ alkyl. In some embodiments, the symbol $A^1$ is =N—, $R^{1A}$ and $R^{2A}$ are joined to form an unsubstituted isoindolin-2-yl-1,3-dione, $R^3$ is —O$R^{14}$, and $R^{14}$ is substituted $C_6$-$C_{20}$ alkyl. In some embodiments, the symbol $A^1$ is =N—, $R^{1A}$ and $R^{2A}$ are joined to form an unsubstituted isoindolin-2-yl-1,3-dione, $R^3$ is —O$R^{14}$, and $R^{14}$ is substituted $C_9$-$C_{20}$ alkyl. In some embodiments, the symbol $A^1$ is =N—, $R^{1A}$ and $R^{2A}$ are joined to form an unsubstituted isoindolin-2-yl-1,3-dione, $R^3$ is —O$R^{14}$, and $R^{14}$ is substituted $C_1$-$C_{10}$ alkyl. In some embodiments, the symbol $A^1$ is =N—, $R^{1A}$ and $R^{2A}$ are joined to form an unsubstituted isoindolin-2-yl-1,3-dione, $R^3$ is —O$R^{14}$, and $R^{14}$ is substituted $C_1$-$C_{12}$ alkyl. In some embodiments, the symbol $A^1$ is =N—, $R^{1A}$ and $R^{2A}$ are joined to form an unsubstituted isoindolin-2-yl-1,3-dione, $R^3$ is —O$R^{14}$, and $R^{14}$ is substituted $C_1$-$C_9$ alkyl. In some embodiments, the symbol $A^1$ is =N—, $R^{1A}$ and $R^{2A}$ are joined to form an unsubstituted isoindolin-2-yl-1,3-dione, $R^3$ is —O$R^{14}$, and $R^{14}$ is substituted $C_6$-$C_{12}$ alkyl. In some embodiments, the symbol $A^1$ is =N—, $R^{1A}$ and $R^{2A}$ are joined to form an unsubstituted isoindolin-2-yl-1,3-dione, $R^3$ is —O$R^{14}$, and $R^{14}$ is substituted $C_8$-$C_{10}$ alkyl.

In some embodiments of the compounds provided herein, $R^{1A}$ is independently hydrogen, halogen, —CF$_3$, —COOH, —CONH$_2$, —C(O)CH$_3$, $R^{20A}$-substituted or unsubstituted alkyl, $R^{20A}$-substituted or unsubstituted heteroalkyl, $R^{20A}$-substituted or unsubstituted cycloalkyl, $R^{20A}$-substituted or unsubstituted heterocycloalkyl, $R^{20A}$-substituted or unsubstituted aryl, or $R^{20A}$-substituted or unsubstituted heteroaryl.

$R^{20A}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{21A}$-substituted or unsubstituted alkyl, $R^{21A}$-substituted or unsubstituted heteroalkyl, $R^{21A}$-substituted or unsubstituted cycloalkyl, $R^{21A}$-substituted or unsubstituted heterocycloalkyl, $R^{21A}$-substituted or unsubstituted aryl, or $R^{21A}$-substituted or unsubstituted heteroaryl.

$R^{21A}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{22A}$-substituted or unsubstituted alkyl, $R^{22A}$-substituted or unsubstituted heteroalkyl, $R^{22A}$-substituted or unsubstituted cycloalkyl, $R^{22A}$-substituted or unsubstituted heterocycloalkyl, $R^{22A}$-substituted or unsubstituted aryl, or $R^{22A}$-substituted or unsubstituted heteroaryl.

In some embodiments of the compounds provided herein, $R^{1B}$ is independently hydrogen, halogen, —CF$_3$, —COOH, —CONH$_2$, —C(O)CH$_3$, $R^{20B}$-substituted or unsubstituted alkyl, $R^{20B}$-substituted or unsubstituted heteroalkyl, $R^{20B}$-substituted or unsubstituted cycloalkyl, $R^{20B}$-substituted or unsubstituted heterocycloalkyl, $R^{20B}$-substituted or unsubstituted aryl, or $R^{20B}$-substituted or unsubstituted heteroaryl.

$R^{20B}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{21B}$-substituted or unsubstituted alkyl, $R^{21B}$-substituted or unsubstituted heteroalkyl, $R^{21B}$-substituted or unsubstituted cycloalkyl, $R^{21B}$-substituted or unsubstituted heterocycloalkyl, $R^{21B}$-substituted or unsubstituted aryl, or $R^{21B}$-substituted or unsubstituted heteroaryl.

$R^{21B}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{22B}$-substituted or unsubstituted alkyl, $R^{22B}$-substituted or unsubstituted heteroalkyl, $R^{22B}$-substituted or unsubstituted cycloalkyl, $R^{22B}$-substituted or unsubstituted heterocycloalkyl, $R^{22B}$-substituted or unsubstituted aryl, or $R^{22B}$-substituted or unsubstituted heteroaryl.

In some embodiments of the compounds provided herein, $R^{2A}$ is independently hydrogen, halogen, —$CF_3$, —COOH, —$CONH_2$, —C(O)$CH_3$, $R^{23A}$-substituted or unsubstituted alkyl, $R^{23A}$-substituted or unsubstituted heteroalkyl, $R^{23A}$-substituted or unsubstituted cycloalkyl, $R^{23A}$-substituted or unsubstituted heterocycloalkyl, $R^{23A}$-substituted or unsubstituted aryl, or $R^{23A}$-substituted or unsubstituted heteroaryl.

$R^{23A}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{24A}$-substituted or unsubstituted alkyl, $R^{24A}$-substituted or unsubstituted heteroalkyl, $R^{24A}$-substituted or unsubstituted cycloalkyl, $R^{24A}$-substituted or unsubstituted heterocycloalkyl, $R^{24A}$-substituted or unsubstituted aryl, or $R^{24A}$-substituted or unsubstituted heteroaryl.

$R^{24A}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{25A}$-substituted or unsubstituted alkyl, $R^{25A}$-substituted or unsubstituted heteroalkyl, $R^{25A}$-substituted or unsubstituted cycloalkyl, $R^{25A}$-substituted or unsubstituted heterocycloalkyl, $R^{25A}$-substituted or unsubstituted aryl, or $R^{25A}$-substituted or unsubstituted heteroaryl.

In some embodiments of the compounds provided herein, $R^{2B}$ is independently hydrogen, halogen, —$CF_3$, —COOH, —$CONH_2$, —C(O)$CH_3$, $R^{23B}$-substituted or unsubstituted alkyl, $R^{23B}$-substituted or unsubstituted heteroalkyl, $R^{23B}$-substituted or unsubstituted cycloalkyl, $R^{23B}$-substituted or unsubstituted heterocycloalkyl, $R^{23B}$-substituted or unsubstituted aryl, or $R^{23B}$-substituted or unsubstituted heteroaryl.

$R^{23B}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{24B}$-substituted or unsubstituted alkyl, $R^{24B}$-substituted or unsubstituted heteroalkyl, $R^{24B}$-substituted or unsubstituted cycloalkyl, $R^{24B}$-substituted or unsubstituted heterocycloalkyl, $R^{24B}$-substituted or unsubstituted aryl, or $R^{24B}$-substituted or unsubstituted heteroaryl.

$R^{24B}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{25B}$-substituted or unsubstituted alkyl, $R^{25B}$-substituted or unsubstituted heteroalkyl, $R^{25B}$-substituted or unsubstituted cycloalkyl, $R^{25B}$-substituted or unsubstituted heterocycloalkyl, $R^{25B}$-substituted or unsubstituted aryl, or $R^{25B}$-substituted or unsubstituted heteroaryl.

In some embodiments of the compounds provided herein, $R^3$ is independently hydrogen, halogen, —$CF_3$, —CN, —OH, —$NH_2$, —COOH, —OC(O)H—$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl.

$R^{26}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, or $R^{27}$-substituted or unsubstituted heteroaryl.

$R^{27}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{28}$-substituted or unsubstituted alkyl, $R^{28}$-substituted or unsubstituted heteroalkyl, $R^{28}$-substituted or unsubstituted cycloalkyl, $R^{28}$-substituted or unsubstituted heterocycloalkyl, $R^{28}$-substituted or unsubstituted aryl, or $R^{28}$-substituted or unsubstituted heteroaryl.

In some embodiments of the compounds provided herein, $R^4$ is independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —C(O)$OCH_3$, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted 4 heterocycloalkyl, $R^{29}$-substituted or unsubstituted aryl, or $R^{29}$-substituted or unsubstituted heteroaryl.

$R^{29}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{30}$-substituted or unsubstituted alkyl, $R^{30}$-substituted or unsubstituted heteroalkyl, $R^{30}$-substituted or unsubstituted cycloalkyl, $R^{30}$ substituted or unsubstituted heterocycloalkyl, $R^{30}$-substituted or unsubstituted aryl, or $R^{30}$-substituted or unsubstituted heteroaryl.

$R^{30}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{31}$-substituted or unsubstituted alkyl, $R^{31}$-substituted or unsubstituted heteroalkyl, $R^{31}$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl.

In some embodiments of the compounds provided herein, $R^{7A}$ is independently hydrogen, $R^{38A}$-substituted or unsubstituted alkyl, $R^{38A}$-substituted or unsubstituted heteroalkyl, $R^{38A}$-substituted or unsubstituted cycloalkyl, $R^{38A}$-substituted or unsubstituted heterocycloalkyl, $R^{38A}$-substituted or unsubstituted aryl, or $R^{38A}$-substituted or unsubstituted membered heteroaryl.

$R^{38A}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{39A}$-substituted or unsubstituted alkyl, $R^{39A}$-substituted or unsubstituted heteroalkyl, $R^{39A}$-substituted or unsubstituted cycloalkyl, $R^{39A}$-substituted or unsubstituted heterocycloalkyl, $R^{39A}$-substituted or unsubstituted aryl, or $R^{39A}$-substituted or unsubstituted heteroaryl.

$R^{39A}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{40A}$-substituted or unsubstituted alkyl, $R^{40A}$-substituted or unsubstituted heteroalkyl, $R^{40A}$-substituted or unsubstituted cycloalkyl, $R^{40A}$-substituted or unsubstituted heterocycloalkyl, $R^{40A}$-substituted or unsubstituted aryl, or $R^{40A}$-substituted or unsubstituted heteroaryl.

In some embodiments of the compounds provided herein, $R^{7B}$ is independently hydrogen, $R^{38B}$-substituted or unsubstituted alkyl, $R^{38B}$-substituted or unsubstituted heteroalkyl, $R^{38B}$-substituted or unsubstituted cycloalkyl, $R^{38B}$-substituted or unsubstituted heterocycloalkyl, $R^{38B}$-substituted or unsubstituted aryl, or $R^{38B}$-substituted or unsubstituted membered heteroaryl.

$R^{38B}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{39B}$-substituted or unsubstituted alkyl, $R^{39B}$-substituted or unsubstituted heteroalkyl, $R^{39B}$-substituted or unsubstituted cycloalkyl, $R^{39B}$-substituted or unsubstituted heterocycloalkyl, $R^{39B}$-substituted or unsubstituted aryl, or $R^{39B}$-substituted or unsubstituted heteroaryl.

$R^{39B}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{40B}$-substituted or unsubstituted alkyl, $R^{40B}$-substituted or unsubstituted heteroalkyl, $R^{40B}$-substituted or unsubstituted cycloalkyl, $R^{40B}$-substituted or unsubstituted heterocycloalkyl, $R^{40B}$-substituted or unsubstituted aryl, or $R^{40B}$-substituted or unsubstituted heteroaryl.

In some embodiments of the compounds provided herein, $R^{8A}$ is independently hydrogen, $R^{41A}$-substituted or unsubstituted alkyl, $R^{41A}$-substituted or unsubstituted heteroalkyl, $R^{41A}$-substituted or unsubstituted cycloalkyl, $R^{41A}$-substituted or unsubstituted heterocycloalkyl, $R^{41A}$-substituted or unsubstituted aryl, or $R^{41A}$-substituted or unsubstituted heteroaryl.

$R^{41A}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{42A}$-substituted or unsubstituted alkyl, $R^{42A}$-substituted or unsubstituted heteroalkyl, $R^{42A}$-substituted or unsubstituted cycloalkyl, $R^{42A}$-substituted or unsubstituted heterocycloalkyl, $R^{42A}$-substituted or unsubstituted aryl, or $R^{42A}$-substituted or unsubstituted heteroaryl.

$R^{42A}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{43A}$-substituted or unsubstituted alkyl, $R^{43A}$-substituted or unsubstituted heteroalkyl, $R^{43A}$-substituted or unsubstituted cycloalkyl, $R^{43A}$-substituted or unsubstituted heterocycloalkyl, $R^{43A}$-substituted or unsubstituted aryl, or $R^{43A}$-substituted or unsubstituted heteroaryl.

In some embodiments of the compounds provided herein, $R^{8B}$ is independently hydrogen, $R^{41B}$-substituted or unsubstituted alkyl, $R^{41B}$-substituted or unsubstituted heteroalkyl, $R^{41B}$-substituted or unsubstituted cycloalkyl, $R^{41B}$-substituted or unsubstituted heterocycloalkyl, $R^{41B}$-substituted or unsubstituted aryl, or $R^{41B}$-substituted or unsubstituted heteroaryl.

$R^{41B}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{42B}$-substituted or unsubstituted alkyl, $R^{42B}$-substituted or unsubstituted heteroalkyl, $R^{42B}$-substituted or unsubstituted cycloalkyl, $R^{42B}$-substituted or unsubstituted heterocycloalkyl, $R^{42B}$-substituted or unsubstituted aryl, or $R^{42B}$-substituted or unsubstituted heteroaryl.

$R^{42B}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{43B}$-substituted or unsubstituted alkyl, $R^{43B}$-substituted or unsubstituted heteroalkyl, $R^{43B}$-substituted or unsubstituted cycloalkyl, $R^{43B}$-substituted or unsubstituted heterocycloalkyl, $R^{43B}$-substituted or unsubstituted aryl, or $R^{43B}$-substituted or unsubstituted heteroaryl.

In some embodiments of the compounds provided herein, $R^{9A}$ is independently hydrogen, $R^{44A}$-substituted or unsubstituted alkyl, $R^{44A}$-substituted or unsubstituted heteroalkyl, $R^{44A}$-substituted or unsubstituted cycloalkyl, $R^{44A}$-substituted or unsubstituted heterocycloalkyl, $R^{44A}$-substituted or unsubstituted aryl, or $R^{44A}$-substituted or unsubstituted heteroaryl.

$R^{44A}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{45A}$-substituted or unsubstituted alkyl, $R^{45A}$-substituted or unsubstituted heteroalkyl, $R^{45A}$-substituted or unsubstituted cycloalkyl, $R^{45A}$-substituted or unsubstituted heterocycloalkyl, $R^{45A}$-substituted or unsubstituted aryl, or $R^{45A}$-substituted or unsubstituted heteroaryl.

$R^{44A}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{46A}$-substituted or unsubstituted alkyl, $R^{46A}$-substituted or unsubstituted heteroalkyl, $R^{46A}$-substituted or unsubstituted cycloalkyl, $R^{46A}$-substituted or unsubstituted heterocycloalkyl, $R^{46A}$-substituted or unsubstituted aryl, or $R^{46A}$-substituted or unsubstituted heteroaryl.

In some embodiments of the compounds provided herein, $R^{9B}$ is independently hydrogen, $R^{44B}$-substituted or unsubstituted alkyl, $R^{44B}$-substituted or unsubstituted heteroalkyl, $R^{44B}$-substituted or unsubstituted cycloalkyl, $R^{44B}$-substituted or unsubstituted heterocycloalkyl, $R^{44B}$-substituted or unsubstituted aryl, or $R^{44B}$-substituted or unsubstituted heteroaryl.

$R^{44B}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{45B}$-substituted or unsubstituted alkyl, $R^{45B}$-substituted or unsubstituted heteroalkyl, $R^{45B}$-substituted or unsubstituted cycloalkyl, $R^{45B}$-substituted or unsubstituted heterocycloalkyl, $R^{45B}$-substituted or unsubstituted aryl, or $R^{45B}$-substituted or unsubstituted heteroaryl.

$R^{45B}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{46B}$-substituted or unsubstituted alkyl, $R^{46B}$-substituted or unsubstituted heteroalkyl, $R^{46B}$-substituted or unsubstituted cycloalkyl, $R^{46B}$-substituted or unsubstituted heterocycloalkyl, $R^{46B}$-substituted or unsubstituted aryl, or $R^{46B}$-substituted or unsubstituted heteroaryl.

In some embodiments of the compounds provided herein, $R^{10A}$ is independently hydrogen, $R^{47A}$-substituted or unsubstituted alkyl, $R^{47A}$-substituted or unsubstituted heteroalkyl, $R^{47A}$-substituted or unsubstituted cycloalkyl, $R^{47A}$-substituted or unsubstituted heterocycloalkyl, $R^{47A}$-substituted or unsubstituted aryl, or $R^{47A}$-substituted or unsubstituted heteroaryl.

$R^{47A}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{48A}$-substituted or unsubstituted alkyl, $R^{48A}$-substituted or unsubstituted heteroalkyl, $R^{48A}$-substituted or unsubstituted cycloalkyl, $R^{48A}$-substituted or unsubstituted heterocycloalkyl, $R^{48A}$-substituted or unsubstituted aryl, or $R^{48A}$-substituted or unsubstituted heteroaryl.

$R^{48A}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{49A}$-substituted or unsubstituted alkyl, $R^{49A}$-substituted or unsubstituted heteroalkyl, $R^{49A}$-substituted or unsubstituted cycloalkyl, $R^{49A}$-substituted or unsubstituted heterocycloalkyl, $R^{49A}$-substituted or unsubstituted aryl, or $R^{49A}$-substituted or unsubstituted heteroaryl.

In some embodiments of the compounds provided herein, $R^{10B}$ is independently hydrogen, $R^{47B}$-substituted or unsubstituted alkyl, $R^{47B}$-substituted or unsubstituted heteroalkyl, $R^{47B}$-substituted or unsubstituted cycloalkyl, $R^{47B}$-substituted or unsubstituted heterocycloalkyl, $R^{47B}$-substituted or unsubstituted aryl, or $R^{47B}$-substituted or unsubstituted heteroaryl.

$R^{47B}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{48B}$-substituted or unsubstituted alkyl, $R^{48B}$-substituted or unsubstituted heteroalkyl, $R^{48B}$-substituted or unsubstituted cycloalkyl, $R^{48B}$-substituted or unsubstituted heterocycloalkyl, $R^{48B}$-substituted or unsubstituted aryl, or $R^{48B}$-substituted or unsubstituted heteroaryl.

$R^{48B}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{49B}$-substituted or unsubstituted alkyl, $R^{49B}$-substituted or unsubstituted heteroalkyl, $R^{49B}$-substituted or unsubstituted cycloalkyl, $R^{49B}$-substituted or unsubstituted heterocycloalkyl, $R^{49B}$-substituted or unsubstituted aryl, or $R^{49B}$-substituted or unsubstituted heteroaryl.

In some embodiments of the compounds provided herein, $R^{11}$ is independently hydrogen, $R^{50}$-substituted or unsubstituted alkyl, $R^{50}$-substituted or unsubstituted heteroalkyl, $R^{50}$-substituted or unsubstituted cycloalkyl, $R^{50}$-substituted or unsubstituted heterocycloalkyl, $R^{50}$-substituted or unsubstituted aryl, or $R^{50}$-substituted or unsubstituted heteroaryl.

$R^{50}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{51}$-substituted or unsubstituted alkyl, $R^{51}$-substituted or unsubstituted heteroalkyl, $R^{51}$-substituted or unsubstituted cycloalkyl, $R^{51}$ substituted or unsubstituted heterocycloalkyl, $R^{51}$-substituted or unsubstituted aryl, or $R^{51}$-substituted or unsubstituted heteroaryl.

$R^{51}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{52}$-substituted or unsubstituted alkyl, $R^{52}$-substituted or unsubstituted heteroalkyl, $R^{52}$-substituted or unsubstituted cycloalkyl, $R^{52}$-substituted or unsubstituted heterocycloalkyl, $R^{52}$-substituted or unsubstituted aryl, or $R^{52}$-substituted or unsubstituted heteroaryl.

In some embodiments of the compounds provided herein, $R^{12}$ is independently hydrogen, $R^{53}$-substituted or unsubstituted alkyl, $R^{53}$-substituted or unsubstituted heteroalkyl, $R^{53}$-substituted or unsubstituted cycloalkyl, $R^{53}$-substituted or unsubstituted heterocycloalkyl, $R^{53}$-substituted or unsubstituted aryl, or $R^{53}$-substituted or unsubstituted heteroaryl.

$R^{53}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{54}$-substituted or unsubstituted alkyl, $R^{54}$-substituted or unsubstituted heteroalkyl, $R^{54}$-substituted or unsubstituted cycloalkyl, $R^{54}$ substituted or unsubstituted heterocycloalkyl, $R^{54}$-substituted or unsubstituted aryl, or $R^{54}$-substituted or unsubstituted heteroaryl.

$R^{54}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{55}$-substituted or unsubstituted alkyl, $R^{55}$-substituted or unsubstituted heteroalkyl, $R^{55}$-substituted or unsubstituted cycloalkyl, $R^{55}$-substituted or unsubstituted heterocycloalkyl, $R^{55}$-substituted or unsubstituted aryl, or $R^{55}$-substituted or unsubstituted heteroaryl.

In some embodiments of the compounds provided herein, $R^{13}$ is independently hydrogen, $R^{56}$-substituted or unsubstituted alkyl, $R^{56}$-substituted or unsubstituted heteroalkyl, $R^{56}$-substituted or unsubstituted cycloalkyl, $R^{56}$-substituted or unsubstituted heterocycloalkyl, $R^{56}$-substituted or unsubstituted aryl, or $R^{56}$-substituted or unsubstituted heteroaryl.

$R^{56}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{57}$-substituted or unsubstituted alkyl, $R^{57}$-substituted or unsubstituted heteroalkyl, $R^{57}$-substituted or unsubstituted cycloalkyl, $R^{57}$ substituted or unsubstituted heterocycloalkyl, $R^{57}$-substituted or unsubstituted aryl, or $R^{57}$-substituted or unsubstituted heteroaryl.

$R^{57}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{58}$-substituted or unsubstituted alkyl, $R^{58}$-substituted or unsubstituted heteroalkyl, $R^{58}$-substituted or unsubstituted cycloalkyl, $R^{58}$-substituted or unsubstituted heterocycloalkyl, $R^{58}$-substituted or unsubstituted aryl, or $R^{58}$-substituted or unsubstituted heteroaryl.

In some embodiments of the compounds provided herein, $R^{14}$ is independently hydrogen, $R^{59}$-substituted or unsubstituted alkyl, $R^{59}$-substituted or unsubstituted heteroalkyl, $R^{59}$-substituted or unsubstituted cycloalkyl, $R^{59}$-substituted or unsubstituted heterocycloalkyl, $R^{59}$-substituted or unsubstituted aryl, or $R^{59}$-substituted or unsubstituted heteroaryl.

$R^{59}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{60}$-substituted or unsubstituted alkyl, $R^{60}$-substituted or unsubstituted heteroalkyl, $R^{60}$-substituted or unsubstituted cycloalkyl, $R^{60}$-substituted or unsubstituted heterocycloalkyl, $R^{60}$-substituted or unsubstituted aryl, or $R^{60}$-substituted or unsubstituted heteroaryl.

$R^{60}$ independently is halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{61}$-substituted or unsubstituted alkyl, $R^{61}$-substituted or unsubstituted heteroalkyl, $R^{61}$-substituted or unsubstituted cycloalkyl, $R^{61}$-substituted or unsubstituted heterocycloalkyl, $R^{61}$-substituted or unsubstituted aryl, or $R^{61}$-substituted or unsubstituted heteroaryl.

In a further embodiment of the compounds provided herein, $R^{15}$ is independently hydrogen, $R^{62}$-substituted or unsubstituted alkyl, $R^{62}$-substituted or unsubstituted heteroalkyl, $R^{62}$-substituted or unsubstituted cycloalkyl, $R^{62}$-substituted or unsubstituted heterocycloalkyl, $R^{62}$-substituted or unsubstituted aryl, or $R^{62}$-substituted or unsubstituted heteroaryl.

$R^{62}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{63}$-substituted or unsubstituted alkyl, $R^{63}$-substituted or unsubstituted heteroalkyl, $R^{63}$-substituted or unsubstituted cycloalkyl, $R^{63}$-substituted or unsubstituted heterocycloalkyl, $R^{63}$-substituted or unsubstituted aryl, or $R^{63}$-substituted or unsubstituted heteroaryl.

$R^{63}$ independently is halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{64}$-substituted or unsubstituted alkyl, $R^{64}$-substituted or unsubstituted heteroalkyl, $R^{64}$-substituted or unsubstituted cycloalkyl, $R^{64}$-substituted or unsubstituted heterocycloalkyl, $R^{64}$-substituted or unsubstituted aryl, or $R^{64}$-substituted or unsubstituted heteroaryl.

In some embodiments of the compounds provided herein, $R^{16}$ is independently hydrogen, $R^{65}$-substituted or unsubstituted alkyl, $R^{65}$-substituted or unsubstituted heteroalkyl, $R^{65}$-substituted or unsubstituted cycloalkyl, $R^{65}$-substituted or unsubstituted heterocycloalkyl, $R^{65}$-substituted or unsubstituted aryl, or $R^{65}$-substituted or unsubstituted heteroaryl.

$R^{65}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{66}$-substituted or unsubstituted alkyl, $R^{66}$-substituted or unsubstituted heteroalkyl, $R^{66}$-substituted or unsubstituted cycloalkyl, $R^{66}$-substituted or unsubstituted heterocycloalkyl, $R^{66}$-substituted or unsubstituted aryl, or $R^{66}$-substituted or unsubstituted heteroaryl.

$R^{66}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{67}$-substituted or unsubstituted alkyl, $R^{67}$-substituted or unsubstituted heteroalkyl, $R^{67}$-substituted or unsubstituted cycloalkyl, $R^{67}$-substituted or unsubstituted heterocycloalkyl, $R^{67}$-substituted or unsubstituted aryl, or $R^{67}$-substituted or unsubstituted heteroaryl.

In some embodiments of the compounds provided herein, $R^{17}$ is independently hydrogen, $R^{68}$-substituted or unsubstituted alkyl, $R^{68}$-substituted or unsubstituted heteroalkyl, $R^{68}$-substituted or unsubstituted cycloalkyl, $R^{68}$-substituted or unsubstituted heterocycloalkyl, $R^{68}$-substituted or unsubstituted aryl, or $R^{68}$-substituted or unsubstituted heteroaryl.

$R^{68}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{69}$-substituted or unsubstituted alkyl, $R^{69}$-substituted or unsubstituted heteroalkyl, $R^{69}$-substituted or unsubstituted cycloalkyl, $R^{69}$-substituted or unsubstituted heterocycloalkyl, $R^{69}$-substituted or unsubstituted aryl, or $R^{69}$-substituted or unsubstituted heteroaryl.

$R^{69}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{70}$-substituted or unsubstituted alkyl, $R^{70}$-substituted or unsubstituted heteroalkyl, $R^{70}$-substituted or unsubstituted cycloalkyl, $R^{70}$-substituted or unsubstituted heterocycloalkyl, $R^{70}$-substituted or unsubstituted aryl, or $R^{70}$-substituted or unsubstituted heteroaryl.

In some embodiments of the compounds provided herein, $R^{18}$ is independently hydrogen, $R^{71}$-substituted or unsubstituted alkyl, $R^{71}$-substituted or unsubstituted heteroalkyl, $R^{71}$-substituted or unsubstituted cycloalkyl, $R^{71}$-substituted or unsubstituted heterocycloalkyl, $R^{71}$-substituted or unsubstituted aryl, or $R^{71}$-substituted or unsubstituted heteroaryl.

$R^{71}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{72}$-substituted or unsubstituted alkyl, $R^{72}$-substituted or unsubstituted heteroalkyl, $R^{72}$-substituted or unsubstituted cycloalkyl, $R^{72}$ substituted or unsubstituted heterocycloalkyl, $R^{72}$-substituted or unsubstituted aryl, or $R^{72}$-substituted or unsubstituted heteroaryl.

$R^{72}$ is independently halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $R^{73}$-substituted or unsubstituted alkyl, $R^{73}$-substituted or unsubstituted heteroalkyl, $R^{73}$-substituted or unsubstituted cycloalkyl, $R^{73}$-substituted or unsubstituted heterocycloalkyl, $R^{73}$-substituted or unsubstituted aryl, or $R^{73}$-substituted or unsubstituted heteroaryl.

$R^{22A}$, $R^{22B}$, $R^{25A}$, $R^{25B}$, $R^{28}$, $R^{31}$, $R^{40A}$, $R^{40B}$, $R^{43A}$, $R^{43B}$, $R^{46A}$, $R^{46B}$, $R^{49A}$, $R^{49B}$, $R^{52}$, $R^{55}$, $R^{58}$, $R^{61}$, $R^{64}$, $R^{67}$, $R^{70}$, and $R^{73}$, are independently hydrogen, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, unsubstituted alkyl, unsubstituted heteroalkyl, unsubstituted cycloalkyl, unsubstituted heterocycloalkyl, unsubstituted aryl, or unsubstituted heteroaryl.

In some embodiments, the compound is any one of the compounds in the Examples section below.

In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound is an eEF-2K modulator. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound is an eEF-2K inhibitor. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound is an eEF-2K activator. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound is an eEF-2 modulator. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound is an eEF-2 inhibitor. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound is an eEF-2 activator. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound is a 5-HTR$_{1B}$ modulator. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound is a 5-HTR$_{1B}$ inhibitor. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound is a 5-HTR$_{1B}$ activator. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound is a 5-HTR$_{1D}$ modulator. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound is a 5-HTR$_{1D}$ inhibitor. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound is a 5-HTR$_{1D}$ activator. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound is a 5-HTR modulator. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound is a 5-HTR inhibitor. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound is a 5-HTR activator. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound reduces the effective amount necessary to treat a disease. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound reduces the effective amount of a second agent (e.g. inhibitor, modulator, compound, drug, chemotherapeutic agent) necessary to treat a disease. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound is an mTOR inhibitor. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound is an Ala inhibitor. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits cancer cell proliferation. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits cancer cell survival. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits cancer cell migration/invasion. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits cancer cell cell cycle progression. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits angiogenesis. In some embodiments of the compound described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits the level of c-myc activity in a cell. In some embodiments of the compound as described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits the level of cyclin-D1 activity in a cell. In some embodiments of the compound as described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits the level of Bcl-2 activity in a cell. In some embodiments of the compound as described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits the level of VEGF activity. In some embodiments of the compound as described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits the level of HIF1alpha activity in a cell. In some embodiments of the compound as described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits the level of c-Src activity in a cell. In some embodiments of the compound as described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits the level of FAK activity in a cell. In some embodiments of the compound as described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits the level of Paxillin activity in a cell. In some embodiments of the compound as described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits the level of IGF-1R activity in a cell. In some embodiments of the compound as described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits the level of Akt activity in a cell. In some embodiments of the compound as described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits the level of mTOR activity in a cell. In some embodiments of the compound as described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits the level of NF-κB activity in a cell. In some embodiments of the compound as described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits the level of ERK1 activity in a cell. In some embodiments of the compound as described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits the level of ERK2 activity in a cell. In some embodiments of the compound as described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), the compound inhibits the level of MAPK activity in a cell.

In another aspect, one or more hydrogens of the compounds provided herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments), may be substituted with an –F. The terms "compounds described herein", "compounds as described herein", "compounds provided herein", "compositions of the present invention", and "compounds of the present invention" may be used interchangeably.

In some embodiments, a compound as described herein may include multiple instances of $R^3$, $R^4$, $R^{11}$, $R^{12}$, $R^{13}$, $R^{14}$, $R^{15}$, $R^{16}$, $R^{17}$, $R^{18}$, $X^3$, $X^4$, u, k, m, n, q, r, t, and/or other variables. In such embodiments, each variable may optional be different and be appropriately labeled to distinguish each group for greater clarity. For example, where each $R^3$, $R^4$, $R^{11}$, $R^{12}$, $R^{13}$, $R^{14}$, $R^{15}$, $R^{16}$, $R^{17}$, $R^{18}$, $X^3$, $X^4$, u, k, m, n, q, r, and t is different, they may be referred to, for example, as $R^{3c}$, $R^{3d}$, $R^{3e}$, $R^{3f}$, $R^{3g}$, $R^{3h}$, $R^{3i}$, $R^{4c}$, $R^{4d}$, $R^{4e}$, $R^{4f}$, $R^{4g}$, $R^{4h}$, $R^{4i}$, $R^{11c}$, $R^{11d}$, $R^{11e}$, $R^{11f}$, $R^{11g}$, $R^{11h}$, $R^{11i}$, $R^{12c}$, $R^{12d}$, $R^{12e}$, $R^{12f}$, $R^{12g}$, $R^{12h}$, $R^{12i}$, $R^{13c}$, $R^{13d}$, $R^{13e}$, $R^{13f}$, $R^{13g}$, $R^{13h}$, $R^{13i}$, $R^{14c}$, $R^{14d}$, $R^{14e}$, $R^{14f}$, $R^{14g}$, $R^{14h}$, $R^{14i}$, $R^{15c}$, $R^{15d}$, $R^{15e}$, $R^{15f}$, $R^{15g}$, $R^{15h}$, $R^{15i}$, $R^{16c}$, $R^{16d}$, $R^{16e}$, $R^{16f}$, $R^{16g}$, $R^{16h}$, $R^{16i}$, $R^{17c}$, $R^{17d}$, $R^{17e}$, $R^{17f}$, $R^{17g}$, $R^{17h}$, $R^{17i}$, $R^{18c}$, $R^{18d}$, $R^{18e}$, $R^{18f}$, $R^{18g}$, $R^{18h}$, $R^{18i}$, $X^{3c}$, $X^{3d}$, $X^{3e}$, $X^{3f}$, $X^{3g}$, $X^{3h}$, $X^{3i}$, $X^{4c}$, $X^{4d}$, $X^{4e}$, $X^{4f}$, $X^{4g}$, $X^{4h}$, $X^{4i}$, $u^c$, $u^d$, $u^e$, $u^f$, $u^g$, $u^h$, $u^i$, $k^c$, $k^d$, $k^e$, $k^f$, $k^g$, $k^h$, $k^i$, $m^c$, $m^d$, $m^e$, $m^f$, $m^g$, $m^h$, $m^i$, $n^c$, $n^d$, $n^e$, $n^f$, $n^g$, $n^h$, $n^i$, $q^c$, $q^d$, $q^e$, $q^f$, $q^g$, $q^h$, $q^i$, $r^c$, $r^d$, $r^e$, $r^f$, $r^g$, $r^h$, $r^i$, $t^c$, $t^d$, $t^e$, $t^f$, $t^g$, $t^h$, $t^i$, respectively, wherein the definition of $R^3$ is assumed by $R^{3c}$, $R^{3d}$, $R^{3e}$, $R^{3f}$, $R^{3g}$, $R^{3h}$, $R^{3i}$, the definition of $R^4$ is assumed by $R^{4c}$, $R^{4d}$, $R^{4e}$, $R^{4f}$, $R^{4g}$, $R^{4h}$, $R^{4i}$, the definition of $R^{11}$ is assumed by $R^{11c}$, $R^{11d}$, $R^{11e}$, $R^{11f}$, $R^{11g}$, $R^{11h}$, $R^{11i}$, the definition of $R^{12}$ is assumed by $R^{12c}$, $R^{12d}$, $R^{12e}$, $R^{12f}$, $R^{12g}$, $R^{12h}$, $R^{12i}$, the definition of $R^{13}$ is assumed by $R^{13c}$, $R^{13d}$, $R^{13e}$, $R^{13f}$, $R^{13g}$, $R^{13h}$, $R^{13i}$, the definition of $R^{14}$ is assumed by $R^{14c}$, $R^{14d}$, $R^{14e}$, $R^{14f}$, $R^{14g}$, $R^{14h}$, $R^{14i}$, the definition of $R^{15}$ is assumed by $R^{15c}$, $R^{15d}$, $R^{15e}$, $R^{15f}$, $R^{15g}$, $R^{15h}$, $R^{15i}$, the definition of $R^{16}$ is assumed by $R^{16c}$, $R^{16d}$, $R^{16e}$, $R^{16f}$, $R^{16g}$, $R^{16h}$, the definition of $R^{17}$ is assumed by $R^{17c}$, $R^{17d}$, $R^{17e}$, $R^{17f}$, $R^{17g}$, $R^{17h}$, $R^{17i}$, the definition of $R^{18}$ is assumed by $R^{18c}$, $R^{18d}$, $R^{18e}$, $R^{18f}$, $R^{18g}$, $R^{18h}$, $R^{18i}$, the definition of $X^3$ is assumed by $X^{3c}$, $X^{3d}$, $X^{3e}$, $X^{3f}$, $X^{3g}$, $X^{3h}$, $X^{3i}$, the definition of $X^4$ is assumed by $X^{4c}$, $X^{4d}$, $X^{4e}$, $X^{4f}$, $X^{4g}$, $X^{4h}$, $X^{4i}$, the definition of u is assumed by $u^c$, $u^d$, $u^e$, $u^f$, $u^g$, $u^h$, $u^i$, the definition of k is assumed by $k^c$, $k^d$, $k^e$, $k^f$, $k^g$, $k^h$, $k^i$, the definition of m is assumed by $m^c$, $m^d$, $m^e$, $m^f$, $m^g$, $m^h$, $m^i$, the definition of n is assumed by $n^c$, $n^d$, $n^e$, $n^f$, $n^g$, $n^h$, $n^i$, the definition of q is assumed by $q^c$, $q^d$, $q^e$, $q^f$, $q^g$, $q^h$, $q^i$, the definition of r is assumed by $r^c$, $r^d$, $r^e$, $r^f$, $r^g$, $r^h$, $r^i$, the definition of t is assumed by $t^c$, $t^d$, $t^e$, $t^f$, $t^g$, $t^h$, $t^i$.

The variables used within a definition of $R^3$, $R^4$, $R^{11}$, $R^{12}$, $R^{13}$, $R^{14}$, $R^{15}$, $R^{16}$, $R^{17}$, $R^{18}$, $X^3$, $X^4$, u, k, m, n, q, r, t, and/or other variables that appear at multiple instances and are different may similarly be appropriately labeled to distinguish each group for greater clarity. For example, in some embodiments, the definition of $R^{3c}$ may employ the symbols $R^{4c}$, $R^{11c}$, $R^{12c}$, $R^{13c}$, $R^{14c}$, $X^{3c}$, $u^c$, $k^c$, $m^c$, and $n^c$ which assume the definitions of $R^4$, $R^{11}$, $R^{12}$, $R^{13}$, $R^{14}$, u, k, m, and n, respectively. In some embodiments, the definition of $R^{4c}$ may employ the symbols $R^{15c}$, $R^{16c}$, $R^{17c}$, $R^{18c}$, $X^{4c}$, $q^c$, $r^c$, and $t^c$ which assume the definitions of $R^{15}$, $R^{16}$, $R^{17}$, $R^{18}$, $X^4$, q, r, and t, respectively. In some embodiments, the definition of $R^{3d}$ may employ the symbols $R^{4d}$, $R^{11d}$, $R^{12d}$, $R^{13d}$, $R^{14d}$, $X^{3d}$, $u^d$, $k^d$, $m^d$, and $n^d$ which assume the definitions of $R^4$, $R^{11}$, $R^{12}$, $R^{13}$, $R^{14}$, $X^3$, u, k, m, and n, respectively. In some embodiments, the definition of $R^{4d}$ may employ the symbols $R^{15d}$, $R^{16d}$, $R^{17d}$, $R^{18d}$, $X^{4d}$, $q^d$, $r^d$, and $t^d$ which assume the definitions of $R^{15}$, $R^{16}$, $R^{17}$, $R^{18}$, $X^4$, q, r, and t, respectively. In some embodiments, the definition of $R^{3e}$ may employ the symbols $R^{4e}$, $R^{11e}$, $R^{12e}$, $R^{13e}$, $R^{14e}$, $X^{3e}$, $u^e$, $k^e$, $m^e$, and $n^e$ which assume the definitions of $R^4$, $R^{11}$, $R^{12}$, $R^{13}$, $R^{14}$, $X^3$, u, k, m, and n, respectively. In some embodiments, the definition of $R^{4e}$ may employ the symbols $R^{15e}$, $R^{16e}$, $R^{17e}$, $R^{18e}$, $X^{4e}$, $q^e$, $r^e$, and $t^e$ which assume the definitions of $R^{15}$, $R^{16}$, $R^{17}$, $R^{18}$, $X^4$, q, r, and t, respectively. In some embodiments, the definition of $R^{3f}$ may employ the symbols $R^{4f}$, $R^{11f}$, $R^{12f}$, $R^{13f}$, $R^{14f}$, $X^{3f}$, $u^f$, $k^f$, $m^f$, and $n^f$ which assume the definitions of $R^4$, $R^{11}$, $R^{12}$, $R^{13}$, $R^{14}$, $X^3$, u, k, m, and n, respectively. In some embodiments, the definition of $R^{4f}$ may employ the symbols $R^{15f}$, $R^{16f}$, $R^{17f}$, $R^{18f}$, $X^{4f}$, $q^f$, $r^f$, and $t^f$ which assume the definitions of $R^{15}$, $R^{16}$, $R^{17}$, $R^{18}$, $X^4$, q, r, and t, respectively. In some embodiments, the definition of $R^{3g}$ may employ the symbols $R^{4g}$, $R^{11g}$, $R^{12g}$, $R^{13g}$, $R^{14g}$, $X^{3g}$, $u^g$, $k^g$, $m^g$, and $n^g$ which assume the definitions of $R^4$, $R^{11}$, $R^{12}$, $R^{13}$, $R^{14}$, $X^3$, u, k, m, and n, respectively. In some embodiments, the definition of $R^{4g}$ may employ the symbols $R^{15g}$, $R^{16g}$, $R^{17g}$, $R^{18g}$, $X^{4g}$, $q^g$, $r^g$, and $t^g$ which assume the definitions of $R^{15}$, $R^{16}$, $R^{17}$, $R^{18}$, $X^4$, q, r, and t, respectively. In some embodiments, the definition of $R^{3h}$ may employ the symbols $R^{4h}$, $R^{11h}$, $R^{12h}$, $R^{13h}$, $R^{14h}$, $X^{3h}$, $u^h$, $k^h$, $m^h$, and $n^h$ which assume the definitions of $R^4$, $R^{11}$, $R^{12}$, $R^{13}$, $R^{14}$, $X^3$, u, k, m, and n, respectively. In some embodiments, the definition of $R^{4h}$ may employ the symbols $R^{15h}$, $R^{16h}$, $R^{17h}$, $R^{18h}$, $X^{4h}$, $q^h$, $r^h$, and $t^h$ which assume the definitions of $R^{15}$, $R^{16}$, $R^{17}$, $R^{18}$, $X^4$, q, r, and t, respectively. In some embodiments, the definition of $R^{3i}$ may employ the symbols $R^{4i}$, $R^{11i}$, $R^{12i}$, $R^{13i}$, $R^{14i}$, $X^{3i}$, $u^i$, $k^i$, $m^i$, and $n^i$ which assume the definitions of $R^4$, $R^{11}$, $R^{12}$, $R^{13}$, $R^{14}$, $X^3$, u, k, m, and n, respectively. In some embodiments, the definition of $R^{4i}$ may employ the symbols $R^{15i}$, $R^{16i}$, $R^{17i}$, $R^{18i}$, $X^{4i}$, $q^i$, $r^i$, and $t^i$ which assume the definitions of $R^{15}$, $R^{16}$, $R^{17}$, $R^{18}$, $X^4$, q, r, and t, respectively.

Pharmaceutical Compositions and Methods of Treatment

In a second aspect, a pharmaceutical composition is provided that includes a pharmaceutically acceptable excipient and a compound as described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments).

In another aspect, a pharmaceutical composition is provided that includes a pharmaceutically acceptable excipient and an anti-eEF-2K inhibitory nucleic acid, anti-5-HTR$_{1B}$ inhibitory nucleic acid, anti-5-HTR$_{1D}$ inhibitory nucleic acid, or an anti-5-HTR inhibitory nucleic acid. In some embodiments, the pharmaceutical composition includes a pharmaceutically acceptable excipient and an inhibitory nucleic acid, the inhibitory nucleic acid is an anti-eEF-2K siRNA, anti-5-HTR$_{1B}$ siRNA, anti-5-HTR$_{1D}$ siRNA, or anti-5-HTR siRNA. In some embodiments of the pharmaceutical composition, the inhibitory nucleic acid is an anti-eEF-2K antisense nucleic acid, anti-5-HTR$_{1B}$ antisense nucleic acid, anti-5-HTR$_{1D}$ antisense nucleic acid, or an anti-5-HTR antisense nucleic acid. In some embodiments of the pharmaceutical composition that includes a pharmaceutically acceptable excipient and an antisense nucleic acid, the antisense nucleic acid is an anti-eEF-2K siRNA, anti-5-HTR$_{1B}$ siRNA, anti-5-HTR$_{1D}$ siRNA, or anti-5-HTR siRNA.

In some embodiments of the pharmaceutical compositions provided herein, the pharmaceutical composition includes a pharmaceutically acceptable excipient, a liposome, and a compound or inhibitory (e.g. antisense) nucleic acid as described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments). In some embodiments of the pharmaceutical composition, the liposome includes dioleoyl-sn-glycero-3-phosphocholine. In some embodiments of the pharmaceutical composition, the liposome includes dimyristoyl-phosphatidylcholine. In some embodiments of the pharmaceutical composition, the compound or inhibitory (e.g. antisense) nucleic acid (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments) is inside the liposome. In some embodiments of the pharmaceutical composition, the compound or inhibitory (e.g. antisense) nucleic acid (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments) is part of the liposome. In some embodiments of the pharmaceutical composition, the liposome includes a targeting moiety. In some embodiments of the pharmaceutical composition, the targeting moiety is folate. A targeting moiety that is part of a liposome, as the term used herein, refers to a moiety that directs the liposome to a particular location (e.g. tissue type, cell type, organ). In some embodiments, a targeting moiety is a compound. In some embodiments, a targeting moiety is a protein. In some embodiments, a targeting moiety is a nucleic acid. In some embodiments, a targeting moiety binds a cell. In some embodiments, a targeting moiety binds a protein. In some embodiments, a targeting moiety binds a protein on a cell. In some embodiments, a targeting moiety binds a protein in a cell. In some embodiments, a targeting moiety binds a cancer cell.

In a third aspect, a method of treating a disease in a patient in need of such treatment is provided. The method includes administering a therapeutically effective amount of a compound as described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments).

In another aspect, a method of treating a disease in a patient in need of such treatment is provided. The method includes administering a therapeutically effective amount of an anti-eEF-2K inhibitory (e.g. antisense) nucleic acid, anti-5-HTR$_{1B}$ inhibitory (e.g. antisense) nucleic acid, anti-5-HTR$_{1D}$ inhibitory (e.g. antisense) nucleic acid, or an anti-5-HTR inhibitory (e.g. antisense) nucleic acid. In some embodiments of the method of treating a disease in a patient in need of such treatment that includes administering a therapeutically effective amount of an inhibitory (e.g. antisense) nucleic acid, the inhibitory (e.g. antisense) nucleic acid is an anti-eEF-2K siRNA, anti-5-HTR$_{1B}$ siRNA, anti-5-HTR$_{1D}$ siRNA, or anti-5-HTR siRNA.

In some embodiments of the method of treating a disease, the disease is cancer. In some embodiments of the method of treating a disease, the disease is breast cancer. In some embodiments of the method of treating a disease, the disease is ovarian cancer. In some embodiments of the method of treating a disease, the disease is pancreatic cancer. In some embodiments of the method of treating a disease, the disease is melanoma. In some embodiments of the method of treating a disease, the disease is lung cancer. In some embodiments of the method of treating a disease, the disease is glioblastoma. In some embodiments of the method of treating a disease, the disease is glioma. In some embodiments of the method of treating a disease, the disease is bladder cancer. In some embodiments of the method of treating a disease, the disease is liver cancer. In some embodiments of the method of treating a disease, the disease is depression. In some embodiments of the method of treating a disease, the disease is metastatic cancer. In some embodiments of the method of treating a disease, the disease is metastatic breast cancer. In some embodiments of the method of treating a disease, the disease is metastatic ovarian cancer. In some embodiments of the method of treating a disease, the disease is metastatic pancreatic cancer. In some embodiments of the method of treating a disease, the disease is metastatic melanoma. In some embodiments of the method of treating a disease, the disease is metastatic lung cancer. In some embodiments of the method of treating a disease, the disease is metastatic glioblastoma. In some embodiments of the method of treating a disease, the disease is metastatic glioma. In some embodiments of the method of treating a disease, the disease is metastatic bladder cancer. In some embodiments of the method of treating a disease, the disease is metastatic liver cancer. In some embodiments of the method of treating a disease, the cancer has metastasized to a different location in the body from the primary tumor. In some embodiments of a method of treating cancer, the cancer is associated with an increased level of activity of eEF-2K. In some embodiments of a method of treating cancer, the cancer is associated with an increased amount of eEF-2K. In some embodiments of a method of treating cancer, the cancer is associated with an increased level of activity of 5-HTR$_{1B}$. In some embodiments of a method of treating cancer, the cancer is associated with an increased amount of 5-HTR$_{1B}$. In some embodiments of a method of treating cancer, the cancer is associated with an increased level of activity of 5-HTR$_{1D}$. In some embodiments of a method of treating cancer, the cancer is associated with an increased amount of 5-HTR$_{1D}$. In some embodiments of a method of treating cancer, the cancer has failed to be treated by a compound not provided herein. In some embodiments of a method of treating cancer, the cancer has failed to be treated by a compound approved for treating the cancer by a government regulator agency. In some embodiments of the method of treating cancer, the disease is a primary tumor. In some embodiments of the method of treating a disease, the disease is a hyperproliferative disorder. In some embodiments of the method of treating a disease, the disease is estrogen receptor positive breast cancer. In some embodiments of the method of treating a disease, the disease is estrogen receptor (ER) negative breast cancer. In some embodiments of the method of treating a disease, the disease is tamoxifen resistant breast cancer. In some embodiments of the method of treating a disease, the disease is HER2 negative breast cancer. In some embodiments of the method of treating a disease, the disease is HER2 positive breast cancer. In some embodiments of the method of treating a disease, the disease is low grade (well differentiated) breast cancer. In some embodiments of the method of treating a disease, the disease is intermediate grade (moderately differentiated) breast cancer. In some embodiments of the method of treating a disease, the disease is high grade (poorly differentiated) breast cancer. In some embodiments of the method of treating a disease, the disease is stage 0 breast cancer. In some embodiments of the method of treating a disease, the disease is stage I breast cancer. In some embodiments of the method of treating a disease, the disease is stage II breast cancer. In some embodiments of the method of treating a disease, the disease is stage III breast cancer. In some embodiments of the method of treating a disease, the disease is stage IV breast cancer.

In some embodiments of the method of treating a disease, the compound or inhibitory (e.g. antisense) nucleic acid is co-administered with a chemotherapeutic agent. The term "chemotherapeutic agent" is used in accordance with its plain ordinary meaning and refers to a composition or compound that is an antineoplastic drug (e.g. alkylating agents, antimetabolites, anthracyclines, alkaloids, topoisomerase inhibitors, select monoclonal antibodies, kinase inhibitors, tyrosine kinase inhibitors, select cytotoxic antibiotics, taxanes, actinomycin, bleomycin, plicamycin, mitomycin, targeted cancer therapies). In some embodiments of the method of treating a disease, the compound or inhibitory (e.g. antisense) nucleic acid is co-administered with an anthracycline. In some embodiments of the method of treating a disease, the compound or inhibitory (e.g. antisense) nucleic acid is co-administered with doxorubicin (dox). In some embodiments of the method of treating a disease, the compound or inhibitory (e.g. antisense) nucleic acid is co-administered with an alkylating agent (e.g. cisplatin, carboplatin, oxaliplatin, mechlorethamine, cyclophosphamide, chlorambucil, ifosfamide)). In some embodiments of the method of treating a disease, the compound or inhibitory (e.g. antisense) nucleic acid is co-administered with an antimetabolite (e.g. azathioprine, mercaptopurine). In some embodiments of the method of treating a disease, the compound or inhibitory (e.g. antisense) nucleic acid is co-administered with a vinca alkaloid (e.g. vincristine, vinblastine, vinorelbine, or vindesine). In some embodiments of the method of treating a disease, the compound or inhibitory (e.g. antisense) nucleic acid is co-administered with a taxane (e.g. paclitaxel (Taxol) or docetaxel). In some embodiments of the method of treating a disease, the compound or inhibitory (e.g. antisense) nucleic acid is co-administered with a topoisomerase inhibitor (e.g. irinotecan, topotecan, amsacrine, etoposide, etoposide phosphate, or teniposide). In some embodiments of the method of treating a disease, the compound or inhibitory (e.g. antisense) nucleic acid is co-administered with actinomycin. In some embodiments of the method of treating a disease, the compound or inhibitory (e.g. antisense) nucleic acid is co-administered with an anthracycline (e.g. doxorubicin, daunorubicin, valrubicin, idarubicin, or epirubicin). In some embodiments of the method of treating a disease, the compound or inhibitory (e.g. antisense) nucleic acid is co-administered with bleomycin. In some embodiments of the method of treating a disease, the compound or inhibitory (e.g. antisense) nucleic acid is co-administered with plicamycin. In some embodiments of the method of treating a disease, the compound or inhibitory (e.g. antisense) nucleic acid is co-administered with mitomycin. In some embodiments of the method of treating a disease, the compound or inhibitory (e.g. antisense) nucleic acid is co-administered with radiation therapy. In some embodiments of the method of treating a disease, the compound or inhibitory (e.g. antisense) nucleic acid is co-administered with hormonal therapy (e.g. aromatase inhibitors, gonadotropin-releasing hormone analogs, selective estrogen receptor modulators, progestins, or antiandrogens). In some embodiments of the method of treating a disease, the compound or inhibitory (e.g. antisense) nucleic acid is co-administered with an aromatase inhibitor (e.g. letrozole, anastrozole, or exemestane). In some embodiments of the method of treating a disease, the compound or inhibitory (e.g. antisense) nucleic acid is co-administered with tamoxifen. In some embodiments of the method of treating a disease, the compound or inhibitory (e.g. antisense) nucleic acid is co-administered with a gonadotropin-releasing hormone analog (e.g. leuprolide or goserelin). In some embodiments of the method of treating a disease, the compound or inhibitory (e.g. antisense) nucleic acid is co-administered with a selective estrogen receptor modulator (e.g. tamoxifen, raloxifene, toremifene, or fulvestrant). In some embodiments of the method of treating a disease, the compound or inhibitory (e.g. antisense) nucleic acid is co-administered with an antiandrogen (e.g. flutamide or bicalutamide). In some embodiments of the method of treating a disease, the compound or inhibitory (e.g. antisense) nucleic acid is co-administered with a progestin (e.g. megestrol or medroxyprogesterone).

In some embodiments, a chemotherapeutic agent is an agent approved by the FDA or similar regulatory agency of a country other than the USA, for treating cancer. Examples of chemotherapeutic agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; jmaspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DES-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™) erlotinib (Tarceva™) cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY 334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

In some embodiments of a method of treating cancer, the cancer is associated with aberrant levels of eEF-2. In some embodiments of a method of treating cancer, the cancer is associated with aberrant levels of eEF-2 activity. In some embodiments of a method of treating cancer, the cancer is associated with aberrant levels of eEF-2K. In some embodiments of a method of treating cancer, the cancer is associated with aberrant levels of eEF-2K activity. In some embodiments of a method of treating cancer, the cancer is associated with aberrant levels of 5-HTR. In some embodiments of a method of treating cancer, the cancer is associated with aberrant levels of 5-HTR activity. In some embodiments of a method of treating cancer, the cancer is associated with aberrant levels of 5-HTR$_{1B}$. In some embodiments of a method of treating cancer, the cancer is associated with aberrant levels of –HTR$_{1B}$ activity. In some embodiments of a method of treating cancer, the cancer is associated with aberrant levels of –HTR$_{1D}$. In some embodiments of a method of treating cancer, the cancer is associated with aberrant levels of –HTR$_{1D}$ activity.

In some embodiments of the method of treating a disease, the disease is depression. In some embodiments of the method of treating a disease, the disease is migraine headaches. In some embodiments of the method of treating a disease, the disease is pain.

The pharmaceutical compositions include optical isomers, diastereomers, or pharmaceutically acceptable salts of the modulators disclosed herein. The compound included in the pharmaceutical composition may be covalently attached to a carrier moiety, as described above. Alternatively, the compound included in the pharmaceutical composition is not covalently linked to a carrier moiety.

The compounds or inhibitory (e.g. antisense) nucleic acid of the invention can be administered alone or can be coadministered to the patient. Coadministration is meant to include simultaneous or sequential administration of the compounds or inhibitory (e.g. antisense) nucleic acids individually or in combination (more than one compound or inhibitory (e.g. antisense) nucleic acid or combination of both). Thus, the preparations can also be combined, when desired, with other active substances (e.g. to reduce metabolic degradation).

The compounds or inhibitory (e.g. antisense) nucleic acids of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds or inhibitory (e.g. antisense) nucleic acids of the present invention can also be administered by injection, that is, intravenously, intramuscularly, intracutaneously, subcutaneously, intraduodenally, or intraperitoneally. Also, the compounds or inhibitory (e.g. antisense) nucleic acids described herein can be administered by inhalation, for example, intranasally. Additionally, the compounds or inhibitory (e.g. antisense) nucleic acids of the present invention can be administered transdermally. It is also envisioned that multiple routes of administration (e.g., intramuscular, oral, transdermal) can be used to administer the compounds or inhibitory (e.g. antisense) nucleic acids of the invention. Accordingly, the present invention also provides pharmaceutical compositions comprising a pharmaceutically acceptable excipient and one or more compounds or inhibitory (e.g. antisense) nucleic acids of the invention.

For preparing pharmaceutical compositions from the compounds or inhibitory (e.g. antisense) nucleic acids of the present invention, pharmaceutically acceptable carriers can be either solid or liquid. Solid form preparations include powders, tablets, pills, capsules, cachets, suppositories, and dispersible granules. A solid carrier can be one or more substance, that may also act as diluents, flavoring agents, binders, preservatives, tablet disintegrating agents, or an encapsulating material.

In powders, the carrier is a finely divided solid in a mixture with the finely divided active component (e.g. a compound or inhibitory (e.g. antisense) nucleic acid provided herein). In tablets, the active component is mixed with the carrier having the necessary binding properties in suitable proportions and compacted in the shape and size desired. The powders and tablets preferably contain from 5% to 70% of the active compound or inhibitory (e.g. antisense) nucleic acid.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds or inhibitory (e.g. antisense) nucleic acids of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds or inhibitory (e.g. antisense) nucleic acids of the invention can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds or inhibitory (e.g. antisense) nucleic acids may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Pharmaceutical compositions provided by the present invention include compositions wherein the active ingredient is contained in a therapeutically effective amount, i.e., in an amount effective to achieve its intended purpose. The actual amount effective for a particular application will depend, inter aria, on the condition being treated. When administered in methods to treat a disease, such compositions will contain an amount of active ingredient effective to achieve the desired result, e.g., modulating the activity of a target molecule (e.g.

a kinase or kinase(s); eEF-2K, eEF-2,5-HTR$_{1B}$, 5-HTR$_{1D}$, 5-HTR), and/or reducing, eliminating, or slowing the progression of disease symptoms (e.g. cancer growth or metastasis, depression). Determination of a therapeutically effective amount of a compound or inhibitory (e.g. antisense) nucleic acid of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. cancer, depression), kind of concurrent treatment, complications from the disease being treated or other health-related problems. Other therapeutic regimens or agents can be used in conjunction with the methods and compounds or inhibitory (e.g. antisense) nucleic acids of Applicants' invention. Adjustment and manipulation of established dosages (e.g., frequency and duration) are well within the ability of those skilled in the art.

For any compound or inhibitory (e.g. antisense) nucleic acid described herein, the therapeutically effective amount can be initially determined from cell culture assays. Target concentrations will be those concentrations of active compound(s) or inhibitory (e.g. antisense) nucleic acid(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds or inhibitory (e.g. antisense) nucleic acids effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound or inhibitory (e.g. antisense) nucleic acid being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. In one embodiment, the dosage range is 0.001% to 10% w/v. In another embodiment, the dosage range is 0.1% to 5% w/v.

Dosage amounts and intervals can be adjusted individually to provide levels of the administered compound or inhibitory (e.g. antisense) nucleic acid effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound or inhibitory (e.g. antisense) nucleic acid by considering factors such as compound or inhibitory (e.g. antisense) nucleic acid potency, relative bioavailability, patient body weight, presence and severity of adverse side effects, preferred mode of administration and the toxicity profile of the selected agent.

The ratio between toxicity and therapeutic effect for a particular compound or inhibitory (e.g. antisense) nucleic acid is its therapeutic index and can be expressed as the ratio between $LD_{50}$ (the amount of compound lethal in 50% of the population) and $ED_{50}$ (the amount of compound or inhibitory (e.g. antisense) nucleic acid effective in 50% of the population). Compounds or inhibitory (e.g. antisense) nucleic acids that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound or inhibitory (e.g. antisense) nucleic acid is used.

Administration

The compositions of the present invention can be delivered by transdermally, by a topical route, formulated as applicator sticks, solutions, suspensions, emulsions, gels, creams, ointments, pastes, jellies, paints, powders, and aerosols. For therapeutic applications, the compounds or inhibitory (e.g. antisense) nucleic acids or drugs of the present invention can be administered alone or co-administered in combination with conventional chemotherapy, radiotherapy, hormonal therapy, and/or immunotherapy.

The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The pharmaceutical compositions of the present invention can be provided as a salt and can be formed with many acids, including but not limited to hydrochloric, sulfuric, acetic, lactic, tartaric, malic, succinic, etc. Pharmaceutical compositions described herein may be salts of a compound or inhibitory (e.g. antisense) nucleic acids or composition which are prepared with relatively nontoxic acids or bases, depending on the particular substituents found on the compounds or inhibitory (e.g. antisense) nucleic acids described herein. When compounds or inhibitory (e.g. antisense) nucleic acids of the present invention contain relatively acidic functionalities, base addition salts can be obtained by contacting the neutral form of such compounds or inhibitory (e.g. antisense) nucleic acids with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds or inhibitory (e.g. antisense) nucleic acids of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

The neutral forms of the compounds or inhibitory (e.g. antisense) nucleic acids may be regenerated by contacting the salt with a base or acid and isolating the parent compound or inhibitory (e.g. antisense) nucleic acids in the conventional manner. The parent form of the compound or inhibitory (e.g. antisense) nucleic acids differs from the various salt forms in certain physical properties, such as solubility in polar solvents, but otherwise the salts are equivalent to the parent form of the compound for the purposes of the present invention.

Certain compositions (compounds or inhibitory (e.g. antisense) nucleic acids described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments)) can exist in unsolvated forms as well as solvated forms, including hydrated forms. In general, the solvated forms are equivalent to unsolvated forms and are intended to be encompassed within the scope of the present invention. Certain compounds or inhibitory (e.g. antisense) nucleic acids described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments) may exist in multiple crystalline or amorphous forms. In general, all physical forms are equivalent for the uses contemplated by the present invention and are intended to be within the scope of the present invention.

In another embodiment, the compositions of the present invention are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The compounds or inhibitory (e.g. antisense) nucleic acids described herein can be used in combination with one another, with other active agents known to be useful in treating a disease (e.g. cancer) associated with cells expressing a particular kinase (e.g. eEF-2K) or receptor (e.g. 5-HTR$_{1B}$, 5-HTR$_{1D}$, 5-HTR), or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

As a non-limiting example, the compounds or inhibitory (e.g. antisense) nucleic acids described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments, or any compounds described in the Examples section) can be co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin, etc.), other kinase inhibitors, other 5-HTR modulators, and the like.

The compounds or inhibitory (e.g. antisense) nucleic acids described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments, or any compounds described in the Examples section) can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

Additionally, the compounds or inhibitory (e.g. antisense) nucleic acids described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments, or any compounds described in the Examples section) can be co-administered with conventional immunotherapeutic agents including, but not limited to, immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

In a further embodiment, the compounds or inhibitory (e.g. antisense) nucleic acids described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments, or any compounds described in the Examples section) can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

The pharmaceutical compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate.

Formulations suitable for oral administration can comprise: (a) liquid solutions, such as an effective amount of a packaged compound or inhibitory (e.g. antisense) nucleic acid described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments, or any compounds described in the Examples section) or drug suspended in diluents, e.g., water, saline, or PEG 400; (b) capsules, sachets, or tablets, each containing a predetermined amount of a compound or inhibitory (e.g. antisense) nucleic acid described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments, or any compounds described in the Examples section), as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a compound or inhibitory (e.g. antisense) nucleic acid described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments, or any compounds described in the Examples section) or drug in a flavor, e.g., sucrose, as well as pastilles comprising the compounds or inhibitory (e.g. antisense) nucleic acids described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments, or any compounds described in the Examples section) in an inert base, such as gelatin and glycerin or sucrose and acacia emulsions, gels, and the like, containing, in addition to the compounds or inhibitory (e.g. antisense) nucleic acids described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (Ig), (IIIg), (Ih), (IIIh), including embodiments, or any compounds described in the Examples section), carriers known in the art.

The compounds or inhibitory (e.g. antisense) nucleic acids described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (Ig), (IIIg), (Ih), (IIIh), including embodiments, or any compounds described in the Examples section) of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which comprises an effective amount of a packaged compound or inhibitory (e.g. antisense) nucleic acid described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (Ig), (IIIg), (Ih), (IIIh), including embodiments, or any compounds described in the Examples section) or drug with a suppository base. Suitable suppository bases include natural or synthetic triglycerides or paraffin hydrocarbons. In addition, it is also possible to use gelatin rectal capsules which contain a combination of the compounds or inhibitory (e.g. antisense) nucleic acids described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (Ig), (IIIg), (Ih), (IIIh), including embodiments, or any compounds described in the Examples section) or drug of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, orally, topically, intraperitoneally, intravesically, or intrathecally. Parenteral administration, oral administration, and intravenous administration are the preferred methods of administration. The formulations of compounds or inhibitory (e.g. antisense) nucleic acids can be presented in unit-dose or multi-dose sealed containers, such as ampoules and vials.

The pharmaceutical preparation is preferably in unit dosage form. In such form the preparation is subdivided into unit doses containing appropriate quantities of the active component, e.g., a compound or inhibitory (e.g. antisense) nucleic acid described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (Ig), (IIIg), (Ih), (IIIh), including embodiments, or any compounds described in the Examples section). The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

In therapeutic use for the treatment of cancer or depression, compounds or inhibitory (e.g. antisense) nucleic acids described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments, or any compounds described in the Examples section) utilized in the pharmaceutical compositions of the present invention are administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound or inhibitory (e.g. antisense) nucleic acid described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (Ig), (IIIg), (Ih), (IIIh), including embodiments, or any compounds described in the Examples section) or drug being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a kinase or receptor modulator compound or inhibitory (e.g. antisense) nucleic acid in a particular patient. Determination of the proper dosage for a particular situation is within the skill of the practitioner. Generally, treatment is initiated with smaller dosages which are less than the optimum dose of the compound or inhibitory (e.g. antisense) nucleic acid described herein (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih), (IIIh), including embodiments, or any compounds described in the Examples section). Thereafter, the dosage is increased by small increments until the optimum effect under circumstances is reached. For convenience, the total daily dosage may be divided and administered in portions during the day, if desired.

The compounds or inhibitory (e.g. antisense) nucleic acids described herein can be used in combination with one another, with other active agents known to be useful in treating cancer or depression or a disease capable of being treated with a compound or inhibitory (e.g. antisense) nucleic acid as described herein, with adjunctive agents that may not be effective alone, but may contribute to the efficacy of the active agent (e.g. compounds or inhibitory (e.g. antisense) nucleic acids as described herein).

In some embodiments of the compounds (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih) or (IIIh)), pharmaceutical compositions, and/or methods described herein, the compound is selected from any of the compounds described in the Examples section herein. In some embodiments of the compounds (e.g. Formula (I), (II), (III), (IV), (V), (Ia), (IIa), (IIIa), (IVa), (Va), (Ib), (IIb), (IIIb), (IVb), (Vb), (Ic), (IIc), (IIIc), (IVc), (Vc), (Id), (IId), (IIId), (IVd), (Vd), (Ie), (IIIe), (If), (IIIf), (Ig), (IIIg), (Ih) or (IIIh)), pharmaceutical compositions, and/or methods described herein, the compound is selected from the group consisting of:

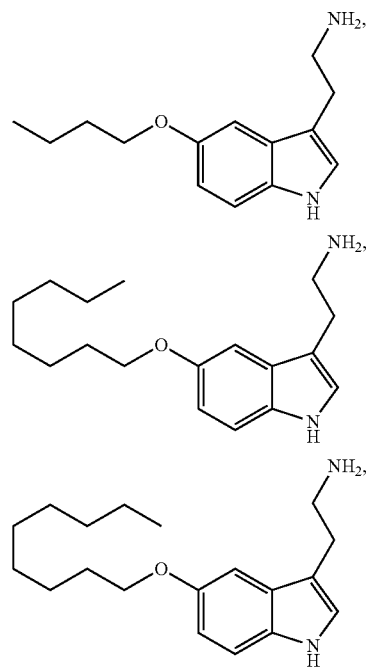

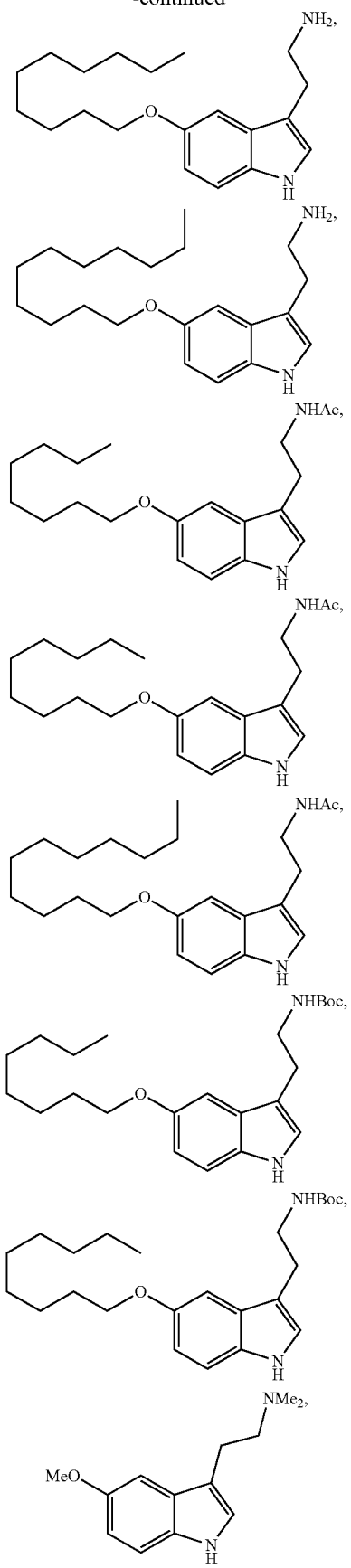
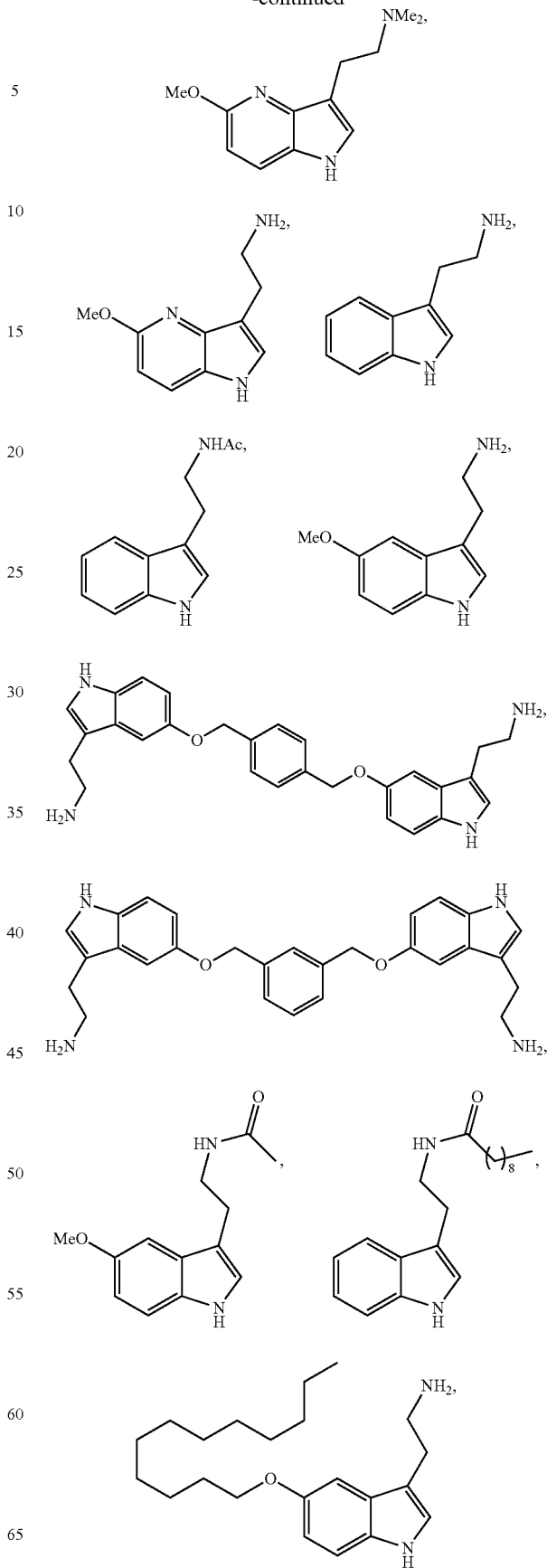

99
-continued
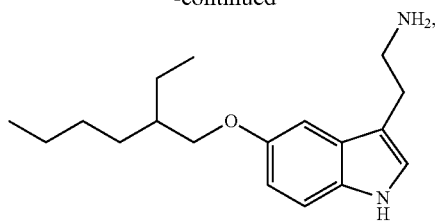
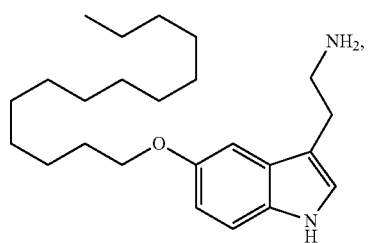
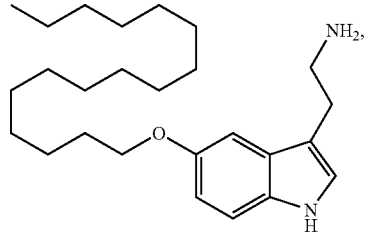
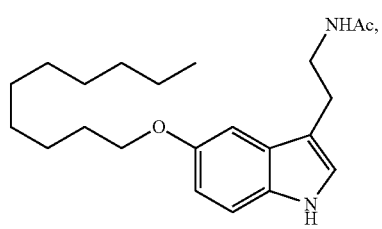
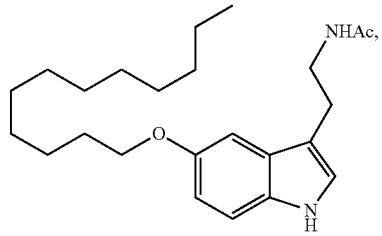
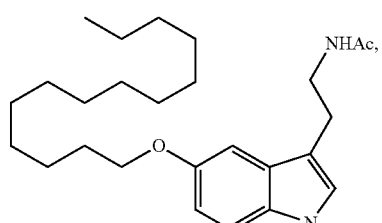
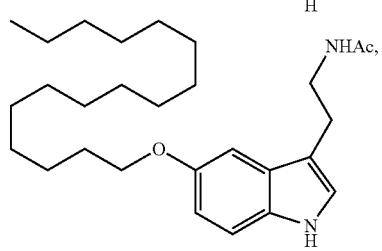
100
-continued
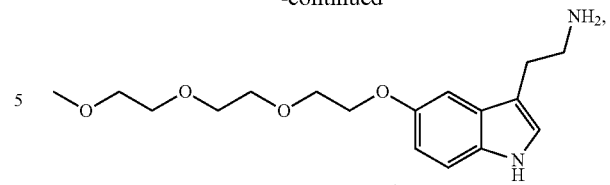
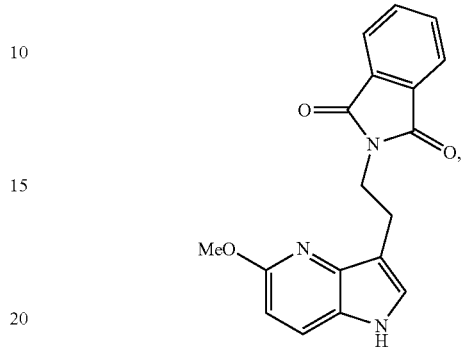
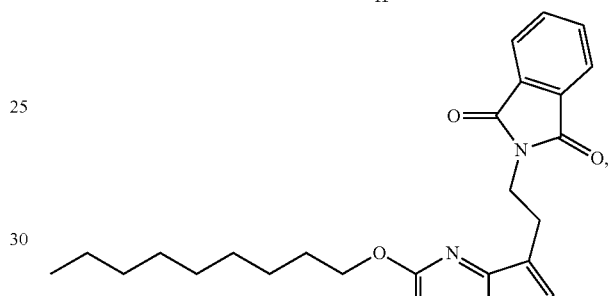
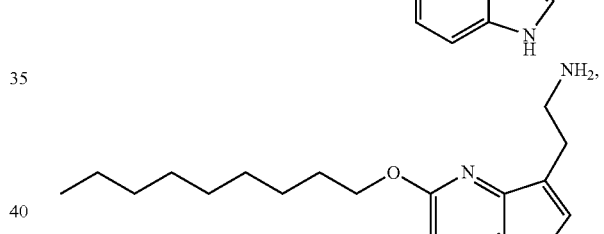
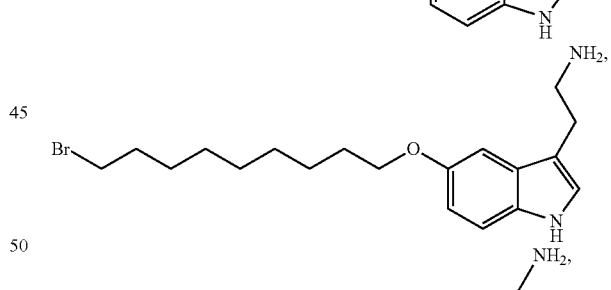
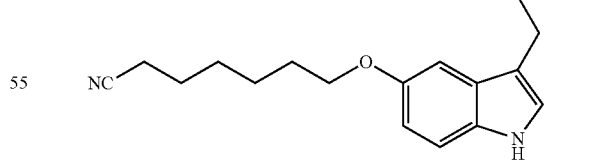
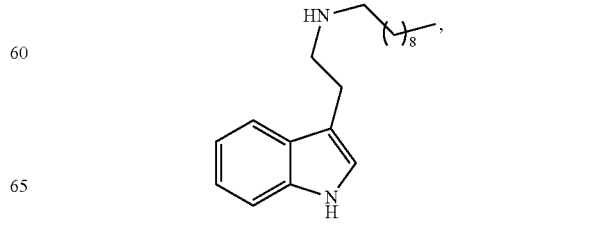

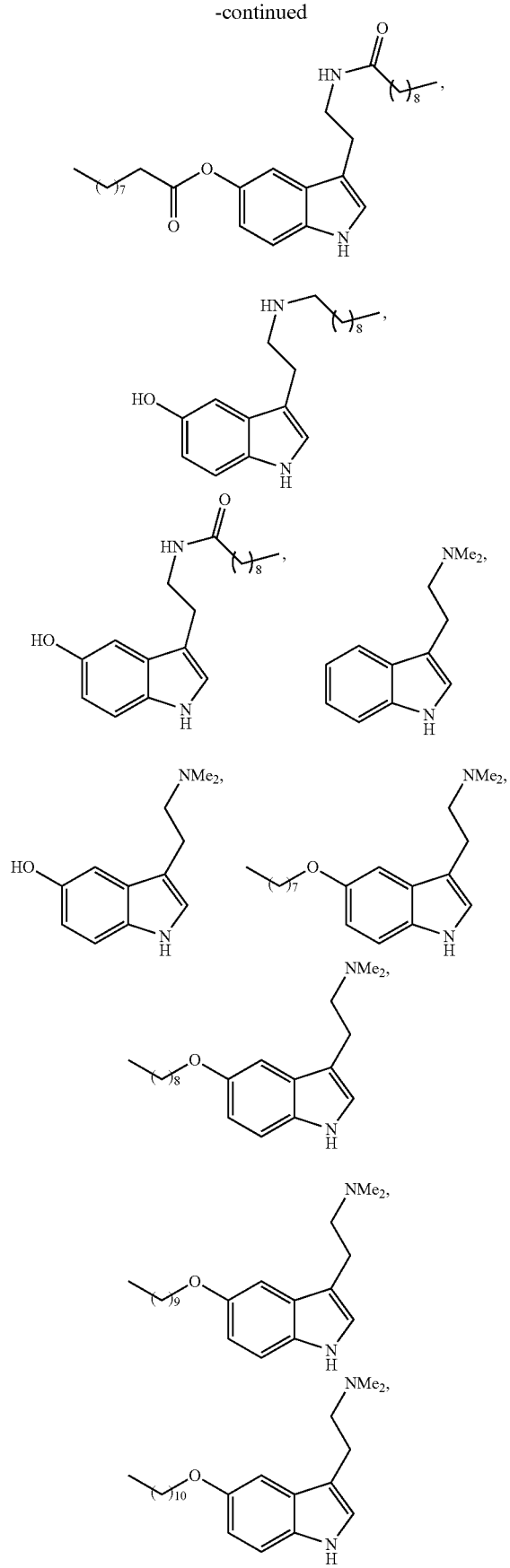
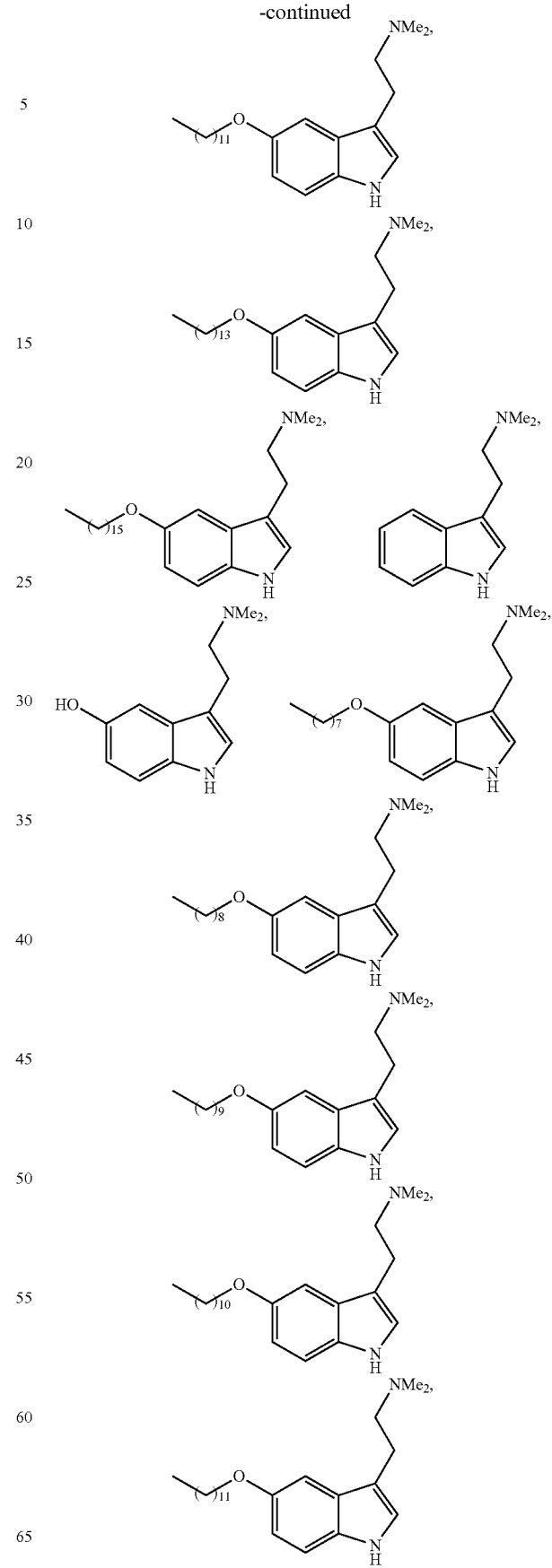

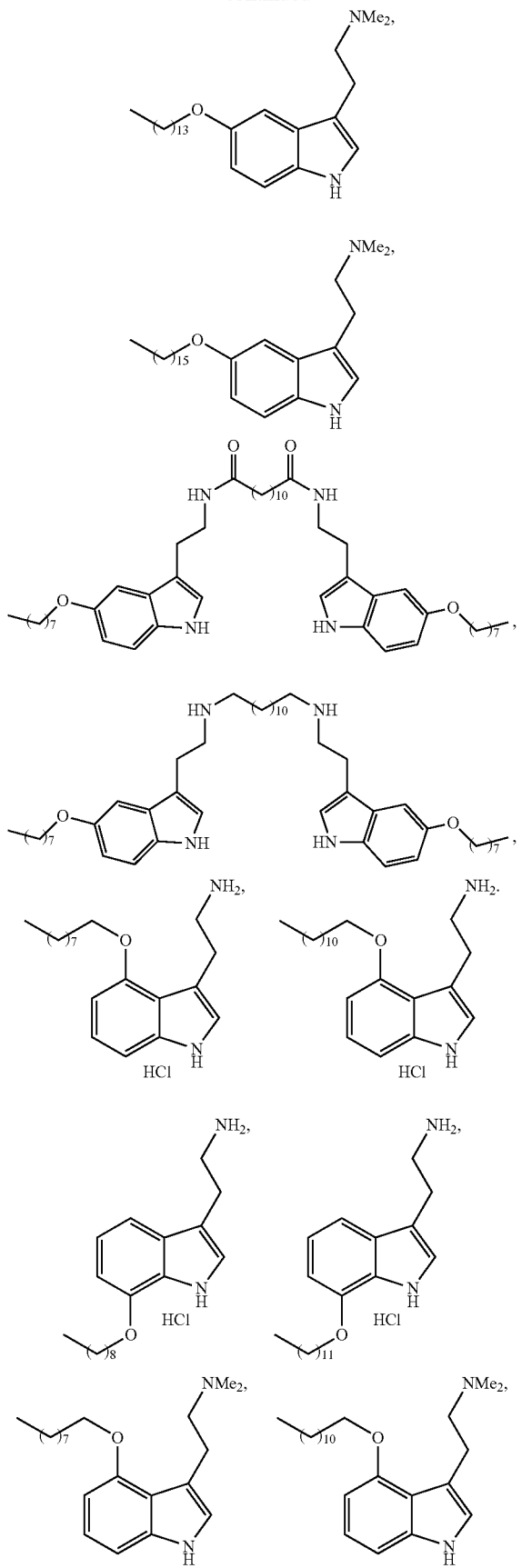
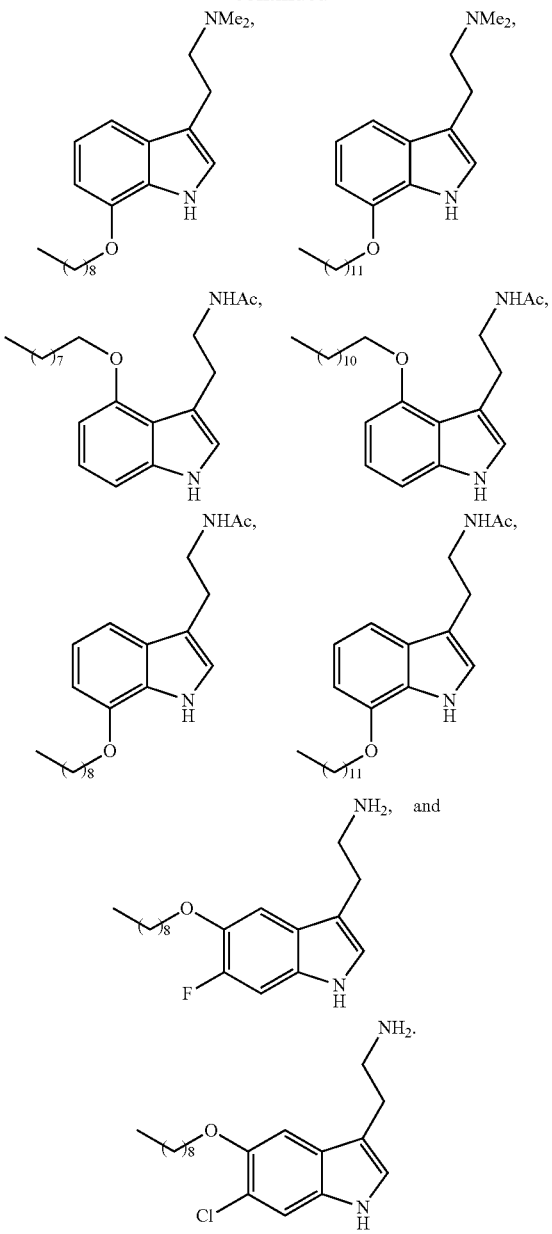
Additional Embodiments
1. A compound having the formula:
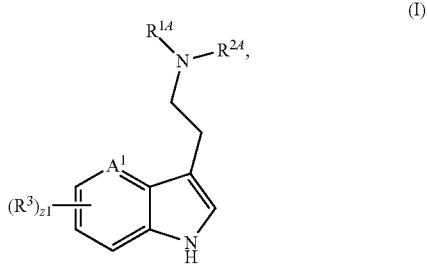

-continued

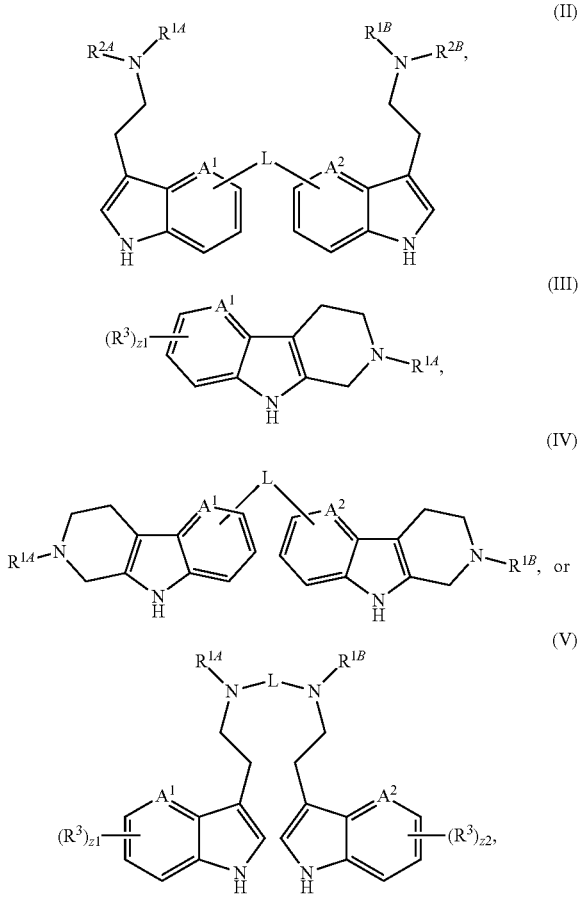

wherein $R^{1A}$ is independently hydrogen, halogen, —$CX^{1A}_3$, —$C(O)R^{7A}$, —$C(O)$—$OR^{7A}$, —$C(O)NR^{7A}R^{8A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1B}$ is independently hydrogen, halogen, —$CX^{1B}_3$, —$C(O)R^{7B}$, —$C(O)$—$OR^{7B}$, —$C(O)NR^{7B}R^{8B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2A}$ is independently hydrogen, halogen, —$CX^{2A}_3$, —$C(O)R^{9A}$, —$C(O)$—$OR^{9A}$, —$C(O)NR^{9A}R^{10A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{2B}$ is independently hydrogen, halogen, —$CX^{2B}_3$, —$C(O)R^{9B}$, —$C(O)$—$OR^{9B}$, —$C(O)NR^{9B}R^{10B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein $R^{1A}$ and $R^{2A}$ are optionally joined to form a substituted or unsubstituted heterocycloalkyl or substituted or unsubstituted heteroaryl; wherein $R^{1B}$ and $R^{2B}$ are optionally joined to form a substituted or unsubstituted heterocycloalkyl or substituted or unsubstituted heteroaryl; $R^3$ is independently hydrogen, halogen, —$CX^3_3$, —CN, —$SO_2Cl$, —$SO_nR^{14}$, —$SO_kNR^{11}R^{12}$, —$NHNH_2$, —$ONR^{11}R^{12}$, —$NHC=(O)NHNH_2$, —$NHC=(O)NR^{11}R^{12}$, —$N(O)_m$, —$NR^{11}R^{12}$, —$C(O)R^{13}$, —$C(O)$—$OR^{13}$, —O—$C(O)$—$R^{13}$, —$C(O)NR^{11}R^{12}$, —$NR^{11}C(O)R^{13}$, —$OR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{7A}$, $R^{7B}$, $R^{8A}$, $R^{8B}$, $R^{9A}$, $R^{9B}$, $R^{10A}$, $R^{10B}$, $R^{11}$, $R^{12}$, $R^{13}$, and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $A^1$ and $A^2$ are independently =N— or =$CR^3$—; L is independently a bond, —O—, —NH—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene,

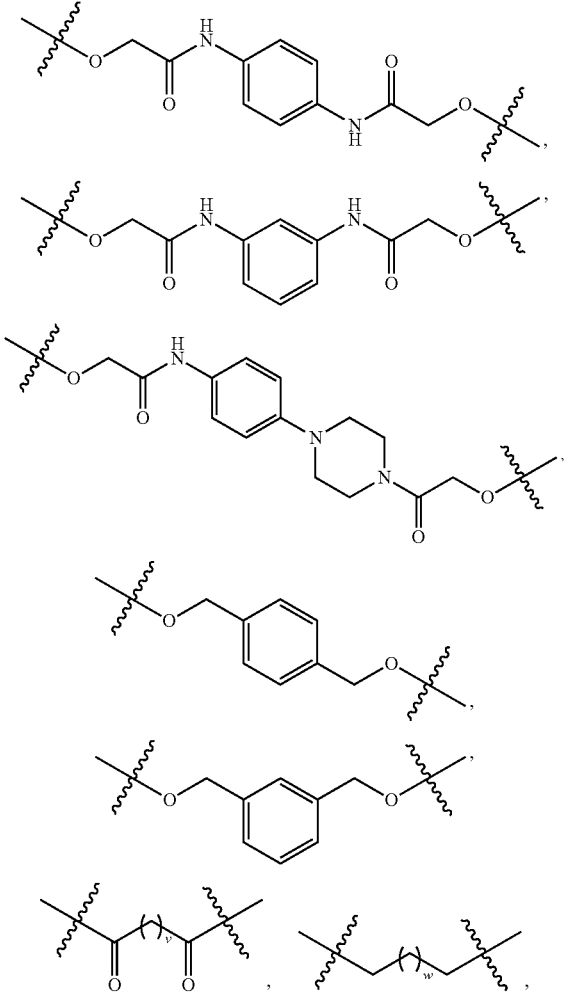

or —O—$(CH_2)_p$—O—; k and m are independently 1 or 2; n is independently an integer from 0 to 4; p, v, and w are independently an integer from 1 to 20; z1 and z2 are independently an integer from 0 to 3; $X^{1A}$, $X^{1B}$, $X^{2A}$, $X^{2B}$, and $X^3$ are independently —Cl, —Br, —I, or —F.

2. A compound of embodiment 1 having the formula:
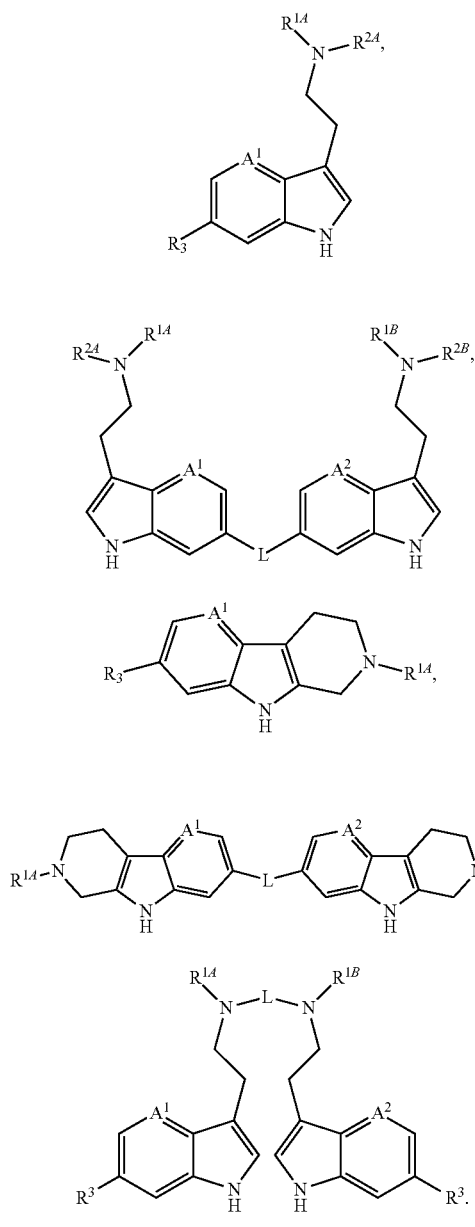
3. A compound of embodiment 1 having the formula:
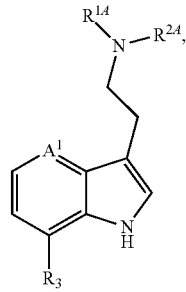
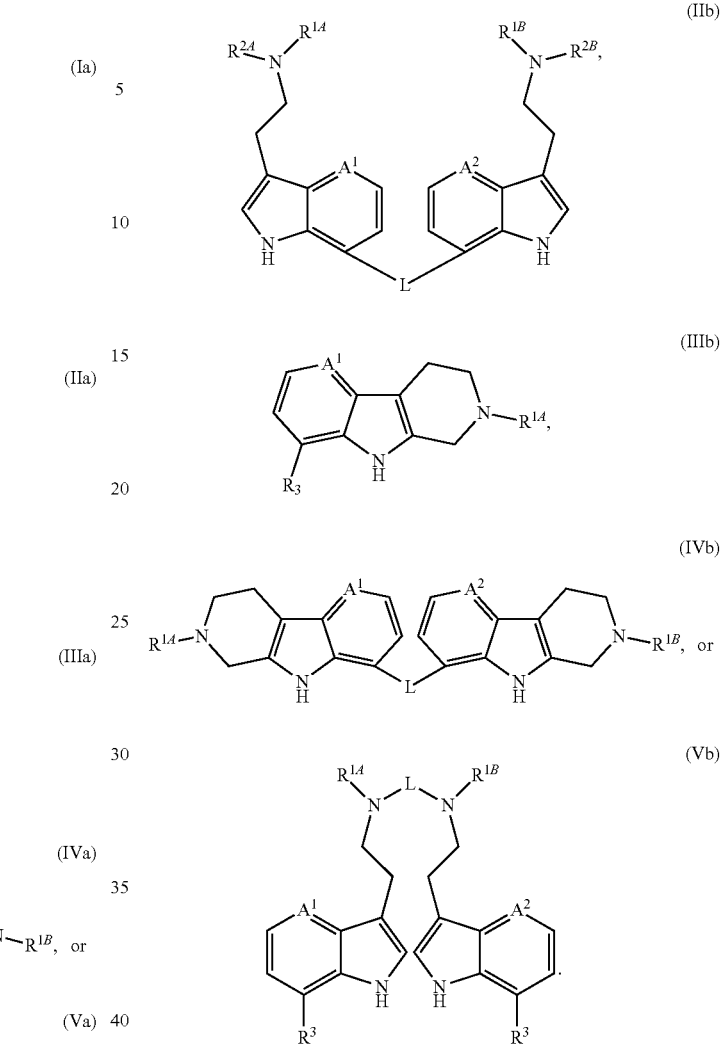
4. A compound of embodiment 1 having the formula:
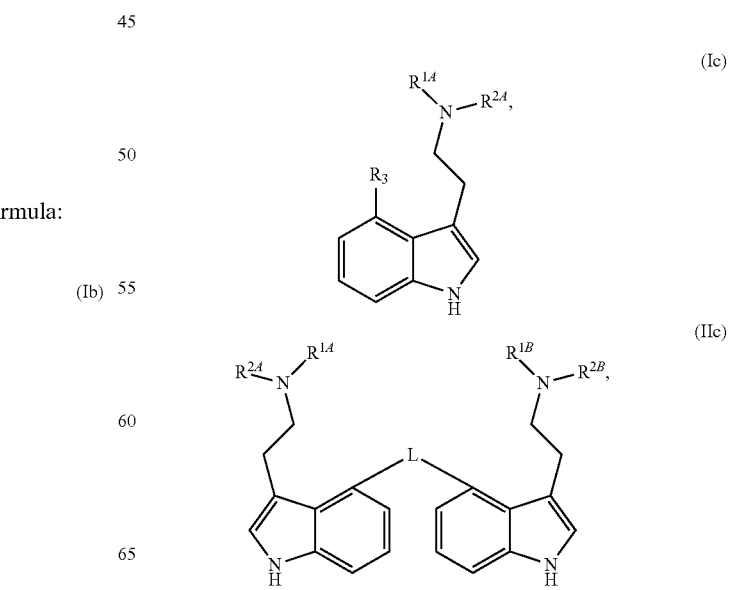

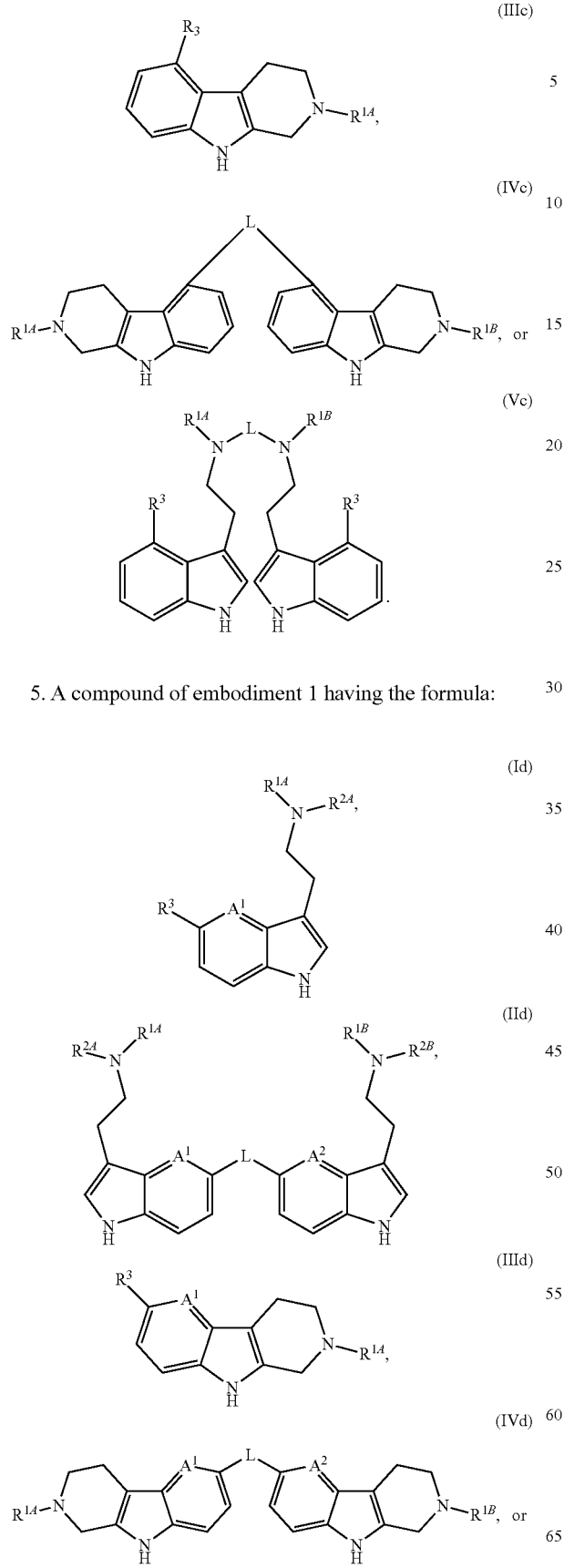
5. A compound of embodiment 1 having the formula:
6. A compound of embodiment 1 having the formula:

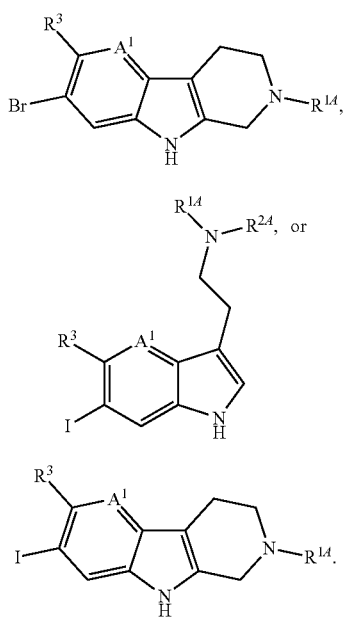

7. The compound of any one of embodiments 1 to 6, wherein $R^{1A}$ is independently —C(O)$R^{7A}$ or —C(O)—O$R^{7A}$; $R^{1B}$ is independently —C(O)$R^{7B}$ or —C(O)—O$R^{7B}$; $R^{7A}$ is independently hydrogen, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl; and $R^{7B}$ is independently hydrogen, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

8. The compound of any one of embodiments 1 to 7, wherein $R^{7A}$ is independently hydrogen, substituted or unsubstituted $C_1$-$C_{10}$ alkyl or substituted or unsubstituted 2 to 10 membered heteroalkyl.

9. The compound of any one of embodiments 1 to 8, wherein $R^{7B}$ is independently hydrogen, substituted or unsubstituted $C_1$-$C_{10}$ alkyl or substituted or unsubstituted 2 to 10 membered heteroalkyl.

10. The compound of any one of embodiments 1 to 9, wherein $R^{7A}$ is independently hydrogen or substituted or unsubstituted $C_1$-$C_{10}$ alkyl.

11. The compound of any one of embodiments 1 to 10, wherein $R^{7B}$ is independently hydrogen or substituted or unsubstituted $C_1$-$C_{10}$ alkyl.

12. The compound of any one of embodiments 1 to 11, wherein $R^{7A}$ is independently methyl.

13. The compound of any one of embodiments 1 to 12, wherein $R^{7B}$ is independently methyl.

14. The compound of any one of embodiments 1 to 11, wherein $R^{7A}$ is independently hydrogen.

15. The compound of any one of embodiments 1 to 12, wherein $R^{7B}$ is independently hydrogen.

16. The compound of any one of embodiments 1 to 15, wherein $R^{1A}$ is —C(O)$R^{7A}$.

17. The compound of any one of embodiments 1 to 15, wherein $R^{1B}$ is —C(O)$R^{7B}$.

18. The compound of any one of embodiments 1 to 15, wherein $R^{1A}$ is —C(O)—O$R^{7A}$.

19. The compound of any one of embodiments 1 to 15, wherein $R^{1B}$ is —C(O)—O$R^{7B}$.

20. The compound of any one of embodiments 1 to 15, wherein $R^{1A}$ is unsubstituted alkyl.

21. The compound of any one of embodiments 1 to 15, wherein $R^{1B}$ is unsubstituted alkyl.

22. The compound of any one of embodiments 1 to 21, wherein $R^{2A}$ is independently —C(O)$R^{9A}$ or —C(O)—O$R^{9A}$; $R^{2B}$ is independently —C(O)$R^{9B}$ or —C(O)—O$R^{9B}$; $R^{9A}$ is independently hydrogen, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl; and $R^{9B}$ is independently hydrogen, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl.

23. The compound of any one of embodiments 1 to 22, wherein $R^{9A}$ is independently hydrogen, substituted or unsubstituted $C_1$-$C_{10}$ alkyl or substituted or unsubstituted 2 to 10 membered heteroalkyl.

24. The compound of any one of embodiments 1 to 23, wherein $R^{9B}$ is independently hydrogen, substituted or unsubstituted $C_1$-$C_{10}$ alkyl or substituted or unsubstituted 2 to 10 membered heteroalkyl.

25. The compound of any one of embodiments 1 to 24, wherein $R^{9A}$ is independently hydrogen or substituted or unsubstituted $C_1$-$C_{10}$ alkyl.

26. The compound of any one of embodiments 1 to 25, wherein $R^{9B}$ is independently hydrogen or substituted or unsubstituted $C_1$-$C_{10}$ alkyl.

27. The compound of any one of embodiments 1 to 26, wherein $R^{9A}$ is methyl.

28. The compound of any one of embodiments 1 to 26, wherein $R^{9B}$ is methyl.

29. The compound of any one of embodiments 1 to 26, wherein $R^{9A}$ is hydrogen.

30. The compound of any one of embodiments 1 to 26, wherein $R^{9B}$ is hydrogen.

31. The compound of any one of embodiments 1 to 30, wherein $R^{2A}$ is —C(O)$R^{9A}$.

32. The compound of any one of embodiments 1 to 30, wherein $R^{2B}$ is —C(O)$R^{9B}$.

33. The compound of any one of embodiments 1 to 30, wherein $R^{2A}$ is —C(O)—O$R^{9A}$.

34. The compound of any one of embodiments 1 to 30, wherein $R^{2B}$ is —C(O)—O$R^{9B}$.

35. The compound of any one of embodiments 1 to 30, wherein $R^{2A}$ is unsubstituted alkyl.

36. The compound of any one of embodiments 1 to 30, wherein $R^{2B}$ is unsubstituted alkyl.

37. The compound of any one of embodiments 1 to 36, wherein $R^{1A}$ and $R^{2A}$ are joined to form a substituted or unsubstituted heterocycloalkyl or substituted or unsubstituted heteroaryl.

38. The compound of any one of embodiments 1 to 37, wherein $R^{1B}$ and $R^{2B}$ are joined to form a substituted or unsubstituted heterocycloalkyl or substituted or unsubstituted heteroaryl.

39. The compound of any one of embodiments 1 to 38, wherein $R^{1A}$ and $R^{2A}$ are joined to form a substituted or unsubstituted heterocycloalkyl.

40. The compound of any one of embodiments 1 to 39, wherein $R^{1B}$ and $R^{2B}$ are joined to form a substituted or unsubstituted heterocycloalkyl.

41. The compound of any one of embodiments 1 to 40, wherein $R^{1A}$ and $R^{2A}$ are joined to form a heterocycloalkyl fused to an aryl.

42. The compound of any one of embodiments 1 to 41, wherein $R^{1B}$ and $R^{2B}$ are joined to form a heterocycloalkyl fused to an aryl.

43. The compound of any one of embodiments 1 to 42, wherein $R^{1A}$ and $R^{2A}$ are joined to form a substituted or unsubstituted isoindolin-2-yl-1,3-dione.

44. The compound of any one of embodiments 1 to 43, wherein $R^{1B}$ and $R^{2B}$ are joined to form a substituted or unsubstituted isoindolin-2-yl-1,3-dione.

45. The compound of any one of embodiments 1 to 44, wherein $R^3$ is independently hydrogen, halogen, —C(O)$R^{13}$, —O—C(O)—$R^{13}$, —C(O)—O$R^{13}$, —O$R^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

46. The compound of any one of embodiments 1 to 44, wherein $R^3$ is independently hydrogen, —C(O)$R^{13}$, —O—C(O)—$R^{13}$, —C(O)—O$R^{13}$, or —O$R^{14}$; and $R^{13}$ and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

47. The compound of any one of embodiments 1 to 46, wherein $R^{13}$ and $R^{14}$ are independently hydrogen, substituted or unsubstituted alkyl, or substituted or unsubstituted heteroalkyl.

48. The compound of any one of embodiments 1 to 46, wherein $R^{13}$ and $R^{14}$ are independently hydrogen.

49. The compound of any one of embodiments 1 to 46, wherein $R^{13}$ and $R^{14}$ are independently substituted or unsubstituted alkyl.

50. The compound of any one of embodiments 1 to 46, wherein $R^{13}$ and $R^{14}$ are independently substituted or unsubstituted $C_1$-$C_{20}$ alkyl.

51. The compound of any one of embodiments 1 to 46, wherein $R^{13}$ and $R^{14}$ are independently substituted or unsubstituted $C_6$-$C_{16}$ alkyl.

52. The compound of any one of embodiments 1 to 46, wherein $R^{13}$ and $R^{14}$ are independently unsubstituted $C_6$-$C_{16}$ alkyl.

53. The compound of any one of embodiments 1 to 46, wherein $R^{13}$ and $R^{14}$ are independently substituted $C_6$-$C_{16}$ alkyl.

54. The compound of any one of embodiments 1 to 46, wherein $R^{13}$ and $R^{14}$ are independently unsubstituted $C_{12}$-$C_{16}$ alkyl.

55. The compound of any one of embodiments 1 to 46, wherein $R^{13}$ and $R^{14}$ are independently substituted $C_{12}$-$C_{16}$ alkyl.

56. The compound of any one of embodiments 1 to 46, wherein $R^{13}$ and $R^{14}$ are independently substituted or unsubstituted heteroalkyl.

57. The compound of any one of embodiments 1 to 46, wherein $R^{13}$ and $R^{14}$ are independently substituted or unsubstituted 2 to 20 membered heteroalkyl.

58. The compound of any one of embodiments 1 to 46, wherein $R^{13}$ and $R^{14}$ are independently substituted or unsubstituted 6 to 16 membered heteroalkyl.

59. The compound of any one of embodiments 1 to 46, wherein $R^{13}$ and $R^{14}$ are independently substituted 6 to 16 membered heteroalkyl.

60. The compound of any one of embodiments 1 to 46, wherein $R^{13}$ and $R^{14}$ are independently unsubstituted 6 to 16 membered heteroalkyl.

61. The compound of any one of embodiments 1 to 46, wherein $R^{14}$ is:

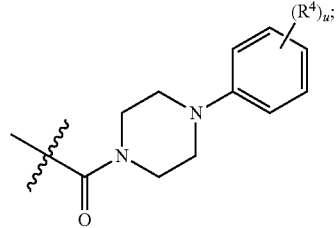

$R^4$ is independently hydrogen, halogen, —C$X^4_3$, —CN, —SO$_2$Cl, —SO$_q$$R^{18}$, —SO$_r$N$R^{15}$$R^{16}$, —NHNH$_2$, —ON$R^{15}$$R^{16}$, —NHC=(O)NHNH$_2$, —NHC=(O)N$R^{15}$$R^{16}$, —N(O)$_r$, —N$R^{15}$$R^{16}$, —C(O)$R^{17}$, —C(O)—O$R^{17}$, —C(O)N$R^{15}$$R^{16}$, —O$R^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15}$, $R^{16}$, $R^{17}$, and $R^{18}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; r and t are independently 1 or 2; q is independently an integer from 0 to 4; u is independently an integer from 0 to 5; and $X^4$ is independently —Cl, —Br, —I, or —F.

62. The compound of any one of embodiments 1 to 45, wherein $R^3$ is independently halogen.

63. The compound of any one of embodiments 1 to 46, wherein $R^3$ is independently hydrogen.

64. The compound of any one of embodiments 1 to 63, wherein $R^3$ is independently —C(O)$R^{13}$.

65. The compound of any one of embodiments 1 to 63, wherein $R^3$ is independently —O—C(O)—$R^{13}$.

66. The compound of any one of embodiments 1 to 63, wherein $R^3$ is independently —C(O)—O$R^{13}$.

67. The compound of any one of embodiments 1 to 63, wherein $R^3$ is independently —O$R^{14}$.

68. The compound of any one of embodiments 1 to 46, wherein $R^3$ is independently —C(O)$R^{13}$ or —O—C(O)—$R^{13}$; $R^{13}$ is

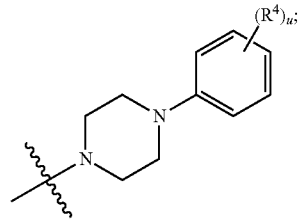

$R^4$ is independently hydrogen, halogen, —C$X^4_3$, —CN, —SO$_2$Cl, —SO$_q$$R^{18}$, —SO$_r$N$R^{15}$$R^{16}$, —NHNH$_2$, —ONR$^{15}$R$^{16}$, —NHC═(O)NHNH$_2$, —NHC═(O)NR$^{15}$R$^{16}$, —N(O)$_p$, —NR$^{15}$R$^{16}$, —C(O)R$^{17}$, —C(O)—OR$^{17}$, —C(O)NR$^{15}$R$^{16}$, —OR$^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{15}$, R$^{16}$, R$^{17}$, and R$^{18}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; r and t are independently 1 or 2; q is independently an integer from 0 to 4; u is independently an integer from 0 to 5; and X$^4$ is independently —Cl, —Br, —I, or —F.

69. The compound of any one of embodiments 1 to 68, wherein A$^1$ is ═CR$^3$—.

70. The compound of any one of embodiments 1 to 69, wherein A$^2$ is ═CR$^3$—.

71. The compound of any one of embodiments 1 to 68, wherein A$^1$ is ═N—.

72. The compound of any one of embodiments 1 to 69, wherein A$^2$ is ═N—.

73. The compound of any one of embodiments 1 to 72, wherein the compound is

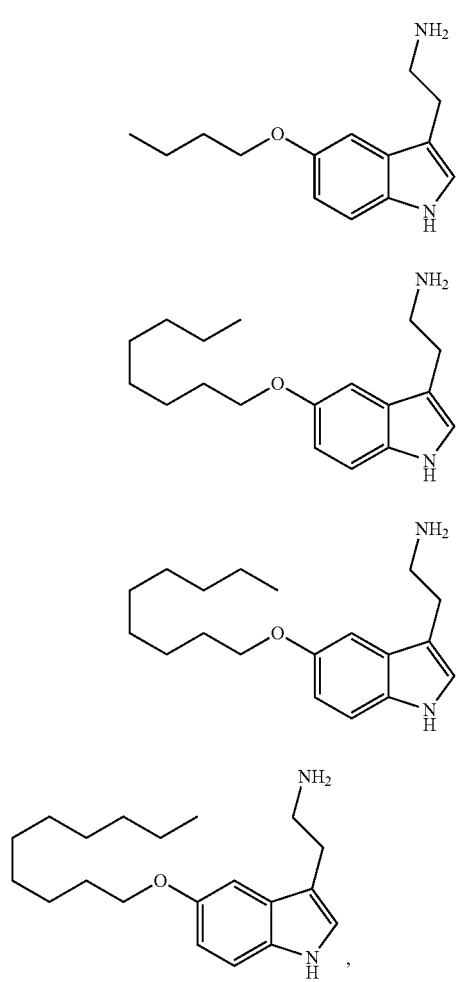

-continued

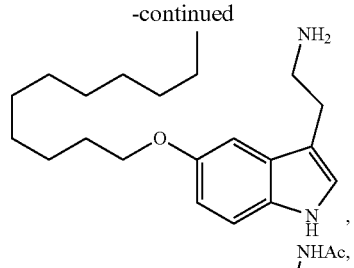

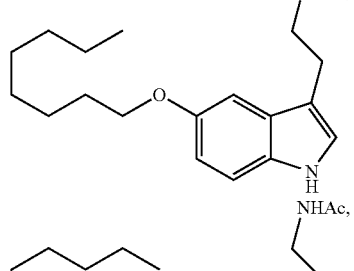

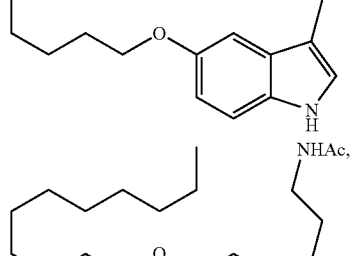

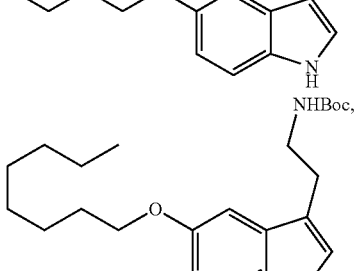

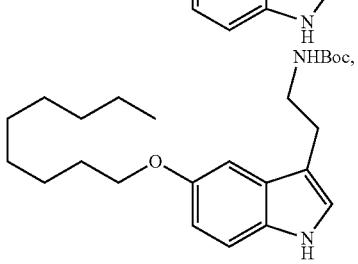

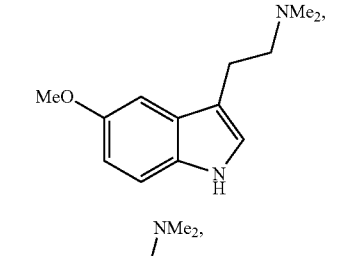

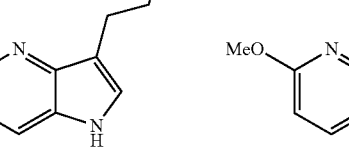

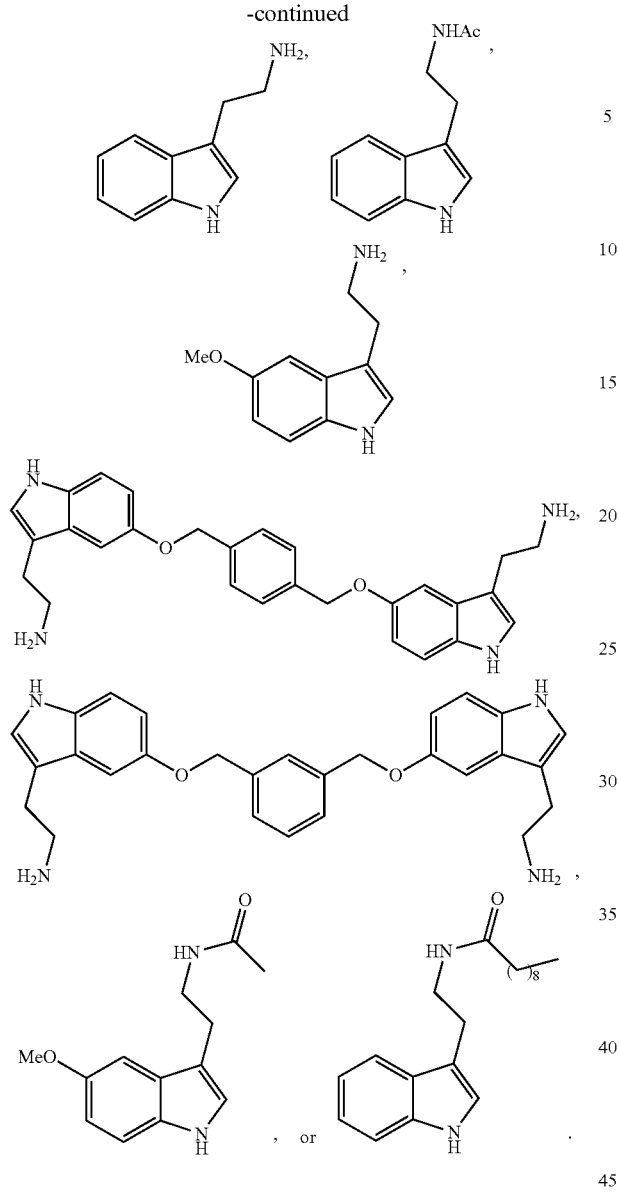
74. The compound of any one of embodiments 1 to 73, wherein the compound
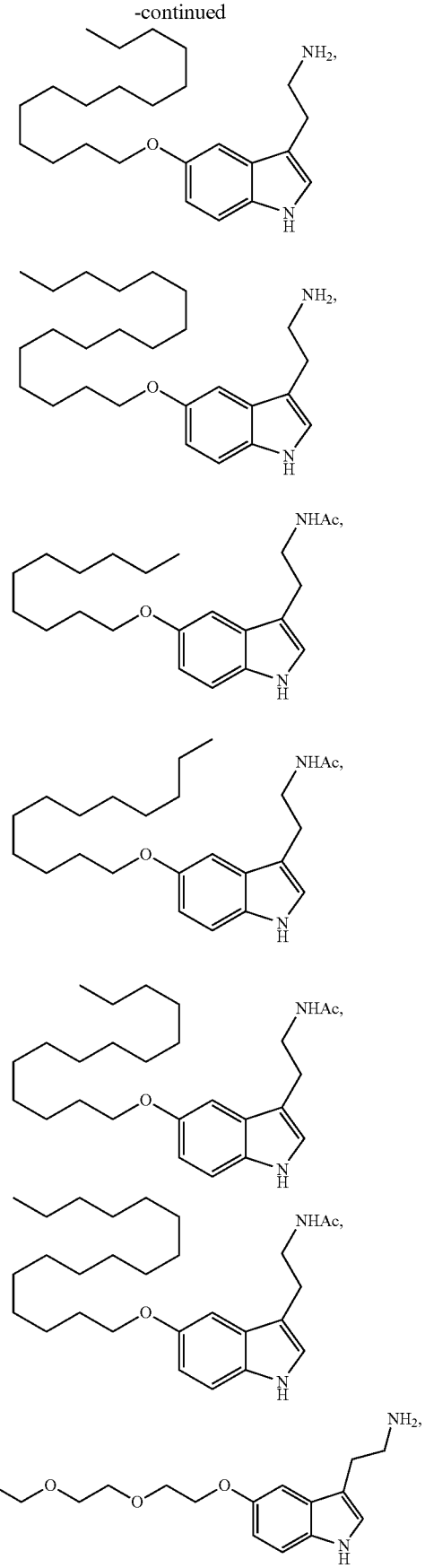

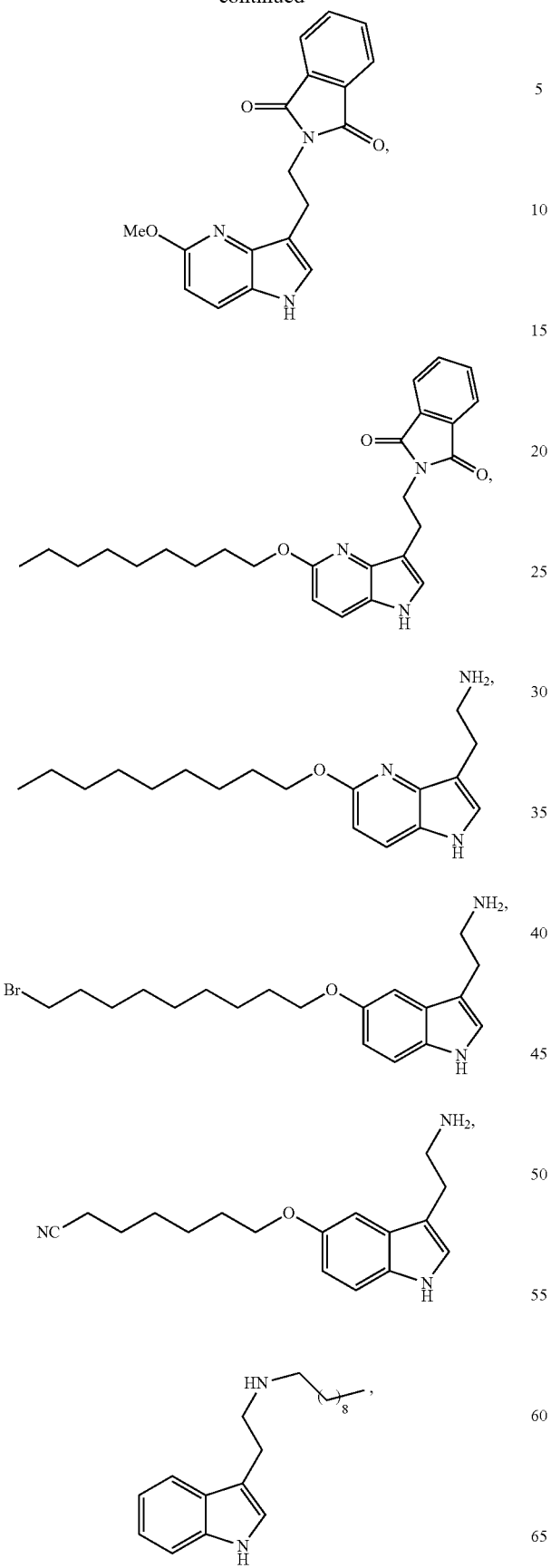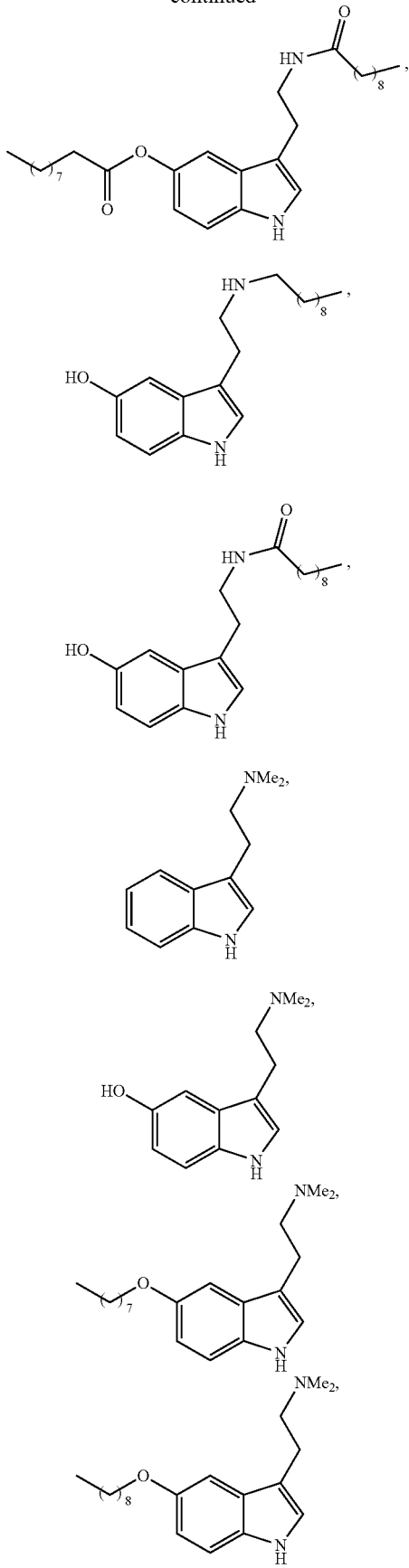

121
-continued
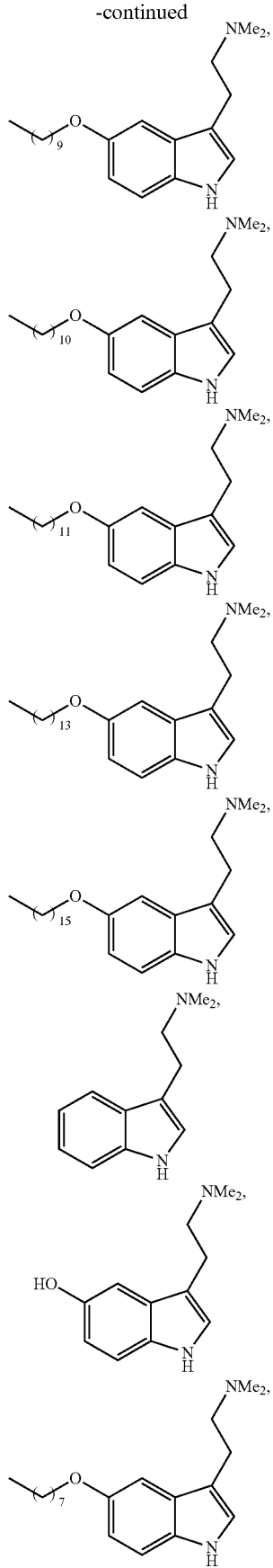
122
-continued
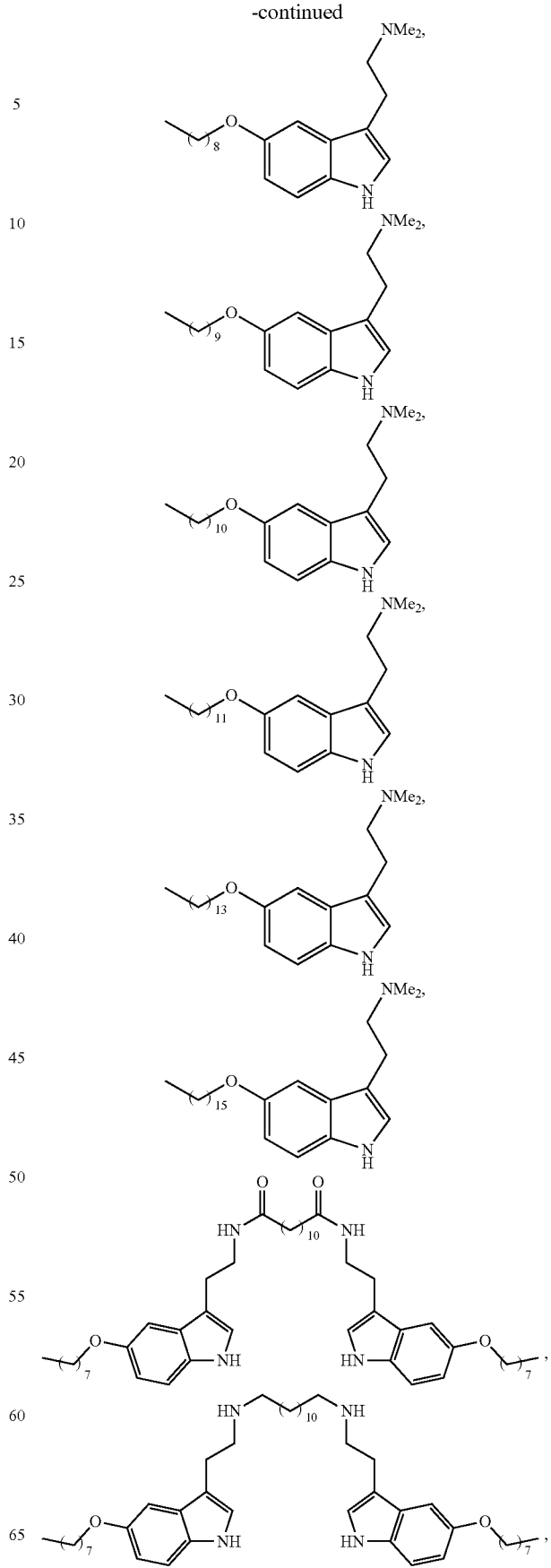

123
-continued

124
-continued

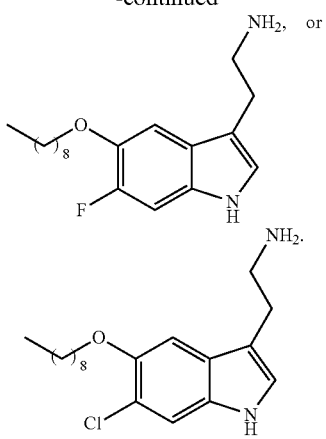

75. A pharmaceutical composition comprising a pharmaceutically acceptable excipient and a compound of any one of embodiments 1 to 74.

76. A pharmaceutical composition comprising a pharmaceutically acceptable excipient, a liposome, and a compound of any one of embodiments 1 to 74.

77. The pharmaceutical composition of embodiment 76, wherein the liposome comprises dioleoyl-sn-glycero-3-phosphocholine.

78. The pharmaceutical composition of embodiment 76, wherein the liposome comprises dimyristoyl-phosphatidylcholine.

79. The pharmaceutical composition of embodiment 76, wherein said compound is in said liposome.

80. The pharmaceutical composition of embodiment 76, wherein said liposome comprises a targeting moiety.

81. The pharmaceutical composition of embodiment 80, wherein said targeting moiety is folate.

82. A method of treating a disease in a patient in need of such treatment, said method comprising administering a therapeutically effective amount of a compound of any one of embodiments 1 to 74.

83. A method of treating a disease in a patient in need of such treatment, said method comprising administering a therapeutically effective amount of a pharmaceutical composition of any one of embodiments 75 to 81.

84. The method of any one of embodiments 82 to 83, wherein said disease is cancer.

85. The method of any one of embodiments 82 to 84, wherein said disease is breast cancer, ovarian cancer, pancreatic cancer, liver cancer, glioblastoma, glioma, lung cancer, prostate cancer, leukemia, or melanoma.

86. The method of any one of embodiments 82 to 85, wherein said disease is metastatic cancer.

87. The method of any one of embodiments 82 to 83, wherein said disease is a migraine headache.

88. The method of any one of embodiments 82 to 83, wherein said disease is depression.

89. The method of any one of embodiments 82 to 88, wherein said compound or pharmaceutical composition is co-administered with a chemotherapeutic agent.

EXAMPLES

Example 1

CaMK-III is Overexpressed in Breast Cancer Cells

Figure 13:
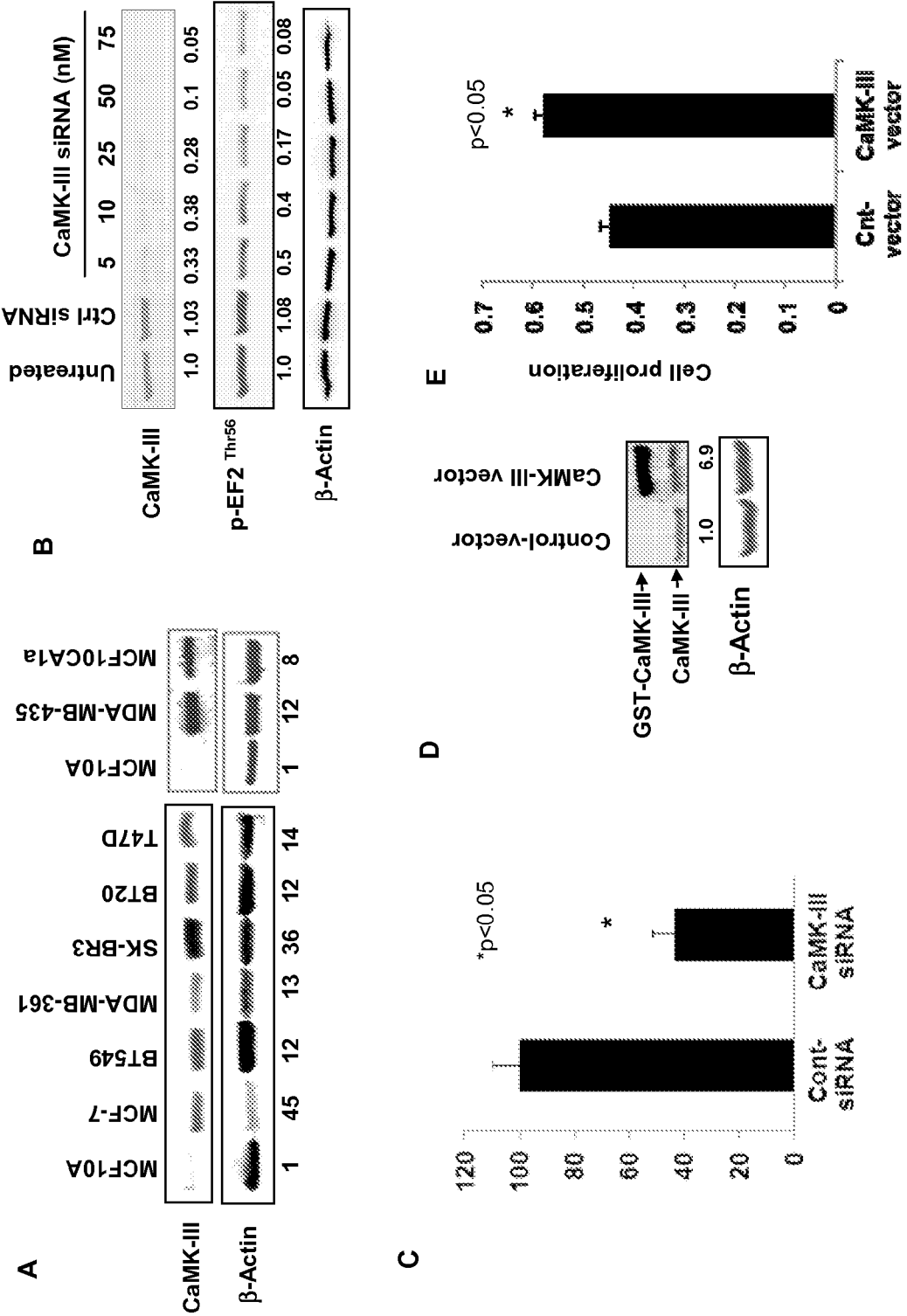
FIG. 13. (A). CaMK-III protein is overexpressed in a panel of breast cancer cells compared to non-tumorigenic normal breast epithelium (MCF10A).(B). A specific siRNA inhibits protein expression of CaMK-III in MDA-MB-231. Cells were transfected by CaMK-III siRNA (5-75 nM) for 48 h and cell lysates were subjected to Western blot analysis. (C). Knockdown of CaMK-III inhibits proliferation of MDA-MB-231 cells detected by MTS assay (*p<0.05).(D). Knockdown of CaMK-III by siRNA (50 nM) induces PARP cleavage (48 h). (E). CaMK-III overexpression increases cell proliferation of MDA-MB-231 cells. Cells were transiently transfected with CaMK-III or a vector control and cell viability was measured using an MTS assay at 96 h.

CaMK-III protein expression was assessed by Western blot analysis in the non-tumorigenic breast epithelium MCF10A cell line and compared to other breast cancer cell lines. These included estrogen receptor-negative, ER(−) cells including MDA-MB-231, MDA-MB-435, BT549, BT20, and SK-BR3 (HER2 overexpressing); ER(+) cells including MCF-7, MDA-MB-361 (HER2 overexpressing), and T47D) and metastatic (MCF10CA1a; CA1a) breast cancer cells (FIG. 13A). Overall, CaMK-III levels were increased in all breast cancer cell lines.

Cell Lines, Culture Conditions, and Reagents.

The human breast cancer cell lines were obtained from ATCC. Cells were cultured at 37° C. in DMEM supplemented with 5% FBS in a humid incubator with 5% $CO_2$.

Cell Viability and Growth Assays.

Viable and dead cells were detected by the trypan blue exclusion assay, the viability and/or proliferation of cells a MTS assay was used [Akar U, et al. Autophagy 2008: 4:669-79].

Plasmids.

EGB2T-CaMK-III (aka eEF-2K) cDNA from the bacterial expression vector p32TCaMK-III, encoding the human Trx-His6-tagged CaMK-III/eEf2K (GenBank accession number NM_013302), was used as a template in a PCR reaction (Franken N A, et al. Nat Protoc 2006: 1:2315-9). To clone the human CaMK-III cDNA, the desired sequence was amplified by PCR using a specifically designed forward primer, 5'-TTT GGTACC ATG GCA GAC GAC GAA GAT CTC ATC-3'(SEQ ID NO:1) (KpnI recognition site underlined) and reverse primer, 5'-AAA TGCGGCCGC TTA CTC CTC CAT CTG GGC CCA-3' (SEQ ID NO:2) (NotI recognition site underlined), and ligated into the EGB-2T vector (Lu K P, Endocr Rev 1993: 14:40-58).

Western Blot Analysis.

After treatment the cells were collected and Western blot was performed as previously described [Akar U, et al. Autophagy 2008: 4:669-79]. The membranes were blocked with 5% dry milk and probed with primary antibodies anti-CaMK-III (eEF-2K) monoclonal antibody, p-EF2 (Thr-56), EF2, cyclin D1, p27, p-Aid (Ser-473), Akt, pIGF-1R (Tyr-1131), IGF-IRβ (#3027), p-Src (Tyr-416), p-paxillin (Tyr-31), p-mTOR (Ser-2448) (Cell signaling); VEGF, HIF1α, p-Fak (Tyr-397) (BD Transfection); c-myc, Bcl-2, caspase 9 (cleaved), poly ADP-ribose polymerase (PARP) (Santa Cruz, Calif.). Horseradish peroxidase-conjugated anti-rabbit or anti-mouse secondary antibody (Amersham Life Science, Cleveland, Ohio). Mouse anti-β-actin and donkey anti-mouse secondary antibodies (Sigma Chemical, St. Louis, Mo.) were used to monitor β-actin expression to ensure equal loading of proteins.

Example 2

Knockdown of CaMK-III Inhibits Cell Proliferation of Breast Cancer Cells

After determining that CaMK-III expression is increased in breast cancer cell lines, we examined possible effect of CaMK-III on breast cancer cell growth in vitro. First, we designed siRNA sequences to target CaMK-III and assessed its ability to down-regulate CaMK-III expression in cells. As shown in FIG. 13B, 50 and 75 nM of siRNA targeting CaMK-III efficiently decreased CaMK-III protein expression about 90% or more at 48 h time point in MDA-MB231 cells. Inhibition of CaMK-III by siRNA resulted in reduction of phosphorylation (Thr56) of its downstream target eEF2 and significant inhibition of cell proliferation in MDA-MB231 cells ($p<0.05$) (FIGS. 13B and C). Similar results were obtained using MCF-7 cells.

To further demonstrate that CaMK-III is involved in cell proliferation we transiently transfected MDA-MB231 cells with GST-conjugated CaMK-III using an expression vector containing DNA encoding for wild type CaMK-111 (FIG. 13D). CaMK-III overexpression significantly increased proliferation of MDA-MB-231 cells compared with those transfected with empty control vector (p<0.05) (FIG. 13E). These data suggest that CaMK-III is involved in proliferation of breast cancer cells.

Example 3

Knockdown of CaMK-III Inhibits the In Vitro Growth Rate and Colony Formation of Breast Cancer Cells To study the effect of CaMK-III growth of ER(−) and ER(+) breast cancer cells we performed a clonogenic assay, which is based on the ability of a single cell to grow into a colony (Franken N A, et al. Nat Protoc 2006: 1:2315-9), using MDA-MB-231 and MCF-7 cells, respectively. Cells were transfected with either CaMK-III or control siRNA (50 nM) every 4 days over a period of two weeks. The knockdown of CaMK-III significantly reduced growth rates and number of colonies (>75%) of both MDA-MB-231 (FIG. 14A) and MCF-7 cells (FIG. 14B) compared to control siRNA treatment (p<0.05). These data indicate that CaMK-III makes significant contributions to breast cancer cell growth in vitro.

Clonogenic Survival Assay.

This assay is an in vitro cell survival assay based on the ability of a single cell to grow into a colony. Briefly, cells (500 cells/well) were transfected with control siRNA or CaMK-III siRNA every week and grown for 2 to 3 weeks. Cells were stained with crystal violet and colonies were counted. Each experiment was repeated twice.

Example 4

Figure 14:
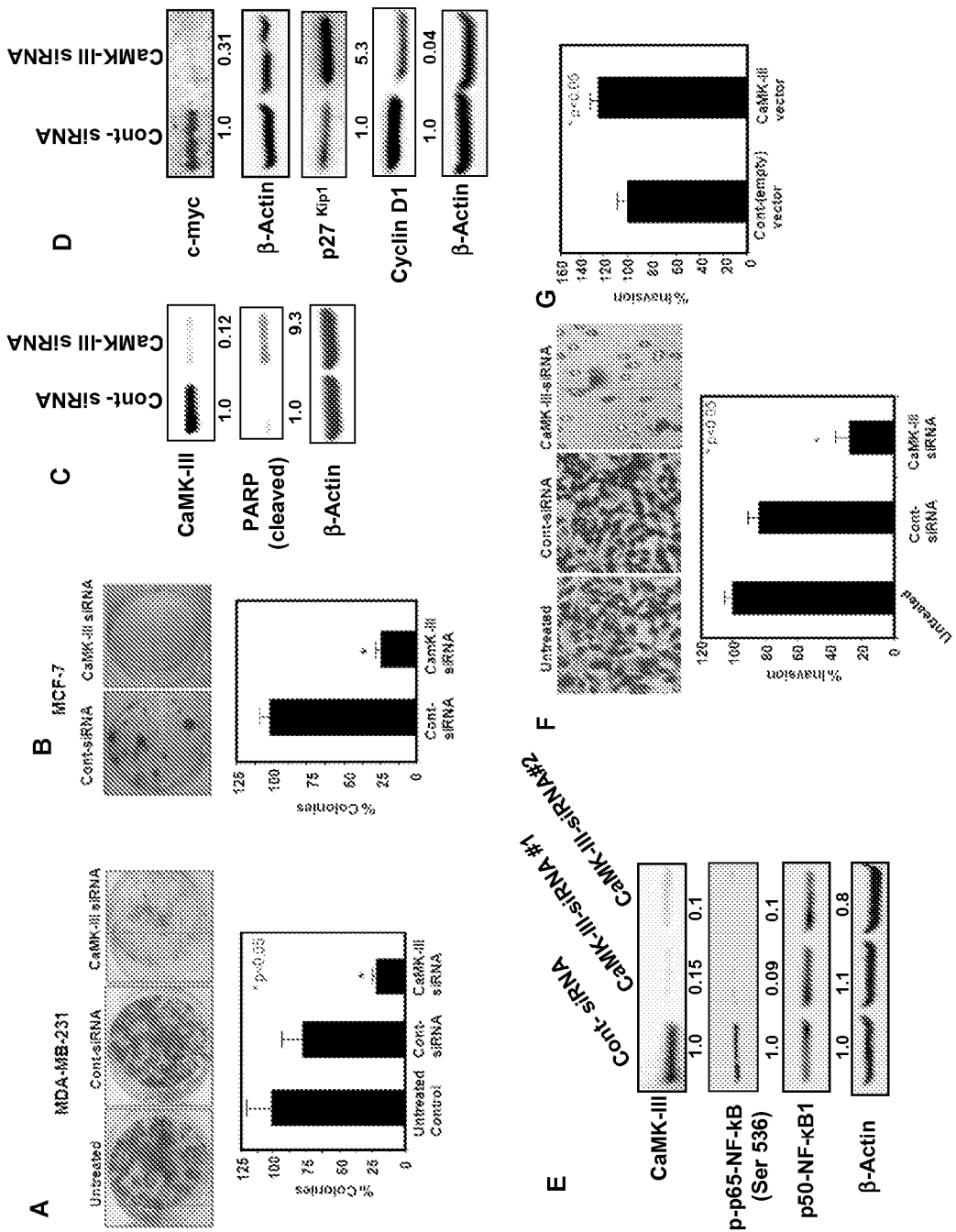
FIG. 14. (A) Knockdown of CaMK-III by siRNA (50 nM) significantly inhibited number of colonies formed by MDA-MB-231 (B) and in MCF7 cells (*p<0.05). (C). Cells were transtected with siRNA every 4 days. (D) Knockdown of CaMK-III siRNA c-myc, cyclin D1 and increased the protein expression of the CDK-Inhibitor $p27^{Kip1}$ (72 h). (E) The knockdown of CaMK-III also reduced the expression of a transcriptionally active form of NF-κB (p-p65-ser-356). (F) Depletion of CaMK-III by siRNA inhibits invasion of MDA-MB-231 cells in matrigel (G) Overexpression of CaMK-III increases invasion of MDA-MB-231 cells in matrigel (72 h).
Figure 18:
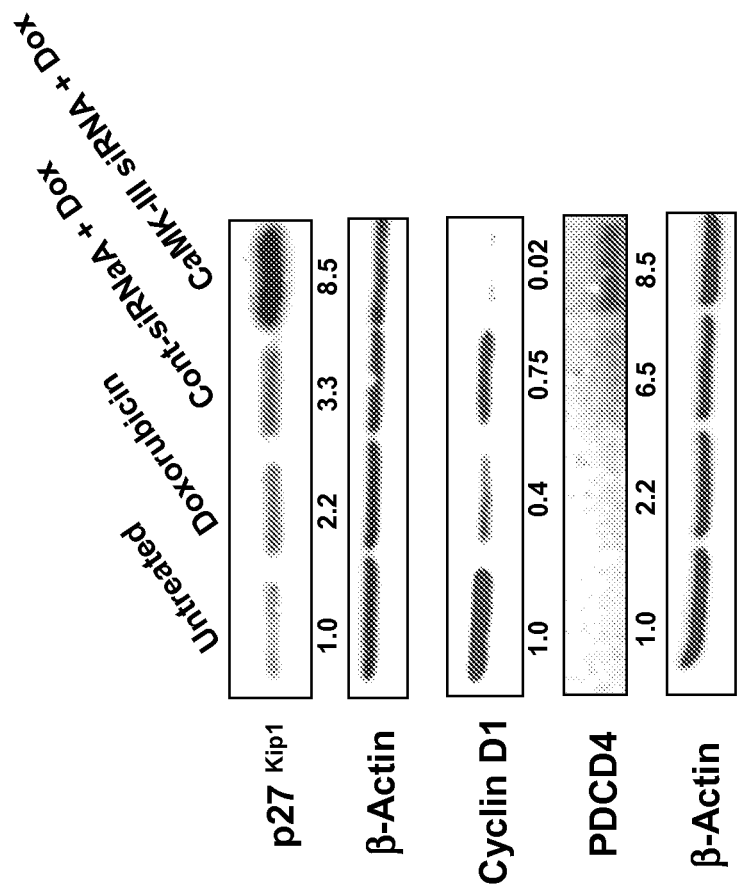
FIG. 18. Western blot analysis demonstrated that inhibition of CaMK-III in MDA-MB231 cells further reduced cyclin D1 was and increased the cycline-dependent kinase (CDK)-inhibitor $p27^{Kip1}$ and PDCD4 tumor suppressor protein, a regulator of $p27^{Kip1}$, response to doxorubicin.

Knockdown of CaMK-III is Inhibits c-myc, Cyclin D1, NF-kB and Induces p27$^{Kip1}$ Expression To gain a mechanistic insight into how CaMK-III inhibition leads to growth inhibition, we knocked down CaMK-III by siRNA and examined expression of proteins critical to growth, cell cell cycle and survival. We first examined if CaMK-III inhibition induced cell death. As shown in FIG. 14C CaMK-III knockdown resulted in induction of apoptosis as indicated by PARP cleavage. The c-myc oncogene is amplified or overexpressed in the majority of human breast cancers and contributes to cell proliferation and is an indicator of risk of recurrence and poor prognosis in patients (Liao D J, Dickson R B. Endocr Relat Cancer 2000: 7:143-64). As shown in FIG. 14D, CaMK-knockdown significantly reduced c-myc expression in MDA-MB-231 cells compared to control cells treated with control siRNA. The cyclin D1 proto-oncogene and p27$^{Kip1}$ cyclin-dependent kinase inhibitor (CDK) are important regulators of G1 to S phase progression. CyclinD1 plays a role in malignant transformation and progression and the overexpression of cyclin D1 and the reduced expression of p27$^{Kip1}$ are indicative of a poor prognostic factor in breast cancer (Musgrove E A. Growth Factors 2006: 24:13-9; Abukhdeir A M, Park B H. Expert Rev Mol Med 2008; 10:e19). Western blot analysis revealed that knockdown of CaMK-III markedly reduced the expression of cyclin D1 and increased the expression of p27$^{Kip1}$ in MDA-MB-231 cells (FIG. 14D). When combined with doxorubicin, a commonly used chemotherapeutic agent, CaMK-III inhibition led to a further reduction in cyclin D1 and further enhancement of p27$^{Kip1}$ expression (FIG. 18). The tumor suppressor PDCD4, which previously we have shown to up-regulate p27$^{Kip1}$ expression (Ozpolat B, et al. Mol Cancer Res 2007: 5:95-108) was induced by the down-regulation of CaMK-III (FIG. 18).

Furthermore, we examined NF-κB, which is known to promote survival and angiogenesis and prevents apoptosis (Shibata A, et al. Breast cancer research and treatment 2002: 73:237-43). The knockdown of CaMK-III also reduced the expression of a transcriptionally active form of NF-κB (p-p65-ser-356) (FIG. 14E). These data indicate that knockdown CaMK-III inhibits expression of key cellular proteins contributing growth and survival of breast cancer cells.

Transfections with siRNA and Plasmid.

Cells were transfected with siRNA as previously described [Akar U, et al. Autophagy 2008: 4:669-79]. siRNA sequence targeting CaMK-III was designed using siRNA-designing software (Qiagen): CAMK-III (EF2KsiRNA) siRNA-1 #1, 5'-GCCAACCAGUACUACCAAA-3' (SEQ ID NO:3). A previously published siRNA sequence was also used target CAMK-III: siRNA #2; 5'-AAGCUCGAACCAGAAU-GUC-3' (SEQ ID NO:4) [Li H M, et al. Proc Amer Assoc Cancer Res 48: 4917, 2007]. Control non-silencing siRNA sequence 5'-AAUUCUCCGAACGUGUCACGU-3' (SEQ ID NO:5) [Abukhdeir A M, Park B H. Expert Rev Mol Med 2008; 10:e19]. siRNA targeting c-Src was purchased from Sigma Aldrich. 1 μg of siRNA, mixed with the transfection reagent (Hyperfect Transfection Reagent, Qiagen), and added to each well. Plasmid vector (1-3 μg) containing human GST-tagged CaMK-III was transfected into cells using the Qiagen plasmid transfection reagent according to the manufacturer's protocol.

Example 5

Depletion of CaMK-III Inhibits Invasion of MDA-MB-231 Cells

The ability of tumor cells to invade is one of the hallmarks of the metastatic phenotype. To determine a role for CaMK-III in mediating breast cancer cell invasion, in vitro invasion assays were performed using Matrigel-coated Boyden chambers. This assay mimics the in vivo invasion process and measures the number of cancer cells passing through a basement membrane matrix (Matrigel) towards media containing chemo-attractants (Shaw L M. Methods Mol Biol 2005: 294: 97-105). While depletion of CaMK-II by siRNA significantly reduced (~80%) invasion of MDA-MB231 cells (p<0.05) (FIG. 14F), the overexpression of CaMK-III significantly increases invasion of MDA-MB-231 breast cancer cells (p<0.05) (FIG. 14G). This suggests that inhibition of CaMK-III can reduce the invasion and metastatic potential of breast cancer cells.

Matrigel Invasion Assay.

MDA-MB-231 cells were transfected with CaMK-III or control siRNA and 24 h later cells ($1 \times 10^5$ cells per well) were seeded onto Matrigel-coated Transwell filters (8-μm pore size) in Matrigel invasion chambers (BD Biosciences, San Jose, Calif.), and the number of cells that invaded the lower side of the membrane were determined at 72 h by counting cells in a minimum of four randomly selected areas.

Example 6

Figure 15:
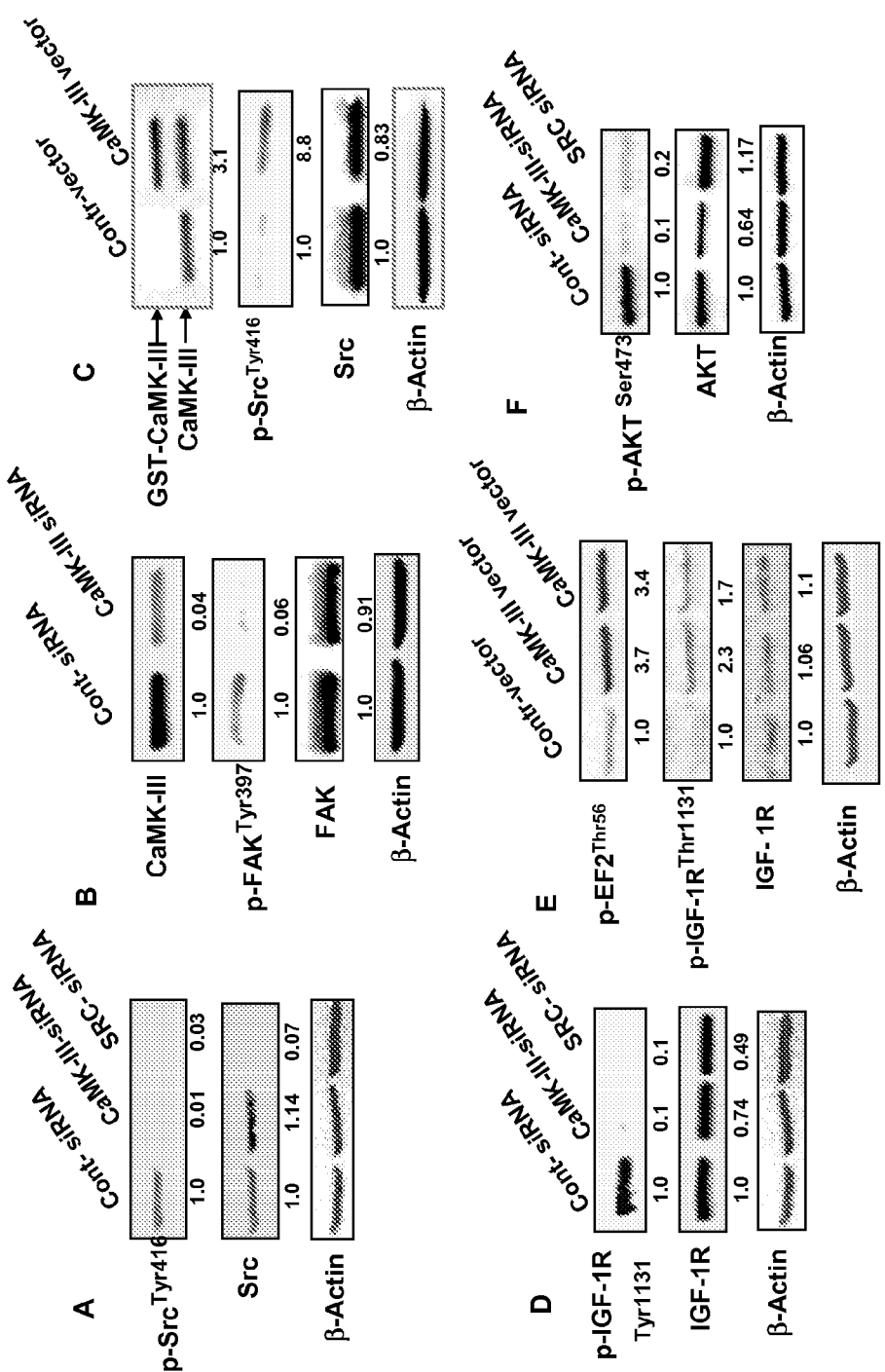
FIG. 15. Knockdown of CaMK-III by siRNA inhibits the activity of c-Src, Fak, PI3K/Akt and IGF-1R as indicated by reduced (A) p-Src (Thr-416), (B) p-Fak (Thr-397) (D) p-IGF1R (Tyr1131) in MDA-MB231 cells (72 h). Depletion of CaMK-III also inhibits p-mTOR, p-Paxillin and VEGF. Knockdown Src by siRNA leads to reduction of Akt and IGF1R activity, suggesting that CaMK-III particiates regulation of AKT. Overexpression of CaMK-III increases (C) p-Src and (E) p-IGFR in MDA-MB231 cells. Cells were transiently transfected with GST-CaMK-III plasmid and 72 h later cells were collected for Western blot analysis. (F) Knockdown of CaMK-III by siRNA inhibits the activity of p-Akt (Ser473).
Figure 19:
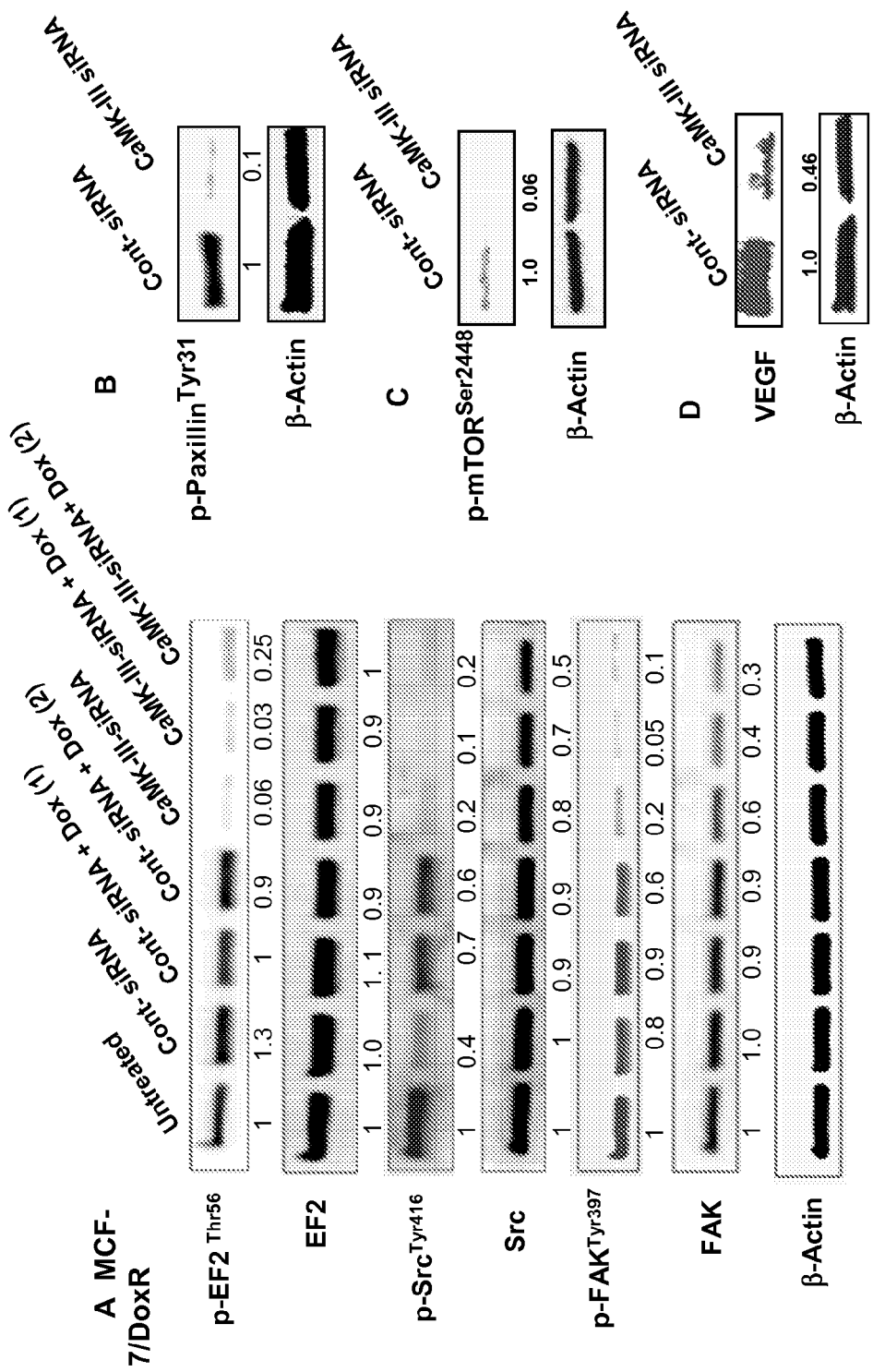
FIG. 19. (A). Knockdown of CaMK-III inhibits Src and FAK activity and increases Doxorubicin-induced apoptosis in MCF7/DoxR cells. CaMK-III depletion also inhibited p-EF2 (Thr56), the substrate of CaMK-III. About 48 hours after siRNA transfection cells were treated with doxorubicin and lysed for Western blot analysis. (B) and (C). Inhibition of CaMK-III by siRNA led to reduced (B) p-Paxillin (Tyr-31), (C) phosphorylation of mTOR and (D) VEGF in MDA-MB-231 cells. Cells were collected for Western blot analysis 72 h after transfected with control siRNA or CaMK-III siRNA.

Knockdown of CaMK-III Inhibits Activity of IGF-1R and PI3K/Akt Through Inhibition of c-Src in Breast Cancer Cells Because the above data clearly implicated CaMK-III in the breast cancer cell proliferation, invasion and survival, we examined the possible involvement of c-Src signaling upon CaMK-III depletion and overexpression. The Src family of non-receptor protein tyrosine kinases are known to play critical roles in adhesion, migration/invasion, proliferation and resistance to chemotherapy (Finn R S. Ann Oncol 2008: 19:1379-86). The knock-down of CaMK-III or c-Src by siRNA led to significant reduction of phospho-c-Src (Tyr-416) (FIG. 15A), and phospho-Fak (Tyr-397) (FIG. 15B) levels in MDA-MB231 cells, indicating that CaMK-III contributes to the promotion of the invasion phenotype though the activation of c-Src/Fak signaling. Similar effects of CaMK-III inhibition were observed on c-Src/Fak activation in doxorubicin resistant MCF-7 (MCF-7/DoxR) breast cancer cells (FIG. 19A). CaMK-III knockdown also led to a reduction in the phosphorylation of paxillin on Tyr-31 (a target for Fak) in these cells (FIG. 19B). The overexpression of CaMK-III resulted in a significant increase in p-Src (Tyr416) and p-eEF2(Thr56), suggesting that CaMK-III activity was increased in CaMK-III transfected MDA-MB-231 cells (FIG. 15C). This data indicated that CaMK-III participates in the activity of Src.

The insulin-like growth factors receptor 1 (IGF-1R) is phosphorylated and activated by c-Src (19). More importantly, because IGF-1R plays a central role in the development of mammary tumors, cell growth, differentiation, survival, and invasion/metastasis by regulating proteins including c-myc, cyclin D1 and NF-κB we sought to determine if IGF-1R is inhibited by CaMK-III and Src depletion. As shown in FIG. 15D, downregulation of CaMK-III resulted in a reduction of phosphorylated IGF-1R (Tyr1131). The overexpression of CaMK-III results in an increased level of IGF-1R autophosphorylation on Tyr-1131 (FIG. 15E). This data show that IGF-1R may serve as a potential mediator of a CaMK-III/c-Src axis.

Src and IGF-1R signaling are known to induce PI3K/Akt (PKB) pathway, which is frequently increased in breast cancer and associated with a poor prognosis (Sun M, et al. The American journal of pathology 2001: 159:431-7). Because our data suggest that CaMK-III and c-Src regulate IGF-1R signaling, we then examined whether CaMK-III plays a role in the activity of Akt (Alessi D R, et al. The EMBO journal. 1996; 15:6541-51). The down-regulation of either CaMK-III or c-Src resulted in the down-regulation of Akt activation (p-Ser473) (FIG. 15F) and mTOR activity (reduced p-Ser2448) (FIG. 19C), suggesting that CaMK-III mediates Akt and mTOR activity, which plays essential roles in cellular responses to growth factors and stress.

Example 7

Figure 16:
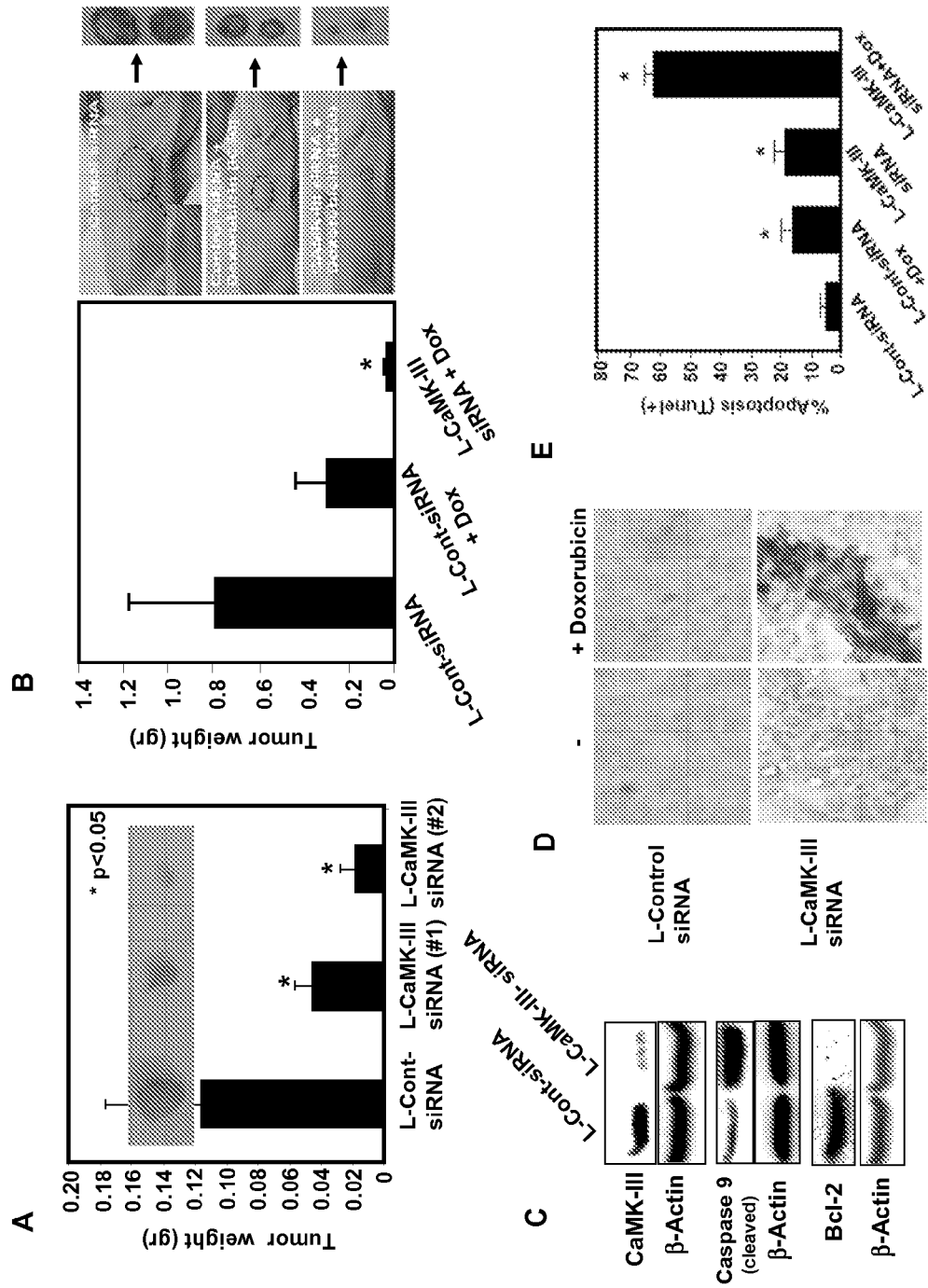
FIG. 16. (A). Therapeutic targeting of the CaMK-III gene was achieved by systemically (i.v.) administered DOPC-liposomal siRNA (L-CaMK-III siRNA #1 and siRNA #2 [42]) or non-silencing DOPC-liposomal siRNA (L-Control siRNA) in nude mice bearing MDA-MB-231 tumors. At the end of week 4, tumor weight was measured. (B). Mice bearing MDA-MB231 tumors were given L-CaMK-III siRNA or L-control siRNA (i.v., twice a week, 150 µg/kg) and doxorubicin once a week (i.p., 2.5 mg/kg) for 4 weeks and tumor weight were measured. (C) Western blot analysis were performed in tumor samples that were resected 48 h after the last siRNA injection showed down modulation target CaMK-III protein and induction apoptosis as indicated by caspase-9 cleavage and (D) TUNELassay. (E) Quantification of TUNEL % positive cells in tumors.

Therapeutic Targeting of CaMK-III by Systemically Administered Liposomal-siRNA Inhibits Orthotopic Tumor Growth in a Breast Cancer Model The studies described above suggest that the CaMK-III gene enhances a number of processes associated with tumorigenesis. To further assess its therapeutic potential the effect of down-regulating CaMK-III in an orthotopic model of MDA-MB-231 breast cancer was assessed in nude mice. To eliminate potential off target-related effects two different siRNAs were used to target CaMK-III siRNA #1 (FIG. 13B) and siRNA #2 [Gross J M, Yee D. Cancer Metastasis Rev 2003: 22:327-36]. Targeting of the CaMK-III gene was achieved by systemic (i.v.) administration of DOPC-liposomal CaMK-III siRNA (150 µg/kg or about 4 µg/mouse) twice a week for a period of 4 weeks. Treatment with both L-CaMK-III siRNA #1 and siRNA #2 inhibited in vivo tumor growth. L-siRNA targeting of CaMK-III results in significant down-regulation of its expression in the tumors (FIG. 22A). These data show that CaMK-III knockdown has growth inhibitory effects on breast cancer tumor growth in vivo and therefore it may be a potential therapeutic target (FIG. 16C).

Moreover, no toxic effects were observed in mice exposed to liposomal CaMK-III siRNA for four weeks compared with the control group. Mice appeared healthy and did not lose weight during the 4 weeks of treatment and the mean weight of L-CaMK-III siRNA and L-control-siRNA groups was 28.3±0.8 g and 28.4±0.4 g, respectively.

Liposomal siRNA Preparation.

For in vivo delivery siRNA was incorporated into dioleoyl-sn-glycero-3-phosphocholine (DOPC). DOPC and siRNA were mixed in the presence of excess tertiary butanol at a ratio of 1:10 (w/w) siRNA/DOPC [Shaw L M. Methods Mol Biol 2005: 294:97-105]. Before in vivo administration, this preparation was hydrated with normal 0.9% saline in 100 µL for i.v injection per mouse.

Orthotopic Xenograft Tumor Model of Breast Cancer.

Athymic female nu/nu mice (5 week old) were obtained from the Department of Experimental Radiation Oncology at M. D. Anderson Cancer Center. All studies were conducted according to an experimental protocol approved by the M. D. Anderson Institutional Animal Care and Use Committee. MDA-MB-231 cells ($1 \times 10^{-6}$) were injected into the right middle mammary fat pad of each mouse. Two weeks after, when tumor size reached about 3-5 mm liposomal siRNA treatments were initiated. Each mouse received 150 µg/kg (equivalent of ~4 ng/mouse) non-silencing control siRNA or CaMK-III siRNA twice a week (i.v. injection from the tail vein in 100 µg saline) for four weeks. After finishing the treatment mice were euthanizedby $CO_2$. Tumor tissues were removed for Western blot, Immunohistochemistry and TUNEL analysis and weighted to measure tumor growth.

Example 8

Figure 23:
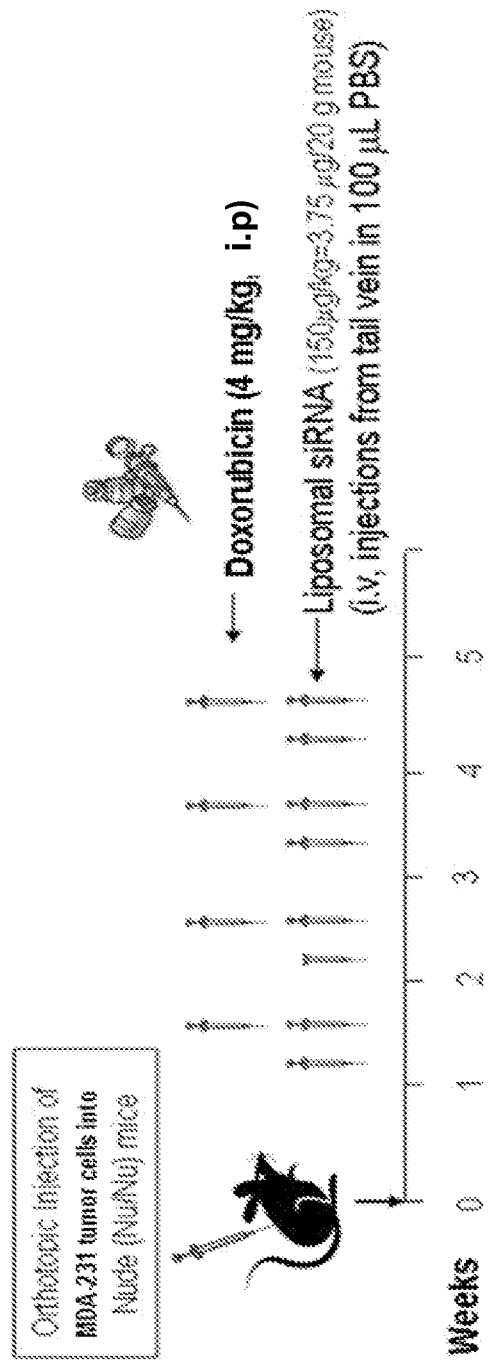
FIG. 23. Treatment schedule of liposomal siRNA (control and CaMK-III) in nude mice bearing MDA-MB231 tumors. About 2 weeks after tumor cell injection MDA-MB-231 cells, the targeting of the CaMK-III gene was achieved by the systemic (i.v. from tail vein) administration of liposomal siRNA (150 μg/kg or about 4 μg/mouse) twice a week for a period of 4 weeks. Treatment with two different siRNA duplexes (siRNA #1 and siRNA #2[42]) targeting CaMK-III.

In Vivo Targeting of CaMK-III Enhances the Efficacy of Chemotherapy in a Breast Cancer Model The in vitro studies described above demonstrate that the inhibition of CaMK-III enhances doxorubicin-induced apoptosis. Doxorubicin is one of the most commonly used chemotherapies in cancer patients. To test whether CaMK-III inhibition sensitizes breast cancer tumors in vivo to chemotherapy, a group of mice were orthotopicaly injected with MDA-MB-231 cells. Two weeks after tumor inoculation, mice were given DOPC-L-CaMK-III siRNA twice a week as described above and doxorubicin once a week (i.p, 4 mg/kg) for 4 weeks (FIG. 23). The group receiving combination therapy (L-CaMK-III siRNA+doxorubicin) had the smallest tumors (p<0.05) compared to liposomal control siRNA+doxorubicin or L-CaMK-III siRNA groups (FIG. 16B). These findings suggest that the silencing of CaMK-III enhances the effect of chemotherapy against breast cancer.

Example 9

Figure 20:
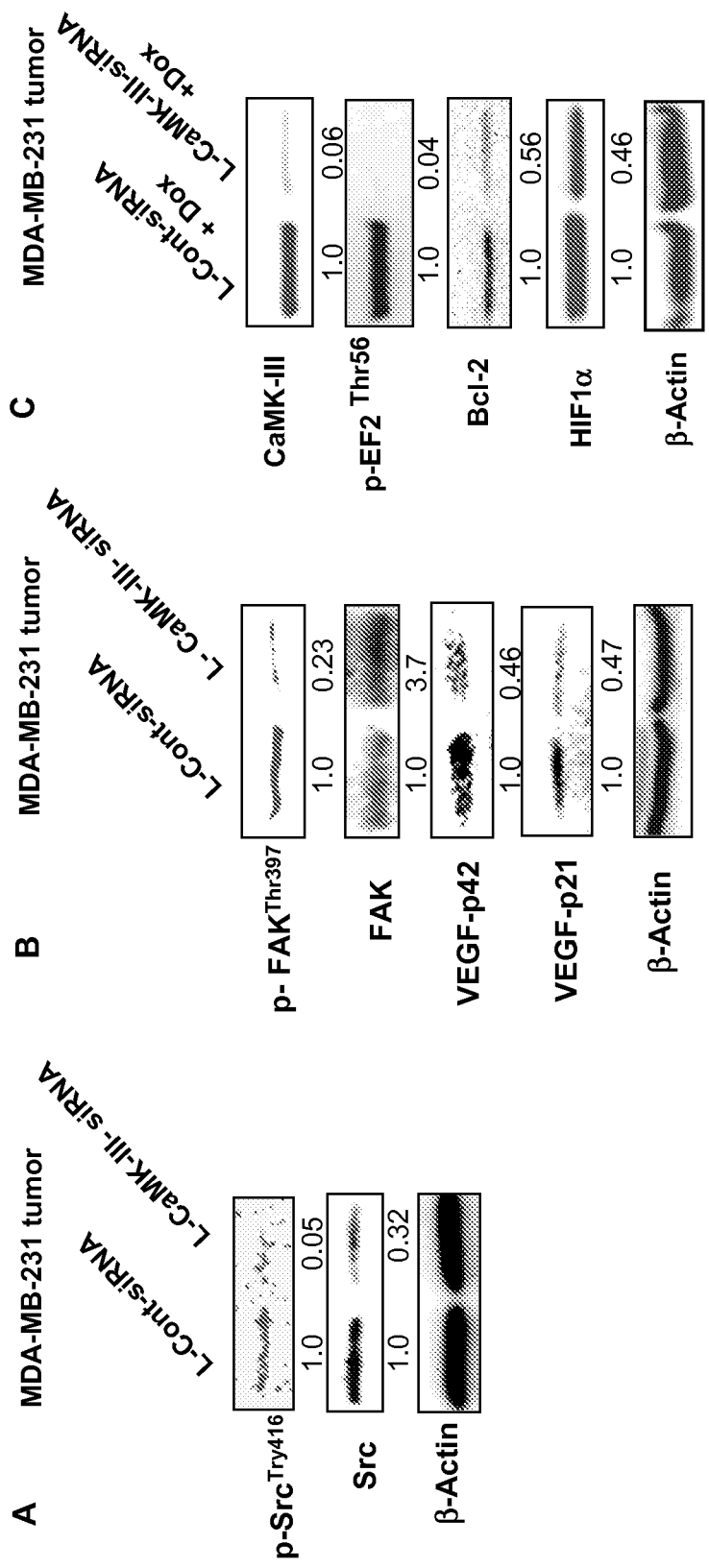
FIG. 20. Analysis of MDA-MB-231 tumors (shown in FIG. 16A) samples resected from mice after 4 weeks of treatment with liposomal-DOPC siRNA. (A) and (B). In vivo therapeutic targeting of CaMK-III by liposomal siRNA decreased expression of Bcl-2 p-Src, p-FAK, VEGF also detected. (C) In vivo administration of L-CaMK-III siRNA inhibits target protein protein CaMK-III and phosphorylation of its downstream target EF2 in MDA-MBA231 tumors shown in FIG. 16B. The combination of liposomal CaMK-III siRNA treatment with doxorubicin enhanced inhibition of Bcl-2 and HIF1α expression.

In Vivo Targeting of CaMK-III Induces Apoptosis and Inhibits Proteins Associated with Apoptosis, Invasion and Angiogenesis in Breast Tumors To determine the mechanisms by which CaMK-III inhibition induces tumor inhibition, tumor samples from in vivo therapeutic experiments were examined for induction apoptosis and proteins that may be critical to tumor growth and progression. Western blot analysis and TUNEL assay of tumors demonstrated marked induction of apoptosis as evidenced by activation of caspase-9 by cleavage and positive staining (brown), respectively (FIGS. 16C, D and E). Inhibition of anti-apoptotic protein Bcl-2 expression was noted in the tumor samples (FIG. 16C). In line with the in vitro studies the phosphorylation of c-Src and Fak were diminished (FIG. 20A) in tumors after L-CaMK-III treatment. In addition, CaMK-III knockdown in tumors increased VEGF and doxorubicin-mediated inhibition of HIF1α (FIG. 20B). We also found that CaMK-III inhibition enhances doxorubicin-induced inhibition of Bcl-2 expression in the tumors (FIG. 20B), consistent with the possibility that Bcl-2 mediates some of the effects of CaMK-III targeted therapy (Akar U, et al. Autophagy 2008: 4:669-79; Ozpolat B, et al. Proceedings of the American Association for Cancer Research-AACR 2010: Abstract #51084).

Example 10

Figure 17:
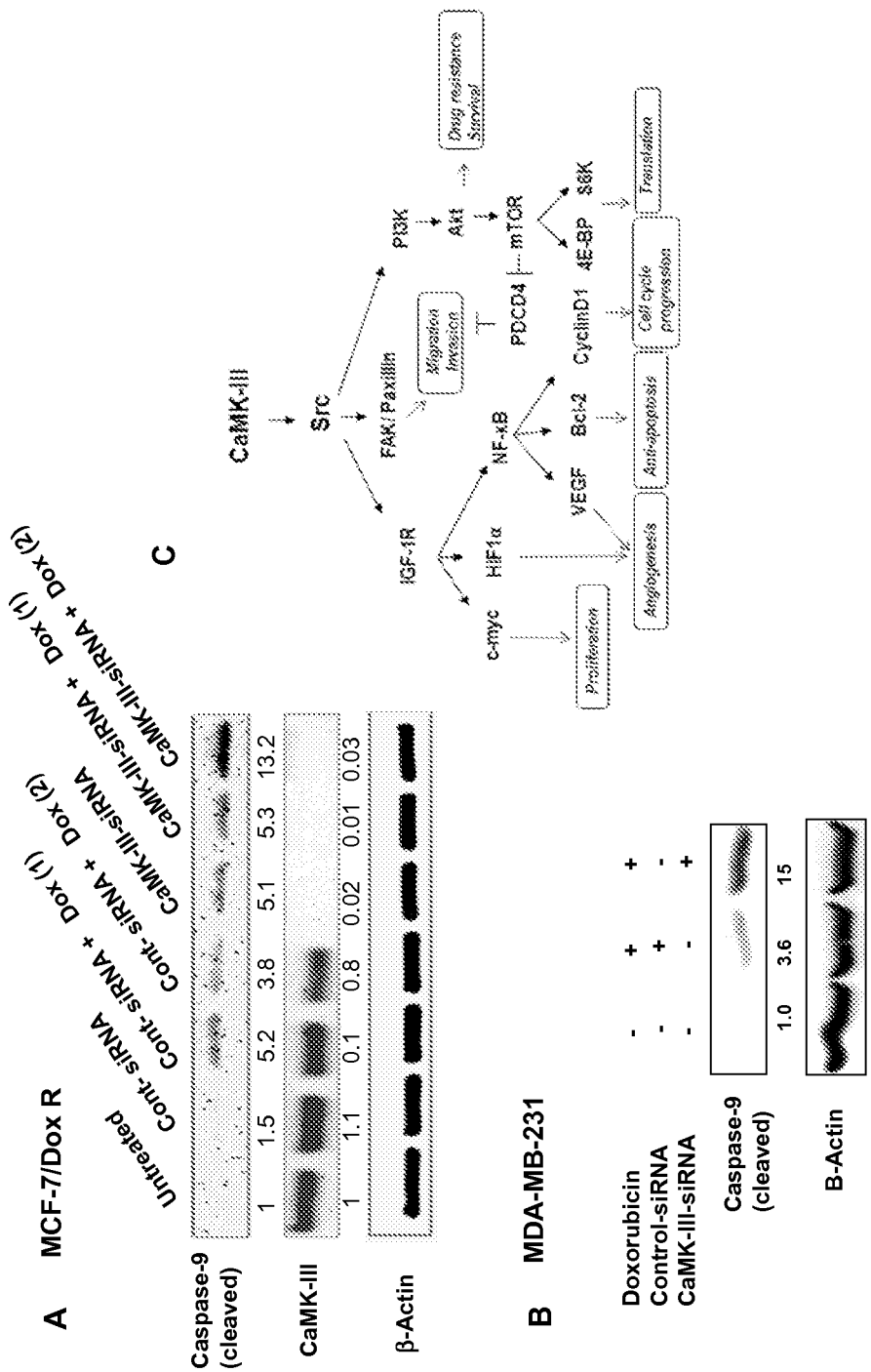
FIG. 17. (A). Knockdown of CaMK-III induces Caspase-9 cleavage and increases Doxorubicin-induced apoptosis in MCF7/DoxR cells. About 48 hours after siRNA transfection cells were treated with doxorubicin and lysed for Western blot analysis.(B). Depletion of CaMK-III enhances orubicin induced Caspase-9 cleavage in MDA-MB231 cells. (C). Proposed mechanism of CaMK-III-mediated pathways and biological endpoints in breast cancer. CaMK-III is involved in cell proliferation, invasion and survival in breast tumors. Inhibition of CaMK-III expression induces apoptosis and activity of c-Src/Fak/paxillin as well as IGF1R and PI3K/Akt. CaMK-III expression is involved in regulation of cell proliferation, survival and angiogenesis by participating to the expression c-myc, NF-κB, cyclinD1, Bcl-2 and VEGF and HIF1α expression that are associated with tumorigenesis. CaMK-III expression suppresses PDCD4, a tumor suppressor protein known to inhibit cell migration/invasion and to induce $p27^{Kip1}$ expression.
Figure 21:
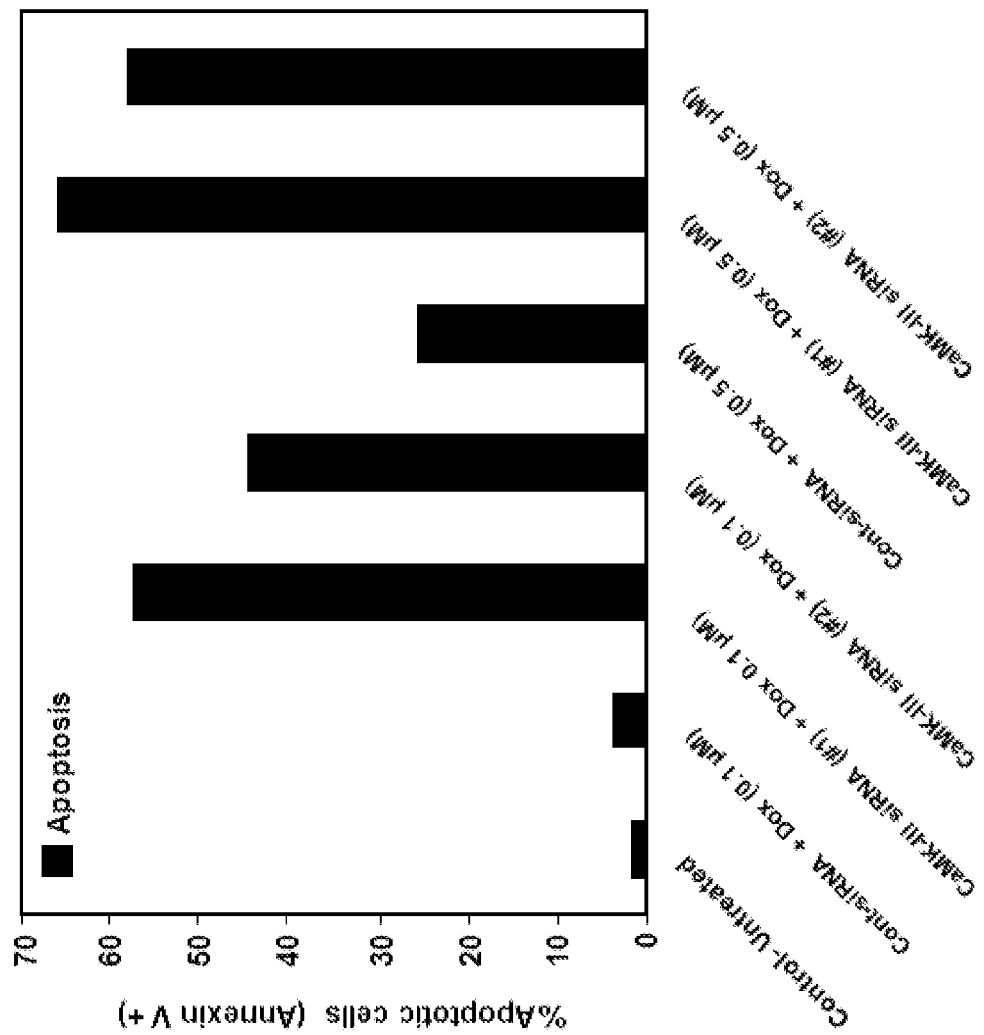
FIG. 21. Knockdown of CaMK-III by two different siRNA duplexes (#1 and #2[42]) enhances efficacy of doxorubicin (0.1 and 0.5 μM) induced apoptosis of MDA-MB231 breast cancer cells. Apoptosis was detected by Annexin V staining and the % of positive cells were quantified by FACS analysis after 48 h of doxorubicin treatment.

Downregulation of CaMK-III Leads to Apoptosis and Enhances Chemotherapy-Induced Cell Death in Drug Resistant Breast Cancer Cells In vitro and in vivo inhibition of CaMK-III resulted in induction of apoptosis (FIGS. 14D and 16C). This suggested a possible mechanism by which CaMK-III inhibition leads to growth inhibition and link between apoptosis protection and CaMK-III expression. To investigate whether inhibition of CaMK-III sensitizes drug (doxorubicin)-resistant MCF7/DoxR and MDA-MB-231 cells to chemotherapy, cells were treated with either CaMK-III (50 nM) or control siRNA (50 nM) for 24 hours and then with doxorubicin ($ED_{50}$ dose) for 48 hours. The ED50 of doxorubicin was determined from a dose-escalation study in a proliferation assay. Inhibition of CaMK-III significantly enhanced doxorubicin-induced apoptosis as indicated by caspase-9 cleavage in MCF7/DoxR and MDA-MB-231 cells compared to controls (FIGS. 17A and B). To determine the percent of cells undergoing apoptosis in response to doxorubicin alone and in combination with CaMK-III siRNA was detected by Annexin V staining and FACS analysis. The inhibition of CaMK-III dramatically increased apoptosis induced by doxorubicin (from 5% to 55%) in these MDAMB-231 cells (FIG. 21).

Figure 22:
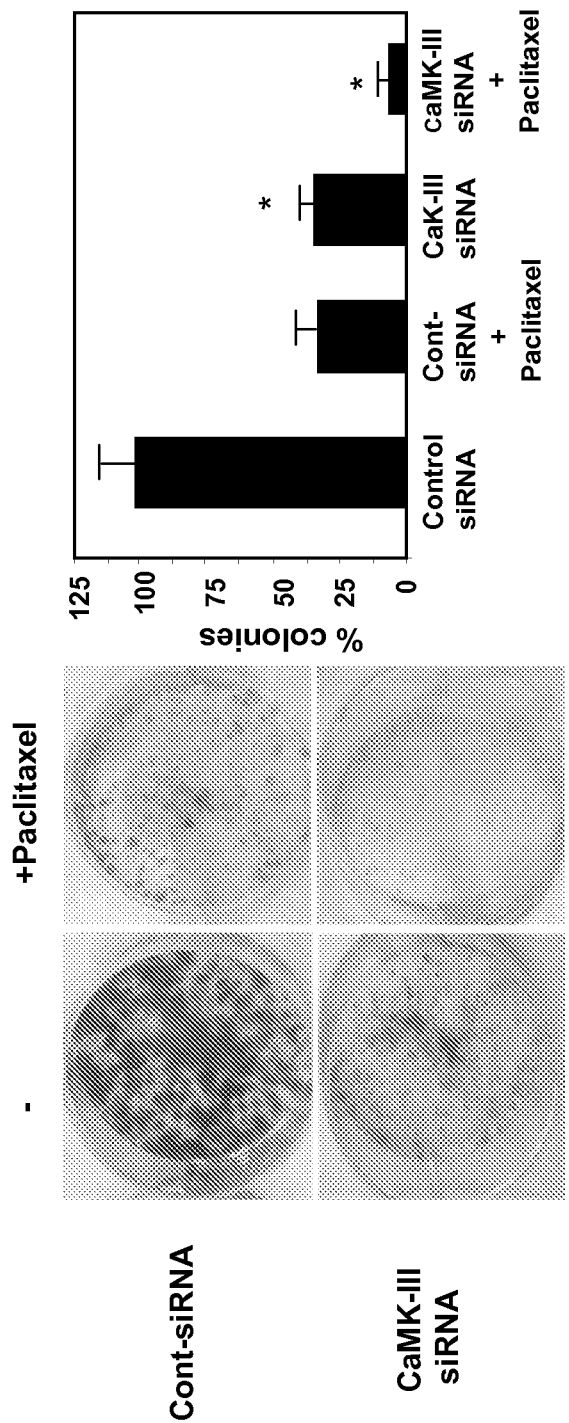
FIG. 22. Inhibition of CaMK-III by siRNA enhances efficacy of paclitaxel (2 nM) inhibited colony formation of highly aggressive and metastatic MDA-MB231 breast cancer cells.

Furthermore, downregulation of CaMK-III also enhanced paclitaxel-induced inhibition of growth (FIG. 22). These data suggested that in vitro and in vivo the inhibition of CaMK-III inhibition sensitize cells to chemotherapy and enhanced the effects of chemotherapy.

Analysis of Cell Death.

Apoptosis was assessed by an Annexin V assay, monitoring PARP and caspase 9 cleavage by Western blot. To provide a comparative assay of apoptosis by Annexin V labeling, tumor cells ($1 \times 10^6$) treated with CaMK-III siRNA or control siRNA for 24 to 96 hours were harvested and washed with PBS. Cells were resuspended in binding buffer and stained with Annexin V and propidium iodide (PI) according to the manufacturer's protocol (BD Pharmingen Annexin V kit, San Diego, Calif.). Positive cells were detected and quantified by FACS analysis.

TdT-Mediated dUTP Nick End Labeling (TUNEL) Assay.

Apoptotic events after treatment with L-siRNA and/or chemotherapy regimens were determined by the TdT-mediated dUTP nick end-labeling (TUNEL) assay (Promega, Madison, Wis.) in tumor sections as described previously according to the manufacturer's protocol [Finn R S. Ann Oncol 2008: 19:1379-86].

Statistical Analysis.

The data were expressed as the means±SD of three or more independent experiments and statistical analysis was performed using the two-tailed and paired Student's t-test. P values less than 0.05 were considered statistically significant and indicated by an asterisk.

Example 11

Analysis of Examples 1 Through 10

Here we provide the first evidence that in vivo therapeutic targeting of CaMK-III expression inhibits growth of established tumors in an orthotopic xenograft model of a highly aggressive and metastatic breast cancer. In addition, our data suggest that targeting CaMK-III may be used as a co-therapy for breast cancer to enhance efficacy of commonly used chemotherapies, such as doxorubicin and paclitaxel.

CaMK-III is a protein kinase whose activity has been shown to be absent in normal tissue adjacent to breast cancer, but significantly increased in breast cancer specimens using kinase assays (Parmer T G, et al. Br J Cancer 1999: 79:59-64). CaMK-III is selectively activated in proliferating cells and especially in the S-phase of the cell cycle (Parmer T G, et al. Cell Growth Differ 1997: 8:327-34). The data presented here demonstrate that CaMK-III is involved in breast cancer cell growth, invasion and sensitize cells to chemotherapy, suggesting that it may be a useful novel therapeutic target in breast cancer.

Our data suggest that siRNA-mediated knockdown of CaMK-III inhibits colony formation in both ER(+) and ER(−) breast cancer cells. Conversely, ectopic expression of CaMK-III significantly increases proliferation of MDA-MB-231 cells in vitro; Our findings, for the first time, show that CaMK-III is involved in the expression of two important regulators of the cell cycle, namely c-myc, cyclin D1 and $p27^{Kip1}$; inhibiting the expression of the c-myc and cyclin D1, and concomitantly inducing the expression of $p27^{Kip1}$. C-myc and cyclin D1, which promotes entry of cells into S phase, induce proliferation, can cause malignant transformation, and is overexpressed in more than 50% of breast cancer patients (Gillett C, et al. Cancer Res 1994: 54:1812-7). $p27^{Kip1}$ is a CDK-inhibitor and a key regulator of G1-to-S phase progression (Alkarain A, et al. J Mammary Gland Biol Neoplasia 2004: 9:67-80).

c-Src is a non-receptor tyrosine kinase, which is over-activated in >70% of breast cancers and recently has been proposed as a target for breast cancer. c-Src plays a critical role in tumorigenesis including, invasion/metastasis, proliferation and angiogenesis as well as chemo-resistance (Finn R S. Ann Oncol 2008: 19:1379-86). Notably, its activity is associated with the worst outcomes in breast cancer patients (Wilson G R, et al. Br J Cancer 2006: 95:1410-4). Our findings suggest that down-regulation of CaMK-III significantly inhibits ~80% of invasion of breast cancer cells (FIG. 14F). The overexpression of CaMK-III significantly increases migration and invasion of MDA-MB-231 cells, suggesting that CaMK-III participates to this process. Knockdown of CaMK-III significantly reduced tyrosine phosphorylation of Src/FAK and Paxillin activity in MDA-MB231 and MCF7/DoxR cells (Finn R S. Ann Oncol 2008: 19:1379-86). Src and FAK are activated by RTKs and integrins (Finn R S. Ann Oncol 2008: 19:1379-86). This seems to occur through an indirect mechanisms or a mediator since CaMK-III is a serine threonine kinase. CaMK-III has been suggested to inhibit translation transiently by phosphorylation of eEF2 (Ryazanov A G, et al. FEBS Lett 1991: 285:170-5). Transient inhibition of protein synthesis is an early event following mitogenic stimulation (Celis J E, et al., Proc Natl Acad Sci USA 1990: 87:4231-5) and has been shown to result in preferential elimination of proteins with short-half lives (White S J, et al. Free Radic Biol Med 2007: 43:1313-21; Tuynder M, et al., Proc Natl Acad Sci USA 2004: 101:15364-9).

Experiments examining the effect of CaMK-III inhibition and overexpression suggest that CaMK-III constitutively induces the activation of IGF-1R through c-Src-mediated phosphorylation of Tyr-1131, which is known to activate IGF-1R (Peterson J E, et al. The Journal of biological chemistry 1996: 271:31562-71). Despite its emerging role in breast and other cancers, targeting IGF-1R has only recently undergone development as a molecular cancer therapeutic (Rosenzweig S A, Atreya H S. Biochem Pharmacol 2010: 80:1115-24). IGF-1R mediates both pro-survival and anti-apoptotic signals and is known to play a role in resistance to chemo and radiation therapies (Rosenzweig S A, Atreya H S. Biochem Pharmacol 2010: 80:1115-24). Furthermore, IGF-1R activation is known to cause transformation of breast epithelium and to increase the tumorigenic potential of a number of cancers (Ozpolat B, et al. Proceedings of the American Association for Cancer Research-AACR 2010: Abstract #51084). The present study suggests that the inhibition of CaMK-III may significantly reduce IGF-1R activity through inhibition of Src (FIG. 15A), suggesting that targeting CaMK-III would have broad therapeutic effects in patients with c-Src and IGF-1R signaling-dependent cancers. Both Src and IGF1R can activate the PI3K/Akt (PKB) pathway, which plays a pivotal role in cell survival and proliferation through a number of downstream effectors and promotes breast cancer cell resistance to chemotherapy, trastuzumab, and tamoxifen (Castaneda C A, et al. Cancer metastasis reviews 2010: 29:751-9). Our findings suggest that targeting CaMK-III inhibits Akt, potentially through c-Src, thereby contributing to the apoptotic effects of inhibiting CaMK-III.

Furthermore, in vivo inhibition of CaMK-III reduced the expression of Bcl-2, which may participate in the induction of apoptosis in tumors (Akar U, et al. Autophagy 2008: 4:669-79; Oltersdorf T, et al., Nature 2005 435:677-81). In fact, we have shown that in vivo targeted silencing of Bcl-2 by liposomal Bcl-2 siRNA inhibits growth of Bcl-2-expressing breast cancer tumors, including MCF7 and MDA-MB-231 tumors in nude mice (Ozpolat B, et al. Proceedings of the American Association for Cancer Research-AACR 2010: Abstract #51084). Therefore in vivo inhibition of Bcl-2 in response to CaMK-III silencing may be important for tumor growth inhibition and enhanced response to chemotherapy.

Our data suggest that the in vivo inhibition of CaMK-III in tumors down-regulates the transcriptionally active form of NT-κB, p-p65 (Ser-536) and VEGF expression and facilitates doxorubicin-induced down-regulation of HIF1α, which are pivotal components of angiogenesis and have been validated as clinical targets in many tumors, including breast cancer. Increased expression of these molecules are linked to the activation of c-Src in breast cells through NF-κB, which is induced by IGF-1R and regulates Bcl-2 (18). Since the down-regulation of NF-κB signaling has been demonstrated to inhibit in vitro and in vivo expression of VEGF, (23) it is possible that CaMK-III may mediate its affects on VEGF expression through the modulation of NF-κB in breast cancer cells.

Example 12

5-HT Induces Proliferation of Breast Cancer Cells

Figure 24:
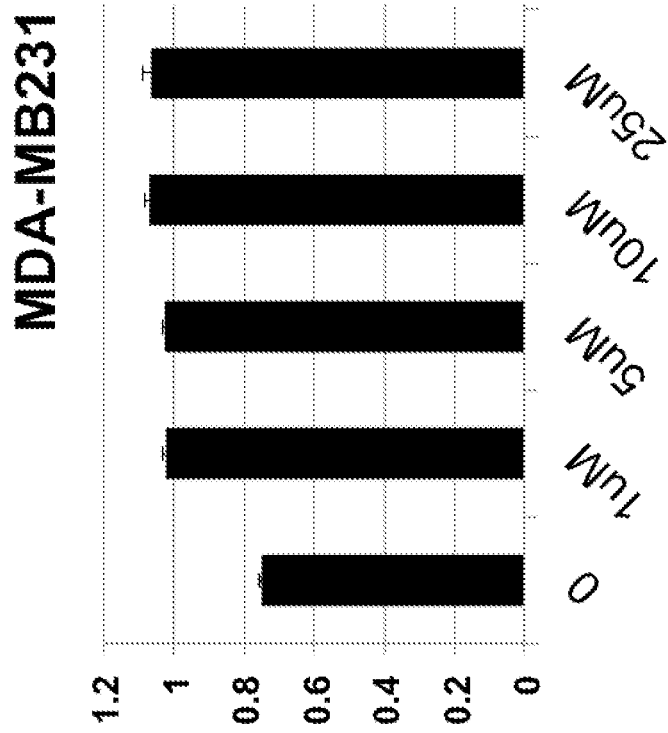
FIG. 24. To demonstrate that 5-HT plays a role in proliferation in breast cancer cells we treated the triple negative (ER-, PR- and Her2/neu-) highly metastatic and aggressive breast cancer cell line MDA-MB-231 with serotonin.

Serotonin (5-HT) has been shown to act as a growth factor on several non-tumoral cells (e.g. vascular smooth muscle cells, lung fibroblasts, renal mesangial cells) [Seuwen K, Pouyssegur J Biochem Pharmacol 1990: 39:985-990; Nemecek G M, et al. Stimulation of aortic smooth muscle cell mitogenesis by serotonin. Proceedings of the National Academy of Sciences of the United States of America 1986: 83:674-678; Takuwa N, et al. The American journal of physiology 1989: 257: F431-439] and induce proliferation in some cancer cell lines, including human lung carcinoma, hepatocellular carcinoma, pancreatic carcinoic cells [Siddiqui E J, et al. BJU Int 2006: 97:634-639; Ishizuka J, et al., Journal of cellular physiology 1992: 150:1-7; Soll C, et al. Hepatology 2010: 51:1244-1254; Cattaneo M G, et al. European journal of pharmacology 1995: 291:209-211]. However, its role in breast cancer proliferation in not well understood. To demonstrate that 5-HT plays a role in proliferation in breast cancer cells we treated the triple negative (ER-, PR- and Her2/neu-) highly metastatic and aggressive breast cancer cell line MDA-MB-231 with serotonin (FIG. 24). Serotonin also induced proliferation of ER+ MCF-7 breast cancer cells.

Cell Lines, Culture Conditions, and Reagents.

The human breast cancer cell lines MDA-MB-231 and MCF-7/R (drug resistant) were obtained from ATTC and Dr. Kapil Mehta, PhD (MD Anderson Cancer Center), respectively. Cells were cultured at 37° C. in DMEM supplemented with 5% FBS in a humid incubator with 5% $CO_2$. For cell proliferation experiments, cells were seeded at a density of $1–2\times10^5$ cells in T-25 tissue culture flasks. Adherent cells were collected by trypsinization, and cell numbers were determined using a Neubauer cell counting chamber. All experiments were repeated at least three times.

Example 13

5-HT1B Receptor is Over Expressed in Breast Cancer Cell Lines

Figure 25:
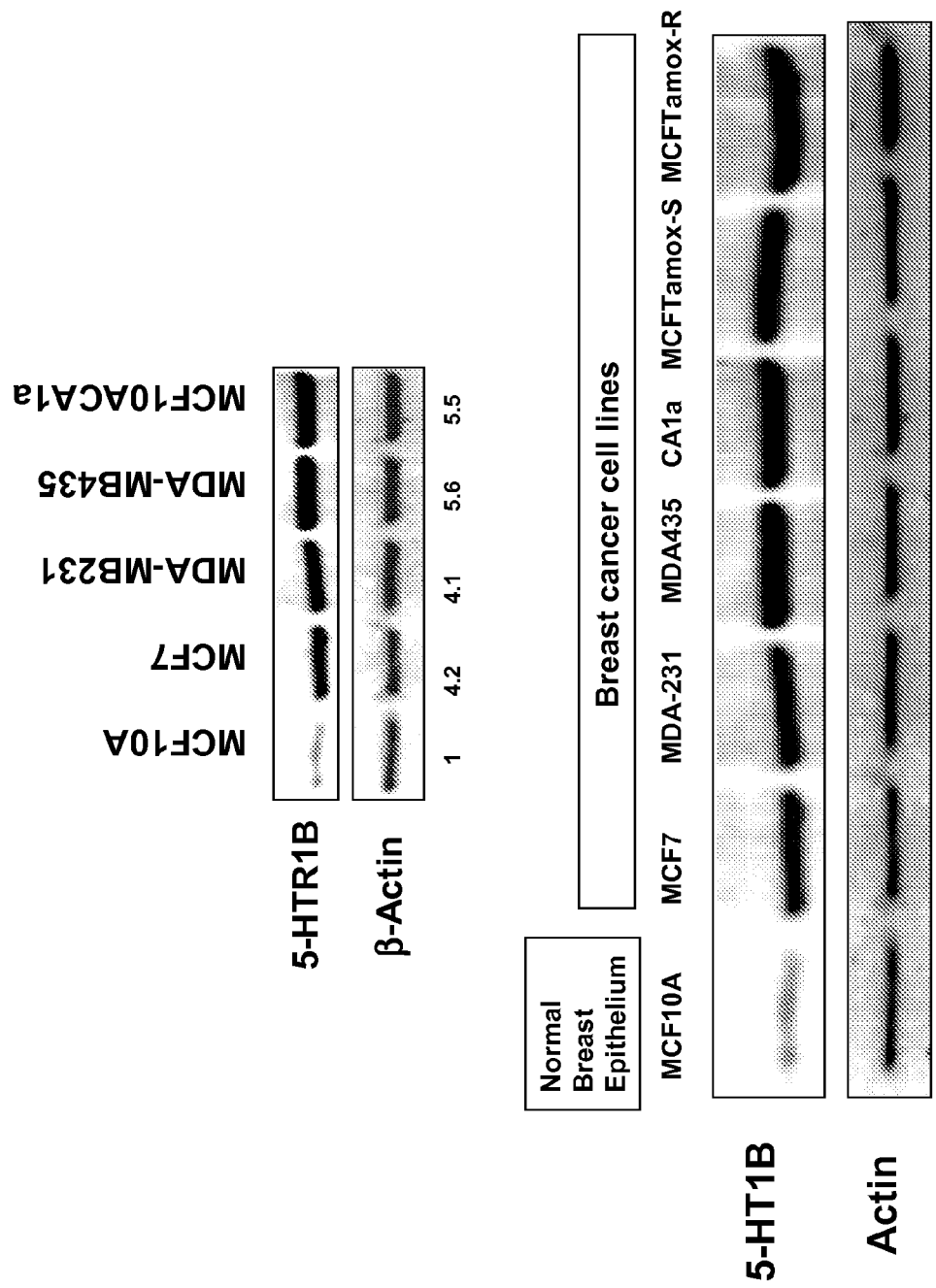
FIG. 25. 5-HT1B receptor is over expressed in breast cancer cell lines To elucidate the mechanism of 5-HT-induced cell proliferation in breast cancer cells, 5-HTR1B receptor protein expression was assessed by Western blot analysis in a normal breast epithelium MCF10A cell line and compared to other breast cancer cell lines. These included the estrogen receptor negative human ER(-) breast cancer cell lines, MDA-MB-231, MDA-MB-435 and the estrogen receptor-positive ER(+) breast cancer cell lines, MCF-7, chemotherapy (doxorubicin) resistant MCF-7/Dox-R cells, MCF10CA1a (CA1a), a metastatic human breast cancer line. All breast cancer cell lines showed higher expression of 5-HTR1B than the normal breast epithelium MCF10A cell line.

To elucidate the mechanism of 5-HT-induced cell proliferation in breast cancer cells, 5-HTR1B receptor protein expression was assessed by Western blot analysis in a normal breast epithelium MCF10A cell line and compared to other breast cancer cell lines. These included the estrogen receptor-negative human ER(-) breast cancer cell lines, MDA-MB-231, MDA-MB-435 and the estrogen receptor-positive ER(+) breast cancer cell lines, MCF-7, chemotherapy (doxorubicin) resistant MCF-7/Dox-R cells, MCF10CA1a (CA1a), a metastatic human breast cancer line. All breast cancer cell lines showed higher expression of 5-HTR1B than the normal breast epithelium MCF10A cell line (FIG. 25), suggesting that 5-HT1B receptor protein levels are upregulated in breast cancer cells.

In our studies we found that 5-HT1B receptor is over expressed in almost all Estrogen receptor ER(+), ER (−) highly aggressive and metastatic cells as well as chemotherapy (doxorubicin) resistant breast cancer cells compared to normal breast epithelium cells (MCF10A). We also found that that serotonin induces proliferation of breast cancer cells and that a specific inhibition of the serotonin 5-HT1B receptors by siRNA and a pharmacological inhibitor inhibits proliferation, colony formation and induce significant apoptosis and autophagic cell death.

Figure 3:
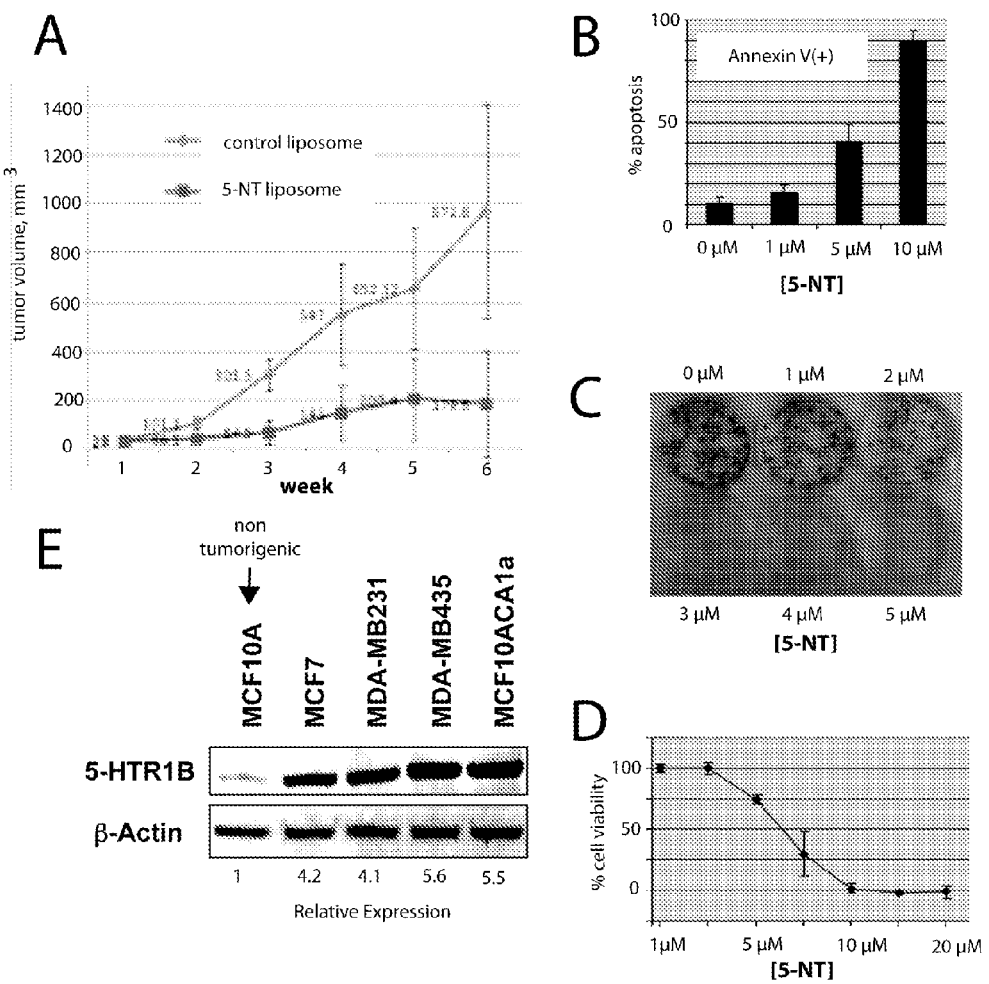
FIG. 3. New role for triptan derivatives targeting the 5-HT$_{1B}$ receptor as a therapeutic modality for breast cancer. (A). In vivo targeting of the 5-HT$_{1B/1D}$ receptor by neutral lipid-based (DOPC)-liposomal 5-NT in nude mice bearing MDA-MB-231 breast cancer xenografts significantly inhibits tumor growth. Treatments, twice per week (4 weeks) were safe and effective. Methods: Phospholipid dioleoylphosphatidylcholine (DOPC) and triptan 5-NT were mixed in tertiary butanol at a lipid:5-NT ratio of 10:1 (w/w). Tween 20 was added at a ratio of 1:20 ratio (w/w) and the mixture lyophilized overnight. The powder was reconstituted in saline and sonicated for one minute. The liposome formulation was injected (100 µl) into the tail vein. (B). 5-NT induces apoptotic cell death of ER(+) MCF-7 cells. (C). 5-NT inhibits colony formation of ER(+) MCF-7 cells. (D). 5-nonylytryptamine (5-NT) (Glennon et al., 1996) inhibits proliferation of triple negative MDA-MB-231, as well as ER(+) MCF-7 and MCF7/Dox resistant cells. (E). The 5-HT$_{1B}$ receptor is over-expressed in triple negative highly aggressive, and metastatic breast cancer cells as well as drug resistant (i.e. tamoxifen and doxorubicin) breast cancer cells. Methods: Blots were visualized with a FluorChem 8900 imager and quantified by a densitometer using the Alpha Imager application program.
Figure 4:
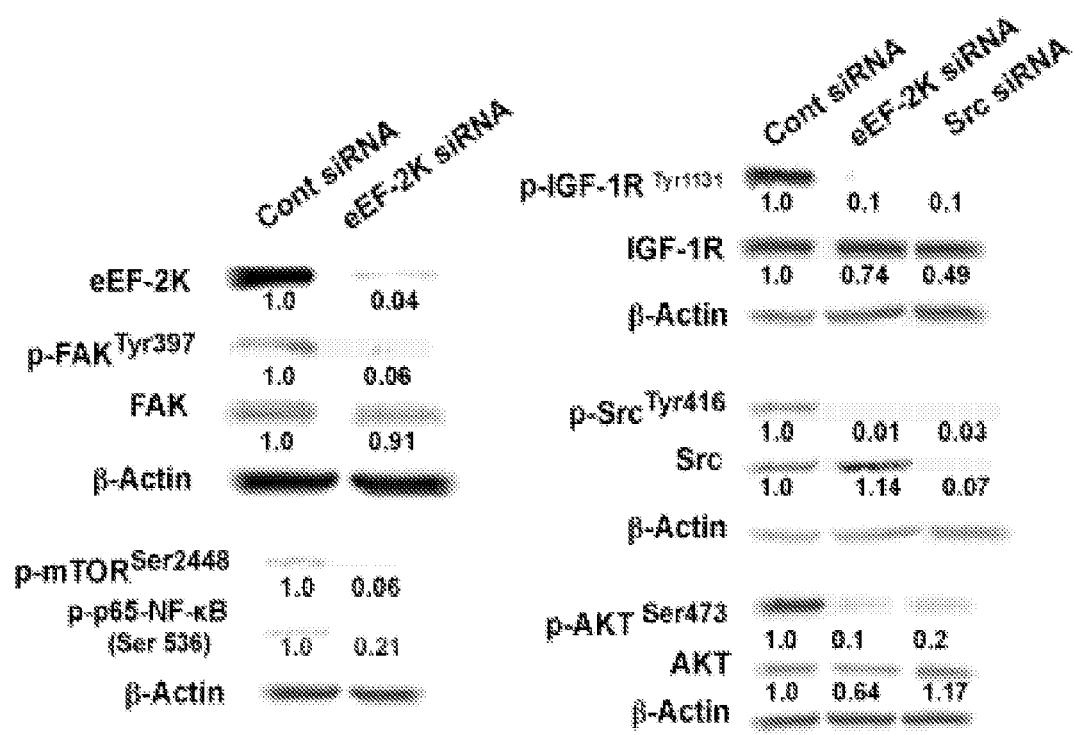
FIG. 4. eEF-2K regulates the activation of IGF-1R, Akt, and mTOR through Src in MDA-MB-231 cells. Western blot analysis shows that eEF-2K siRNA inhibits eEF-2K expression. This leads to the concomitant down-regulation of Src activity (as determined by detection of phospho Tyr-416). The down-regulation of eEF-2K or Src leads to the down-regulation of IGF-1R and Akt activity. Methods: Cells were transfected by eEF-2K or Src siRNA (75 nM) for 48 h and assessed by Western blotting as in FIG. 5.

Several 5-HT receptors (1D, 1F, 2C and 3A) were found to be over-expressed in some breast cancer cells, compared to MCF10A normal breast epithelium (Pai V P, et al., Breast Cancer 2009: Res 11: R81). In addition to the $5\text{-}HT_{1D}$ receptor we found, for the first time that the $5\text{-}HT_{1B}$ receptor is also over-expressed in ER(-), ER(+) and drug resistant breast cancer cells (FIG. 3E). Preliminary studies with SB-224289 a selective 5-HT$_{1B}$ receptor antagonist (Selkirk et al., 1998) provided the first insight into a novel pathway for the regulation of the activity of several signaling pathways by the 5-HT1B serotonin receptor. We found that SB224289 induces apoptosis and inhibits the STAT3 and Bcl-2 pathways, as well as the PI3K/Akt pathway. These are activated in the majority of breast cancers.

Western Blot Analysis.

After treatment the cells were trypsinized and collected by centrifugation, and whole-cell lysates were obtained using a lysis buffer as described previously [Akar U, et al. Mol Cancer Res 2007: 5:241-249]. Total protein concentration was determined using a DC protein assay kit (Bio-Rad, Hercules, Calif.). Aliquots containing 30 g of total protein from each sample were subjected to sodium dodecyl sulfate-polyacrylamide gel electrophoresis (SDS-PAGE) with a 4-20% gradient and electrotransferred to nitrocellulose membranes. The membranes were blocked with 5% dry milk in Tris-buffered saline-Tween 20 (TBST), probed with primary antibodies anti EREK1/2 or p-ERK1/2 (Cell signaling), polyclonal LC3 antibody (Novus biologicals, Littleton, Colo.). The antibodies were diluted in TBST containing 2.5% dry milk and incubated at 4 C overnight. After the membranes were washed with TBST, they were incubated with horseradish peroxidase-conjugated anti-rabbit or anti-mouse secondary antibody (Amersham Life Science, Cleveland, Ohio). Mouse anti-actin and donkey anti-mouse secondary antibodies (Sigma Chemical, St. Louis, Mo.) were used to monitor-actin expression to ensure equal loading of proteins. Chemiluminescent detection was performed with Chemi-glow detection reagents (Alpha Innotech, San Leandro, Calif.). The blots were visualized with a FluorChem 8900 imager and quantified by a densitometer using the Alpha Imager application program (Alpha Innotech, San Leandro, Calif.).

Example 14

Figure 26:
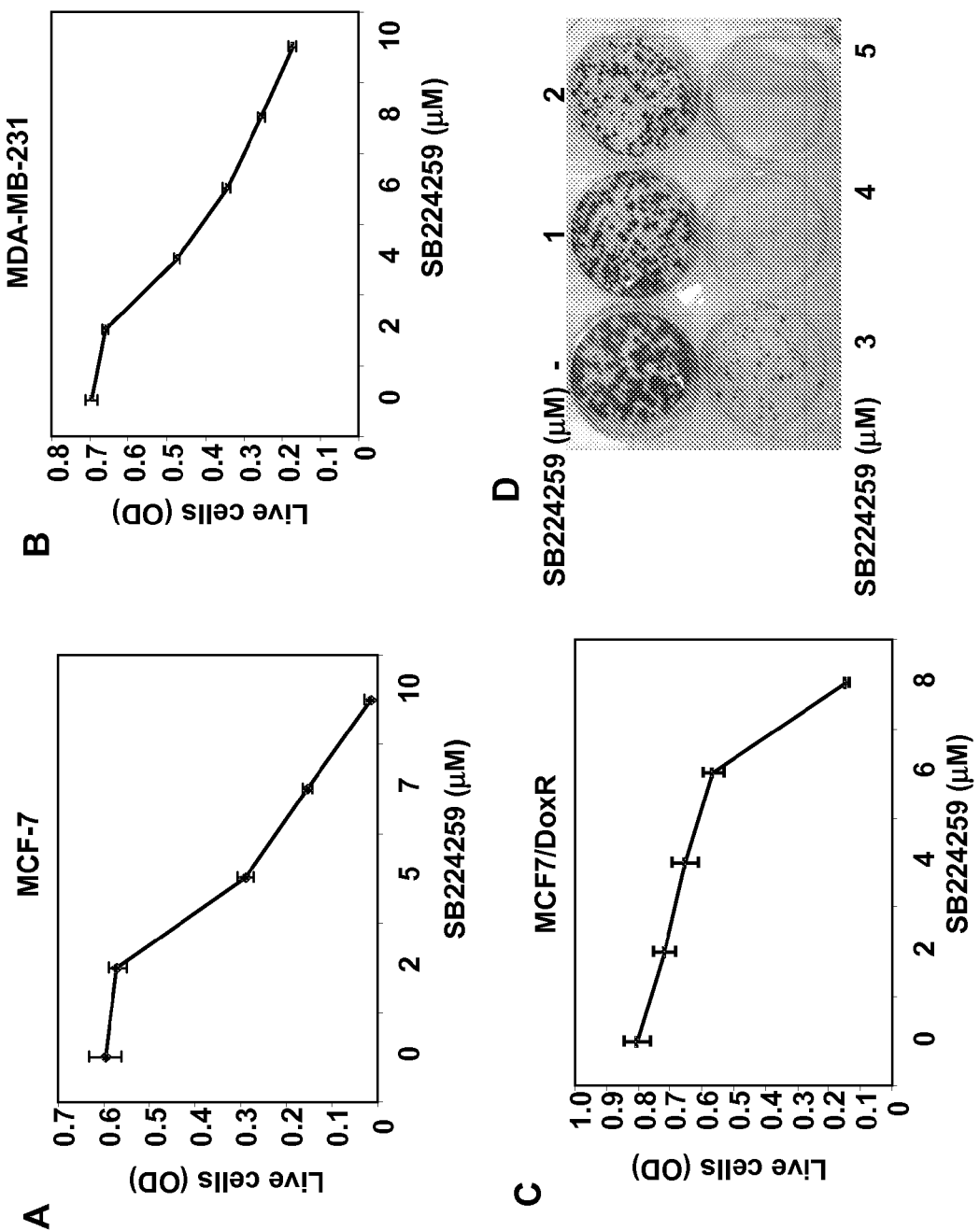
FIG. 26. Specific inhibition of the 5-HT1B receptor inhibits proliferation of breast cancer cells. To determine the role of the 5-HT1B receptor we inhibited 5-HTR1B signaling in breast cancer cells using a specific antagonist SB224289 and assessed cell proliferation of [23]. This resulted in a dose-dependent inhibition of MCF7 (A), MB-231 (B) and MCF7/Dox resistant (C) cell proliferation as detected by an MTS assay. Another specific antagonist (SB216641) of 5-HTR1B also showed a similar ability to inhibit the growth of breast cancer cells. The inhibition of 5-HT1B significantly inhibited the formation of MCF7 cell colonies in a dose dependent manner (D). To study the effect of 5-HT1B on the survival and colony formation of breast cancer cells a clonogenic survival assay was performed using various concentrations of SB224259 over a period of two weeks.

Specific Inhibition of the 5-HT1B Receptor Inhibits Proliferation of Breast Cancer Cells To determine the role of the 5-HT1B receptor we inhibited 5-HTR1B signaling in breast cancer cells using a specific antagonist SB224289 and assessed cell proliferation of [23]. This resulted in a dose-dependent inhibition of MCF7, MB-231 and MCF7/Dox resistant cell proliferation as detected by an MTS assay (FIG. 26A-C). Another specific antagonist (SB216641) of 5-HTR1B also showed a similar ability to inhibit the growth of breast cancer cells.

Cell Viability and Growth Assays.

Viable and dead cells were detected by the trypan blue exclusion assay, where viable cells (non-stained) with intact membrane are able to exclude the dye, while dead cells take up the coloring blue agent from the media. To quantitatively assess the viability and/or proliferation of cells a MTS assay was used, which incorporates a redox indicator that changes color in response to metabolic activity. To study cell viability in response to CaMK-III siRNA or control siRNA and plasmid encoding CaMK-III or empty plasmid transfection cells were seeded in 96-well plates at a density of 3×103 cells per well in 100 μl of medium. Next day the medium was removed and cells were transfected with siRNA at different concentrations in 100 μl of medium plus transfection mix. Two days after transfection, the medium was removed and replaced by 180 μl of medium plus 20 μl of MTS and the cells were incubated under normal conditions until the color changed. Plates were read at dual wavelengths (570-595 nm) in an Elisa plate reader (Kinetic Microplate Reader, Molecular Devices Corporation, Sunnyvale, Calif.).

Example 15

Inhibition of 5-HT1B Leads to Reduce Colony Formation of Breast Cancer Cells

Figure 27:
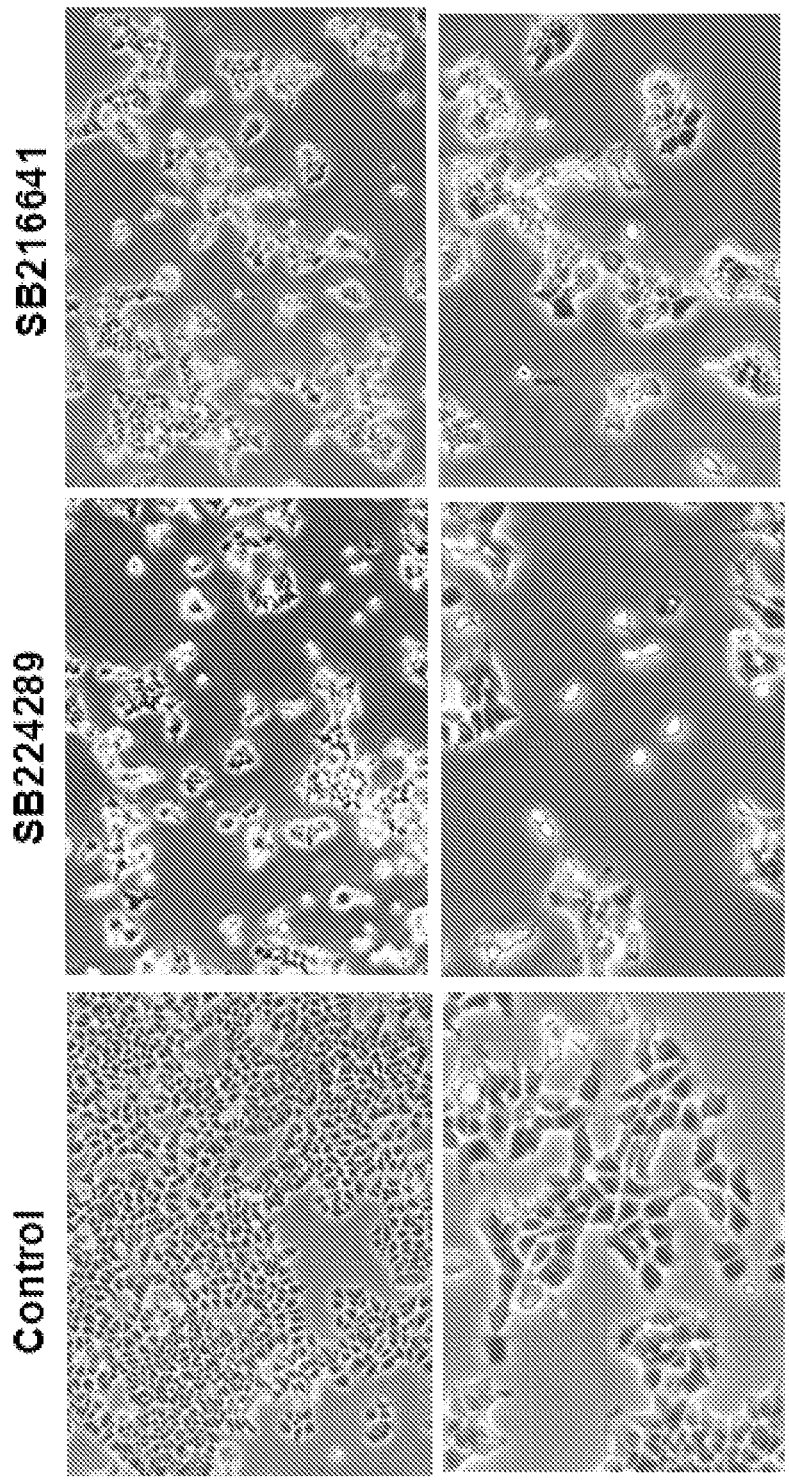
FIG. 27. Inhibition of 5-HT1B leads to reduced colony formation of breast cancer cells. The appearance of cells after 72 h of treatment of MDA-MB231 cells. Cell death and detachment as well as reduced cell number was observed. This assay is based on the ability of a single cell to grow into a colony [24]. Thus, compared to control experiments (untreated), SB224259-treated cells grew more slowly and produced fewer colonies. We found similar effects in MDA-MB-231 cells with SB224289. Overall, these data suggest that 5-HTR1B contributes to colony formation as inhibition of this receptor reduced colonies formed by breast cancer cells.

To study the effect of 5-HT1B on the survival and colony formation of breast cancer cells a clonogenic survival assay was performed using various concentrations of SB224259 over a period of two weeks. This assay is based on the ability of a single cell to grow into a colony [Franken N A, et al. Nat Protoc 2006: 1:2315-2319]. The inhibition of 5-HT1B significantly inhibited the formation of MCF7 cell colonies in a dose dependent manner (FIG. 26D). Thus, compared to control experiments (untreated), SB224259-treated cells grew more slowly and produced fewer colonies. We found similar effects in MDA-MB-231 cells with SB224289. Overall, these data suggest that 5-HTR1B contributes to colony formation as inhibition of this receptor reduced colonies formed by breast cancer cells. FIG. 27 shows the appearance of cells after 72 h of treatment of MDA-MB231 cells. Cell death and detachment as well as reduced cell number was observed.

Clonogenic Survival Assay.

This assay is an in vitro cell survival assay based on the ability of a single cell to grow into a colony. Briefly, cells (500 cells/well) were transfected with different siRNA as described above and at 48 h post-transfection, cells were trypsinized and seeded into 6-well plates in the medium (500 cells/mL). Cells were transfected with control siRNA or CaMK-III siRNA every week and grown for 2 to 3 weeks. Cells were stained with crystal violet and colonies cells were counted. Each group was assayed in triplicate dishes, and each experiment was repeated twice.

Example 16

Figure 28:
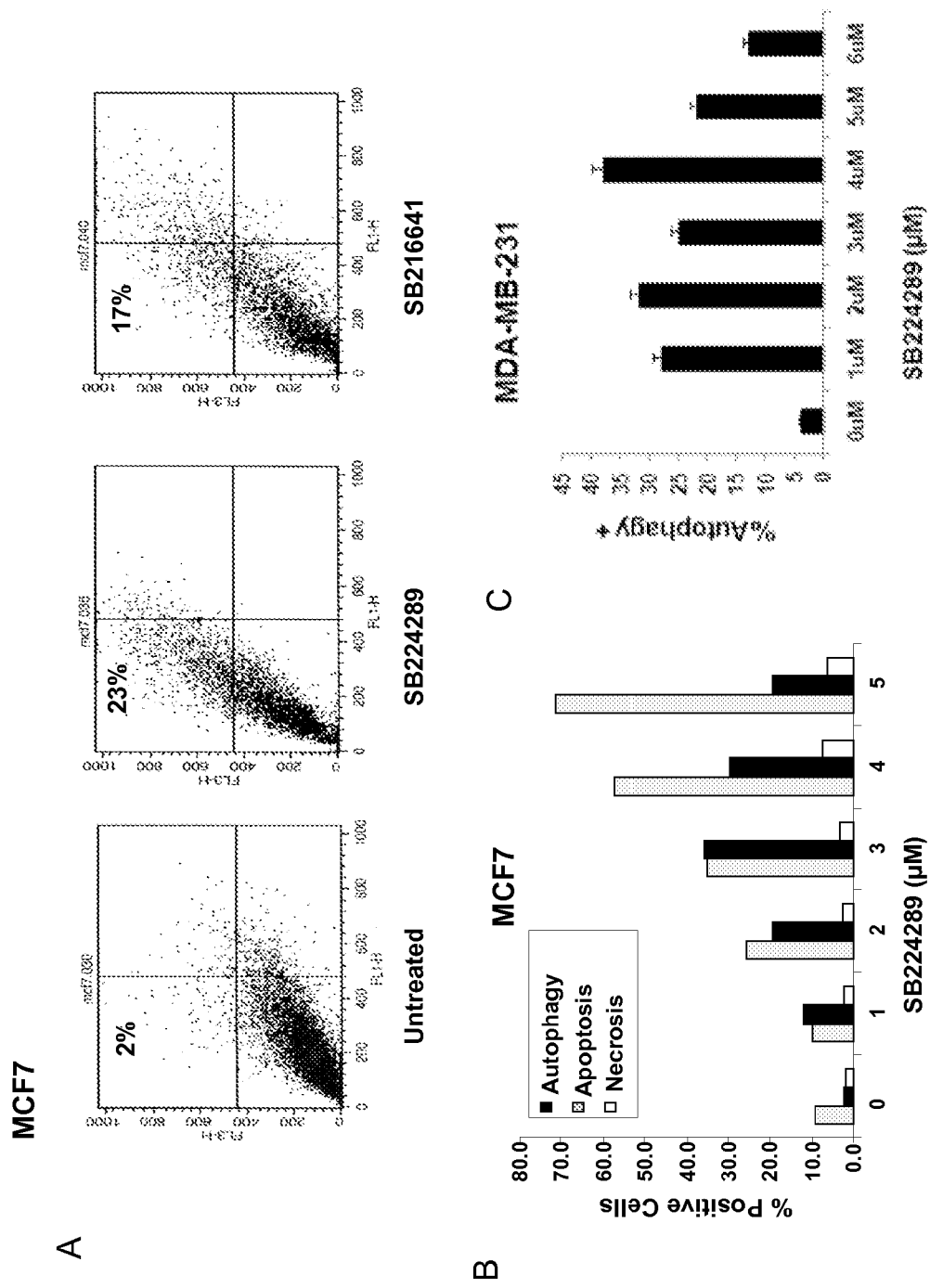
FIG. 28. Inhibition of the 5-HT1B receptor induces autophagy and apoptosis in breast cancer cells. To determine the role of serotonin 5-HT1B receptor in cell survival and the mechanism of growth inhibition induced by HT1B inhibitors we investigated cell death in breast cancer cells. When 5-HT1B was inhibited by either SB224289 or SB216641 we detected marked induction of autophagy in (A) as detected by acridine orange staining, apoptosis by Annexin V and necrosis by propidium iodide (PI) staining and FACS analysis (B) in MCF7 breast cancer cells. Induction of acidic vacuoles by acridine orange staining was also observed in MDA-MB231 cells after SB224289 treatment for 72 hours (p<0.05) (FIG. 28C). Quantification of acridine orange stained vesicular organelles by flow cytometry indicated that the percentage of positive cells in SB224289 or SB216641-treated cells (23% and 17%, respectively) were significantly higher than in the control untreated cells (2%). SB224289 treatment also induced apoptosis in a dose dependent manner in MCF cells (B). As the dose was increased SB224289 (higher than $EC_{50}$ 4.4 μM) a shift from autophagy to apoptosis was observed, with reduced autophagy.

Inhibition of the 5-HT1B Receptor Induces Autophagy and Apoptosis in Breast Cancer Cells To determine the role of serotonin 5-HT1B receptor in cell survival and the mechanism of growth inhibition induced by HT1B inhibitors we investigated cell death in breast cancer cells. When 5-HT1B was inhibited by either SB224289 or SB216641 we detected marked induction of autophagy (FIG. 28A) as detected by acridine orange staining, apoptosis by Annexin V and necrosis by propidium iodide (PI) staining and FACS analysis (FIG. 28B) in MCF7 breast cancer cells. Induction of acidic vacuoles by acridine orange staining was also observed in MDA-MB231 cells after SB224289 treatment for 72 hours (p<0.05) (FIG. 28C). Quantification of acridine orange stained vesicular organelles by flow cytometry indicated that the percentage of positive cells in SB224289 or SB216641-treated cells (23% and 17%, respectively) were significantly higher than in the control untreated cells (2%). SB224289 treatment also induced apoptosis in a dose dependent manner in MCF cells (FIG. 28B). As the dose was increased SB224289 (higher than EC$_{50}$ 4.4 μM) a shift from autophagy to apoptosis was observed, with reduced autophagy. Induction of autophagy was further evidenced by induction of LC3-II, a specific marker of autophagy in response to SB224284 in MCF7 and doxorubicin resistant MCF7 cells (MCF7/Dox-R) (FIG. 29A).

To further demonstrate that inhibition of HTR1B inhibition leads to autophagy in breast cancer cells, we transfected MCF-7 cells with green fluorescent protein-tagged LC3

Figure 29:
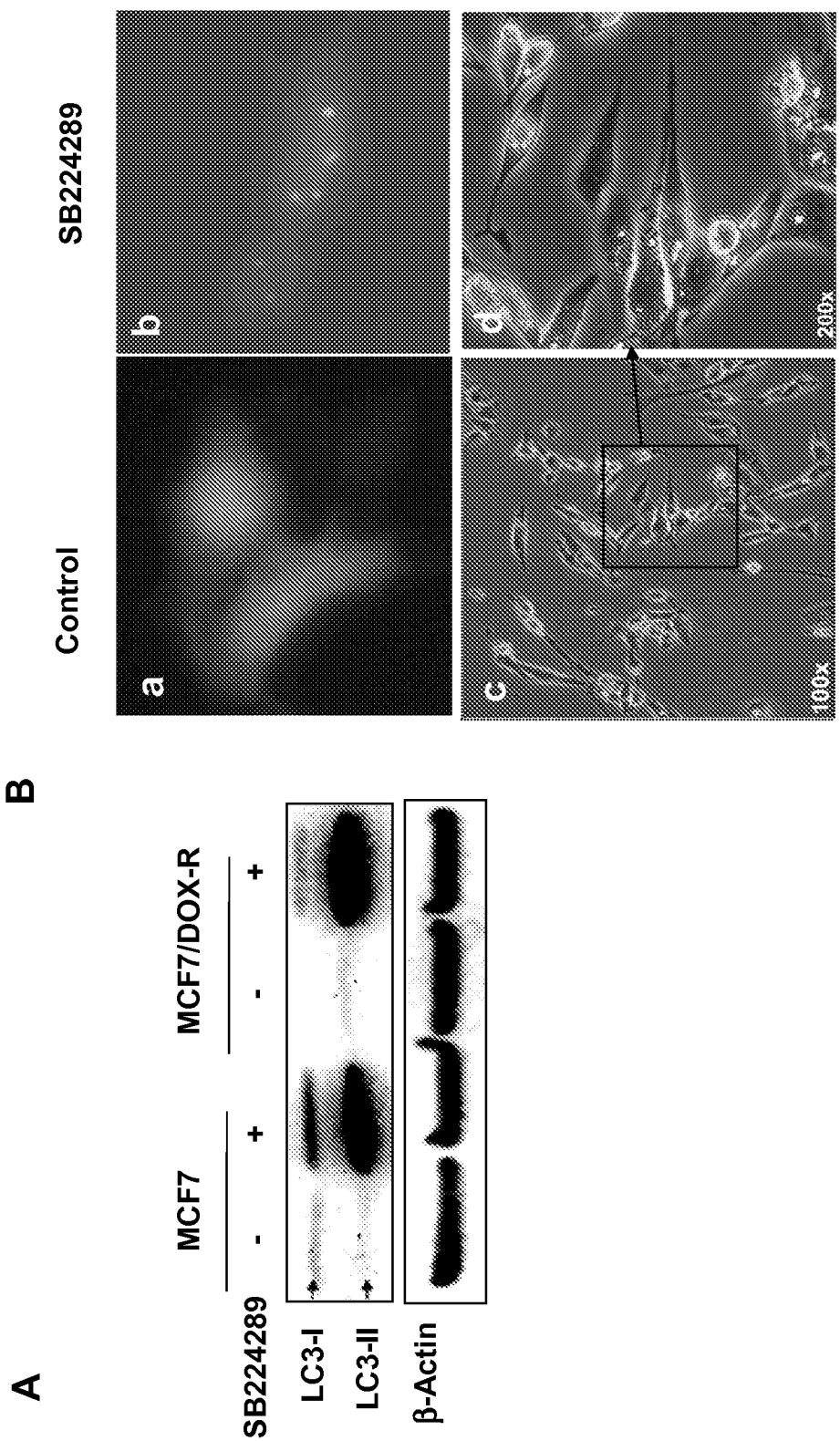
FIG. 29. Induction of autophagy was further evidenced by induction of LC3-II, a specific marker of autophagy in response to SB224284 in MCF7 and doxorubicin resistant MCF7 cells (MCF7/Dox-R) (A). To further demonstrate that inhibition of HTR1B inhibition leads to autophagy in breast cancer cells, we transfected MCF-7 cells with green fluorescent protein-tagged LC3 (GFP-LC3) expression plasmid and determined the accumulation of GFP-LC-II protein in autophagosomes after treatment with HTR1B inhibitor SB224289 (B). When autophagy is induced, LC3-II, a cleaved product of LC3, specifically localizes to the membrane of autophagosomes [17]. Therefore accumulation of GFP-LC3-II in the vacuoles following the SB224289 treatment indicates formation of autophagosomes and induction of autophagy in the cells (B a-b). In control or untreated cells, none of the above changes were observed except diffuse expression pattern of GFP-LC3 detected by fluorescence microscopy. In HTR1B inhibitor treated cells, GFP-LC3 distributes from a diffuse cytoplasmic pattern to form punctuate structures that indicate preautophagosomal and autophagosomal membranes. (Bc-d) shows pictures of the cells with formation of autophagic vacuoles by phase contrast microscopy.

(GFP-LC3) expression plasmid and determined the accumulation of GFP-LC-II protein in autophagosomes after treatment with HTR1B inhibitor SB224289 (FIG. 29B). When autophagy is induced, LC3-II, a cleaved product of LC3, specifically localizes to the membrane of autophagosomes [Akar U, et al. Autophagy 2008: 4:669-679]. Therefore accumulation of GFP-LC3-II in the vacuoles following the SB224289 treatment indicates formation of autophagosomes and induction of autophagy in the cells (FIG. 29B a-b). In control or untreated cells, none of the above changes were observed except diffuse expression pattern of GFP-LC3 detected by fluorescence microscopy. In HTR1B inhibitor treated cells, GFP-LC3 distributes from a diffuse cytoplasmic pattern to form punctuate structures that indicate preautophagosomal and autophagosomal membranes. FIG. 29Bc-d shows pictures of the cells with formation of autophagic vacuoles by phase contrast microscopy.

Figure 30:
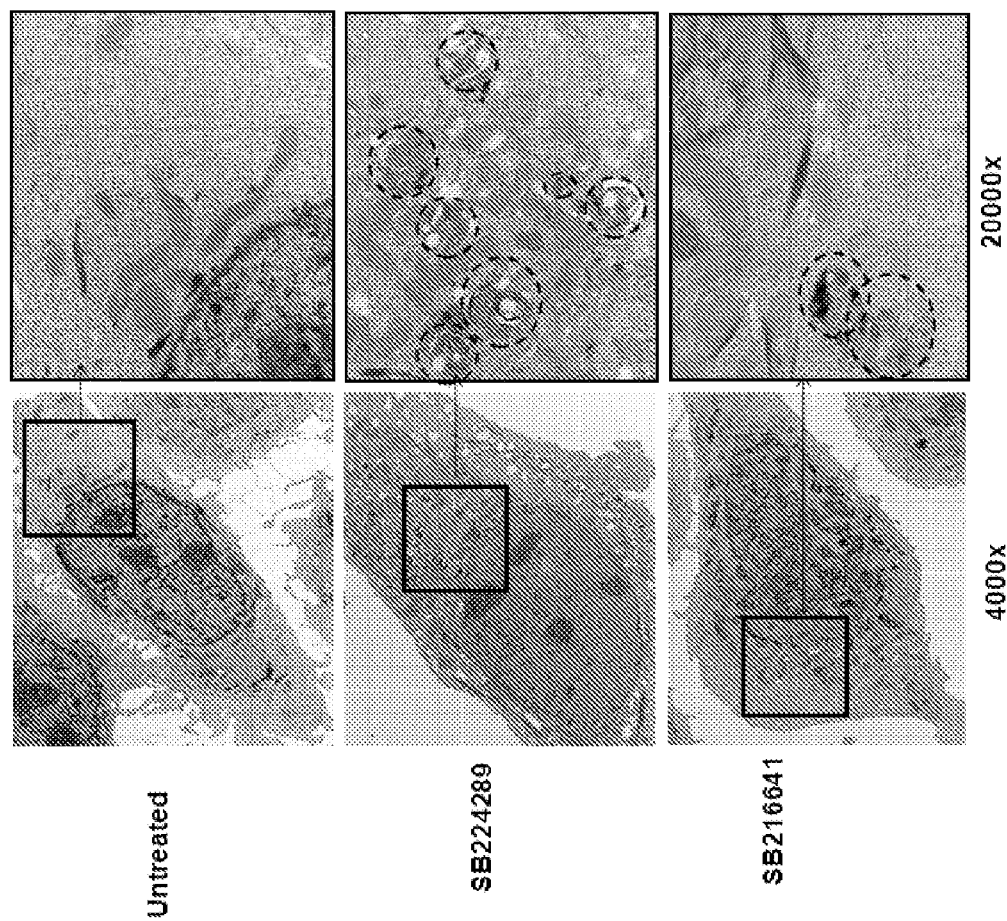
FIG. 30. To further support the findings we analyzed induction of autophagy by transmission electron microscopy, which clearly demonstrated that inhibition of HT1B by SB224289 or SB216641 treatment induced formation of autophagic vesicles containing cellular organelles, with merging of autophagic vesicles with lysosomes and lysed cellular content in the autophagosomes, indicating activity of lysosomal function and degradation. These results suggest that inhibition of HTR1B induces autophagy breast cancer cells.

To further support the findings we analyzed induction of autophagy by transmission electron microscopy, which clearly demonstrated that inhibition of HT1B by SB224289 or SB216641 treatment induced formation of autophagic vesicles containing cellular organelles, with merging of autophagic vesicles with lysosomes and lysed cellular content in the autophagosomes, indicating activity of lysosomal function and degradation (FIG. 30). These results suggest that inhibition of HTR1B induces autophagy breast cancer cells.

Analysis of Cell Death.

Apoptosis was assessed by an Annexin V assay, monitoring PARP and caspase 9 cleavage by Western blot. To provide a comparative assay of apoptosis by Annexin V labeling, tumor cells ($1\times10^6$) treated with CaMK-III siRNA or control siRNA for 24 to 96 hours were harvested and washed with PBS. Cells were resuspended in binding buffer and stained with Annexin V and propidium iodide (PI) according to the manufacturer's protocol (BD Pharmingen Annexin V kit, San Diego, Calif.). Positive cells were detected and quantified by FACS analysis.

Evaluation of Autophagy by Detection of Acidic Vesicular Organelles.

To detect and quantify acidic vesicular organelles, we stained cells with acridine orange as described previously.[31] The number of acridine orange-positive cells was determined by fluorescence-activated cell sorting (FACS) analysis. Cell morphology was examined using fluorescence microscopy (Nikon, Melville, N.Y.) with the cells remaining in their culture flasks.

Transmission Electron Microscopy.

MCF-7 cells were grown on six-well plates, treated with Bcl-2 siRNA or control siRNA or left untreated, fixed for 2 hours with 2.5% glutaraldehyde in 0.1 M cacodylate buffer (pH 7.4), postfixed in 1% $OsO_4$ in the same buffer, and then subjected to the electron microscopic analysis as described previously [Akar U, et al. Mol Cancer Res 2007: 5: 241-249]. Representative areas were chosen for ultra-thin sectioning and viewed with a Hitachi 7600.

Statistical Analysis.

The data were expressed as the means±SD of three or more independent experiments and statistical analysis was performed using the two-tailed and paired Student's t-test. P values less than 0.05 were considered statistically significant and indicated by an asterisk.

Example 17

Figure 31:
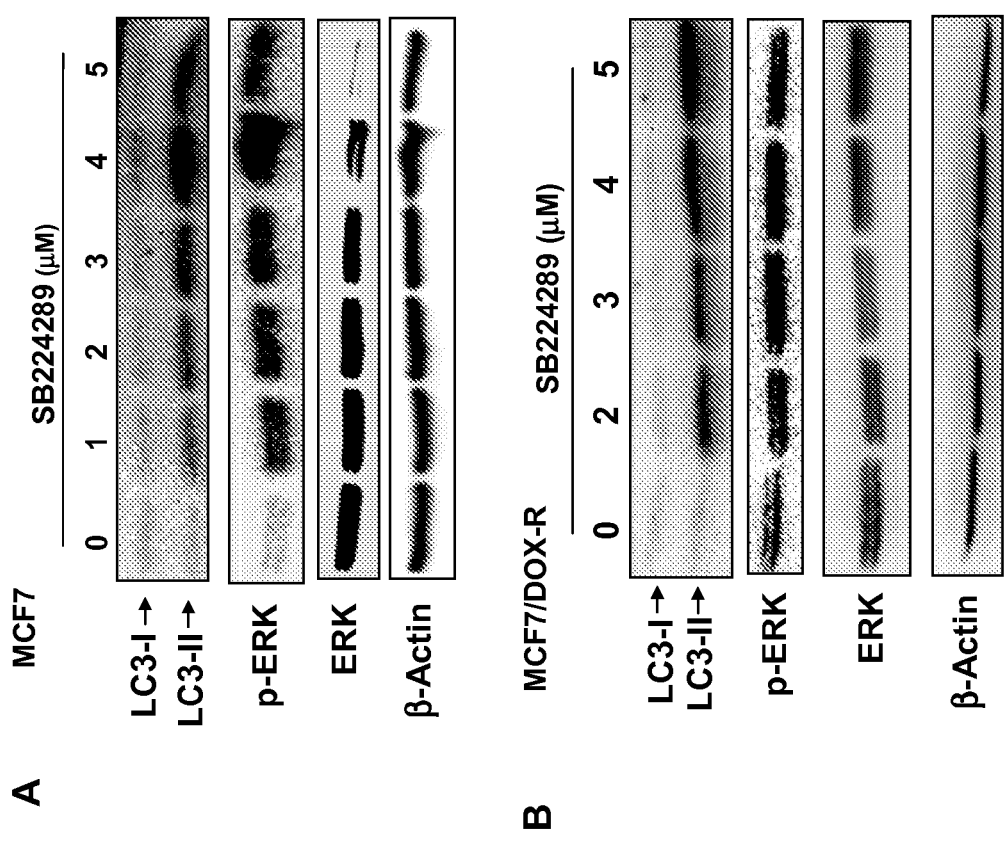
FIG. 31. 5-HT1B modulates autophagy through activity of ERK1/2-MAPK signaling in breast cancer cells. Induction of ERK1/2 has been shown to participate in the induction of autophagy. We investigated whether inhibition of HT1B induces ERK-MAPK signaling in breast cancer cells. (A) and (B) Blockage of the 5-HT1B receptor with SB224289 induced phosphorylation of ERK (p42/p44) in MCF7, MCF7/Dox resistant and MDA-MB-231 as detected by Western blot analysis (FIG. 31-32).
Figure 32:
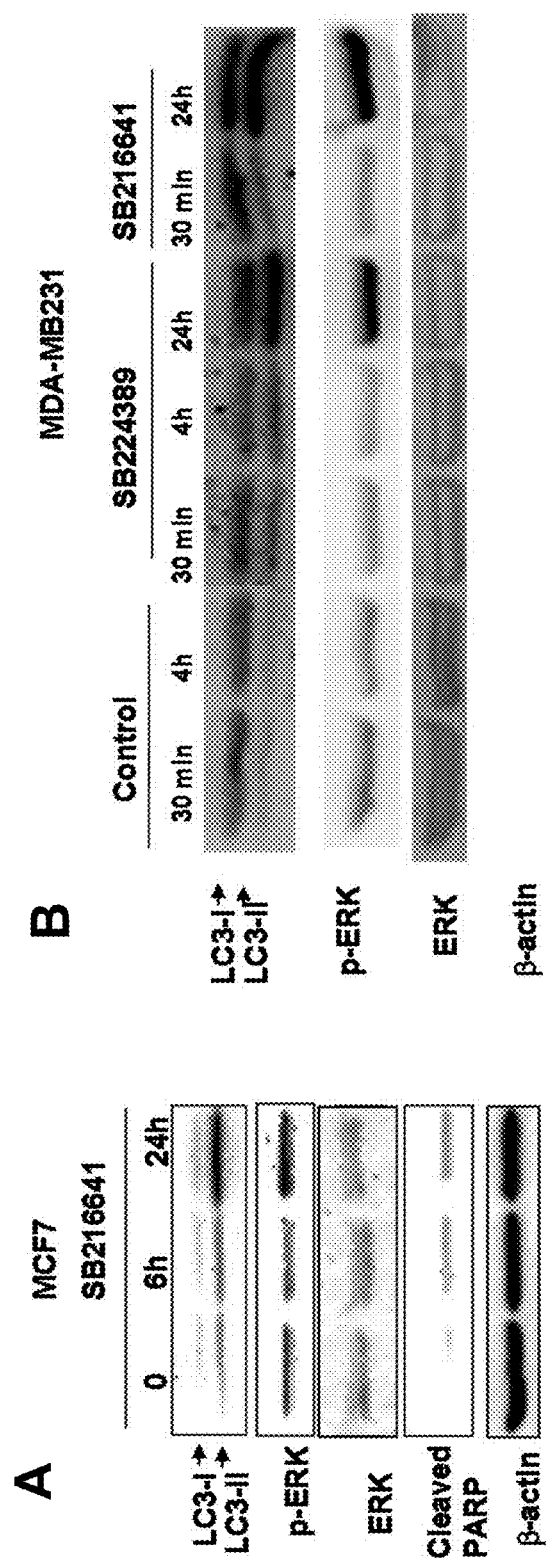
FIG. 32. Induction of ERK1/2 has been shown to participate in the induction of autophagy. We investigated whether inhibition of HT1B induces ERK-MAPK signaling in breast cancer cells. Blockage of the 5-HT1B receptor with SB224289 induced phosphorylation of ERK (p42/p44) in MCF7, MCF7/Dox resistant and MDA-MB-231 as detected by Western blot analysis (FIG. 31-32). SB216641 also induced phosphorylation of ERK (p42/p44) and LC3-III in MCF7 cells (A). Induction of ERK signaling was closely associated with induction of autophagy marker LC3-II in all treatments and breast cancer cell lines tested including MDA-MB231 in response to inhibition of HT1B signaling by 2 different inhibitors (B).

5-HT1B Modulates Autophagy Through Activity of ERK1/2-MAPK Signaling in Breast Cancer Cells induction of ERK1/2 has been shown to participate in the induction of autophagy. We investigated whether inhibition of HT1B induces ERK-MAPK signaling in breast cancer cells. Blockage of the 5-HT1B receptor with SB224289 induced phosphorylation of ERK (p42/p44) in MCF7, MCF7/Dox resistant and MDA-MB-231 as detected by Western blot analysis (FIG. 31-32). SB216641 also induced phosphorylation of ERK (p42/p44) and LC3-III in MCF7 cells (FIG. 32A). Induction of ERK signaling was closely associated with induction of autophagy marker LC3-II in all treatments and breast cancer cell lines tested including MDA-MB231 in response to inhibition of HT1B signaling by 2 different inhibitors.

Figure 33:
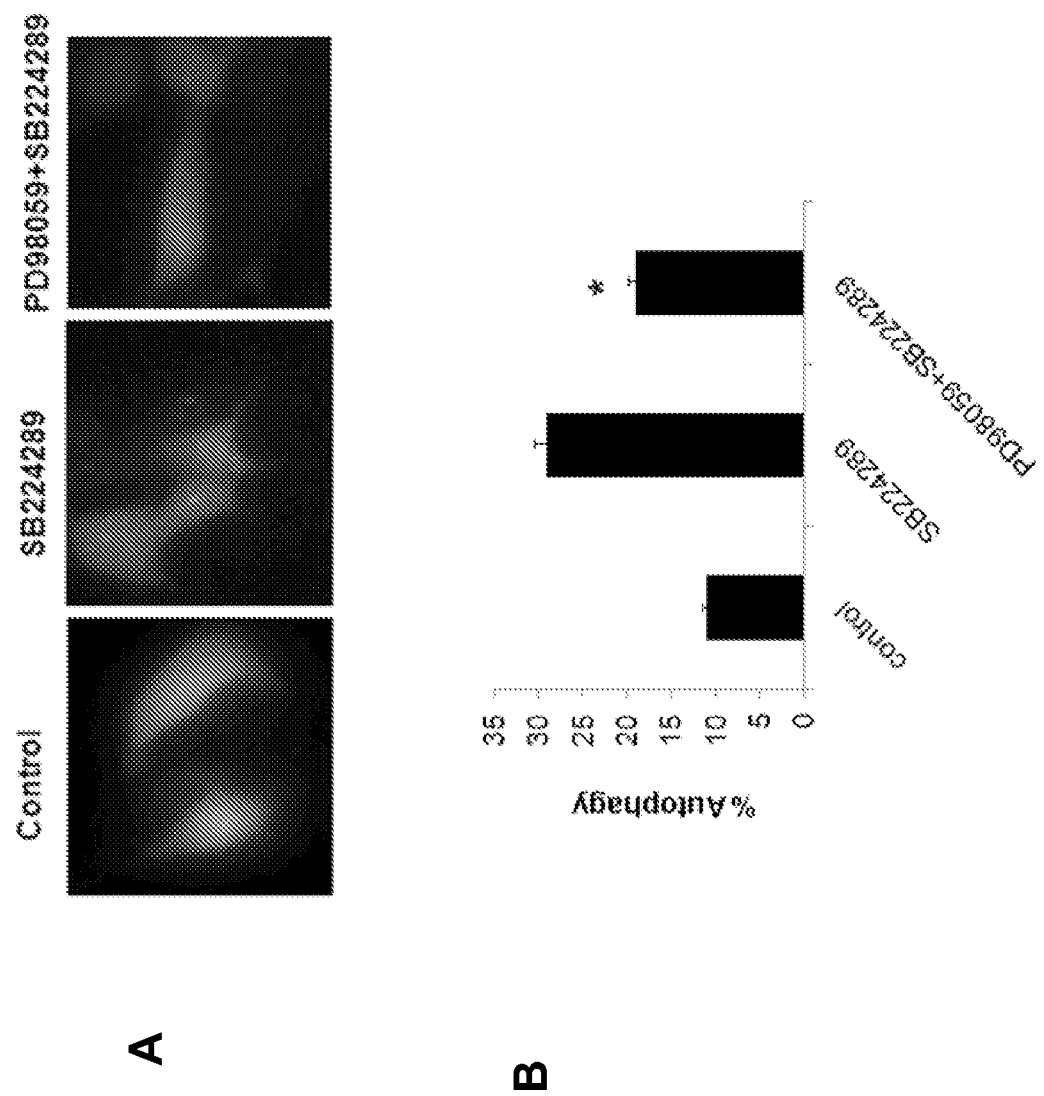
FIG. 33. To demonstrate a link between autophagy induction in response to HTR1B inhibition and ERK activation we inhibited ERK using a MEK inhibitor (PD98059) we transfected MCF-7 cells with green fluorescent protein-tagged LC3 (GFP-LC3) expression plasmid and determined the accumulation of GFP-LC-II protein in autophagosomes after treatment with HTR1B inhibitor SB224289 (A) and (B). Accumulation of GFP-LC3-II in the vacuoles following pretreatment with PD98059 prevented SB224289 induced formation of autophagosomes and punctate pattern indicating induction of autophagy in the cells (FIG. 29B $a$-$b$) detected by fluorescence microscopy. In HTR1B inhibitor treated cells, GFP-LC3 showed punctuate structures that indicate preautophagosomal and autophagosomal membranes. (B) shows number of GFP-LC3 positive cells formation of autophagic vacuoles with or without the treatment of ERK inhibitor.

To demonstrate a link between autophagy induction in response to HTR1B inhibition and ERK activation we inhibited ERK using a MEK inhibitor (PD98059) we transfected MCF-7 cells with green fluorescent protein-tagged LC3 (GFP-LC3) expression plasmid and determined the accumulation of GFP-LC-II protein in autophagosomes after treatment with HTR1B inhibitor SB224289 (FIG. 33A-B). Accumulation of GFP-LC3-II in the vacuoles following pretreatment with PD98059 prevented SB224289 induced formation of autophagosomes and punctate pattern indicating induction of autophagy in the cells (FIG. 29B a-b) detected by fluorescence microscopy. In HTR1B inhibitor treated cells, GFP-LC3 showed punctuate structures that indicate preautophagosomal and autophagosomal membranes. FIG. 33B shows number of GFP-LC3 positive cells formation of autophagic vacuoles with or without the treatment of ERK inhibitor.

Figure 34:
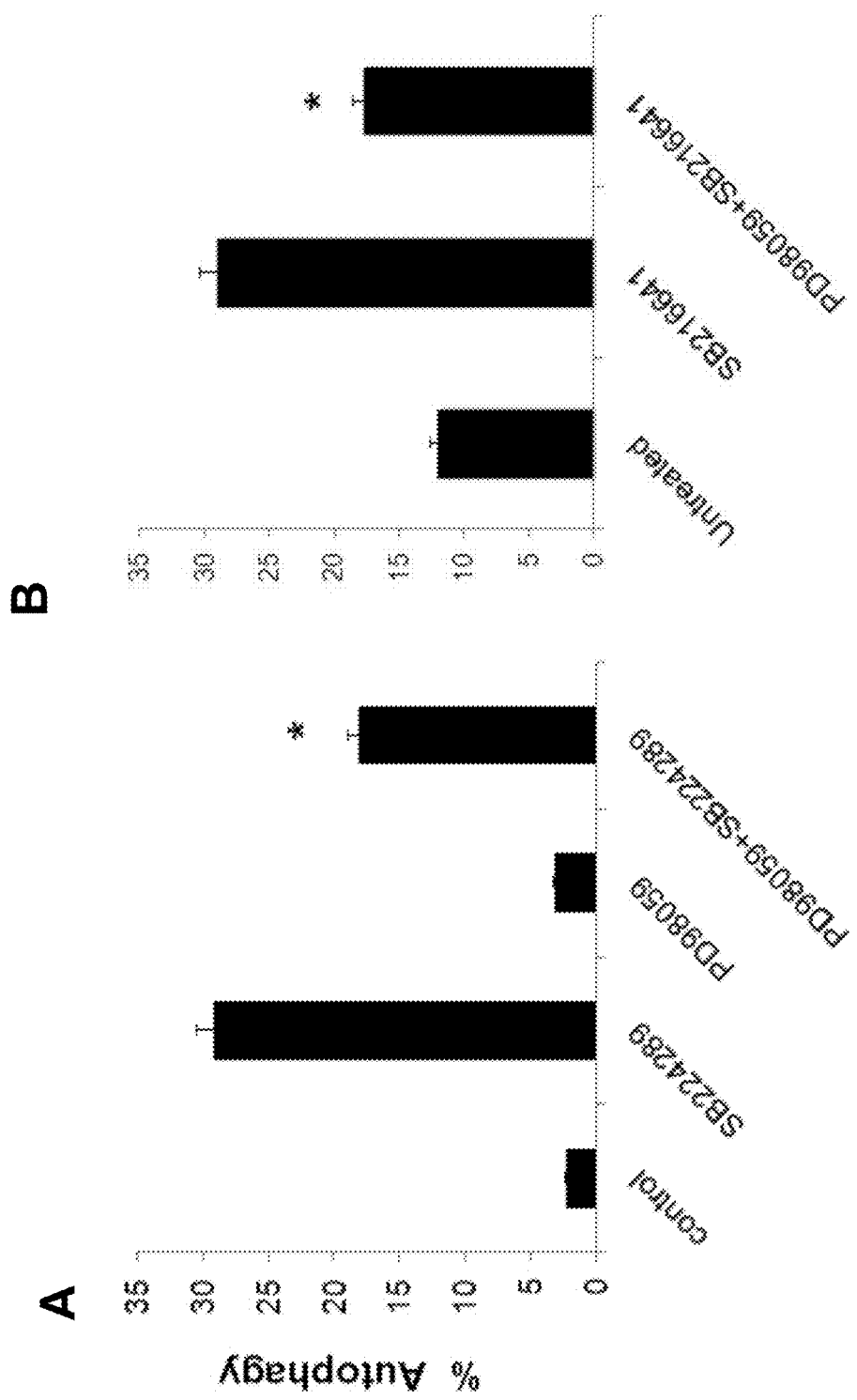
FIG. 34. To further demonstrate that autophagy induced in response to HTR1B inhibition is mediated by ERK activation we inhibited ERK using a MEK inhibitor (PD98059) and found that inhibition of ERK significantly reduced autophagy induction in MCF7 and MDA-MB231 cells detected by acridine orange staining and FACS analysis (p<0.05) (A) and (B). The percent positive cells with autophagy induced by SB224359 was decreased to 18% from 29.2% by ERK inhibitor, suggesting that ERK mediates participates to autophagy induced by inhibition of HTR1B.

To further demonstrate that autophagy induced in response to HTR1B inhibition is mediated by ERK activation we inhibited ERK using a MEK inhibitor (PD98059) and found that inhibition of ERK significantly reduced autophagy induction in MCF7 and MDA-MB231 cells detected by acridine orange staining and FACS analysis (p<0.05) (FIGS. 34A and 34B). The percent positive cells with autophagy induced by SB224359 was decreased to 18% from 29.2% by ERK inhibitor, suggesting that ERK mediates participates to autophagy induced by inhibition of HTR1B.

Example 18

Induction of Autophagy by HT1B Inhibition Contributes to Cell Death

Figure 35:
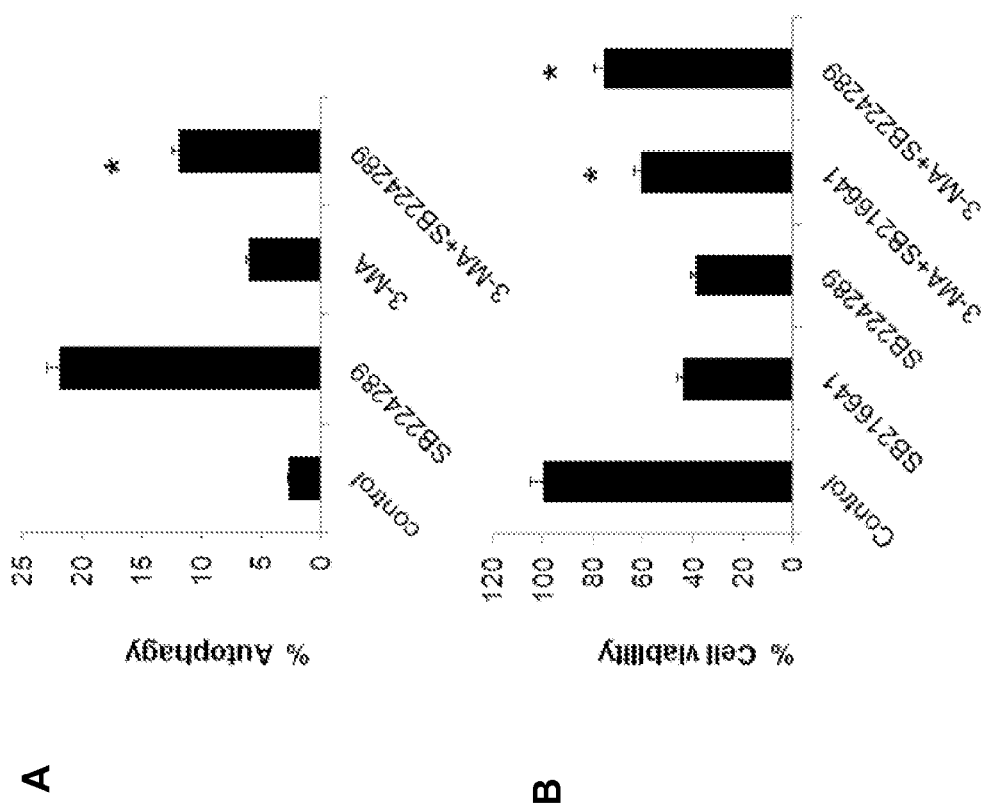
FIG. 35. Induction of autophagy by HT1B inhibition contributes to cell death. Autophagy has been shown to function as a protective survival pathway in response to nutrient or growth factor deprivation, hypoxia, metabolic and therapeutic stress [25]. It was also reported that autophagy induction can lead to cells death [16][19]. To understand the role of autophagy in response to HT1B inhibition by SB224289 we inhibited autophagy by 3-MA (A). The incidence of autophagy induced by SB224359 was decreased to 12% from 22.4% by 3-MA. Cell viability was significantly increased by 3-MA from 42% by SB224289 to 61% and 31% by SB216641 to 71% in MCF7 cells (p<0.05) (B). These results suggest that inhibition of autophagy increases cell viability by HTR1B inhibition and autophagy contributes to cell death.
Figure 36:
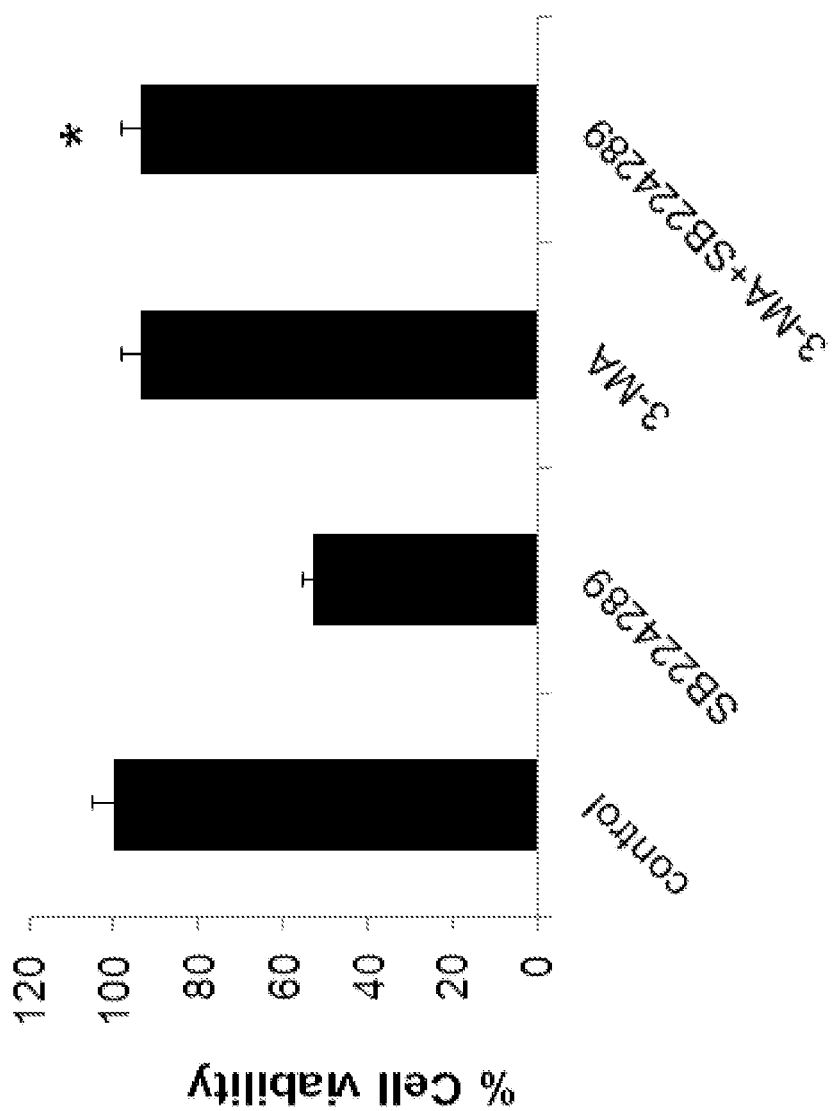
FIG. 36. Cell viability MDA-231 cells.
Figure 37:
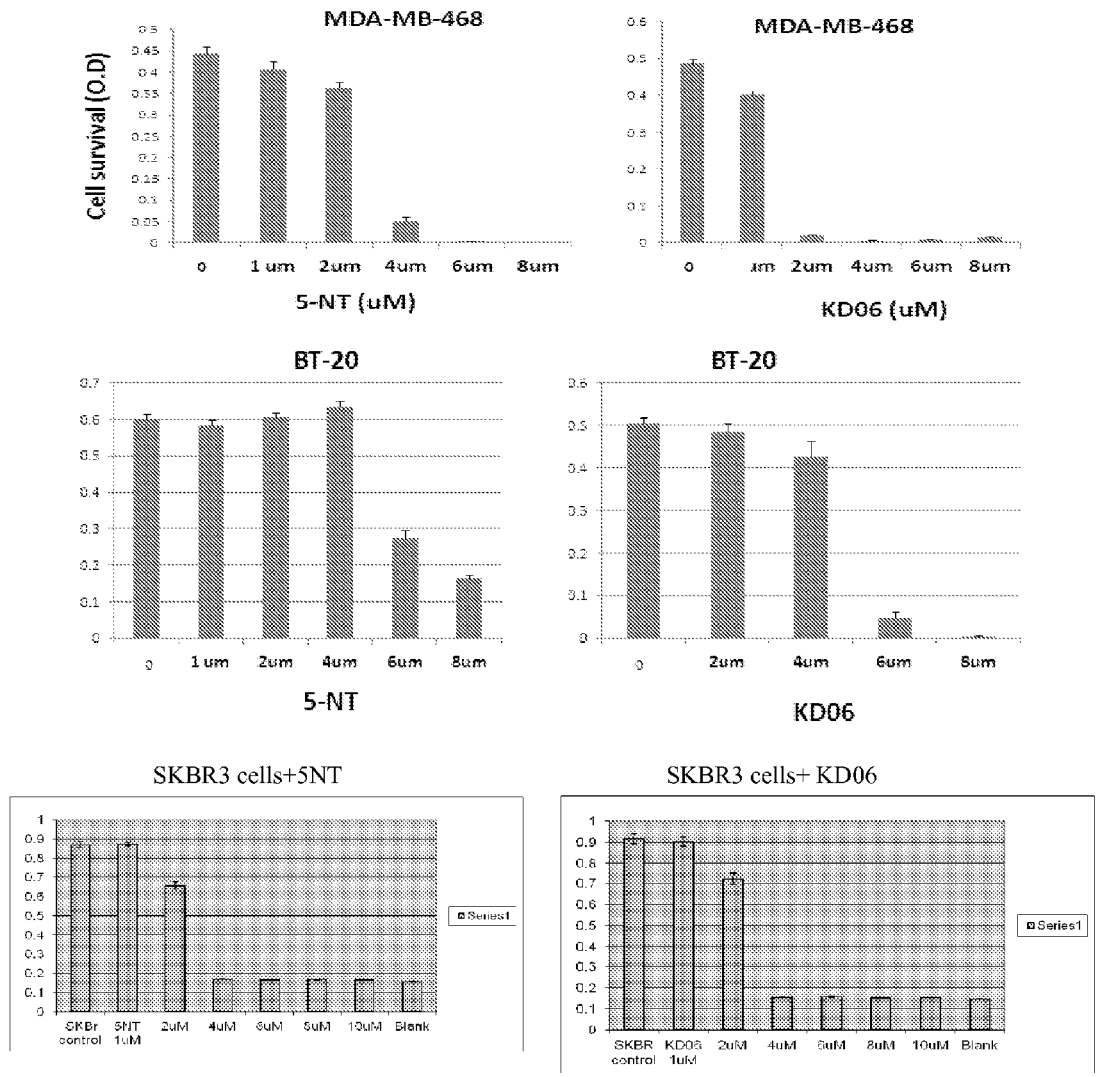
FIG. 37. 5-NT and KD06 tested in a large panel of breast cancer cells. Both compounds are effective against almost all breast cancer cell lines, including: Triple negative (estrogen receptor negative; ER(−), progesterone receptor negative and Her2/neu negative) breast cancer cell lines) including MDA-468, BT20 and MDa-MB231 cells. Triple negative breast cancer patients have poor prognosis and they have resistance to standard therapies and cannot use tamoxifen antiestrogen therapy or herception antibody as targeted therapy since they do not have targets for these therapies. SKBR3, MDA-MB435, T47D, ZR75.1 breast cancer cell lines with different features, such as high SRC, HER2 etc. are sensitive to 5-NT and KD06. Y-axes for all views shown in this figure are cell survival (O.D.).
Figure 38:
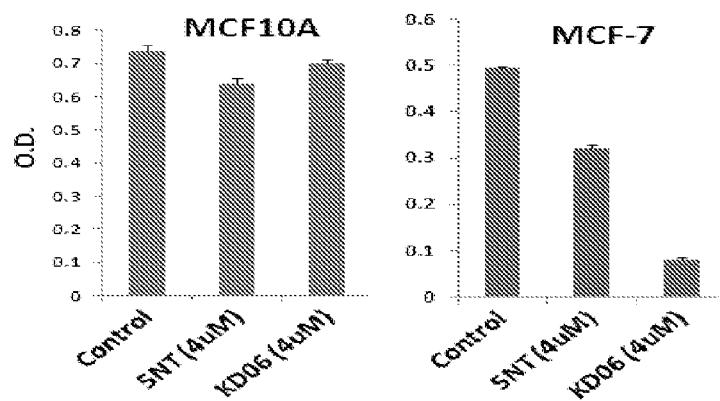
FIG. 38. (A). 5-NT and KD06 at IC50 to IC90 doses in breast cancer cells (MCF7) are not toxic against normal breast cancer epithelium (MCF10A). (B). Animals (mice) that received at least 15 doses of liposome incorporated 5-NT (i.v., 10 mg/kg) for 4 weeks look Ok compared to liposome incorporated control siRNA treated group. (C). Liver (AST, ALT), kidney (BUN, Creatinine) tox markers. Mice that received 5-NT for 4 weeks did not lose any weight and they looked healthy (AST: Aspartate transaminase, ALT: Alanine transaminase, ALP: Alkaline phosphatase, BUN: blood urea nitrogen) (Each grouping is shown left to right AST, ALT, ALP, BUN, creatinine).
Figure 38:
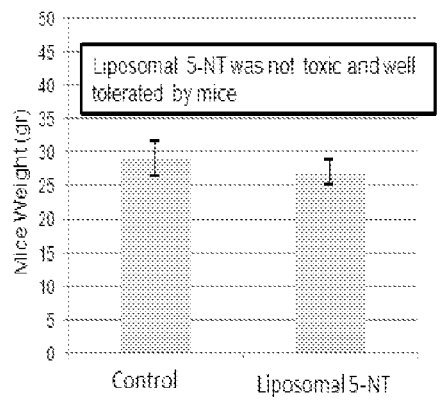
Figure 38:
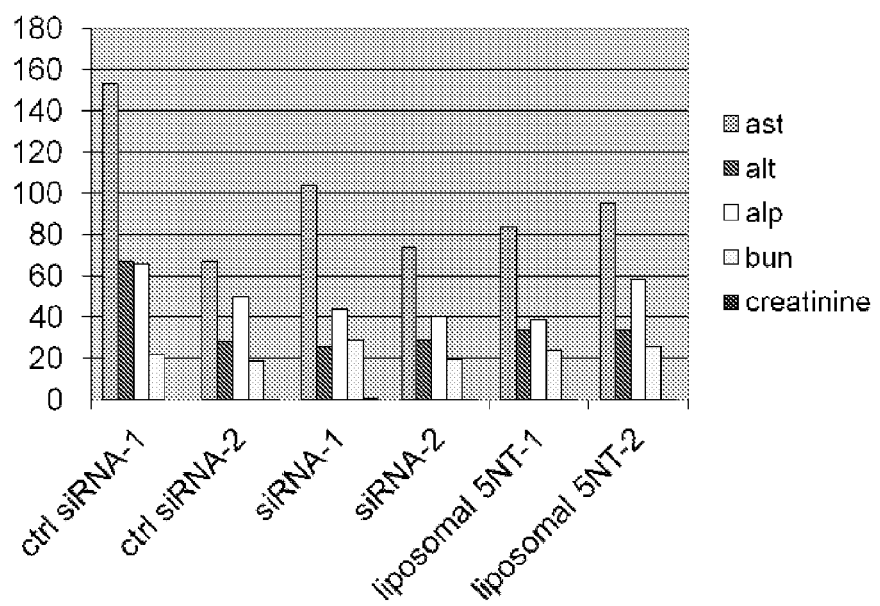
Figure 39:
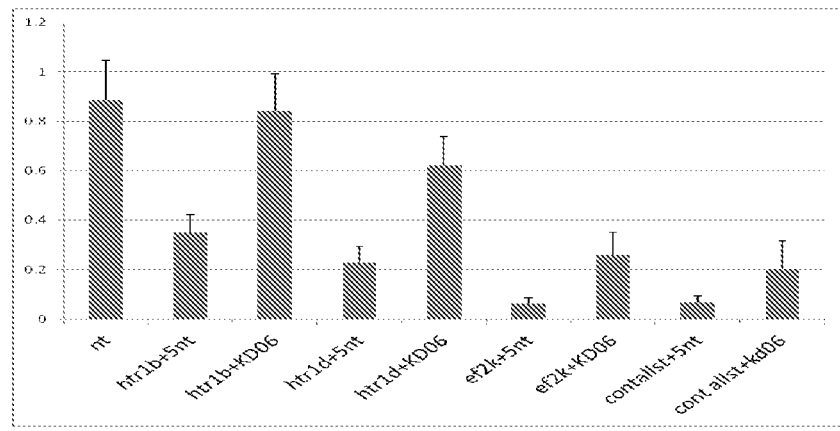
FIG. 39. Inhibition of HTR1B/1D by siRNA mediated gene silencing reverses some of the effect of 5NT and KD06 on cell proliferation inhibition, suggesting that 5NT inhibits cell proliferation through HTR 1B/1D receptors.

Autophagy has been shown to function as a protective survival pathway in response to nutrient or growth factor deprivation, hypoxia, metabolic and therapeutic stress [Dalby K N, et al. Autophagy 2010: 6: 322-329]. It was also reported that autophagy induction can lead to cell death [Kanzawa T, et al. Cancer research 2003: 63: 2103-2108] [Akar U, et al. Mol Cancer Res 2007: 5: 241-249]. To understand the role of autophagy in response to HT1B inhibition by SB224289 we inhibited autophagy by 3-MA (FIG. 35A). The incidence of autophagy induced by SB224359 was decreased to 12% from 22.4% by 3-MA. Cell viability was significantly increased by 3-MA from 42% by SB224289 to 61% and 31% by SB216641 to 71% in MCF7 cells (p<0.05) (FIG. 35B). These results suggest that inhibition of autophagy increases cell viability by HTR1B inhibition and autophagy contributes to cell death.

Example 19

Analysis of Examples 12 Through 18

Serotonin (5-HT), a monoamine neurotransmitter, plays a mitogenic role in some cancer cells. Serotonin mediates its effects through 14 different receptors that are differentially expressed in different tissues. In this study we demonstrated that serotonin induces proliferation of breast cancer cells. Here we showed the expression and role of 5-HT1B receptor is markedly (about 8-10 fold) increased in breast cancer cells. 5-HT1B receptor overexpression was found in ER(+), ER (−) highly aggressive and metastatic breast cancer cell lines compared to normal untranformed breast epithelium. More importantly, we showed 5-HT1B mediates proliferation, survival, and autophagy in breast cancer cells and inhibition of the serotonin 5-HTR-1B by specific inhibitors significantly inhibited growth of ER(+), ER(−) and drug (doxorubicin) resistant MCF7/Dox-R cells inducing both authophagic and apoptotic cell death, which represent a novel mechanism of action by inhibitors and the role of these receptors in cell survival and death.

Inhibition of serotonin 5-HTR-1B also significantly inhibited colony formation of MDA-MB-231 cells, which are considered triple negative (ER-, PR- and Her2-) and resistant to most therapies. Inhibition of the 5-HT1B also was effective in inhibition of proliferation of chemotherapy (doxorubicin) resistant cells (MCF7/DoxR), suggesting that targeting this receptor may provide therapeutic benefit to drug resistant advance stage breast cancers. Specific targeting of HTR1B two different inhibitors (SB224284 or SB216641) exerted similar effects and induced significant apoptosis and autophagy, which was evidenced by electron microscopy, LC3-II expression, a hallmark of autophagy and GFP-LC3 translocation to the autophagosomes. Inhibition of autophagy reduced cell death and increased cell survival in response to HTR1B inhibitors, suggesting that autophagy is involved in cell death induced by $HTR_1B$ inhibition in breast cancer cells. Induction of autophagy was associated induction of MAPK (ERK1/2) activity (FIG. 31 A, B, FIG. 32A). We found ERK activation participates to autophagy induction in response to HTR1B receptor inhibition. ERK activation has been shown to induce autophagy in some cancer cells.

Current literature suggest that autophagic cell death can help elimination of cancer cells following various treatment [Tsujimoto Y, Shimizu S Cell death and differentiation 2005: 12 Suppl 2: 1528-1534] [Kanzawa T, et al. Cancer research 2003: 63: 2103-2108] [Akar U, et al. Autophagy 2008: 4:669-679]. Depending on the stimulus autophagy may contribute to cell death or be associated with cell death [Kroemer G, Levine B Nature reviews Molecular cell biology 2008: 9: 1004-1010]. Our study suggest that in breast cancer cells inhibition of HTR1B growth signaling induces autophagy which participates in cell death.

In conclusion, our findings suggest for the first time that that serotonin 5-HT1B receptors are overexpressed in breast cancer cells and HTR-1B signaling promotes growth and survival of breast cancer cells and that inhibition of these receptors inhibits cell proliferation and induces apoptosis and autophagic cell death.

Example 20

Triptans and Derivatives as Cancer Therapeutics

Our studies show that the serotonin 5-HT1B receptor is over-expressed in primary, metastatic and resistant breast cancer cells and that in vitro modulation of $5\text{-}HT_{1B}$ signaling in breast cancer cells inhibits proliferation and induces apoptosis. Remarkably, a clinically safe triptan, 5-NT, a potent agonist of the $5\text{-}HT_{1B/1D}$ receptors exhibits efficacy in both in vitro and in vivo breast cancer models.

Figure 6:
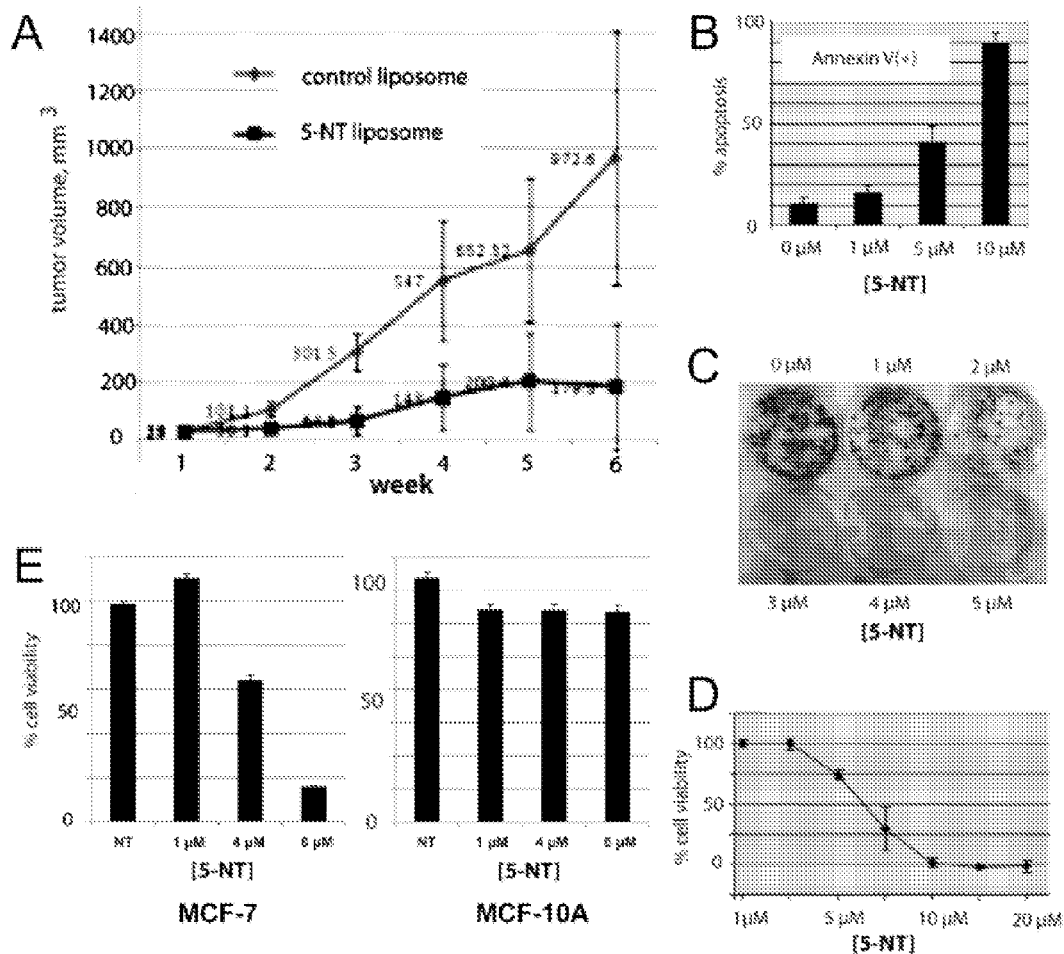
FIG. 6. New role for triptans as a therapeutic modality for breast cancer. (A). In vivo targeting of the 5-HT$_{1B/1D}$ receptor by neutral lipid-based (DOPC)-liposomal 5-nonylytryptamine (5-NT) (Glennon et al., 1996b) in nude mice bearing MDA-MB-231 breast cancer xenografts significantly inhibits tumor growth. Treatments, twice per week (4 weeks) were safe and effective. Methods: Phospholipid dioleoylphosphatidylcholine (DOPC) and triptan 5-NT were mixed in tertiary butanol at a lipid:5-NT ratio of 10:1 (w/w). Tween 20 was added at a ratio of 1:20 ratio (w/w) and the mixture lyophilized overnight. The powder was reconstituted in saline and sonicated for one minute. The liposome formulation was injected (100 µl) into the tail vein. (B). 5-NT induces apoptotic cell death of ER(+) MCF-7 cells. (C). 5-NT inhibits colony formation of ER(+) MCF-7 cells. (D). 5-NT inhibits proliferation of triple negative MDA-MB-231, as well as ER(+) MCF-7 and MCF7/Dox resistant cells. (E). 5-NT shows much higher selectivity towards the tumorigenic cell line MCF-7, when compared to MCF-10A, a non-tumorigenic cell line, and appears to be non-toxic to mice.
Figure 9:
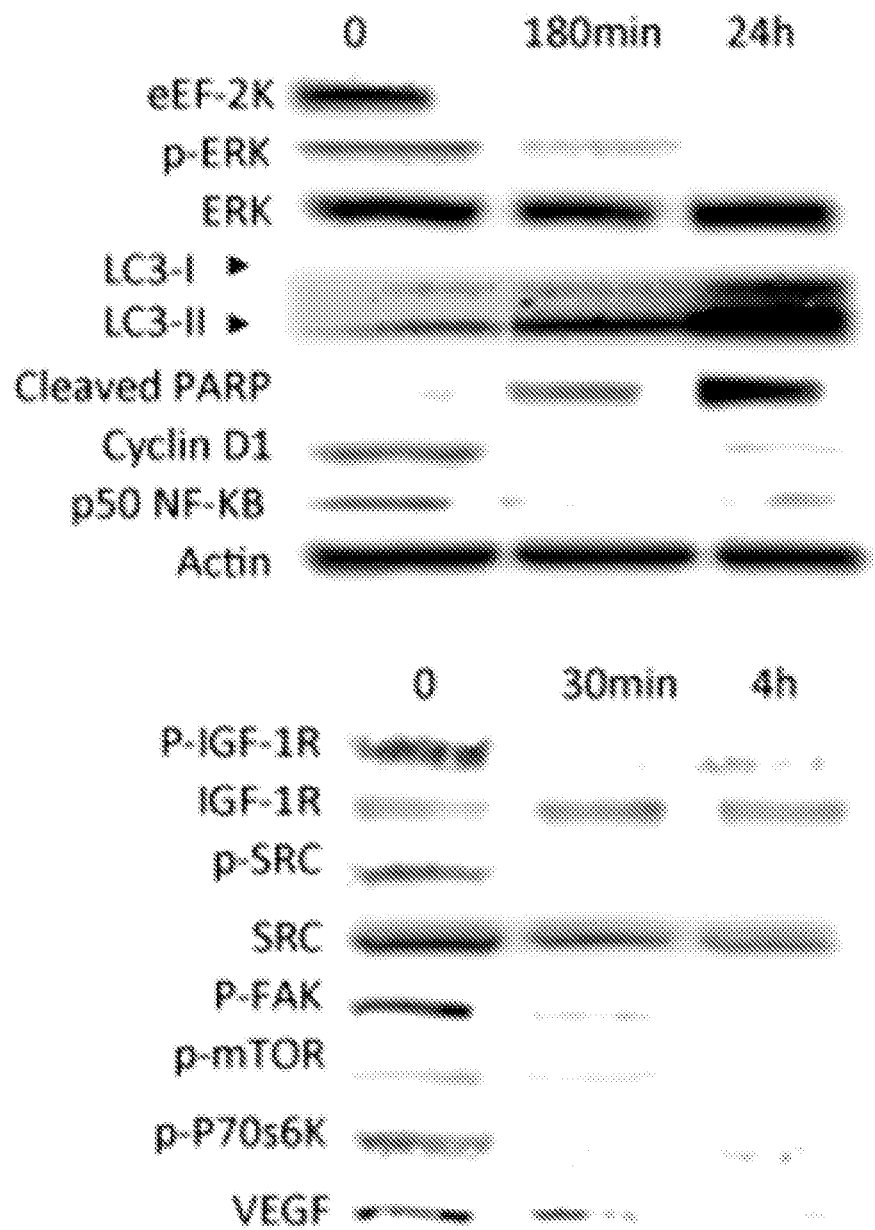
FIG. 9. 5-NT down-regulates critical pro-tumorigenic processes in ER(+) MCF-7 breast cancer cells. Western blot analysis shows that 5-NT (5 µM) down-regulates the expression of eEF-2K, Cyclin D1, NF-kB, and VEGF as well as the phosphorylation of IGF-1R, Src, FAK, mTOR, p70S6K, and ERK2. 5-NT also induces PARP cleavage and LC3-II formation. Methods: MCF7 cells were cultured at 37° C. in DMEM supplemented with 5% FBS in a humid incubator with 5% $CO_2$. Following incubation with or without 5-NT, cells were lysed according to standard protocols for western blotting. Blots were quantified as in FIG. 7.
Figure 10:
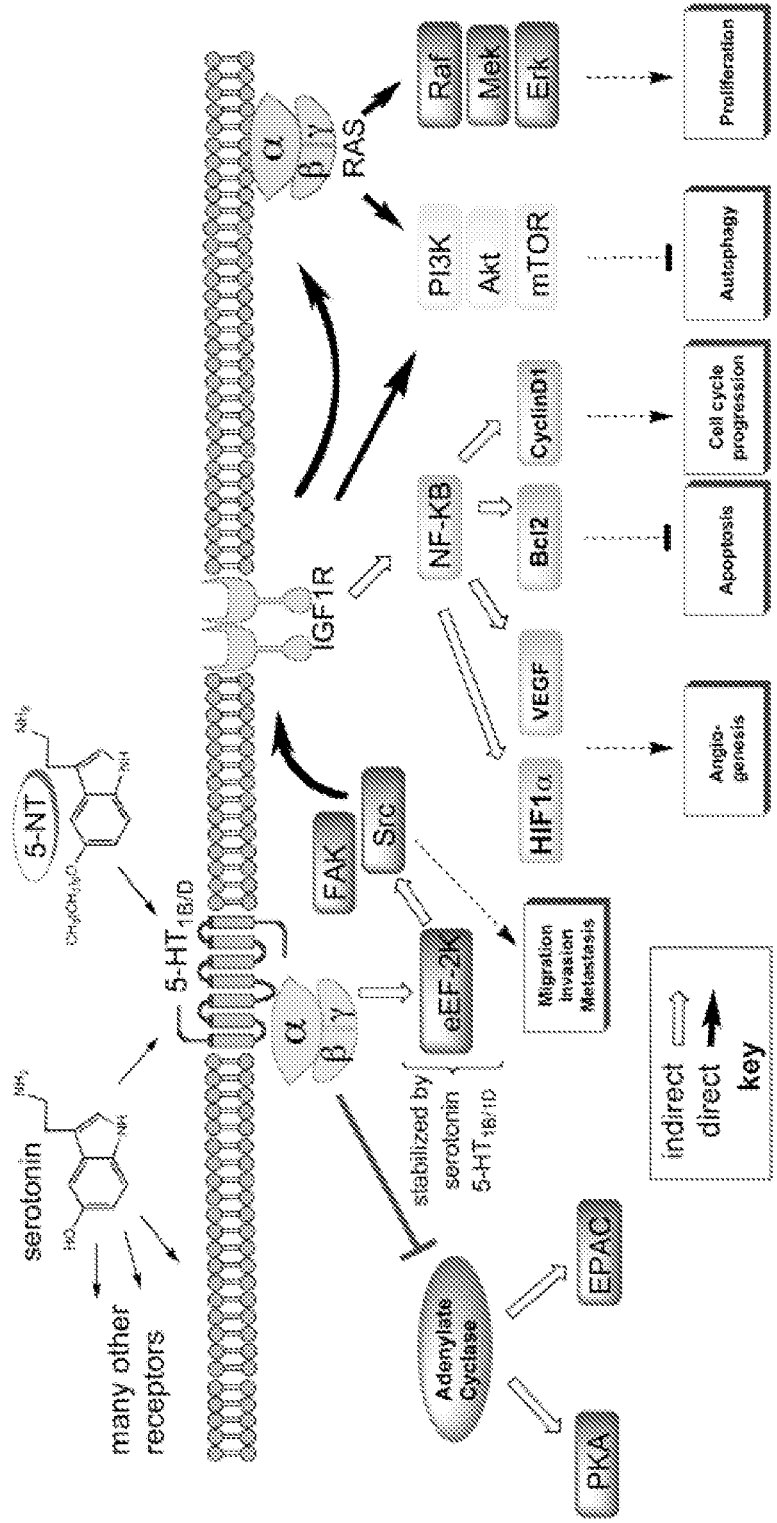
FIG. 10. Possible mechanism for how triptan derivatives, such as 5-NT disrupt tumorigenic signaling of the $5-HT_{1B}$ receptor. Binding of 5-NT to the $5-HT_{1B}$ receptor leads to the down-regulation of eEF-2K expression as well as the inactivation of c-Src and Fak, IGF-1R, Akt/mTor and Erk. These events may contribute to the observed pharmacological effects of 5-NT on breast cancer cells expressing a dysregulated serotonin system. The mechanism in this figure is based on the reported roles of the depicted genes in the literature, and represents a starting point from which to fully evaluate the mechanism of action of triptan derivatives.

Our studies in MCF-7 cells have established that 5-NT down-regulates ERK/cyclin-D, Akt/mTor, IGF1-R and Src/Fak and eEF-2K within 4 hours (FIG. 9). These represent some of the most important therapeutic targets in breast cancer and may underlie the anti-proliferative and pro-apoptotic effects of 5-NT (FIG. 6). Recently, we discovered that the down-regulation of eEF-2K (which is over-expressed in all tumorigenic breast cancer lines tested) disrupts these signaling pathways in both in vitro and in vivo breast cancer models, suggesting that eEF-2K may be an important target for 5-NT therapy. Ovarian cancer where our studies suggests that the 5-HT1B receptor is also over-expressed.

Figure 2:
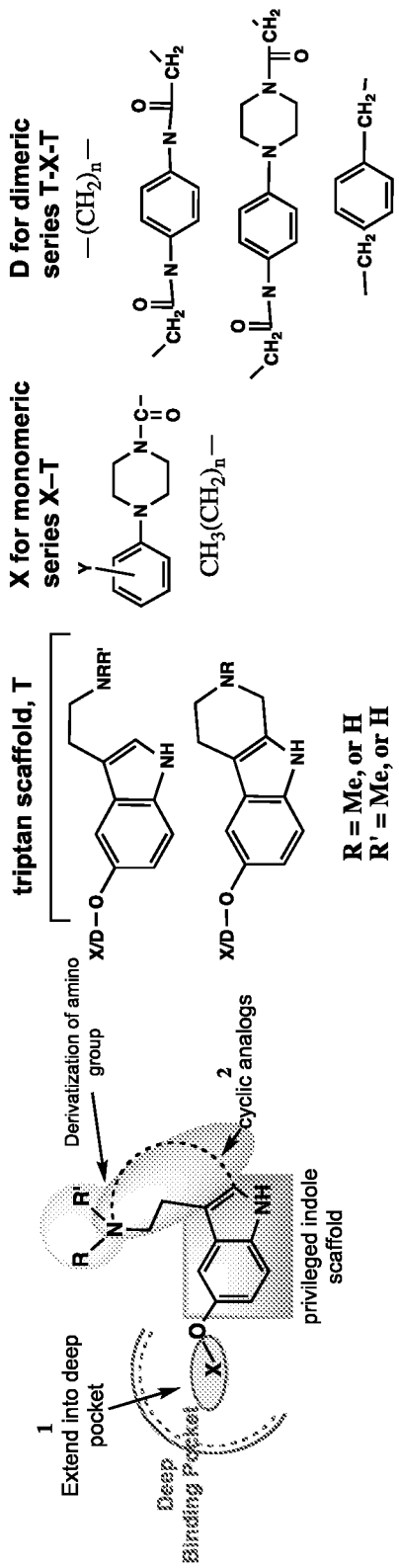
FIG. 2. Synthesis of a library of triptan analogs.

Synthetic procedures for the elaboration of the 5-hydroxytryptamine scaffold are well-established (Glennon, 1996; Glennon et al., 1996; Glennon et al., 1994; Halazy et al., 1996; John et al., 1999; Perez et al., 1995; Perez et al., 1998a; Perez et al., 1998b). In addition, because $5\text{-}HT_{1B/1D}$ receptors form heterodimers dimers (Xie et al., 1999), dimeric derivatives of 5-NT which have been shown to potently bind $5\text{-}HT_{1B/1D}$ (Halazy et al., 1996; Perez et al., 1998a; Perez et al., 1998b) will be synthesized by coupling triptan scaffolds (T) to dimeric linkers (D), as shown in FIG. 2.

We have identified an analog of 5-NT, which displayed a two-fold greater potency towards MDA-MB-231 breast cancer cells than 5-NT confirming the importance of the alkoxy substituent at the 5 position of the triptan, as well as other potent compounds (Examples section).

We found using our previously described approach (Akar et al., 2010; Landen et al., 2005; Ozpolat et al., 2007; Ozpolat et al., 2010; Verma et al., 2008) that a neutral charge nanoliposomal 5-NT formulation prepared from DOPC and Tween-20 was effective at inhibiting tumor growth in an orthotopic model of breast cancer (FIG. 3A). We have used RGD- and folate-modified LCLs to promote tumor delivery of siRNA (Ozpolat et al., 2010). RGD targets liposomes to αvβ3 integrin receptors, which are highly expressed in breast tumors (Ozpolat et al., 2010). In some embodiments, the targeted liposome delivery system is composed of 4 different lipid components e.g. DOPC, tween-20, DSPE-PEG and DSPE-PEG-RGD. In some embodiments, the extrusion process (Hope et al., 1985) will be used to prepare small unilaminar liposomes of ~100 nm, which can be confirmed using a light microscope. Based on preliminary in vitro experiments using RGD-M-LCL a 4-8-fold greater uptake of siRNA into cells was achieved compared to passive liposomes.

Several triptan derivatives possessing either novel bulky substituents at the 5-ring position or possessing a cyclized 3-amino functionality (e.g. frovatriptan) are reported to bind $5\text{-}HT_{1B}$ with higher affinity than 5-NT (Wilson et al., 2011). We have synthesized a triptan derivative, which possesses a slightly longer 5-alkyl substituent than 5-NT and exhibits 2-3 fold greater potency in a viability assay (Examples section).

In studies a number of 5-substituted and cyclic triptan derivatives have been made. The folate receptor-alpha (FRα) provides an excellent alternative target for this purpose, because it is a highly selective tumor marker that is over-expressed in about 90% of breast carcinomas (Garin-Chesa et al., 1993; Holm et al., 1994; Jhaveri et al., 2004; Ross et al., 1994). Most normal cells including breast epithelium do not express FRα. More importantly, about 80% of metastases derived from epithelial cancers express FRα.

In some embodiments, the triptan drug is co-administered with an $ED_{50}$ dose of doxorubicin.

Studies targeting eEF-2K by siRNA in tumors resulted in the down-regulation of c-Src activity in the tumors. We found in studies that the encapsulation of the potential therapeutic drug 5-NT in a passive neutral liposome rendered it effective in animals on a twice-weekly treatment regimen.

We are encouraged that a previous toxicology study found that mice exhibited no weight loss, when treated with a high 50 mg/kg dose of liposomal 5-NT and given the extensive oral use of triptans in the human population for the treatment of migraines.

Eukaryotic elongation factor 2 kinase (eEF-2K) modulates the rate of protein synthesis by inactivating eukaryotic elongation factor 2 (eEF-2) via phosphorylation (Nairn et al., 1985; Ryazanov, 1987). Constitutively activated eEF-2K in human breast cancer has been linked to cell proliferation (Parmer et al., 1998). Glioblastoma and breast cancer cells also employ eEF-2K to regulate autophagy a stress-induced pro-survival pathway (Cheng et al., 2010; Wu et al., 2006). Additionally, eEF-2K has been implicated in aging (Riis et al., 1993). The mTOR pathway negatively regulates eEF-2K activity via phosphorylation by p70 S6 kinase (Wang et al., 2001), the cdc2-cyclin B complex (Smith and Proud, 2008) and an additional kinase (Browne and Proud, 2004). We made the novel discovery that siRNA-mediated down-regulation of eEF-2K in breast cancer cells leads to the down-regulation of critical cell-signaling kinases including mTOR, IGF-1R and Src, while concomitantly inducing apoptosis, and inhibiting cell invasiveness and tumor growth. These observations suggest that mTOR is modulated by eEF-2K.

Remarkably, our studies show that a clinically safe triptan, 5-nonylytryptamine (5-NT) (Glennon and Dukat, 2010), a potent agonist of the 5-HT$_{1B/1D}$ serotonin receptors (Glennon et al., 1996a), exhibits efficacy in both in vitro and in vivo breast cancer models, with the notable down-regulation of eEF-2K as well as c-Src/FAK and the downstream IGF-1R, PI3K/Akt and mTOR signaling pathways. Significantly, we have observed similar downstream effects when eEF-2K is down-regulated by siRNA, with the inhibition of key protumorigenic signaling proteins such as c-Src, FAK, IGF-1R, Aid and mTOR. Critically, 5-NT exhibits high selectivity for cancer cell lines over non-tumorigenic cells, and was shown to be non-toxic to mice. Our data indicates that the targeted down-regulation of eEF-2K by siRNA induces apoptosis, and inhibits cell proliferation and migration. Additionally, critical signaling proteins including mTOR, IGF-1R and Src are down-regulated. The 5-HT1B receptor is over-expressed in breast cancer cells, and significantly, we found that 5-NT down-regulates eEF-2K and exhibits similar effects to the down-regulation of eEF-2K by siRNA in both in vitro and in vivo breast cancer models. We have also synthesized a triptan derivative (KD06) which is more potent than 5-NT.

We made the novel discovery that siRNA-mediated down-regulation of eEF-2K in breast cancer cells leads to the down-regulation of critical cell-signaling kinases including mTOR, IGF-1R and Src, while concomitantly inducing apoptosis, and inhibiting cell invasiveness and tumor growth. These observations suggest that key signaling pathways are modulated by eEF-2K.

Figure 7:
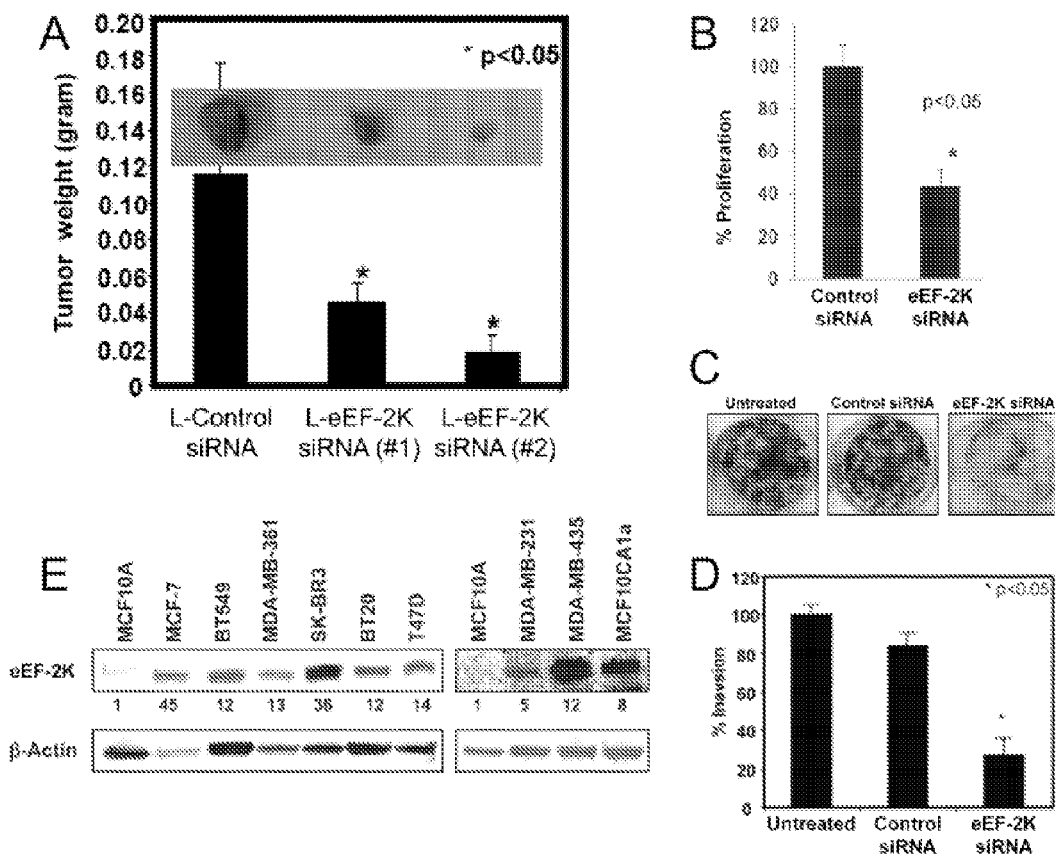
FIG. 7. siRNA targeting of eEF-2K significantly inhibits tumor growth. (A). Therapeutic targeting of eEF-2K by systemically administered liposomal siRNA inhibits orthotopic tumor growth in a breast cancer model. Methods: About 2 weeks after injection of MDA-MB-231 cells ($1 \times 10^6$) into mammary fat pat (orthotopic), therapeutic targeting of the eEF-2K gene was achieved by systemically (i.v.) administered DOPC-nanoliposomal siRNA (L-eEF-2K siRNA) (150 µg/kg or about 4 µg/mouse, twice a week for 4 weeks). Non-silencing DOPC-liposomal siRNA (L-Control siRNA) was used as control. Two different eEF-2K-targeting siRNAs were used; eEF-2K siRNA(#1) and siRNA(#2). At the end of week 4, the experiment was terminated and tumor weight was measured. (B). eEF-2K silencing inhibits proliferation triple negative MDA-MB-231 cells. (C). eEF-2K silencing inhibits colony formation of triple negative MDA-MB-231 cells. (D). eEF-2K silencing inhibits invasion/migration of triple negative MDA-MB-231. (E). eEF-2K is overexpressed across a variety of breast cancer cell lines. Methods: Blots were visualized with a FluorChem 8900 imager and quantified by a densitometer using the Alpha Imager application program.
Figure 8:
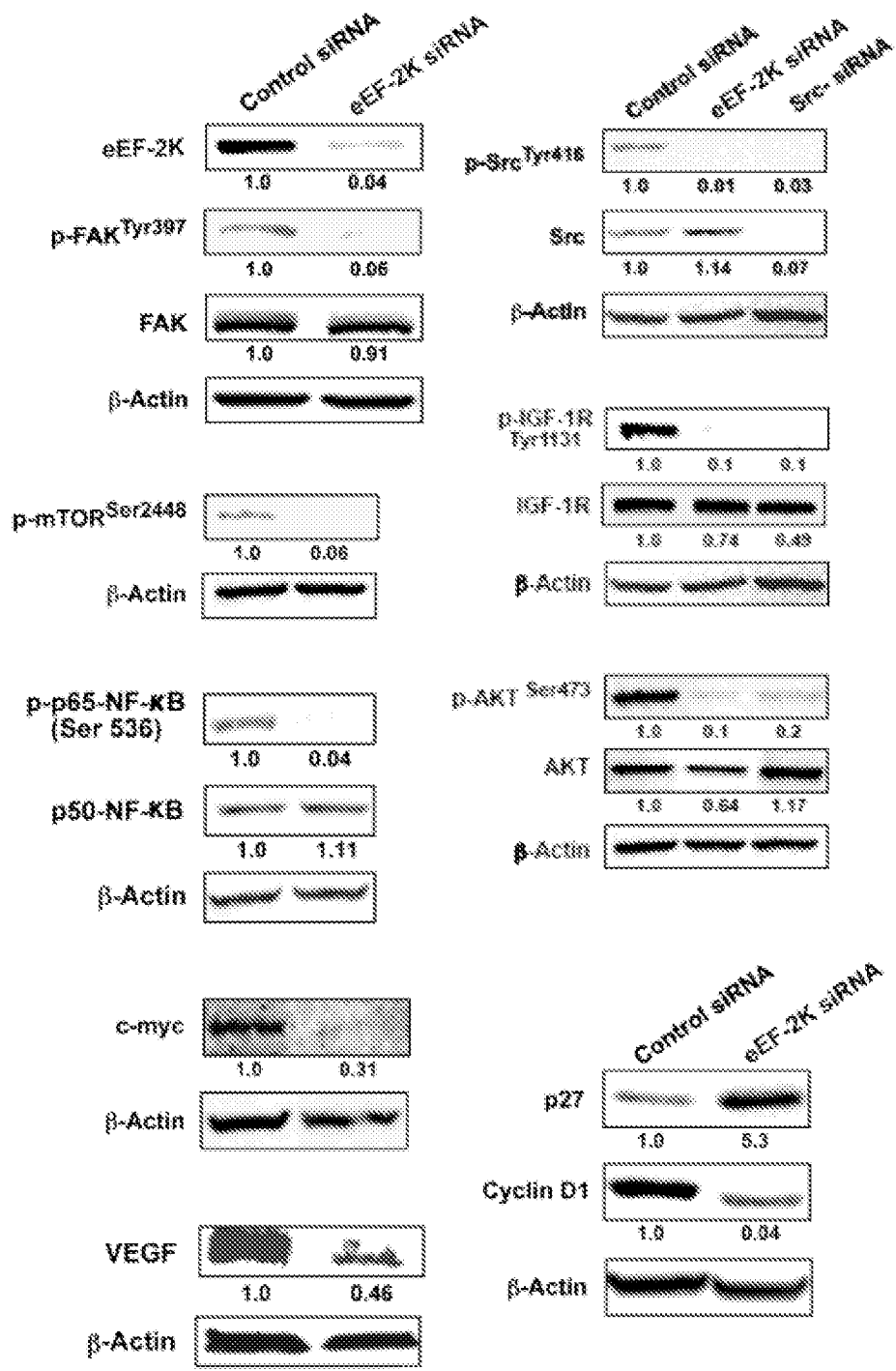
FIG. 8. eEF-2K regulates the activation of IGF-1R, Akt, and mTOR through Src in MDA-MB-231 cells. Western blot analysis shows that eEF-2K siRNA inhibits eEF-2K expression. This leads to the concomitant down-regulation of Src activity (as determined by detection of phospho Tyr-416). The down-regulation of eEF-2K or Src leads to the down-regulation of IGF-1R, Akt and mTOR activity. Additionally FAK, NF-kB, VEGF, cyclin D1 and c-myc are downregulated, while p27 levels increase. Methods: Cells were transfected with eEF-2K or Src siRNA (75 nM) for 48 h and assessed by Western blotting. Blots were quantified as in FIG. 7.

FIG. 7 indicates that knockdown of eEF-2K inhibits in vitro proliferation of breast cancer cells, colony formation and invasion, and induces apoptosis. Silencing of eEF-2K by siRNA significantly inhibits the number of colonies formed by MDA-MB-231 (FIG. 7C) which indicates that eEF-2K promotes cell proliferation (FIG. 7B). In addition, knockdown of eEF-2K inhibits migration/invasion (FIG. 7D). Cleavage of PARP in MDA-MB-231 cells indicates that eEF-2K knockdown induces apoptosis. Overexpression of eEF-2K by transfection increases cell proliferation and invasion. FIG. 7E indicates that eEF-2K is overexpressed across a variety of breast cancer cell lines. The data in FIG. 5 suggests that 5-NT works through the down regulation of eEF-2K. Treatment of MCF-7 cells with 5-NT down-regulates eEF-2K and exhibits similar effects as eEF-2K siRNA, including down-regulation of critical signaling proteins, inhibition of cell growth and induction of apoptosis. The data in FIG. 3A suggest that 5-NT potently inhibits breast cancer tumor growth in a mouse model. Using nanoliposomal delivery technology we discovered that the systemic (i.v.) administration of 5-NT at 5.8 mg/kg (twice weekly) significantly inhibits growth of highly aggressive and metastatic triple negative (Her-, ER-, Pr-) MDA-MB-231 human breast tumors in an in vivo orthotopic xenograft breast cancer model in nude mice. FIG. 7A indicates that eEF-2K siRNA significantly inhibits tumor growth in the MDA-MB-231 orthotopic mouse model. DOPC-liposomes containing two different eEF-2K-targeting siRNAs reduce tumor size significantly in the mouse model. FIG. 8 indicates that inhibition of eEF-2K blocks activity of c-Src/FAK and downstream IGF-1R, PI3K/Akt and mTOR signaling pathways. Knockdown of eEF-2K levels down-regulates critical signaling proteins including Src, FAK, IGF-1R, Ala and mTOR. FIG. 8 indicates that eEF-2K regulates proteins involved in cell cycle progression and angiogenesis. Knockdown of eEF-2K levels affects expression of cell cycle progression markers with increase in p27 and decrease in cyclin D1 levels. Downregulation of eEF-2K also decreases expression of VEGF which is involved in angiogenesis.

Figure 11:
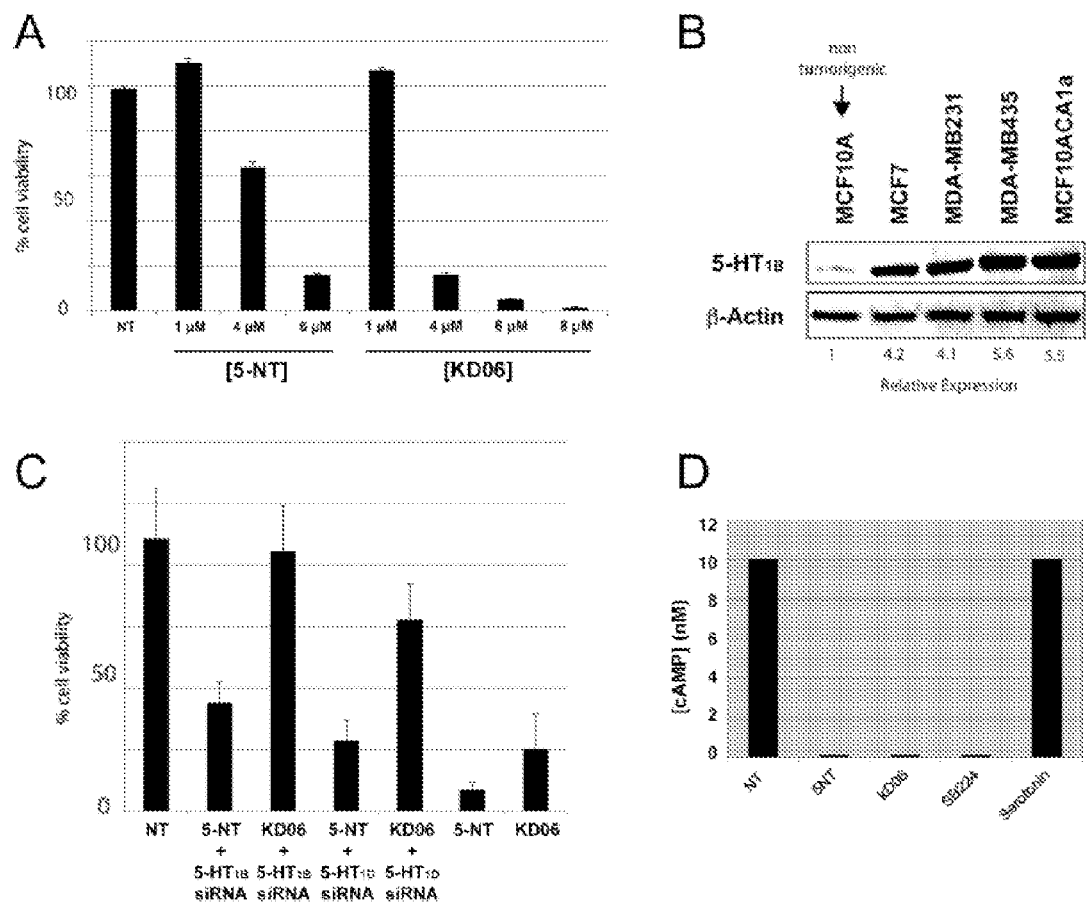
FIG. 11. 5-NT and KD06 exhibit anti-tumor effects by signaling through the $5-HT_{1B/1D}$ receptor. (A). KD06, a triptan derivative that we have synthesized, is more potent than 5-NT. (B). The $5-HT_{1B}$ receptor is over-expressed in triple negative highly aggressive, and metastatic breast cancer cells as well as drug resistant (i.e. tamoxifen and doxorubicin) breast cancer cells. (C). Knockdown of either the $5-HT_{1B}$ or $5-HT_{1D}$ receptor blunts the effect of 5-NT and KD06. (D). 5-NT and KD06 also decrease cAMP levels, which is known to be associated with $5-HT_{1B/1D}$ receptor signaling.
Figure 12:
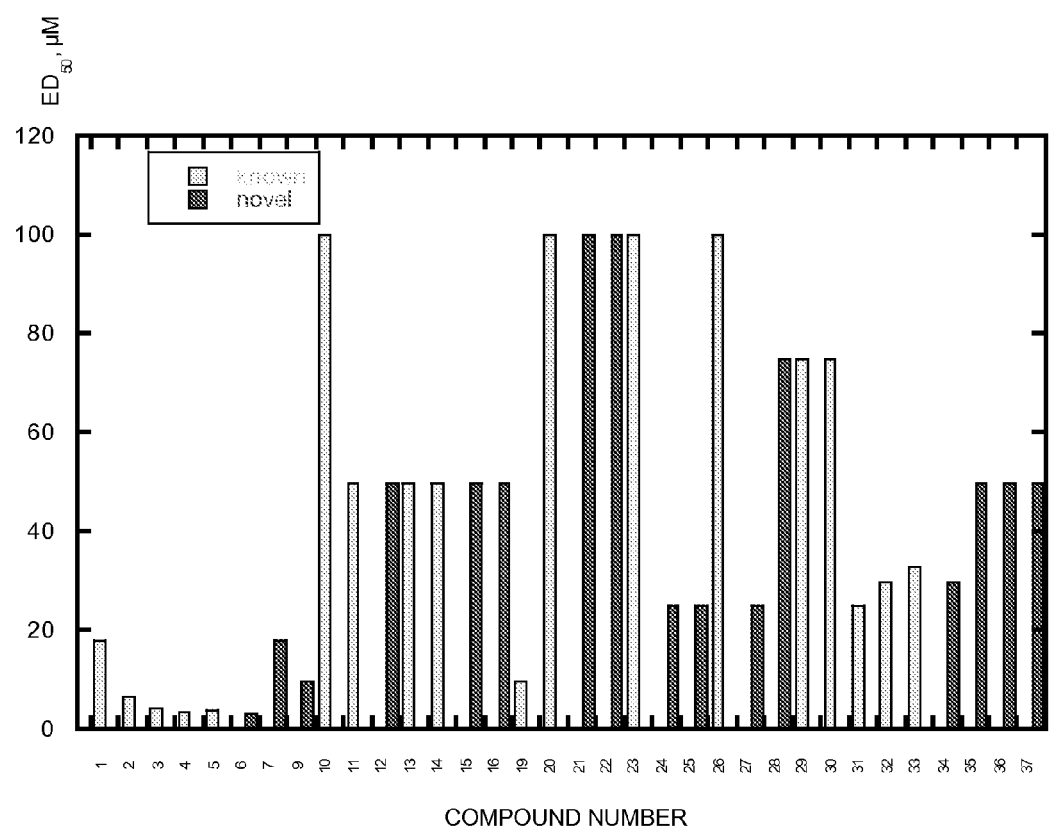
FIG. 12. Characterization of compounds. Compound are numbered with KD numbers Examples (e.g. Compound 1 in FIG. 12 corresponds to compound KD01 in the Examples section, Compound 37 in FIG. 12 corresponds to compound KD37 in the Examples section).

FIG. 6 indicates that 5-NT inhibits in vitro proliferation of breast cancer cells, colony formation and invasion, and induces apoptosis. 5-NT significantly inhibits the number of colonies formed by MCF-7 (FIG. 6C) which indicates that 5-NT inhibits cell proliferation. In addition, 5-NT induces apoptosis (FIG. 6B) and decreases cell viability (FIG. 6D). Cleavage of PARP in MCF-7 cells (FIG. 9) indicates that 5-NT induces apoptosis. FIG. 6E indicates that 5-NT exhibits high selectivity for cancer cell lines over non-tumorigenic cells. The data in FIG. 9 suggest that 5-NT works through the down regulation of eEF-2K. Treatment of MCF-7 cells with 5-NT down-regulates eEF-2K and exhibits similar effects as eEF-2K siRNA, including down-regulation of critical signaling proteins, inhibition of cell growth and induction of apoptosis. 5-NT showed much higher selectivity towards the tumorigenic cell line MCF-7, when compared to MCF-10A, a non-tumorigenic cell line. FIG. 11 suggests that 5-NT works through the 5-HT$_{1B/1D}$ receptor. The serotonin 5-HT$_{1B}$ receptor is over-expressed in primary, metastatic and resistant breast cancer cells (FIG. 11B). Knockdown of either the 5-HT$_{1B}$ or 5-HT$_{1D}$ receptor, blunts the effect of 5-NT (FIG. 11C). 5-NT also decreases cAMP levels (FIG. 11D) which is known to be associated with 5-HT$_{1B/1D}$ receptor signaling.

Using nanoliposomal delivery technology we discovered that the systemic (i.v.) administration of 5-nonylytryptamine (5-NT) (a triptan drug (Glennon et al., 1996)) at 5.8 mg/kg (twice weekly) significantly inhibits growth of highly aggressive and metastatic triple negative (Her-, ER-, Pr-) MDA-231 human breast tumors in an in vivo orthotopic xenograft breast cancer model in nude mice (FIG. 3A). Most importantly, nanoliposomal 5-NT was shown to be non-toxic to mice and to normal cells. However, it induces apoptosis (FIG. 3B), inhibits colony formation (FIG. 3C) and inhibits growth (FIG. 3D) of MDA-231 and MCF-7 cells.

Figure 5:
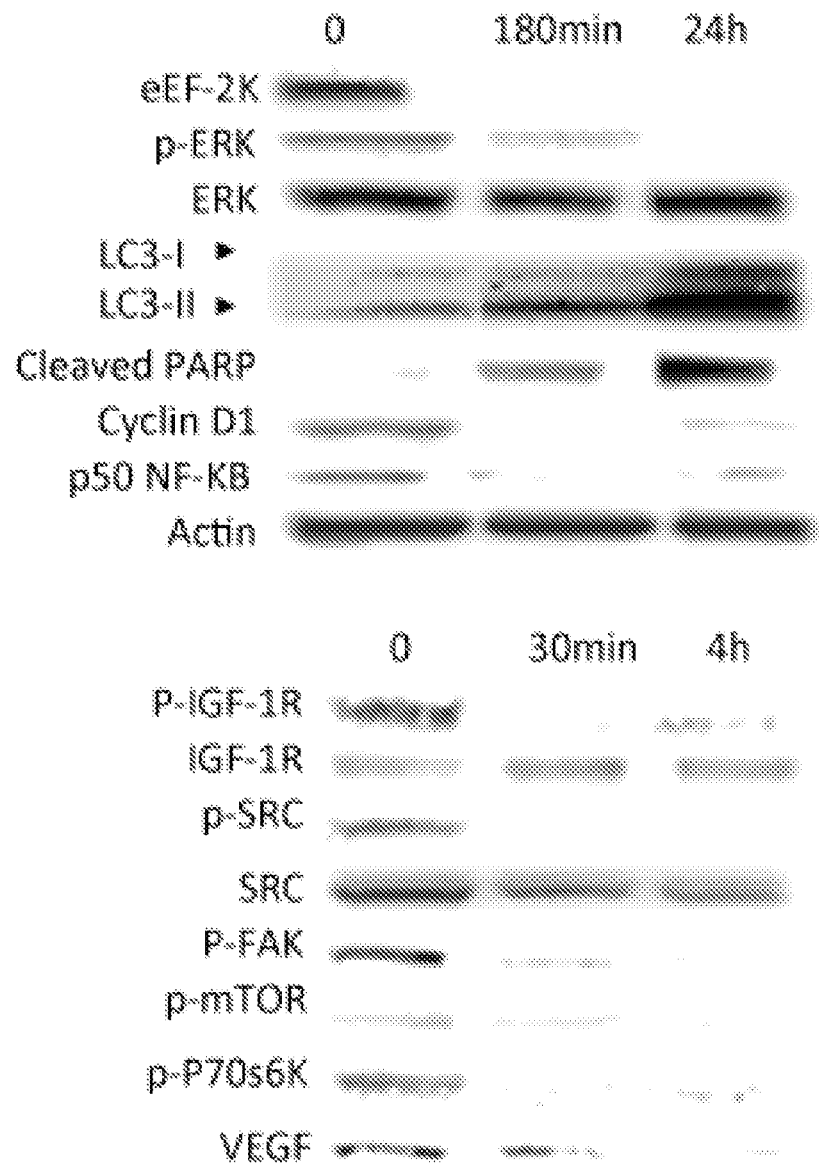
FIG. 5. 5-NT down-regulates critical pro-tumorigenic processes in ER(+) MCF-7 triple negative breast cancer cells. Western blot analysis shows that 5-NT (5 µM) down-regulates the expression of eEF-2K, Cyclin D, NF-κB, and VEGF as well as the phosphorylation of IGF1R, Src, FAK, mTOR, p70S6K, and ERK2. 5-NT also induces PARP cleavage and LC3-II. Methods: MCF7 cells were cultured at 37° C. in DMEM supplemented with 5% FBS in a humid incubator with 5% CO$_2$. Following incubation with or without 5-NT cells were lysed according to standard protocols for western blotting. Blots were quantified as in FIG. 3.

5-NT is a potent and specific ligand for the serotonin 5-HT$_{1B/1D}$ receptors (Glennon et al., 1996). We also found that 5-NT induced robust apoptosis in MCF-7 cells (FIG. 3B), and induced the down-regulation of protein kinases associated with critical survival pathways (e.g. IGF-1R, Akt, mTor, ERK) and/or invasion (e.g. c-Src and Fak) (FIG. 5). In addition it down-regulated proteins important for cell cycle progression (e.g. cyclin D) and angiogenesis (e.g. VEGF) (FIG. 5).

While the antagonist SB224289 was found to be quite toxic in mice, 5-NT was found to potently inhibit breast cancer tumor growth (FIG. 3A) without displaying any toxicity (i.e. weight loss) at a high dose of 50 mg/kg.

Targeted delivery of therapeutics and diagnostics to tumor cells and vasculature is recognized as a powerful approach for the treatment of cancer (Ozpolat et al., 2010). We recently developed a neutral nanoliposome (~mean diameter 65 nm) composed of neutral-charge dioleylphosphatidylcholine (DOPC), which can target siRNA in vivo into tumor cells 10- and 30-fold more effectively than cationic liposomes or naked siRNA, respectively (Ozpolat et al., 2010). We effectively delivered 5-NT to breast tumors in an orthotopic model using the same liposome. 5-NT derivatives are generally metabolized efficiently by first pass through the liver and have a plasma half-life of only 2-3 hours. Significantly, the nanoliposome delivery vehicle required administration of the drug only twice per week at a low 5.8 mg/kg dose to facilitate significant tumor growth inhibition (FIG. 3A).

We discovered that 5-nonylytryptamine (5-NT) (a triptan drug with high specificity for $5-HT_{1B/1D}$) significantly inhibits growth and induces apoptosis and autophagy in highly aggressive and metastatic Her(−) ER(−) PR(−) in vitro models of human breast cancer. We also found that a combination of 5-NT with a low dose of doxorubicin (a common chemotherapy) leads to synergistic cell death in MCF-7 cells and that 5-NT, when combined with doxorubicin, induces the cell-cycle inhibitor (p27) and the translation inhibitor, programmed cell death 4 (PDCD4). We discovered that using nanoliposomal delivery technology the systemic (i.v.) administration of 5-nonylytryptamine (5.8 mg/kg, twice weekly) significantly inhibits growth of tumors in an in vivo orthotopic xenograft breast cancer model in nude mice. We found that nanoliposomal 5-NT is non-toxic to mice and normal cells. Our novel neutrally charged DOPC-based nanovector delivery system has been shown to increase targeting of molecules such as siRNA in vivo into tumor cells by 30-fold. Folate or RGD expressing nanoliposomes exhibit a further 5-9 fold enhancement. We found that the $5-HT_{1B}$ receptor is over-expressed in estrogen receptor ER(−), ER(+), triple negative, highly aggressive metastatic and drug resistant (tamoxifen and chemotherapy) breast cancers. An antagonist of the $5-HT_{1B}$ receptor induces apoptotic cell death, inhibits Bcl-2 expression, as well as the PI3K/Akt/mTOR and STAT3 signaling pathways, all of which are associated with progression, metastasis and resistance to most chemotherapeutics, hormone therapy and radiotherapy.

5-NT analogs may be optimally encapsulated in liposomes at a drug to lipid ratio of approximately 1:10 w/w. Drug-lipid compatibility tests may be performed using differential scanning calorimetry to guide the selection of the optimal lipid composition for entrapment of 5-NT analogs (Chiu and Premier, 2011). Liposomal drug formulations may be prepared as follows: Solution A: The RGD-conjugated neutral lipid DSPE-PEG$_{2000}$-RGD (from Avanti polar lipids Inc.) and DSPE-PEG$_{2000}$ (varied ratio) may be mixed with dioleylphosphatidylcholine (DOPC) in an overall ratio of ~1:11; w/w in the presence of ~5% Tween-20 (w/w). Solution B: DOPC may be mixed with the triptan in a ratio of ~1:10-20 in the presence of excess tertiarybutanol. Solution A and B may then be mixed to give a final ratio of ~(1:10; w/w) drug:lipid. The mixture may then be frozen and lyophilized overnight. Before incubating with cells, the lyophilized powder may be mixed with saline solution to make liposomes and extruded through a 100 nm membrane. The amount of each drug analog successfully encapsulated may be assessed following the method of Liu et al. (Liu et al., 2010) where RGD-M-LCL is separated from unloaded drug using a Sephadex-G50 column. Drug release from RGD-M-LCL may be determined in medium with 50% FBS over 2-120 h using the same approach. To evaluate the uptake of liposomes into breast cancer cells, a fluorescent assay may be adopted that we previously used to characterize liposome uptake (Ozpolat and Lachman, 2003). Following the in vitro tests, verification of 5-NT release in vivo may be investigated in five control animals with tumors, and plasma concentrations may be monitored (0.5-8 h post injection) by HPLC to assess release of the drug following in vivo injections. Tumor and other tissues such as liver, spleen, kidney, heart, lung, small intestine, uterus and muscle may be collected after a single injection of each formulation. The levels of drug may be determined in tissues and expressed per gram of tissue weight.

Example 21

Compound Synthesis

Chemistry: Synthesis of Various Tryptamine Derivatives

General procedure for the synthesis of 3-(2-Aminoethyl)-5-(alkoxy)indole hydrochloride (KD01-KD-09)

A 250 mL round bottom flask was charged with potassium carbonate (650 mg, 4.7 mmol) and serotonin hydrochloride salt (500 mg, 2.35 mmol) and stirred in $H_2O/CH_3CN$ (2/1, 10 mL) till all the solid material had dissolved. Di-tert-butyl dicarbonate (564 mg, 2.59 mmol) was added via syringe, and the resulting yellow solution was allowed to stir at room temperature for 24 h. The reaction mixture was diluted with water 10 ml and the resulting precipitate was extracted with EtOAc (3×75 mL), and the combined organic layer was washed with $H_2O$ (1×5 mL) and brine (1×5 mL). The EtOAc layer was dried over ($Na_2SO_4$) and solvent evaporated under reduced pressure at 25° C. to obtain 610 mg of N-t-BOC-serotonin as brown foam. Yield: 93%, mp 52-54° C. LRMS (ESI): M+ for $C_{15}H_{20}N_2O_3$, calculated 276.14. found 276.14.

N-t-BOC serotonin (0.5 mmol) and potassium carbonate (1 mmol) was dissolved in $CH_3CN$ (4 mL) at 25° C. in a 250 mL round bottom flask fitted with a reflux condenser. Alkyl bromide (0.53 mmol) was added via syringe and the resulting reaction mixture was heated to 80° C. for 24 h. The reaction mixture was allowed to cool to 25° C. and the solvent was evaporated under reduced pressure. The residue obtained was purified using flash chromatography with 20-30% EtOAc/hexanes as eluent. The alkylated serotonin N-t-BOC serotonin derivatives were obtained as pale brown oil.

The above alkylated serotonin N-t-BOC serotonin derivative (0.11 mmol) was dissolved in EtOAc (0.2 mL) in a 100 mL round bottom flask. To the above solution was added HCl (3 M) in EtOAc (0.6 mL) and the reaction mixture was allowed to stir for 2 h. A white precipitate formation was observed after 10 min. Solvent was evaporated under reduced pressure at 25° C. and the product was triturated with anhydrous $Et_2O$. The solid product was collected by filtration and washed well with anhydrous $Et_2O$ and cold EtOAc to obtain the product as white precipitate.

Scheme 1: Synthesis of 2-(5-alkoxy-1H-indol-3-yl)ethanamine hydrochloride (KD01-KD09)

Scheme 2: synthesis of N-(2-(5-alkoxy-1H-indol-3-yl)ethyl)acetamide (KD10-KD16).

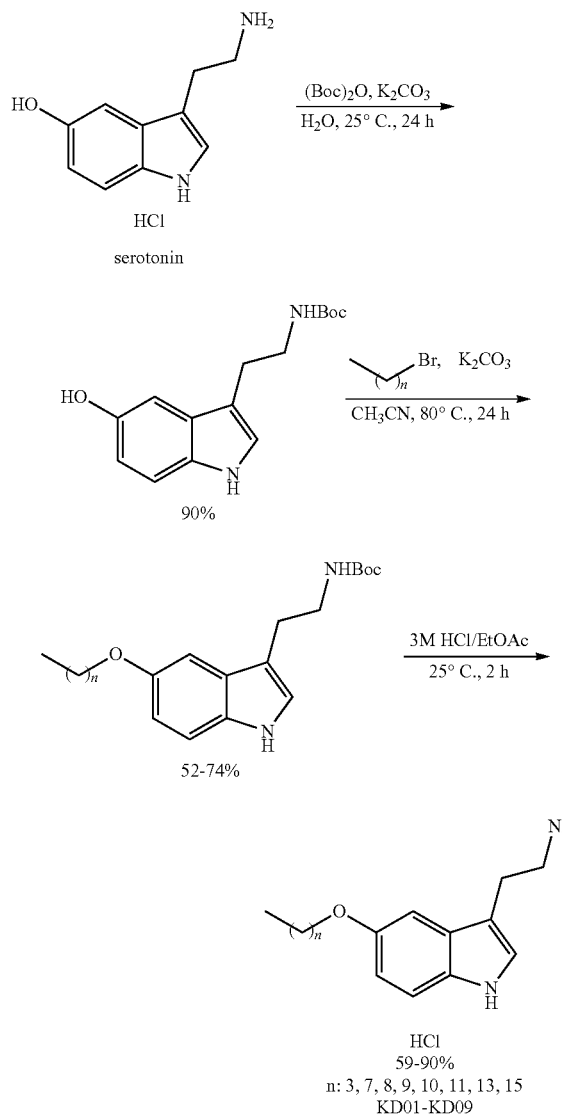

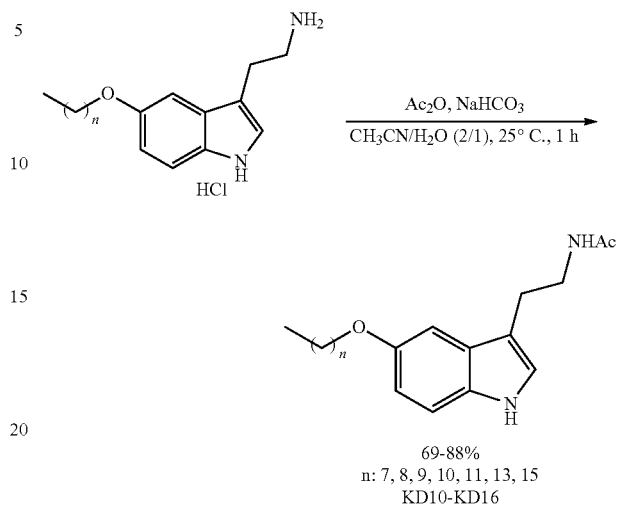

Scheme 3: synthesis of 2-(5-methoxy-1H-indol-3-yl)-N,N-dimethylethanamine (KD19) and 2-(5-methoxy-1H-pyrrolo[3,2-b]pyridin-3-yl)-N,N-dimethylethanamine (KD20)

A reported procedure was followed to prepare the compounds(1).

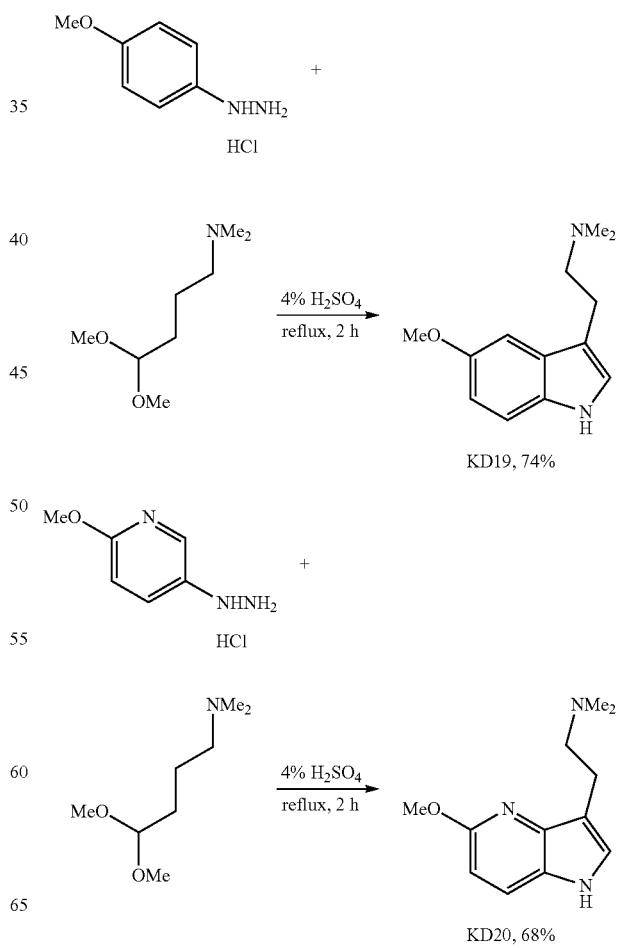

General procedure for the synthesis of N-(2-(5-alkoxy-1H-indol-3-yl)ethyl)acetamide (KD10-KD16)

The 3-(2-Aminoethyl)-5-(alkoxy)indole hydrochloride (0.05 mmol) was dissolved in $CH_3CN/H_2O$ (2/1, 0.5 mL), followed by addition of $NaHCO_3$ (0.25 mmol) in a 5 mL dram vial. To the cloudy white solution was then added $Ac_2O$ (0.15 mmol) and the reaction mixture was stirred at 25° C. for 4 h. The reaction mixture wad then diluted with water (4 mL) and extracted with EtOAc (3×2 mL). The EtOAc layer was washed with water (1×2 mL) and brine (1×2 mL) and dried over $Na_2SO_4$. The solvent was evaporated under reduced pressure at 30° C. to obtain the corresponding 3-(2-acetylaminoethyl)-5-(alkoxy)indoles as pale yellow oil which solidifies upon standing.

Scheme 4: synthesis of 2-(5-(2-(2-(2-methoxyethoxy)ethoxy)ethoxy)-1H-indol-3-yl)ethanamine hydrochloride (KD21)

This compound was prepared by the procedure similar to syntheses of 2-(5-alkoxy-1H-indol-3-yl) ethanamine hydrochloride.

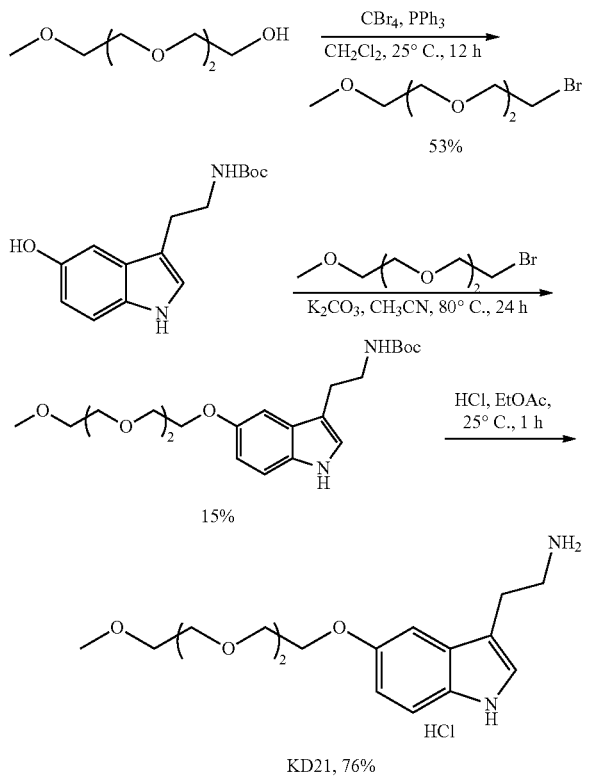

Procedure for synthesis of 2-(5-(nonyloxy)-1H-pyrrolo[3,2-b]pyridin-3-yl)ethanamine (KD25)

The N-phthaloyl protected 5-methoxy-4-azaindole was prepared by heating the 5-hydrazinyl-2-methoxypyridine hydrochloride (502 mg, 2.86 mmole) and 2-(4,4-diethoxybutyl)isoindoline-1,3-dione (1 g, 3.43 mmole) in 50 mL of 4% sulfuric acid and 8 mL ethanol at 95° C. for 2 h in a 250 mL round bottom flask. The reaction mixture was cooled to 25° C. and neutralized with 30% NH$_4$OH. The reaction mixture was extracted with EtOAc (1×20 mL) and washed with water and brine. The organic layer was dried over Na2SO4 and solvent evaporated to obtain 820 mg of product as pale brown solid. Yield: 88%.

The N-phthaloyl protected 5-methoxy-4-azaindole (300 mg, 0.94 mmole) was refluxed in HBr/CH3CO2H (3 mL) for 48 h in a 100 mL round bottom flask fitted with a refluxing condensor. The reaction mixture was cooled to 25° C. and diluted with water (10 mL). The reaction mixture was neutralized with 10% NaOH solution and extracted with EtOAc (3×5 mL) and washed thoroughly with water (2×5 mL) and brine (2×5 mL). The organic layer was dried over Na2SO4 and solvent evaporated to obtain 190 mg of product, N-phthaloyl protected 5-hydroxy-4-azaindole as pale brown solid.

N-phthaloyl protected 5-hydroxy-4-azaindole (80 mg, 0.26 mmole) and DIPEA (0.15 mL, 0.63 mmole) was dissolved in 2 mL DMF and stirred at 25° C. for 5 min in a 25 mL round bottom flask. To the reaction mixture was then added n-nonyl bromide (60 mg, 0.29 mmole) and reaction continued at 110° C. for 24 h. The reaction mixture was cooled to 25° C. and solvent removed under reduced pressure. The residue was purified by flash chromatography eluting with 50% EtOAc/hexanes to afford product N-phthaloyl protected 5-nonyloxy-4-azaindole as a dark yellow solid (31 mg, 42%). Rf 0.4 (50% EtOAc/hexanes).

N-phthaloyl protected 5-nonyloxy-4-azaindole (20 mg, 0.05 mmole) and hydrazine (3 mg, 0.09 mmole) was dissolved in CH2Cl2 (0.5 mL) in a 25 mL round bottom flask. EtOH (1 mL) was added to the reaction mixture and allowed to stir overnight at 25° C. for 12 h, after which it was cooled to 0° C., and filtered, and the white solid material was washed with 3 mL of cold CH2Cl2. The filtrate was evaporated under reduced pressure to afford 7 mg (50%) of 2-aminoethyl-5-nonyloxy-4-azaindole as a yellow solid. LRMS (ESI): M+1 for C18H29N3O calcd 304.4. found 304.4.

Scheme 5: synthesis of 4-azaindoles (KD22-KD25)

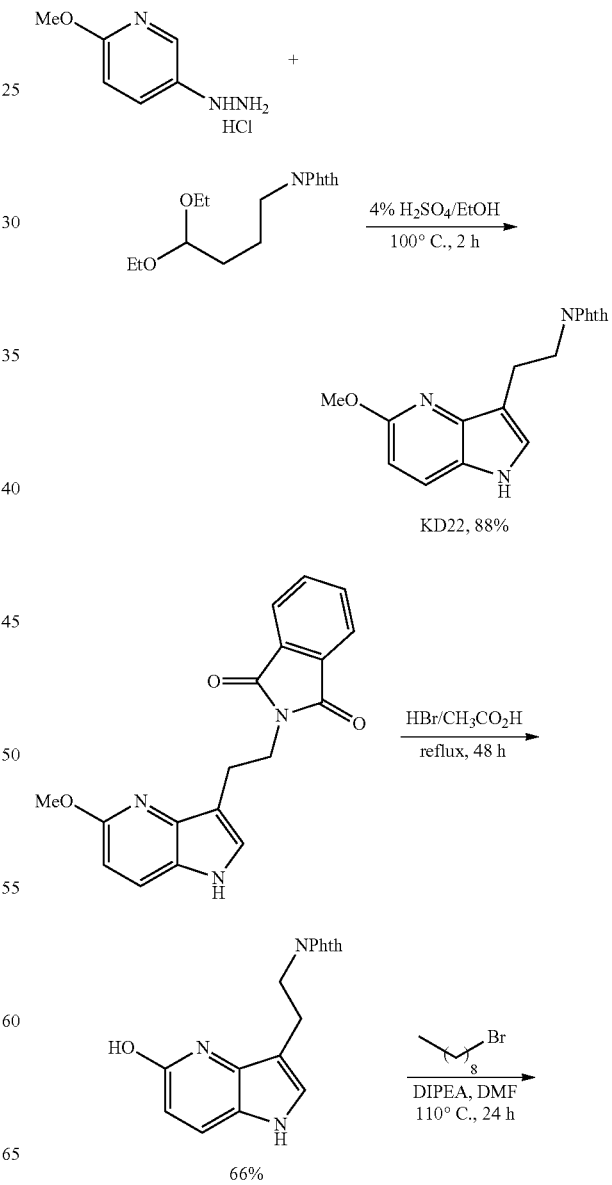

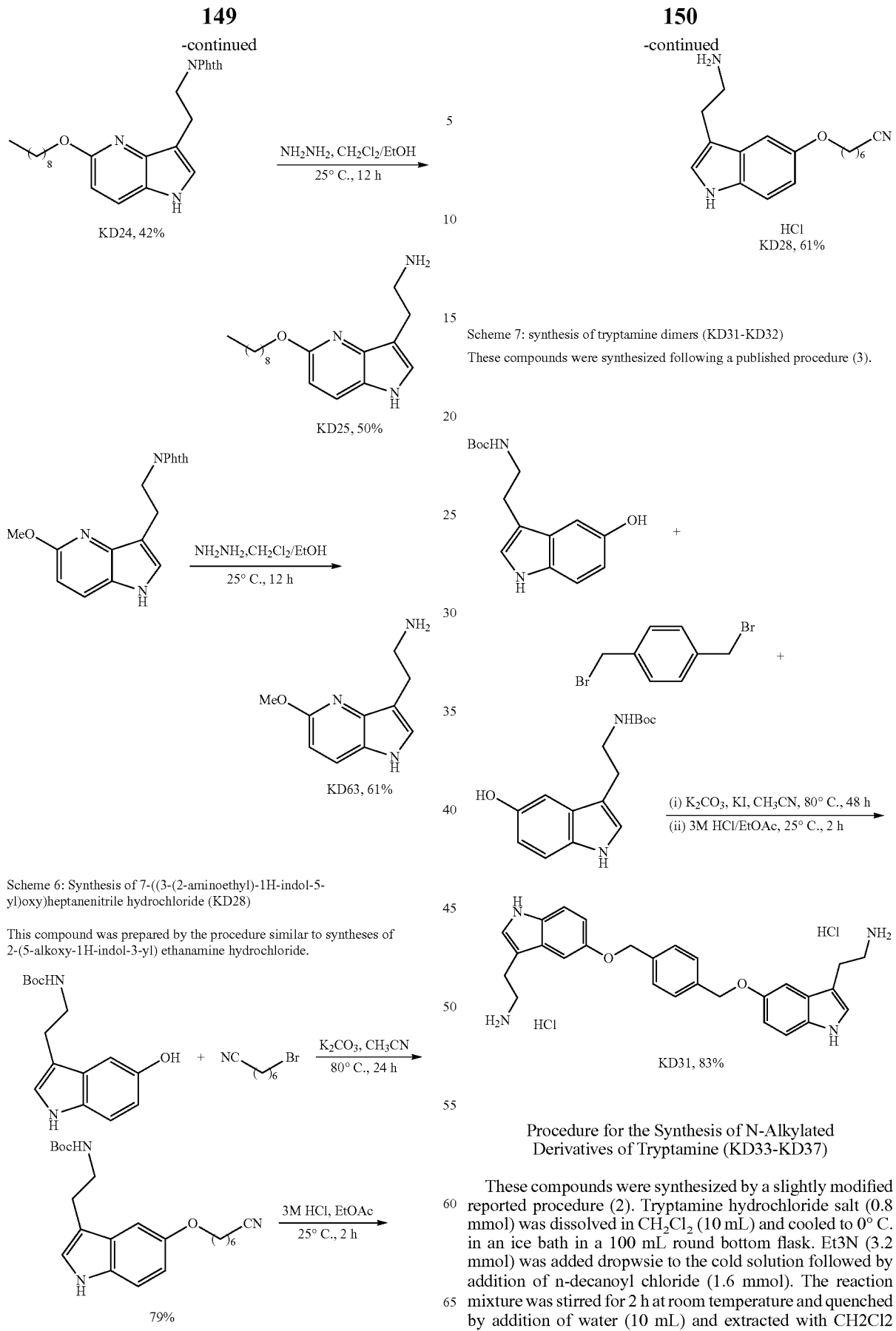

Scheme 7: synthesis of tryptamine dimers (KD31-KD32)

These compounds were synthesized following a published procedure (3).

Scheme 6: Synthesis of 7-((3-(2-aminoethyl)-1H-indol-5-yl)oxy)heptanenitrile hydrochloride (KD28)

This compound was prepared by the procedure similar to syntheses of 2-(5-alkoxy-1H-indol-3-yl) ethanamine hydrochloride.

Procedure for the Synthesis of N-Alkylated Derivatives of Tryptamine (KD33-KD37)

These compounds were synthesized by a slightly modified reported procedure (2). Tryptamine hydrochloride salt (0.8 mmol) was dissolved in $CH_2Cl_2$ (10 mL) and cooled to 0° C. in an ice bath in a 100 mL round bottom flask. Et3N (3.2 mmol) was added dropwsie to the cold solution followed by addition of n-decanoyl chloride (1.6 mmol). The reaction mixture was stirred for 2 h at room temperature and quenched by addition of water (10 mL) and extracted with CH2Cl2 (3×10 mL). The organic layer was then dried over Na2SO4, filtered and concentrated in vacuo. The residue was purified by flash chromatography eluting with 100% hexanes and 20-30% EtOAc/hexanes to afford N-decanoylamide of tryptamine as an yellow solid (236 mg, 92%). $R_f$=0.5 (20% EtOAc/hexanes).

To a solution of above amide (50 mg, 0.16 mmol) in tetrahydrofuran (10 mL) was added LiAlH4 (1.59 mL (1 M solution in THF, 1.59 mmol) at 0° C. in a 100 mL round bottom flask. The reaction mixture was refluxed for 4 h and then cooled to 25° C. and further to 0° C. in an icebath. The reaction was quenched with water (10 mL) and extracted with EtOAc (3×5 mL). The EtOAc layer was washed with water (1×5 mL), brine (1×5 mL) and dried over Na2SO4. Evaporation of the solvent under reduced pressure afforded the desired product as yellow semisolid (42 mg, 88%).

Scheme 8: synthesis of N-alkylated derivatives of tryptamine and serotonin (KD33-KD37)

A similar procedure was followed to obtain the N-alkylated derivative of serotonin.

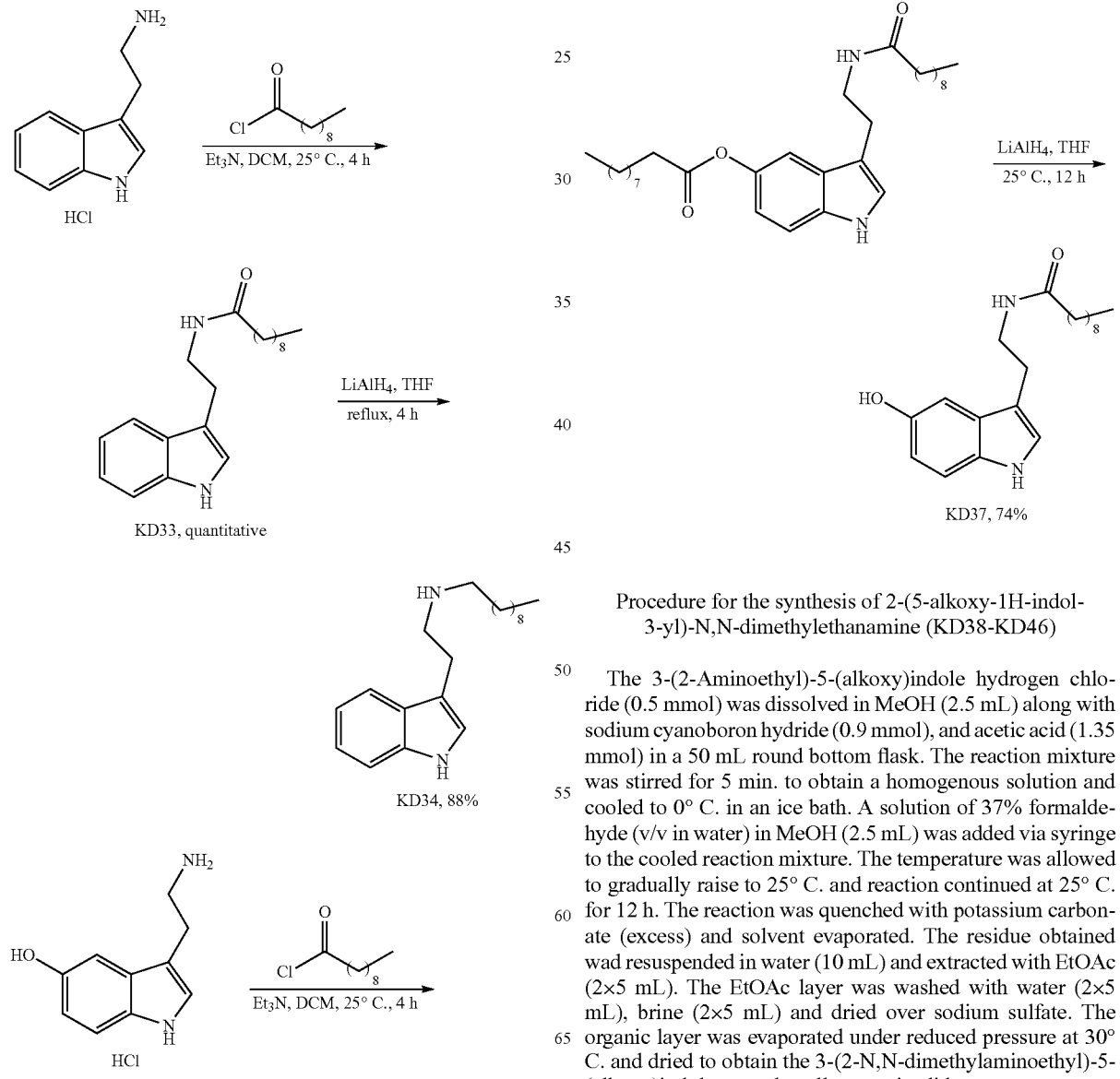

Procedure for the synthesis of 2-(5-alkoxy-1H-indol-3-yl)-N,N-dimethylethanamine (KD38-KD46)

The 3-(2-Aminoethyl)-5-(alkoxy)indole hydrogen chloride (0.5 mmol) was dissolved in MeOH (2.5 mL) along with sodium cyanoboron hydride (0.9 mmol), and acetic acid (1.35 mmol) in a 50 mL round bottom flask. The reaction mixture was stirred for 5 min. to obtain a homogenous solution and cooled to 0° C. in an ice bath. A solution of 37% formaldehyde (v/v in water) in MeOH (2.5 mL) was added via syringe to the cooled reaction mixture. The temperature was allowed to gradually raise to 25° C. and reaction continued at 25° C. for 12 h. The reaction was quenched with potassium carbonate (excess) and solvent evaporated. The residue obtained wad resuspended in water (10 mL) and extracted with EtOAc (2×5 mL). The EtOAc layer was washed with water (2×5 mL), brine (2×5 mL) and dried over sodium sulfate. The organic layer was evaporated under reduced pressure at 30° C. and dried to obtain the 3-(2-N,N-dimethylaminoethyl)-5-(alkoxy)indoles as pale yellow semi solid.

Scheme 9: synthesis of 2-(5-alkoxy-1H-indol-3-yl)-N,N-dimethylethanamine (KD38-KD46)

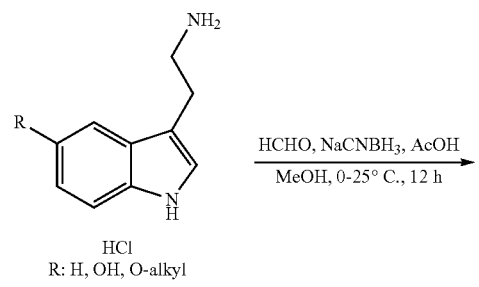

HCl
R: H, OH, O-alkyl

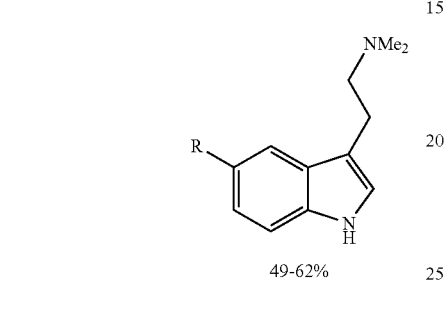

49-62%

KD38

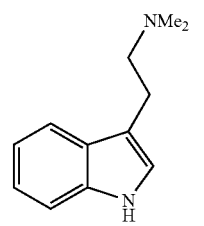

KD39

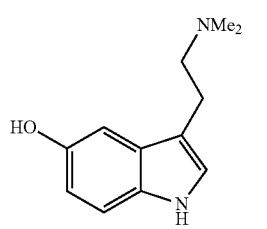

KD40

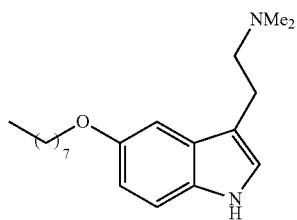

KD41

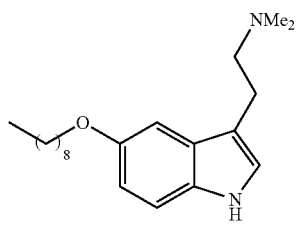

KD42

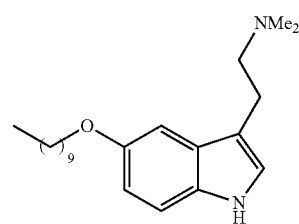

KD43

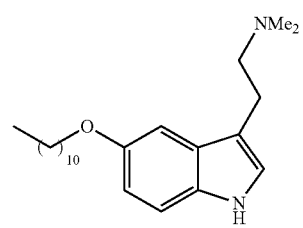

KD44

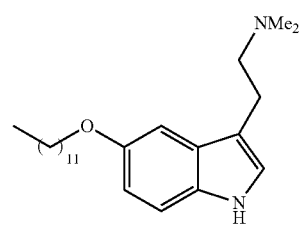

KD45

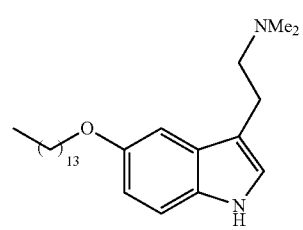

KD46

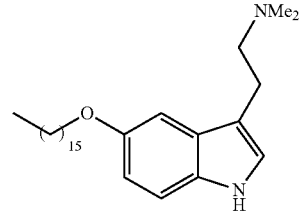

Procedure for the synthesis of 4- and 7-alkoxy tryptamine (KD48-KD51)

4-Hydroxyindole (500 mg, 3.76 mmol), K2CO3 (1.04 g, 7.51 mmol), and n-nonylbromide (817 mg, 3.94 mmol) was dissolved in acetonitrile (10 mL) and stirred at 25° C. for 10 min in a 250 mL round bottom flask. The reaction mixture was refluxed for 24 h and cooled to 25° C. The reaction mixture filtered to remove insoluble impurities and solvent evaporated under reduced pressure. The residue was purified by flash chromatography eluting with 100% hexanes and 30% EtOAc/hexanes to afford 4-nonyloxyindole as pale yellow solid (847 mg, 87%). $R_f$=0.8 (30% EtOAc/hexanes).

A solution of 4-nonyloxyindole (500 mg, 1.93 mmol), 1-dimethylamino-2-nitroethylene (224 mg, 1.93 mmol), and TEA (286 μL) in CH2Cl2 (10 mL) was stirred at 25° C. for 1 h in a 250 mL round bottom flask. The reaction mixture was cooled to 0° C. and quenched with saturated NaHCO3 solution (10 mL). The organic layer was dried over Na2SO4 and solvent evaporated. The residue thus obtained was purified by flash chromatography eluting with 100% hexanes to 20-30% EtOAc/hexanes to afford 3-(2-nitroethylene)-4-(nonyloxy) indole as a yellow solid (234 mg, 37%). R$_f$=0.4 (30% EtOAc/hexanes).

3-(2-nitroethylene)-4-(nonyloxy)indole (230 mg, 0.7 mmol) was dissolved in THF (6 mL) in 100 mL round bottom flask and cooled to 0° C. in an ice bath. LiAlH4 (1 M Solution in THF, 4.2 mL, 4.2 mmol) was added drop wise to the cooled reaction mixture and the temperature was slowly raised to 25° C. The reaction mixture was refluxed for 4 h and cooled to 0° C. followed by quenching with water (10 mL). The reaction mixture was extracted with EtOAc (3×10 mL) and washed with water (1×10 mL) and brine (1×10 mL), dried over Na2SO4 and filtered. The filtrate was acidified with 3 M HCl in EtOAc (1 mL) and solvent evaporated. The residue obtained was triturated with ether and precipitate obtained filtered and washed with cold EtOAc and dried to obtain 138 mg of 3-(2-aminoethyl)-4-(nonyloxy)indole hydrochloride as a pale yellow solid (138 mg, 58%).

Scheme 10: synthesis of 4- and 7-alkoxy tryptamine (KD48-KD51)

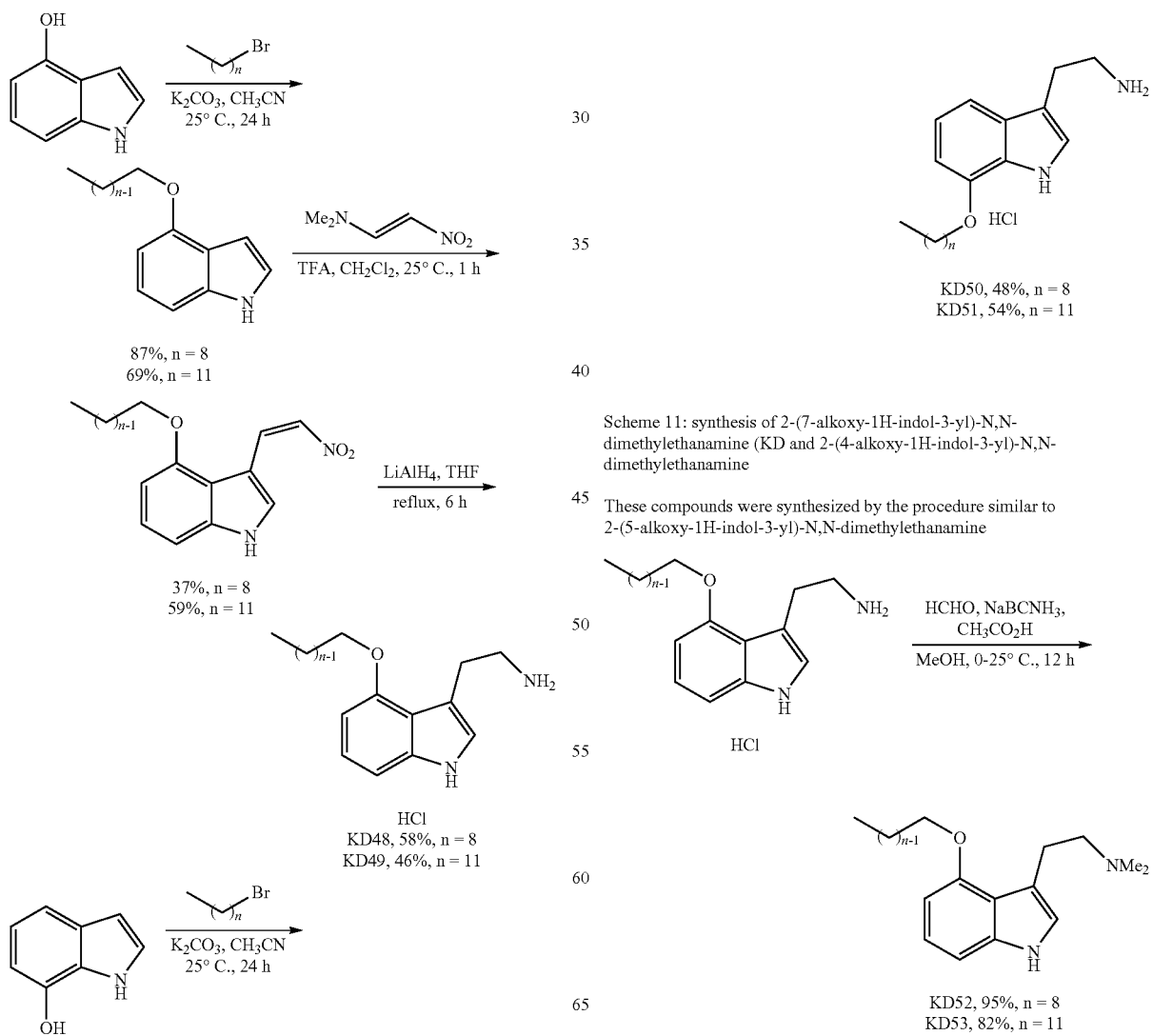

Scheme 11: synthesis of 2-(7-alkoxy-1H-indol-3-yl)-N,N-dimethylethanamine (KD and 2-(4-alkoxy-1H-indol-3-yl)-N,N-dimethylethanamine These compounds were synthesized by the procedure similar to 2-(5-alkoxy-1H-indol-3-yl)-N,N-dimethylethanamine -continued

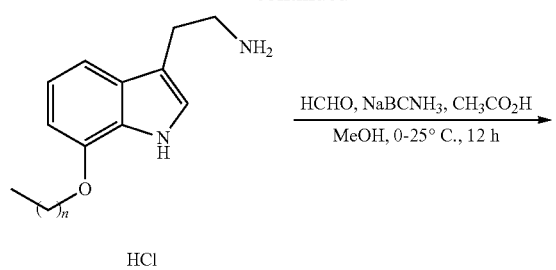

HCHO, NaBCNH$_3$, CH$_3$CO$_2$H
MeOH, 0-25° C., 12 h

HCl

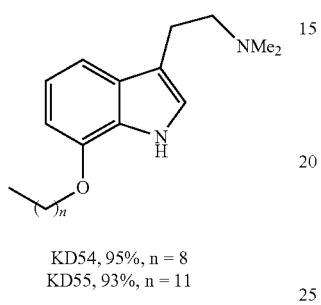

KD54, 95%, n = 8
KD55, 93%, n = 11

Scheme 12: synthesis of N-(2-(4-alkoxy-1H-indol-3-yl)ethyl)acetamide (KD56-KD57) and N-(2-(4-alkoxy-1H-indol-3-yl)ethyl)Acetamide (KD58-KD59)

These compounds were synthesized by the procedure similar to N-(2-(5-alkoxy-1H-indol-3-yl)ethyl)acetamide

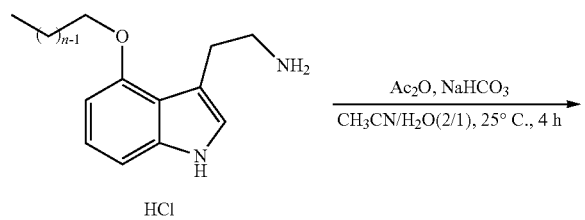

HCl

Ac$_2$O, NaHCO$_3$
CH$_3$CN/H$_2$O(2/1), 25° C., 4 h

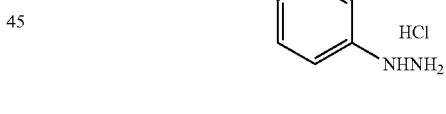

KD56, 87%, n = 8
KD57, 98%, n = 11

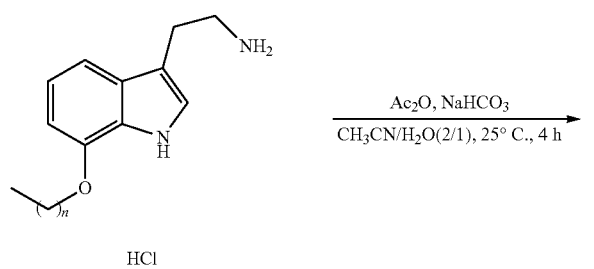

HCl

Ac$_2$O, NaHCO$_3$
CH$_3$CN/H$_2$O(2/1), 25° C., 4 h

-continued

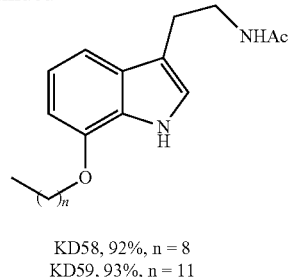

KD58, 92%, n = 8
KD59, 93%, n = 11

General Experimental Methods

All reactions were carried out under an atmosphere of dry nitrogen. Glasswares were oven-dried prior to use. Unless otherwise indicated, common reagents or materials were obtained from commercial sources and used without further purification. All solvents were dried prior to use with appropriate drying agents. Dry distilled DMF, DIPEA were obtained from Acros and used as such. Flash column chromatography was performed using silica gel 60 (230-400 mesh). Analytical thin layer chromatography (TLC) was carried out on Merck silica gel plates with QF-254 indicator and visualized by UV. $^1$H and $^{13}$C NMR spectra were measured on a Varian Direct Drive 400s, a Varian MERCURY 400, or Varian UNITY+300s and referenced to Me4Si for $^1$H. The purity of the compounds (≥95%) were determined using HPLC conducted on an Surveyor 1100 system, using a reversed phase C8 column with diode array detection. All LC-MS data were collected on a Surveyor HPLC (autosampler, quaternary pump, and diode array detector) and a Thermo LTQ-XL linear ion trap mass spectrometer with electrospray source. The method of elution used was CH$_3$CN:H$_2$O with 0.1% formic acid, with a flow rate of 0.5 mL/min. HR electrospray ionization (ESI) mass spectra were recorded on a Waters QTOF Premier micromass instrument or a Varian 9.4T QFT-ESI ICR system.

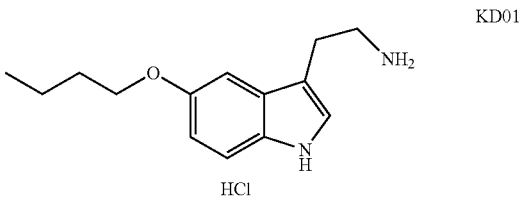 [SMILES: CCCCOc1ccc2[nH]cc(CCN)c2c1 ; Cl]

$^1$H (300 MHz DMSO-d$_6$) δ 10.05 (br, 3H), 7.0 (d, J=9.0 Hz, 2H), 6.89 (d, J=9.0 Hz, 2H), 3.71 (s, 3H) $^{13}$C (100.6 MHz DMSO-d$_6$) δ 155.23, 139.28, 117.56, 114.76, 55.73.

KD01

HCl $^1$H (400 MHz DMSO-d$_6$) δ 10.84 (br, 1H), 8.12 (br, 2H), 7.25 (d, J=8.8 Hz, 1H), 7.19 (d, J=3.8 Hz, 1H), 7.08 (d, J=3.8 Hz, 1H), 6.73 (dd, J=8.8 Hz, 1H), 3.99 (t, J=6.4 Hz, 2H), 3.06-2.995 (m, 4H), 1.75-1.67 (m, 2H), 1.51-1.42 (m, 2H), 0.95 (t, J=7.2 Hz, 3H); $^{13}$C (100.6 MHz DMSO-d$_6$) δ 152.89, 131.85, 127.62, 124.39, 112.54, 112.11, 109.64, 101.54, 68.08, 31.53, 23.54(2C), 19.33, 14.26. LRMS (ESI): 233.2 HRMS calculated 233.1654. found 233.1650 (M+1).

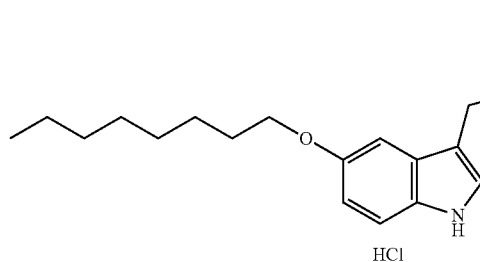

KD02

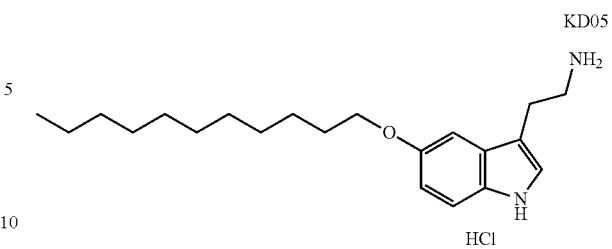

KD05

$^1$H (400 MHZ DMSO-$d_6$) δ 10.77 (br, 1H), 7.82 (br, 2H), 7.22 (d, J=8.1 Hz, 1H), 7.16 (d, J=3.9 Hz, 1H), 7.03 (d, J=4.1 Hz, 1H), 6.71 (dd, J=8.2 Hz, 4.1 Hz, 1H), 3.93 (t, J=8.2 Hz, 2H), 3.03-2.99 (m, 2H), 2.95-2.91 (m, 2H), 1.75-1.65 (m, 2H), 1.41 (br, 2H), 1.24 (br, 14H), 0.84 (t, J=8.1 Hz, 3H); $^{13}$C (100.6 MHz DMSO-$d_6$) δ 152.75, 131.80, 127.81, 124.04, 112.85, 111.72, 109.99, 109.73, 101.65, 68.37, 31.75, 29.51, 29.48(2C), 29.46, 29.32, 29.17, 26.10, 23.62, 22.55, 14.42. LRMS (ESI) 331.3, HRMS calculated 331.2744. found 331.2743 (M+1).

$^1$H (400 MHZ DMSO-$d_6$) δ 10.77 (br, 1H), 7.85 (br, 2H), 7.22 (d, J=8.0 Hz, 1H), 7.16 (d, J=4.0 Hz, 1H), 7.03 (d, J=4.0 Hz, 1H), 6.71 (dd, J=8.0 Hz, 4.0 Hz, 1H), 3.94 (t, J=8.0 Hz, 2H), 3.03-2.99 (m, 2H), 2.95-2.91 (m, 2H), 1.75-1.65 (m, 2H), 1.42 (br, 2H), 1.26 (br, 8H), 0.85 (t, J=8.0 Hz, 3H); $^{13}$C (100.6 MHz DMSO-$d_6$) δ 152.9, 131.86, 127.62, 124.42, 112.54, 112.1, 109.59, 101.55, 68.39, 31.71, 29.46, 29.29 (2C), 29.15, 26.13, 23.56, 22.55, 14.42. LRMS (ESI): 289.3, HRMS calculated 289.2274. found 289.2272 (M+1).

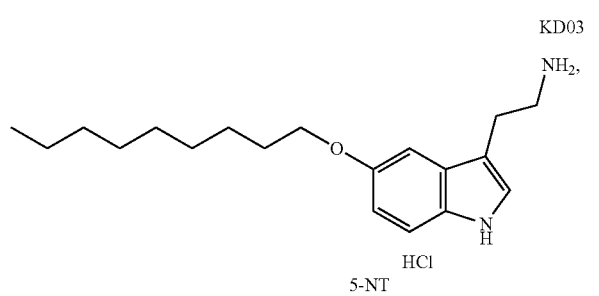 [SMILES: CCCCCCCCCOc1ccc2[nH]cc(CCN)c2c1 ; Cl]

KD03
5-NT

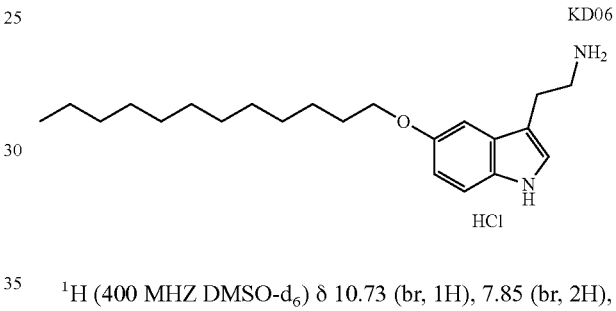

KD06

$^1$H (400 MHZ DMSO-$d_6$) δ 10.76 (br, 1H), 7.86 (br, 2H), 7.21 (d, J=7.9 Hz, 1H), 7.15 (d, J=4.0 Hz, 1H), 7.04 (d, J=4.0 Hz, 1H), 6.70 (dd, J=8.0 Hz, 4.0 Hz, 1H), 3.93 (t, J=8.0 Hz, 2H), 3.03-2.99 (m, 2H), 2.95-2.91 (m, 2H), 1.75-1.65 (m, 2H), 1.42 (br, 2H), 1.26 (br, 10H), 0.85 (t, J=8.0 Hz, 3H); $^{13}$C (100.6 MHz DMSO-$d_6$) δ 152.9, 131.87, 127.61, 124.46, 112.56, 112.1, 109.52, 101.55, 68.39, 31.73, 29.45(2C), 29.33 (2C), 29.13, 26.12, 23.58, 22.55, 14.42. LRMS (ESI) 303.3, HRMS calculated 303.2431. found 303.2437 (M+1).

$^1$H (400 MHZ DMSO-$d_6$) δ 10.73 (br, 1H), 7.85 (br, 2H), 7.17 (d, J=8.2 Hz, 1H), 7.11 (d, J=4.2 Hz, 1H), 6.98 (d, J=4.2 Hz, 1H), 6.66 (dd, J=8.2 Hz, 4.2 Hz, 1H), 3.88 (t, J=8.1 Hz, 2H), 2.98-2.94 (m, 2H), 2.90-2.86 (m, 2H), 1.67-1.62 (m, 2H), 1.41 (br, 2H), 1.24 (br, 16H), 0.78 (t, J=8.0 Hz, 3H); $^{13}$C (100.6 MHz DMSO-$d_6$) δ 152.8, 131.87, 127.7, 124.46, 112.54, 112.09, 109.48, 101.53, 68.39, 31.72, 29.5, 29.48, 29.43(2C), 29.36, 29.32, 29.16, 27.31, 26.12, 23.6, 22.55, 14.42. LRMS (ESI) 345.4, HRMS calculated 345.2900. found 345.2902 (M+1).

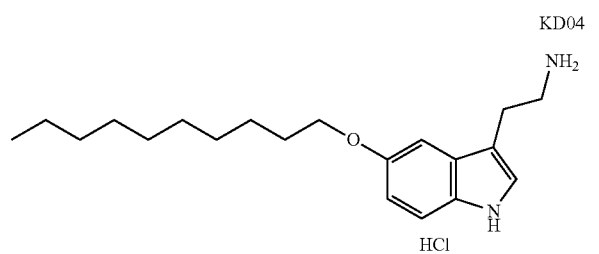 [SMILES: CCCCCCCCCCOc1ccc2[nH]cc(CCN)c2c1 ; Cl]

KD04

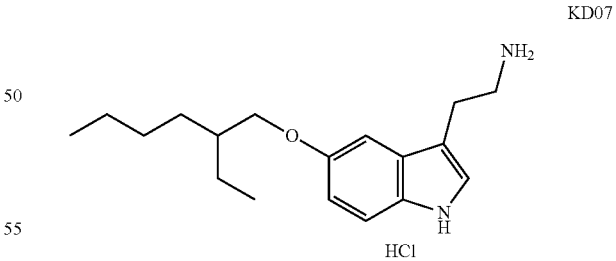

KD07

$^1$H (400 MHZ DMSO-$d_6$) δ 10.78 (br, 1H), 7.92 (br, 2H), 7.21 (d, J=7.8 Hz, 1H), 7.16 (d, J=3.9 Hz, 1H), 7.03 (d, J=3.8 Hz, 1H), 6.71 (dd, J=7.8 Hz, 4.0 Hz, 1H), 3.93 (t, J=7.9 Hz, 2H), 3.03-2.99 (m, 2H), 2.95-2.91 (m, 2H), 1.75-1.65 (m, 2H), 1.41 (br, 2H), 1.24 (br, 12H), 0.84 (t, J=7.9 Hz, 3H); $^{13}$C (100.6 MHz DMSO-$d_6$) δ 152.9, 131.88, 127.6, 124.47, 112.56, 112.09, 109.49, 101.54, 68.38, 31.74, 29.5, 29.43 (2C), 29.32, 29.16, 27.31, 26.12, 23.6, 22.55, 14.42. LRMS (ESI) 317.4, HRMS calculated 317.25874. found 317.2588 (M+1).

$^1$H (400 MHZ DMSO-$d_6$) δ 10.77 (br, 1H), 7.84 (br, 2H), 7.22 (d, J=8.2 Hz, 1H), 7.16 (d, J=4.1 Hz, 1H), 7.03 (d, J=4.1 Hz, 1H), 6.72 (dd, J=8.1 Hz, 4.0 Hz, 1H), 3.84 (d, J=4.1 Hz, 2H), 3.01 (br, 2H), 2.95-2.91 (m, 2H), 1.70-1.67 (m, 1H), 1.47-1.23 (m, 8H), 0.91-0.85 (m, 6H); $^{13}$C (100.6 MHz DMSO-$d_6$) δ 153.17, 131.89, 127.61, 124.49, 112.56, 112.12, 109.51, 101.59, 70.99, 30.52, 28.97, 23.88 (2C), 23.58 (2C), 22.99, 14.44, 11.45. LRMS (ESI) 289.3, HRMS calculated 289.2274. found 289.2275 (M+1).

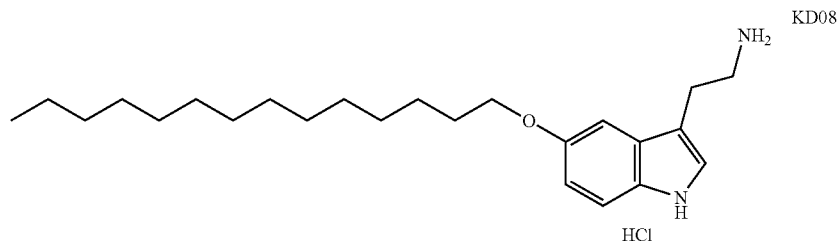 [SMILES: CCCCCCCCCCCCCCOc1ccc2[nH]cc(CCN)c2c1 ; Cl]

KD08

¹H (400 MHz DMSO-d₆) δ 10.78 (br, 1H), 7.94 (br, 2H), 7.22 (d, J=7.9 Hz, 1H), 7.16 (d, J=3.9 Hz, 1H), 7.03 (d, J=4.0 Hz, 1H), 6.70 (dd, J=7.9 Hz, 4.0 Hz, 1H), 3.93 (t, J=6.8 Hz, 2H), 3.06-2.97 (br, 2H), 2.95-2.91 (m, 2H), 1.73-1.66 (m, 2H), 1.45-1.36 (m, 2H), 1.27 (br, 20H), 0.83 (t, J=6.8 Hz, 3H); ¹³C NMR (101 MHz, DMSO-d₆) δ 152.90, 131.87, 127.61, 124.43, 112.54, 112.09, 109.73, 101.53, 68.38, 31.74, 29.50 (2C), 29.46, 29.43, 29.41, 29.40, 29.38, 29.37, 29.33, 29.16, 26.13, 23.57, 22.55, 14.42. LRMS (ESI) 373.4, HRMS calculated 373.3213. found 373.3215 (M+1).

5.52 (br, 1H), 3.99 (t, J=6.8 Hz, 2H), 3.59 (q, J=12.8 Hz, 5.6 Hz, 2H), 2.93 (t, J=6.8 Hz, 2H), 1.93 (s, 3H), 1.84-1.77 (m, 2H), 1.48 (br, 2H), 1.32 (br, 8H), 0.89 (t, J=6.0 Hz, 3H); ¹³C (100.6 MHz CDCl₃) δ 170.10, 153.57, 131.48, 127.74, 122.69, 113.0, 112.69, 111.87, 101.59, 68.90, 39.68, 31.83, 29.52, 29.42, 29.27, 26.15, 25.25, 23.42, 22.67, 14.11. LRMS (ESI) 331.2 (M+1) HRMS calculated 353.2199. found 353.2202 (M+Na⁺).

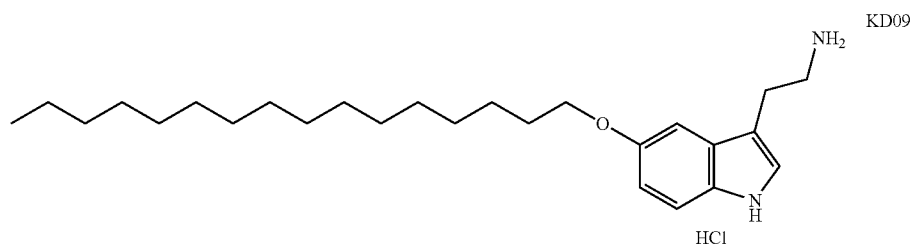 [SMILES: CCCCCCCCCCCCCCCCOc1ccc2[nH]cc(CCN)c2c1 ; Cl]

KD09

¹H (400 MHz DMSO-d₆) δ 10.78 (br, 1H), 8.0 (br, 2H), 7.22 (d, J=8.8 Hz, 1H), 7.16 (s, 1H), 7.03 (s, 1H), 6.71 (dd, J=8.6 Hz, 4.3 Hz, 1H), 3.94 (t, J=6.4 Hz, 2H), 3.0 (br, 2H), 2.93 (br, 2H), 1.74-1.67 (m, 2H), 1.41 (br, 2H), 1.23 (br, 24H), 0.84 (t, J=6.8 Hz, 3H); ¹³C NMR (101 MHz, DMSO-d₆) δ 145.99, 128.83, 126.99, 123.37, 119.55, 111.19, 109.99, 103.01, 67.92, 31.75, 29.50(2C), 29.46, 29, 42, 29.38, 29.35, 29.33, 29.30, 29.27, 29.21, 29.15, 25.99, 23.64, 22.55, 14.42. LRMS (ESI) 401.4, HRMS calculated 401.3526. found 401.3528.

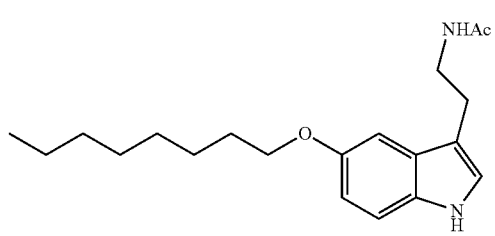

KD10

¹H (400 MHZ CDCl₃) δ 7.96 (br, 1H), 7.26 (d, J=7.9 Hz, 1H), 7.0 (d, J=7.9 Hz, 2H), 6.88 (dd, J=7.8 Hz, 4.0 Hz, 1H),

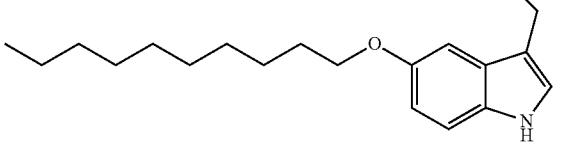

KD11

¹H (400 MHZ CDCl₃) δ 7.95 (br, 1H), 7.26 (d, J=7.8 Hz, 1H), 7.02 (d, J=7.8 Hz, 2H), 6.90 (dd, J=7.9 Hz, 4.0 Hz, 1H), 5.53 (br, 1H), 4.01 (t, J=6.9 Hz, 2H), 3.61 (q, J=12.4 Hz, 5.6 Hz, 2H), 2.95 (t, J=6.8 Hz, 2H), 1.94 (s, 3H), 1.86-1.79 (m, 2H), 1.50 (br, 2H), 1.31 (br, 10H), 0.90 (t, J=6.0 Hz, 3H); ¹³C (100.6 MHz CDCl₃) δ 170.10, 153.58, 131.47, 127.75, 122.68, 113.02, 112.72, 111.86, 101.59, 68.90, 39.67, 31.88, 29.57, 29.52, 29.46, 29.28, 26.14, 25.25, 23.43, 22.67, 14.11. LRMS (ESI) 345.2 (M+1), HRMS calculated 367.2356. found 367.2361 (M+Na⁺).

KD12

¹H (400 MHZ CDCl₃) δ 7.94 (br, 1H), 7.25 (d, J=7.8 Hz, 1H), 7.02 (d, J=7.8 Hz, 2H), 6.88 (dd, J=7.9 Hz, 4.0 Hz, 1H), 5.52 (br, 1H), 3.99 (t, J=6.9 Hz, 2H), 3.59 (q, J=12.4 Hz, 5.6 Hz, 2H), 2.93 (t, J=6.8 Hz, 2H), 1.93 (s, 3H), 1.84-1.77 (m, 2H), 1.48 (br, 2H), 1.27 (br, 12H), 0.88 (t, J=6.0 Hz, 3H); ¹³C (100.6 MHz CDCl₃) δ 170.02, 153.59, 131.47, 127.74, 122.67, 113.02, 112.72, 111.86, 101.58, 68.89, 39.67, 31.89, 29.61, 29.57, 29.52, 29.46, 29.33, 26.14, 25.25, 23.43, 22.68, 14.12. LRMS (ESI) 359.2 (M+1), HRMS calculated 381.2513. found 381.2515 (M+Na⁺).

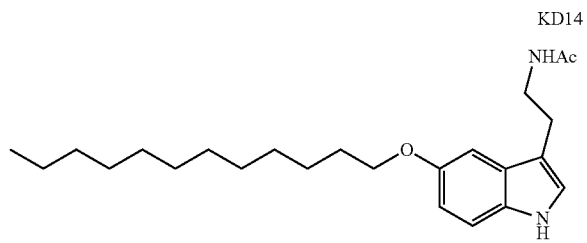 [SMILES: CCCCCCCCCCCCOc1ccc2[nH]cc(CCNC(C)=O)c2c1]
KD14

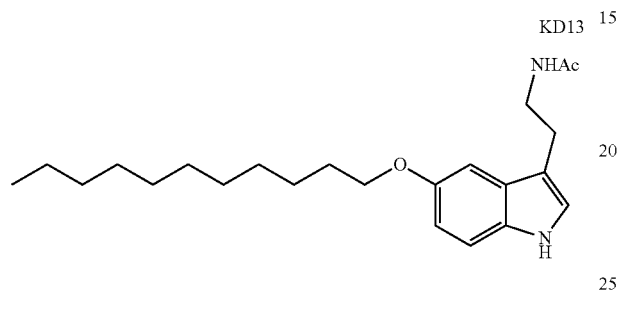
KD13

¹H (400 MHZ CDCl₃) δ 7.99 (br, 1H), 7.28 (d, J=7.8 Hz, 1H), 7.04 (d, J=7.8 Hz, 2H), 6.90 (dd, J=7.9 Hz, 4.0 Hz, 1H), 5.54 (br, 1H), 4.02 (t, J=6.9 Hz, 2H), 3.62 (q, J=12.4 Hz, 5.6 Hz, 2H), 2.96 (t, J=6.8 Hz, 2H), 1.95 (s, 3H), 1.83-1.79 (m, 2H), 1.48 (br, 2H), 1.29 (br, 16H), 0.90 (t, J=6.0 Hz, 3H); ¹³C (100.6 MHz CDCl₃) δ 170.02, 153.58, 131.48, 127.74, 122.69, 113.00, 112.70, 111.87, 101.58, 68.90, 39.67, 31.91, 29.67, 29.64(2C), 29.62, 29.52, 29.47, 29.35, 26.15, 25.25, 23.42, 22.68, 14.12. LRMS (ESI) 387.3 (M+1), HRMS calculated 409.2823. found 409.2822 (M+Na⁺).

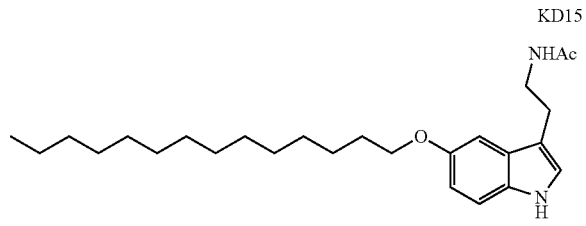 [SMILES: CCCCCCCCCCCCCCOc1ccc2[nH]cc(CCNC(C)=O)c2c1]
KD15

¹H (400 MHZ CDCl₃) δ 7.98 (br, 1H), 7.28 (d, J=7.8 Hz, 1H), 7.05 (d, J=7.8 Hz, 2H), 6.90 (dd, J=7.9 Hz, 4.0 Hz, 1H), 5.54 (br, 1H), 4.02 (t, J=6.9 Hz, 2H), 3.62 (q, J=12.4 Hz, 5.6 Hz, 2H), 2.96 (t, J=6.8 Hz, 2H), 1.95 (s, 3H), 1.83-1.79 (m, 2H), 1.48 (br, 2H), 1.29 (br, 14H), 0.90 (t, J=6.0 Hz, 3H); ¹³C (100.6 MHz CDCl₃) δ 170.02, 153.58, 131.47, 127.74, 126.68, 113.01, 112.70, 111.87, 101.58, 68.90, 39.67, 31.90, 29.62 (3C), 29.52, 29.46, 29.34, 26.15, 25.25, 23.42, 22.68, 14.12. LRMS (ESI) 373.2 (M+1), HRMS calculated 395.2669. found 395.2672 (M+Na⁺).

¹H (400 MHz CDCl₃) δ 7.94 (br, 1H), 7.26 (d, J=7.8 Hz, 1H), 7.02 (d, J=7.8 Hz, 2H), 6.88 (dd, J=7.9 Hz, 4.0 Hz, 1H), 5.51 (br, 1H), 3.99 (t, J=6.9 Hz, 2H), 3.60 (q, J=12.4 Hz, 5.6 Hz, 2H), 2.93 (t, 2H, J=6.8 Hz), 1.93 (s, 3H), 1.82-1.78 (m, 2H), 1.48 (br, 2H), 1.26 (br, 20H), 0.88 (t, J=6.0 Hz, 3H); ¹³C (100.6 MHz CDCl₃) δ 170.02, 153.59, 131.47, 127.75, 122.67, 113.02, 112.72, 111.86, 101.58, 68.90, 39.66, 31.91, 29.68, 29.65(3C), 29.62 (2C), 29.52, 29.47, 29.35, 26.15, 25.26, 23.43, 22.69, 14.12. LRMS (ESI) 415.3 (M+1), HRMS calculated 437.3139. found 437.3140 (M+Na⁺).

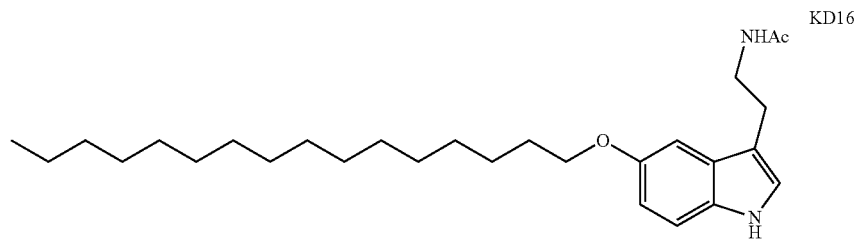 [SMILES: CCCCCCCCCCCCCCCCOc1ccc2[nH]cc(CCNC(C)=O)c2c1]
KD16

¹H (400 MHz CDCl₃) δ 8.01 (br, 1H), 7.26 (d, J=7.8 Hz, 1H), 7.02 (d, J=7.8 Hz, 2H), 6.88 (dd, J=7.9 Hz, 4.0 Hz, 1H), 5.55 (br, 1H), 3.99 (t, J=6.9 Hz, 2H), 3.60 (q, J=12.4 Hz, 5.6 Hz, 2H), 2.94 (t, J=6.8 Hz, 2H), 1.93 (s, 3H), 1.82-1.78 (m, 2H), 1.45 (br, 2H), 1.21 (br, 24H), 0.88 (t, J=6.0 Hz, 3H); ¹³C (100.6 MHz CDCl₃) δ 170.12, 153.56, 131.49, 127.74, 122.71, 112.99, 112.65, 111.88, 101.58, 68.91, 39.69, 31.92, 29.69(6C), 29.65, 29.63, 29.53, 29.48, 29.36, 26.15, 25.24, 23.40, 22.69, 14.12. LRMS (ESI) 443.3 (M+1), HRMS calculated 465.3452. found 465.3451 (M+Na⁺).

KD18

¹H NMR (400 MHz, cdcl₃) δ 7.90 (br, 1H), 7.17 (d, J=7.1 Hz, 1H), 6.96 (d, J=2.3 Hz, 1H), 6.93 (s, 1H), 6.79 (dd, J=7.1, 2.3 Hz, 1H), 4.53 (br, 1H), 3.93 (t, J=6.6 Hz, 2H), 2.84 (t, J=6.7 Hz, 2H), 1.73 (m, 2H), 1.41 (m, 2H), 1.36 (s, 9H), 1.21 (s, 12H), 0.81 (t, J=6.9 Hz, 3H). ¹³C NMR (101 MHz, cdcl₃) δ 155.66, 153.52, 131.63, 127.76, 122.91, 112.83, 111.76, 111.24, 101.88, 68.82, 32.08, 29.60, 29.54, 29.49, 29.28, 28.44, 26.15, 22.71, 14.12 (2C overlapping). LRMS (ESI) 403.3 (M+1) HRMS calculated 425.2775. found 425.2772 (M+Na⁺).

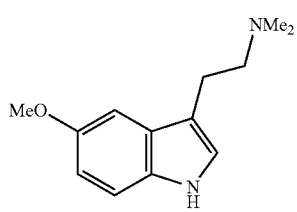

KD19

¹H NMR (400 MHz, CD₃OD) δ 7.20 (d, J=8.7 Hz, 1H), 7.00 (br, 2H), 6.75 (d, J=8.7 Hz, 1H), 3.80 (s, 3H), 2.88 (t, J=7.9 Hz, 2H), 2.62 (t, J=7.9 Hz, 2H), 2.31 (s, 6H); ¹³C NMR (101 MHz, CD₃OD) δ 153.64, 131.56, 127.57, 122.37, 111.87, 111.72, 110.84, 99.64, 59.74, 54.87, 43.66, 22.72. LRMS (ESI) 219.2 HRMS calculated 219.1492. found 219.1493 (M+1).

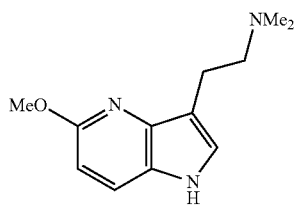

KD20

¹H NMR (400 MHz, CD₃OD) δ 7.58 (d, J=8.7 Hz, 1H), 7.21 (d, J=8.7 Hz, 1H), 6.52 (d, J=8.0 Hz, 1H), 3.92 (s, 3H), 2.94 (br, 2H), 2.77 (br, 2H), 2.37 (s, 6H); ¹³C NMR (101 MHz, CD₃OD) δ 159.70, 141.34, 124.92, 121.48, 114.92, 111.73, 103.73, 59.73, 56.30, 43.98, 21.82. LRMS (ESI) 220.2, HRMS calculated 220.1444. found 220.1444 (M+1).

KD21

5-Hexaethylene glycol tryptamine ¹H (400 MHZ DMSO-d₆) δ 10.79 (br, 1H), 7.87 (br, 2H), 7.23 (d, J=7.8 Hz, 1H), 7.17 (d, J=4.0 Hz, 1H), 7.06 (d, J=4.0 Hz, 1H), 6.73 (dd, J=4.0 Hz, 8.0 Hz, 1H), 4.07 (t, J=5.8 Hz, 2H), 3.73 (t, J=5.8 Hz, 2H), 3.58 (m, 2H), 3.50 (m, 4H), 3.41 (m, 2H), 3.21 (s, 3H), 2.93 (br, 4H); ¹³C (100.6 MHz DMSO-d₆) δ 152.64, 131.96, 127.60, 124.53, 112.61, 112.06, 109.59, 101.64, 71.70, 70.39, 70.26, 69.66, 68.07, 66.79, 58.49, 41.70, 23.59. LRMS (ESI) 323.2 HRMS calculated 323.1965. found 323.1967 (M+1)

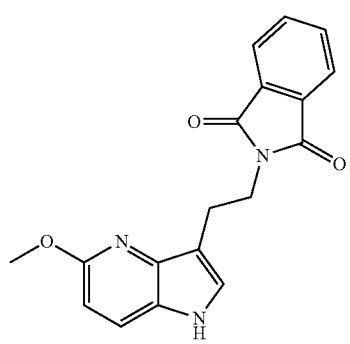

KD-22

¹H NMR (400 MHz, CDCl₃) δ 8.05 (s, 1H), 7.73 (br, 4H), 7.48 (d, J=8.6 Hz, 1H), 7.16 (s, 1H), 6.51 (d, J=8.6 Hz, 1H), 4.11 (t, J=7.1 Hz, 2H), 3.91 (s, 3H), 3.22 (t, J=7.1 Hz, 2H); ¹³C NMR (101 MHz, CDCl₃) δ 168.39, 159.60, 141.86, 133.68, 132.23, 124.43, 124.26, 122.99, 121.53, 112.84, 105.42, 53.03, 38.55, 23.39. LRMS (ESI) 322.2 (M+1), HRMS calculated 344.1006. found 344.1004 (M+Na⁺).

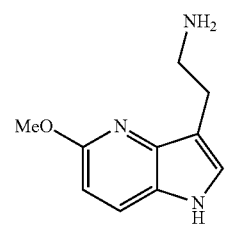

KD23

¹H NMR (400 MHz, DMSO-d₆) δ 11.08 (br, 1H), 8.05 (br, 2H), 7.70 (d, J=8.7 Hz, 1H), 6.56 (m, J=8.7 Hz, 2H), 3.86 (s, 3H), 3.19 (m, 2H), 2.97 (t, J=7.2 Hz, 2H); ¹³C NMR (101 MHz, DMSO-d₆) δ 159.07, 133.24, 126.68, 124.92, 118.37, 110.04, 105.17, 53.18, 23.27 (1C submerged with DMSO-d₆ peak). LRMS (ESI) 192.2, HRMS calculated 192.1131. found 192.113 (M+1).

KD24

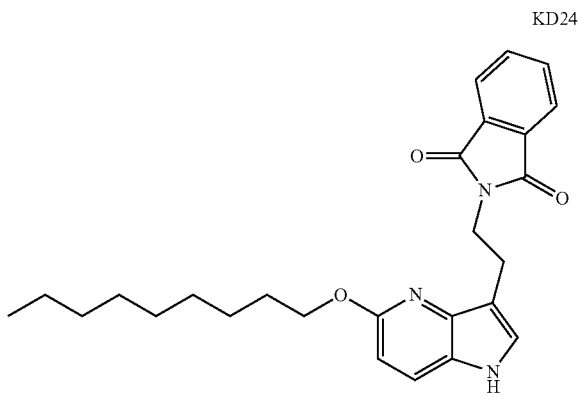 [SMILES: CCCCCCCCCOc1ccc2[nH]cc(CCN3C(=O)c4ccccc4C3=O)c2n1]

¹H NMR (400 MHz, CD₃OD) δ 7.65 (br, 4H), 7.42 (d, J=7.9 Hz, 1H), 7.08 (s, 1H), 6.31 (d, J=7.9 Hz, 1H), 4.04 (t, J=6.6 Hz, 2H), 3.91 (t, J=6.8 Hz, 2H), 3.03 (t, J=6.8 Hz, 2H), 1.60 (m, 2H), 1.20 (br, 12H), 0.79 (t, J=6.7 Hz, 3H); ¹³C NMR (101 MHz, CD₃OD) δ 168.59, 158.83, 134.12, 131.80, 125.24, 122.37, 122.32, 121.24, 111.40, 110.05, 104.29, 65.18, 38.55, 31.59, 29.40, 29.21, 29.12, 28.98, 25.90, 23.27, 22.48, 13.27 (1C). LRMS (ESI) 434.2, HRMS calculated 434.2438. found 434.2439 (M+1).

KD25

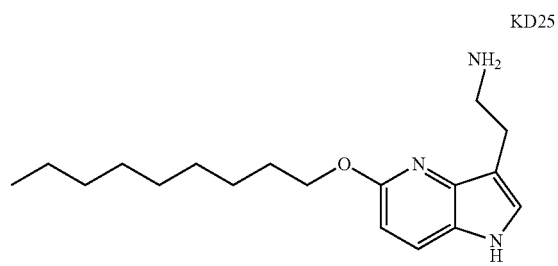 [SMILES: CCCCCCCCCOc1ccc2[nH]cc(CCN)c2n1]

¹H NMR (400 MHz, DMSO-d₆) δ 11.06 (br, 1H), 7.93 (br, 2H), 7.68 (d, J=8.7 Hz, 1H), 7.37 (s, 1H), 6.54 (d, J=8.7 Hz, 1H), 4.23 (t, J=6.6 Hz, 2H), 3.21-3.14 (m, 2H), 2.96 (t, J=7.2 Hz, 2H), 1.84-1.64 (m, 2H), 1.40 (br, 2H), 1.24 (br, 10H), 0.84 (t, J=6.9 Hz, 3H). LRMS (ESI) 304.4, HRMS calculated 304.2383. found 304.2385 (M+1).

KD27

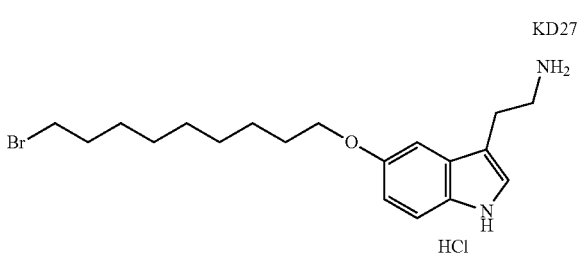 [SMILES: NCCc1c[nH]c2ccc(OCCCCCCCCCBr)cc12 ; Cl]

¹H (400 MHz DMSO-d₆) δ 10.78 (br, 1H), 7.95 (br, 2H), 7.22 (d, J=8.8 Hz, 1H), 7.16 (s, 1H), 7.04 (s, 1H), 6.91 (dd, J=10.8 Hz, 2.0 Hz, 1H); 3.94 (t, J=6.4 Hz, 2H), 3.0 (br, 2H), 3.5 (t, J=4.8 Hz, 2H), 2.97-2.93 (m, 2H), 1.805-1.67 (m, 4H), 1.29 (br, 10H). ¹³C NMR (101 MHz, DMSO-d₆) δ 152.90, 131.87, 127.61, 124.36, 112.84, 112.04, 109.55, 101.65, 68.38, 45.98, 35.70, 32.68, 29.44, 29.32, 29.22, 28.52, 27.96, 26.09, 23.57. LRMS (ESI) 381.2, HRMS calculated 381.1536. found 381.1535 (M+1).

KD28

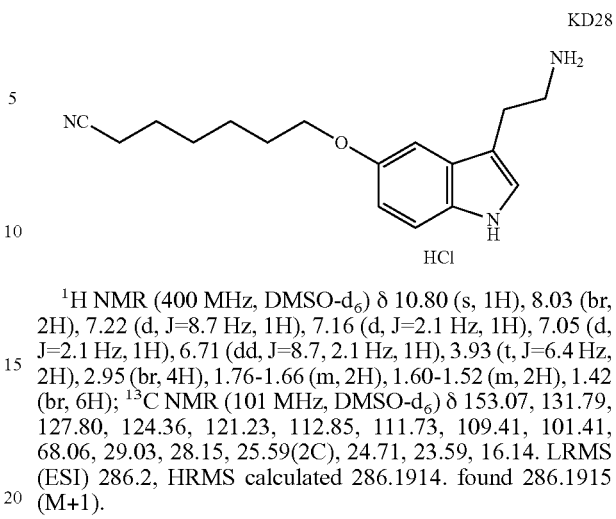

¹H NMR (400 MHz, DMSO-d₆) δ 10.80 (s, 1H), 8.03 (br, 2H), 7.22 (d, J=8.7 Hz, 1H), 7.16 (d, J=2.1 Hz, 1H), 7.05 (d, J=2.1 Hz, 1H), 6.71 (dd, J=8.7, 2.1 Hz, 1H), 3.93 (t, J=6.4 Hz, 2H), 2.95 (br, 4H), 1.76-1.66 (m, 2H), 1.60-1.52 (m, 2H), 1.42 (br, 6H); ¹³C NMR (101 MHz, DMSO-d₆) δ 153.07, 131.79, 127.80, 124.36, 121.23, 112.85, 111.73, 109.41, 101.41, 68.06, 29.03, 28.15, 25.59(2C), 24.71, 23.59, 16.14. LRMS (ESI) 286.2, HRMS calculated 286.1914. found 286.1915 (M+1).

KD29

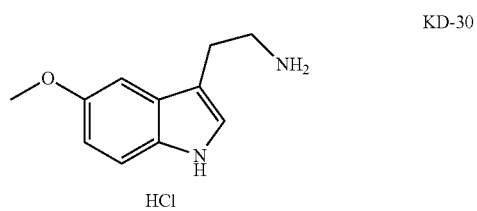

Acetyltryptamine ¹H (400 MHz CDCl₃) δ 8.01 (br, 1H), 7.54 (d, J=7.9 Hz, 1H), 7.32 (d, J=8.2 Hz, 1H), 7.15 (t, J=7.6 Hz, 1H), 7.07 (t, J=7.6 Hz, 1H), 6.98 (s, 1H), 5.54 (br, 1H), 3.56-3.52 (m, 2H), 2.92 (t, J=7.2 Hz, 2H), 1.86 (s, 3H). ¹³C (100.6 MHz CDCl₃) δ 163.82, 136.37, 127.31, 122.26, 122.0, 119.55, 118.69, 112.98, 112.25, 39.87, 25.21, 23.29. LRMS (ESI) 225.1, HRMS calculated 225.0998. found 225.0998 (M+1).

KD-30

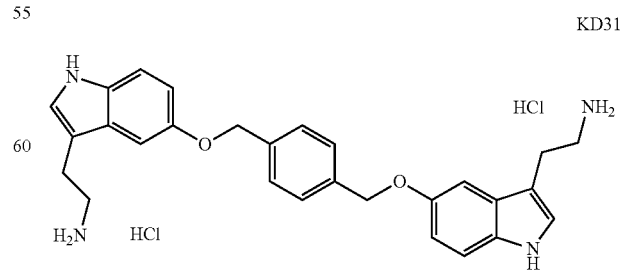

¹H NMR (400 MHz, DMSO-d₆) δ 10.60 (s, 1H), 8.01 (br, 2H), 7.27-7.11 (m, 1H), 7.05 (d, J=2.0 Hz, 1H), 6.98 (d, J=2.0 Hz, 1H), 6.75-6.62 (dd, J=6.3 Hz, 2.0 Hz, 1H), 3.73 (s, 3H), 2.86-2.61 (m, 4H). ¹³C NMR (101 MHz, DMSO-d₆) δ 153.29, 131.82, 128.06, 123.69, 112.81, 112.36, 111.37, 100.57, 55.76, 43.13, 30.08. LRMS (ESI) 191.2, HRMS calculated 191.1179. found 191.1180 (M+1).

KD31

¹H NMR (400 MHz, DMSO-d₆) δ 10.85 (br, 2H), 7.97 (br, 4H), 7.49 (br, 4H), 7.25 (d, J=8.7 Hz, 2H), 7.19 (m, 4H), 6.80

(dd, J=8.7, 2.4 Hz, 2H), 5.10 (s, 4H), 3.02 (br, 4H), 2.95 (br, 4H); $^{13}$C NMR (101 MHz, DMSO-$d_6$) δ 152.53, 137.59, 132.04, 128.20, 127.60, 124.57, 112.67, 112.26, 109.64, 102.14, 70.08, 23.72 (2C overlapping). LRMS (ESI) 455.2, HRMS calculated 455.2442. found 455.2446 (M+1).

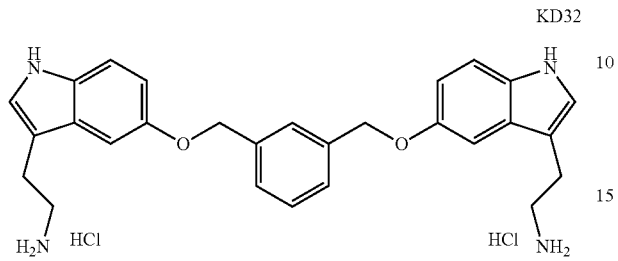

KD32

$^1$H NMR (400 MHz, DMSO-$d_6$) δ 10.83 (br, 2H), 8.01 (br, 4H), 7.60 (s, 1H), 7.42 (br, 4H), 7.30-7.11 (m, 5H), 6.81 (dd, J=8.7, 2.3 Hz, 2H), 5.12 (s, 4H), 2.99 (br, 8H); $^{13}$C NMR (101 MHz, DMSO-$d_6$) δ 152.34, 138.38, 132.06, 128.87, 127.49, 124.80, 112.85, 112.17, 109.72, 102.05, 70.17, 23.72 (2C overlapping). LRMS (ESI) 455.2, HRMS calculated 455.2442. found 455.2445 (M+1).

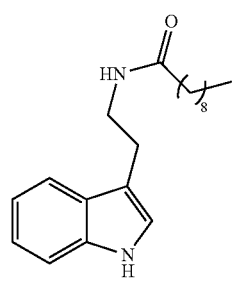

KD33

$^1$H NMR (400 MHz, CDCl$_3$) δ 8.23 (br, 1H), 7.61 (d, J=7.9 Hz, 1H), 7.38 (d, J=7.9 Hz, 1H), 7.21 (t, J=7.6 Hz, 1H), 7.13 (t, J=7.6 Hz, 1H), 7.03 (s, 1H), 5.56 (br, 1H), 3.61 (q, J=6.4 Hz, 2H), 2.98 (t, J=6.7 Hz, 2H), 2.10 (t, J=6.7 Hz, 2H), 1.57 (br, 2H), 1.25 (br, 12H), 0.88 (t, J=6.7 Hz, 3H); $^{13}$C NMR (101 MHz, CDCl$_3$) δ 173.47, 136.39, 127.33, 122.18, 122.02, 119.46, 118.71, 113.01, 111.26, 39.67, 36.90, 31.86, 30.15, 29.44, 29.35, 29.28, 25.76, 25.34, 22.67, 14.09. LRMS (ESI) 315.4, HRMS calculated 337.2250. found 337.2251 (M+Na$^+$).

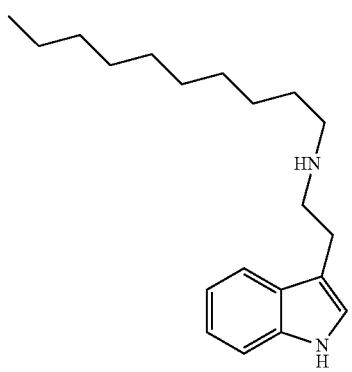

KD34

$^1$H (400 MHZ CDCl$_3$) δ 8.39 (br, 1H), 7.65 (d, J=8.1 Hz, 1H), 7.38 (d, J=8.1 Hz, 1H), 7.21 (t, J=11.9 Hz, 1H), 7.13 (t, J=11.9 Hz, 1H), 7.05 (s, 1H), 3.65 (t, J=11.8 Hz, 2H), 3.09-2.96 (br, 4H), 2.66 (t, J=12.0 Hz, 2H), 1.26 (br, 2H), 1.29 (br, 12), 0.91 (t, J=12.0 Hz, 3H); $^{13}$C (101 MHz CDCl$_3$) δ 136.67, 127.61, 122.37, 122.21, 119.47, 119.06, 113.74, 111.43, 49.93, 37.75, 33.10, 32.16, 30.0, 29.76, 29.59, 27.58, 26.04, 25.61, 22.94, 14.38. LRMS (ESI) 301.2, HRMS calculated 301.2638. found 301.2638 (M+1).

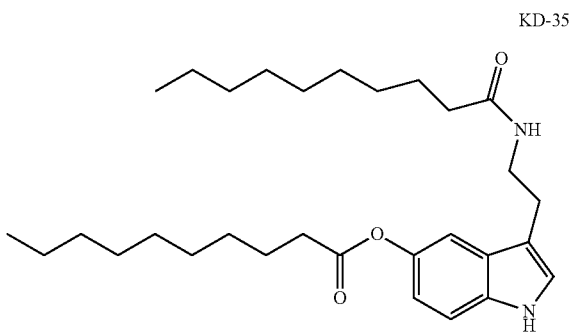 [SMILES: CCCCCCCCCC(=O)NCCc1c[nH]c2ccc(OC(=O)CCCCCCCCC)cc12]

KD-35

$^1$H NMR (400 MHz, CDCl$_3$) δ 8.34 (br, 1H), 7.48 (d, J=8.6 Hz, 1H), 7.18 (s, 1H), 7.06 (d, J=8.6 Hz, 1H), 5.76 (br, 1H), 3.71 (br, 2H), 3.07 (t, J=6.2 Hz, 2H), 2.73 (t, J=7.6 Hz, 2H), 2.27 (t, J=7.6 Hz, 2H), 2.00-1.88 (m, 2H), 1.73 (br, 2H), 1.59 (br, 2H), 1.42 (br, 22H), 1.03 (t, J=6.4 Hz, 6H); $^{13}$C NMR (101 MHz, CDCl$_3$) δ 176.91, 173.45, 143.87, 134.12, 127.56, 123.50, 116.36, 113.17, 112.04, 110.84, 39.64, 36.86, 34.56, 33.86, 31.87, 29.46, 29.45, 29.37, 29.31, 29.29, 29.20, 29.13, 25.77, 25.25, 25.07, 24.84, 22.67, 14.12. LRMS (ESI) 485.2, HRMS calculated 507.3557. found 507.3555 (M+Na$^+$).

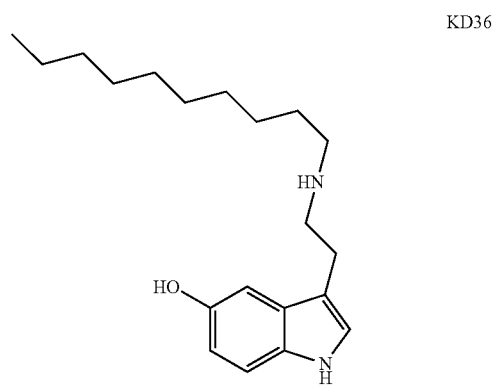 [SMILES: CCCCCCCCCCNCCc1c[nH]c2ccc(O)cc12]

KD36

$^1$H NMR (400 MHz, CD$_3$OD) δ 7.14 (d, J=8.7 Hz, 1H), 6.99 (s, 1H), 6.92 (d, J=2.7 Hz, 1H), 6.65 (dd, J=8.7, 2.7 Hz, 1H), 3.44 (t, J=7.2 Hz, 2H), 2.85 (t, J=8.0 Hz, 2H), 2.14 (t, J=8.0 Hz, 2H), 1.56 (br, 2H), 1.28 (br, 14H), 0.89 (t, J=9.5 Hz, 3H): $^{13}$C NMR (75 MHz, CDCl$_3$) δ 150.66, 131.53, 128.25, 123.16, 123.03, 112.86, 111.82, 103.46, 49.26, 33.04, 32.15, 29.88, 29.82, 29.71, 29.68, 29.58, 29.55, 26.03, 22.93, 14.37. LRMS (ESI) 317.2, HRMS calculated 317.2587. found 317.2591 (M+1).

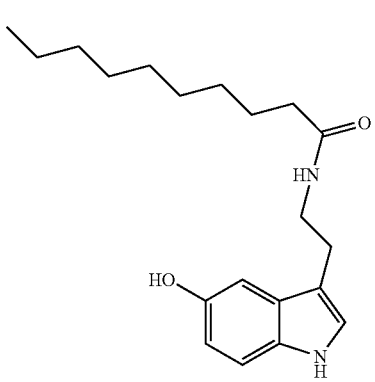

KD37

¹H (400 MHZ CDCl₃) δ 8.11 (br, 1H), 7.17 (d, J=8.0 Hz, 1H), 7.02 (d, J=4.1 Hz, 1H), 6.93 (d, J=4.0 Hz, 1H), 6.80 (dd, J=8.1 Hz, 4.0 Hz, 1H), 5.74 (br, 1H), 3.52 (q, J=8.2, 3.8 Hz, 2H), 2.84 (t, J=8.0 Hz, 2H), 2.10 (t, J=7.9 Hz, 2H), 1.56 (br, 2H), 1.22 (br, 12), 0.86 (t, J=7.8 Hz, 3H); ¹³C (101 MHz CDCl₃) δ 174.11, 150.31, 131.70, 128.26, 123.25, 112.50, 112.39, 112.15, 103.43, 39.95, 37.12, 32.11, 29.70, 29.60 (2C), 29.54, 26.02, 25.65, 22.92, 14.37. LRMS (ESI) 331.2 (M+1), HRMS calculated 353.21995. found 353.22 (M+Na⁺).

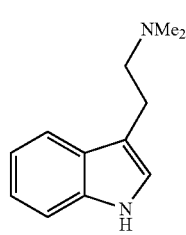

KD38

¹H (400 MHz CDCl₃) δ 8.47 (br, 1H), 7.52 (d, J=7.7 Hz, 1H), 7.21 (d, J=7.9 Hz, 1H), 7.08 (t, J=7.2 Hz, 1H), 7.02 (t, J=7.2 Hz, 1H), 6.84 (br, 1H), 2.87 (t, J=7.8 Hz, 2H), 2.58 (t, J=7.8 Hz, 2H), 2.27 (s, 6H); ¹³C (101 MHz CDCl₃) δ 136.36, 127.42, 121.83, 121.73, 119.09, 118.73, 113.90, 111.25, 60.49, 45.37, 23.60. LRMS (ESI) 189.2, HRMS calculated 189.1386. found 189.1387 (M+1).

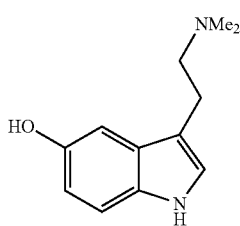

KD39

¹H NMR (400 MHz, CD₃OD) δ 7.10 (d, J=8.6 Hz, 1H), 6.93 (s, 1H), 6.86 (d, J=2.3 Hz, 1H), 6.62 (dd, J=8.6, 2.3 Hz, 1H), 2.87 (t, J=7.9 Hz, 2H), 2.64 (t, J=7.9 Hz, 2H), 2.29 (s, 6H); ¹³C NMR (101 MHz, CD₃OD) δ 149.98, 131.66, 127.91, 122.40, 111.30, 111.24, 110.95, 102.01, 60.03, 43.96, 23.14. LRMS (ESI) 205.2, HRMS calculated 205.1335. found 205.1336 (M+1).

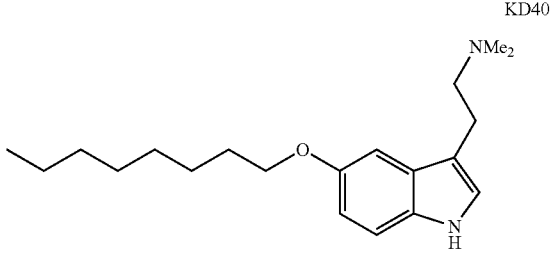 [SMILES: CCCCCCCCOc1ccc2[nH]cc(CCN(C)C)c2c1]

KD40

¹H (400 MHz CDCl₃) δ 7.93 (br, 1H), 7.24 (d, J=8.8 Hz, 1H), 7.06 (d, J=2.4 Hz, 1H), 7.0 (d, J=2.4 Hz, 1H), 6.86 (dd, J=8.8.0 Hz, 2.4 Hz, 1H), 4.01 (d, J=6.8 Hz, 2H), 2.91 (t, J=7.6 Hz, 2H), 2.63 (t, J=7.6 Hz, 2H), 2.35 (s, 6H), 1.85-1.78 (m, 2H), 1.50 (br, 2H), 1.33 (br, 8H), 0.90 (t, J=7.2 Hz, 3H); ¹³C NMR (101 MHz, CDCl₃) δ 153.39, 131.57, 127.80, 122.36, 114.29, 112.85, 111.40, 101.65, 68.70, 60.07, 45.42, 32.22, 29.54, 29.35, 29.28, 26.15, 23.59, 22.71, 14.07. LRMS (ESI) 317.3, HRMS calculated 317.2587. found 317.2587 (M+1).

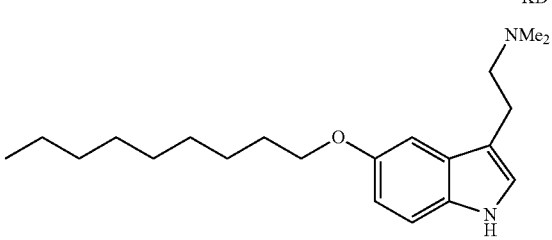

KD41

¹H NMR (300 MHz, CDCl₃) δ 7.93 (br, 1H), 7.25 (d, J=8.8 Hz, 1H), 7.08 (s, 1H), 7.02 (s, 1H), 6.88 (d, J=8.8 Hz, 1H), 4.03 (t, J=6.7 Hz, 2H), 2.93 (t, J=9.6 Hz, 2H), 2.66 (t, J=9.6 Hz, 2H), 2.38 (s, 6H), 1.88-1.78 (m, 2H), 1.50 (br, 2H), 1.31 (br, 10H), 0.91 (t, J=6.7 Hz, 3H). ¹³C NMR (101 MHz, CDCl₃) δ 153.39, 131.56, 127.57, 122.04, 113.49, 112.61, 111.41, 101.65, 68.95, 60.06, 45.43, 31.89, 29.58, 29.55, 29.49, 29.29, 26.46, 23.91, 22.47, 14.07. LRMS (ESI) 331.3, HRMS calculated 331.2744. found 331.2744 (M+1).

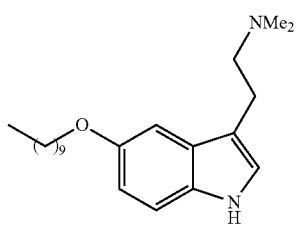

KD42

¹H NMR (300 MHz, CDCl₃) δ 7.94 (br, 1H), 7.25 (d, J=8.7 Hz, 1H), 7.08 (s, 1H), 7.02 (s, 1H), 6.88 (d, J=8.7 Hz, 1H), 4.03 (t, J=6.6 Hz, 2H), 2.99-2.88 (t, J=9.1 Hz, 2H), 2.68 (t, J=9.1 Hz, 2H), 2.39 (s, 6H), 1.89-1.75 (m, 2H), 1.51 (br, 2H), 1.30 (br, 12H), 0.91 (t, J=6.8 Hz, 3H); ¹³C NMR (101 MHz, CDCl₃) δ 153.41, 131.54, 127.58, 122.02, 113.51, 112.60, 111.43, 101.64, 68.94, 60.06, 45.43, 31.89, 29.59, 29.54, 29.51, 29.47, 29.29, 26.46, 23.91, 22.47, 14.07. LRMS (ESI) 345.3, HRMS calculated 345.2900. found 345.2899 (M+1).

173

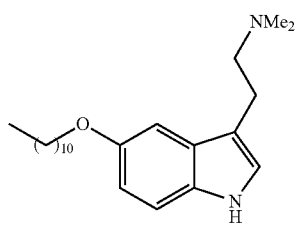

KD43

¹H NMR (300 MHz, CDCl₃) δ 7.91 (br, 1H), 7.25 (d, J=7.8 Hz, 1H), 7.07 (s, 1H), 7.01 (s, 1H), 6.88 (d, J=7.8 Hz, 1H), 4.03 (t, J=6.6 Hz, 2H), 2.94 (t, J=9.6 Hz, 2H), 2.66 (t, J=9.6 Hz, 2H), 2.37 (s, 6H), 1.90-1.76 (m, 2H), 1.51 (br, 2H), 1.29 (br, 14H), 0.90 (t, J=6.5 Hz, 3H); ¹³C NMR (101 MHz, CDCl₃) δ 153.08, 131.00, 127.56, 122.36, 113.73, 112.84, 111.70, 101.96, 69.26, 60.06, 45.10, 31.91, 29.63(2C), 29.54, 29.49(2C), 29.35, 26.15, 23.59, 22.69, 14.40. LRMS (ESI) 359.4, HRMS calculated 359.3057. found 359.3058 (M+1).

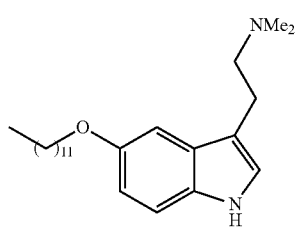

KD44

¹H NMR (300 MHz, CDCl₃) δ 7.92 (br, 1H), 7.26 (d, J=8.9 Hz, 2H), 7.07 (s, 1H), 7.02 (s, 1H), 6.88 (d, J=8.9 Hz, 1H), 4.03 (t, J=7.4 Hz, 2H), 2.96 (t, J=9.6 Hz, 2H), 2.72 (t, J=9.6 Hz, 2H), 2.42 (s, 6H), 1.90-1.75 (m, 2H), 1.51 (br, 2H), 1.29 (br, 16H), 0.95-0.86 (t, J=9.6 Hz, 3H); ¹³C NMR (101 MHz, CDCl₃) δ 153.40, 131.55, 127.56, 122.36, 113.48, 112.61, 111.72, 101.64, 69.26, 59.74, 45.11, 32.22, 29.68(2C), 29.64, 29.63, 29.55, 29.49, 29.35, 26.16, 23.27, 22.71, 14.07. LRMS (ESI) 373.4, HRMS calculated 373.3213. found 373.3212 (M+1).

174

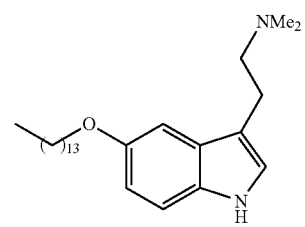

KD45

¹H NMR (300 MHz, CDCl₃) δ 7.93 (br, 1H), 7.25 (d, J=8.7 Hz, 1H), 7.07 (s, 1H), 7.01 (s, 1H), 6.88 (d, J=8.7 Hz, 1H), 4.03 (t, J=6.7 Hz, 2H), 2.93 (t, J=10.8 Hz, 2H), 2.67 (t, J=9.6 Hz, 2H), 2.38 (s, 6H), 1.90-1.76 (m, 2H), 1.49 (br, 2H), 1.28 (br, 20H), 0.90 (t, J=6.8 Hz, 3H); ¹³C NMR (101 MHz, CDCl₃) δ 153.40, 131.56, 127.80, 122.05, 113.72, 112.60, 111.70, 101.65, 68.96, 60.05, 45.09, 31.91, 29.70(2C), 29.69, 29.66(2C), 29.63, 29.55, 29.50, 29.36, 26.16, 23.91, 22.47, 13.82. LRMS (ESI) 401.4, HRMS calculated 401.3526. found 401.3527 (M+1).

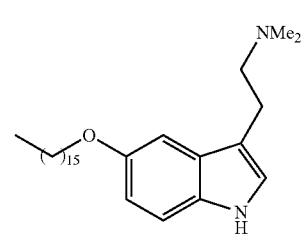

KD46

¹H NMR (300 MHz, CDCl₃) δ 7.89 (br, 1H), 7.25 (d, J=8.6 Hz, 1H), 7.08 (s, 1H), 7.02 (s, 1H), 6.88 (d, J=8.6 Hz, 1H), 4.02 (t, J=7.2 Hz, 2H), 2.93 (t, J=9.6 Hz, 2H), 2.66 (t, J=9.6 Hz, 2H), 2.37 (s, 6H), 1.89-1.75 (m, 2H), 1.50 (br, 2H), 1.28 (br, 24H), 0.90 (t, J=8.0 Hz, 3H); ¹³C NMR (101 MHz, CDCl₃) δ 153.39, 131.23, 127.80, 122.04, 113.71, 112.61, 111.41, 101.97, 68.95, 60.07, 45.42, 32.24, 29.70(4C), 29.66, 29.63, 29.55, 29.50, 29.36, 26.16, 23.58, 22.69, 14.06. LRMS (ESI) 429.4, HRMS calculated 429.3839. found 429.3837 (M+1).

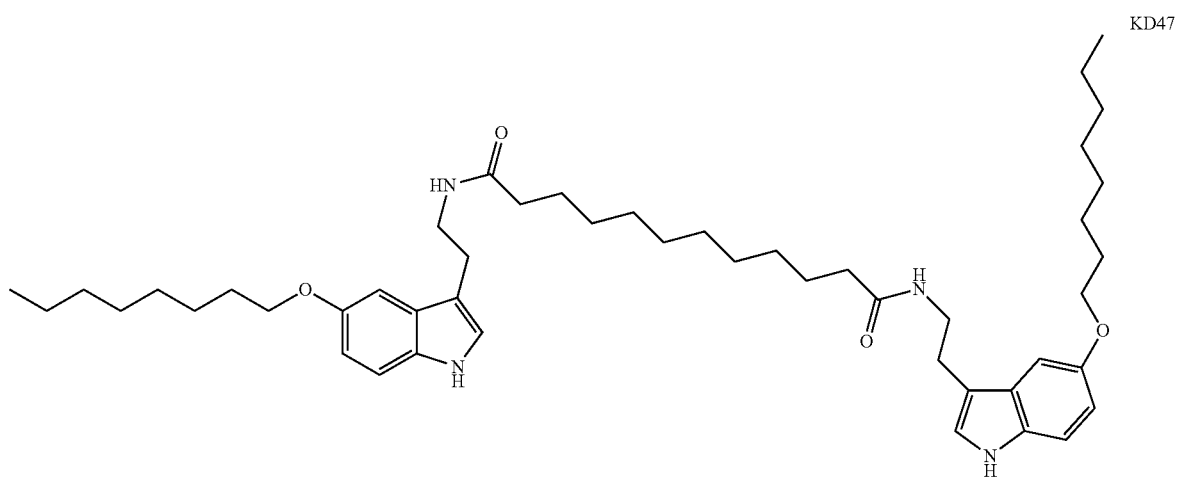 [SMILES: CCCCCCCCOc1ccc2[nH]cc(CCNC(=O)CCCCCCCCCCC(=O)NCCc3c[nH]c4ccc(OCCCCCCCC)cc34)c2c1]

KD47

Bisoctatryptaminedecanoyl $^1$H (400 MHz CDCl$_3$) δ 8.29 (br, 2H), 7.26 (d, J=7.8 Hz, 2H), 7.02 (d, J=16.0 Hz, 4H), 6.88 (dd, J=7.6 Hz, 4.0 Hz, 2H), 5.56 (br, 2H), 3.99 (t, J=8.0 Hz, 2H), 3.61 (q, J=12.4 Hz, 5.6 Hz,), 2.94 (t, J=8.0 Hz, 2H), 2.10 (t, J=7.8 Hz,), 1.84-1.77 (m, 4H), 1.57 (br, 4H), 1.48 (br, 4H), 1.32 (br, 18H), 1.24 (br, 14H), 0.90 (t, J=7.6 Hz, 6H); $^{13}$C (101 MHz CDCl$_3$) δ 173.13, 153.51, 131.57, 127.69, 122.78, 112.89, 112.56, 111.93, 109.99, 101.59, 68.91, 39.39, 36.84, 31.83, 29.53, 29.43, 29.28, 29.07, 29.00, 26.16, 25.61, 25.35, 22.67, 14.12. LRMS 769.2 (M−1).

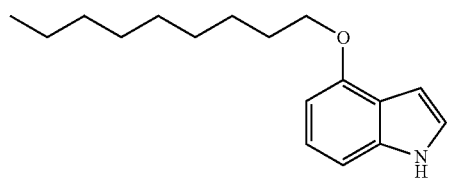 [SMILES: CCCCCCCCCOc1cccc2[nH]ccc12]

4-nonylindole $^1$H (400 MHz CDCl$_3$) δ 8.13 (br, 1H), 7.11 (m, 2H), 7.0 (d, J=7.8 Hz, 1H), 6.68 (t, J=6.0 Hz, 1H), 6.52 (d, 7.8 Hz, 1H,), 4.12 (t, J=8.0 Hz, 2H), 1.91 (m, 2H), 1.52 (m, 2H), 1.30 (br, 10H), 0.91 (t, J=8.0 Hz, 3H). LRMS (ESI) 260.2 (M+1).

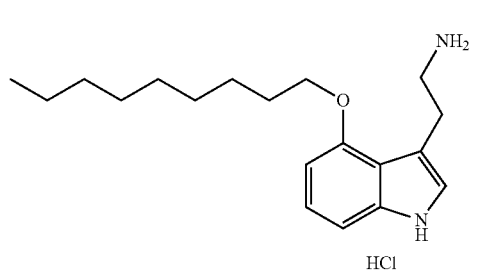

KD48

$^1$H (400 MHZ DMSO-d$_6$) δ 10.91 (br, 1H), 7.78 (br, 2H), 7.03 (s, 1H), 6.92 (m, 2H), 6.43 (d, J=7.2 Hz, 1H), 4.01 (t, J=8.0 Hz, 2H), 3.06 (br, 4H), 1.78 (m, 2H), 1.42 (br, 2H), 1.24 (br, 10H), 0.83 (t, J=7.2 Hz, 3H); $^{13}$C (101 MHz DMSO-d$_6$) δ 153.61, 138.66, 122.84, 122.55, 116.96, 109.74, 105.25, 99.93, 67.54, 31.75, 29.46 (2C), 29.29, 29.23, 29.18, 26.13, 25.44, 22.57, 14.43. LRMS (ESI) 303.2, HRMS calculated 303.2431. found 303.2429 (M+1).

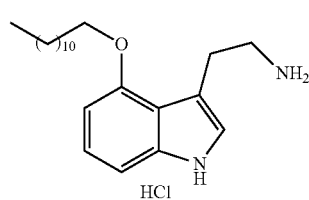

KD49

$^1$H (400 MHZ DMSO-d$_6$) δ 10.90 (br, 1H), 7.74 (br, 2H), 7.01 (br, 1H), 6.92 (m, 2H), 6.43 (d, J=7.8 Hz, 1H), 4.01 (t, J=8.0 Hz, 2H), 3.06 (br, 4H), 1.78 (m, 2H), 1.43 (br, 2H), 1.15 (br, 16H), 0.84 (t, J=8.0 Hz, 3H); $^{13}$C (101 MHz DMSO-d$_6$) δ 145.99, 128.83, 126.99, 123.36, 119.54, 111.19, 110.36, 109.99, 103.00, 67.91, 31.75, 29.52(2C), 29.49, 29.47, 29.31 (2C), 29.17, 25.98, 23.63, 22.55, 14.41. LRMS (ESI) 345.2, HRMS calculated 345.2900. found 345.2899 (M+1).

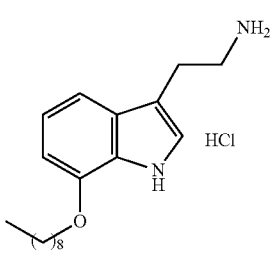

KD50

$^1$H (400 MHz DMSO-d$_6$) δ 10.91 (br, 1H), 8.0 (br, 2H), 6.89 (t, J=8.0 Hz, 1H), 6.62 (d, J=7.2 Hz, 1H), 7.1 (s, 1H), 7.12 (br, 1H), 4.1 (t, J=6.8 Hz, 2H), 3.0 (br, 2H), 2.98-2.93 (m, 2H), 1.80-1.72 (m, 2H), 1.50-1.43 (m, 2H), 1.25 (br, 10H), 0.84 (t, J=6.8 Hz, 3H); $^{13}$C NMR (101 MHz, DMSO-d$_6$) δ 152.89, 131.87, 127.63, 124.35, 112.54, 112.08, 109.71, 101.53, 68.38, 31.74, 29.49, 29.46, 29.33, 29.16, 26.13, 23.90, 22.55, 14.42. LRMS (ESI) 303.2, HRMS calculated 303.2431. found 303.2430 (M+1).

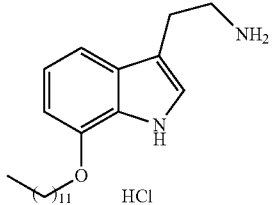

KD51

7-dodecaoxy tryptamine $^1$H (400 MHZ DMSO-d$_6$) δ 10.90 (br, 1H), 8.03 (br, 2H), 7.11 (m, 2H), 6.68 (t, J=7.9 Hz, 1H), 6.61 (d, J=7.9 Hz, 1H), 4.07 (t, J=8.0 Hz, 2H), 2.98 (br, 4H), 1.76 (m, 2H), 1.46 (br, 2H), 1.25 (br, 16H), 0.83 (t, J=8.0 Hz, 3H); $^{13}$C (101 MHz DMSO-d$_6$) δ 145.99, 128.83, 126.99, 123.36, 119.54, 111.19, 110.36, 109.99, 103.00, 67.91, 31.75, 29.52(2C), 29.49, 29.47, 29.31 (2C), 29.17, 25.98, 23.63, 22.55, 14.41. LRMS (ESI) 345.2, HRMS calculated 345.2900. found 345.2901 (M+1).

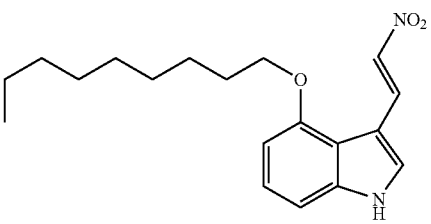 [SMILES: CCCCCCCCCOc1cccc2[nH]cc(/C=C/[N+](=O)[O-])c12]

4-nonylindole-3-nitroethylene $^1$H (400 MHz CDCl$_3$) δ 8.64 (br, 1H), 8.56 (d, J=16.0 Hz, 1H), 8.06 (d, J=16.0 Hz, 1H), 7.60 (br, 1H), 7.24 (t, J=7.9 Hz, 1H), 7.05 (d, J=8.0 Hz, 1H), 6.69 (d, J=7.9 Hz, 1H), 4.18 (t, J=8.0 Hz, 2H), 1.99 (m, 2H), 1.57 (br, 2H), 1.30 (br, 10H), 0.90 (t, J=8.0 Hz, 3H). LRMS (ESI) 331.2 (M+1).

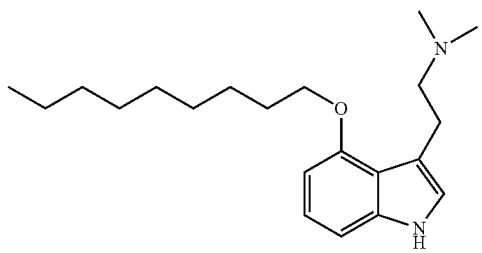

KD52

¹H (400 MHz CDCl₃) δ 8.10 (br, 1H), 7.07 (t, J=7.9 Hz, 1H), 6.95 (d, J=7.8 Hz, 1H), 6.90 (s, 1H), 6.50 (d, J=7.9 Hz, 1H), 4.10 (t, J=6.6 Hz, 2H), 3.12 (t, J=8.2 Hz, 2H), 2.71 (t, J=8.2 Hz, 2H), 2.37 (s, 6H), 1.98 (m, 2H), 1.52 (br, 2H), 1.23 (br, 10H), 0.91 (t, J=6.6 Hz, 3H); ¹³C (101 MHz CDCl₃) δ 154.16, 138.06, 122.68, 120.38, 117.29, 114.68, 104.17, 99.83, 67.67, 61.41, 45.26, 31.88, 29.61 (2C), 29.49, 29.46, 29.30, 24.94, 22.67, 14.11. LRMS (ESI) 331.2, HRMS calculated 331.2744. found 331.2747 (M+1).

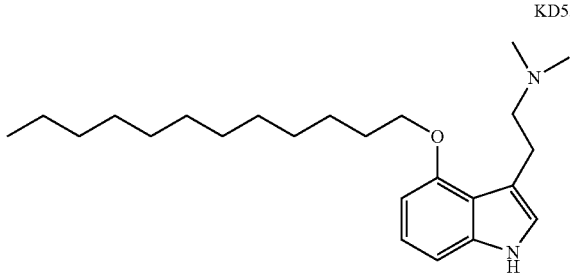

KD53

¹H (400 MHz CDCl₃) δ 8.02 (br, 1H), 7.05 (t, J=7.8 Hz, 1H), 6.91 (d, J=7.8 Hz, 1H), 6.91 (s, 1H), 6.50 (d, J=7.8 Hz, 1H), 4.09 (t, J=6.7 Hz, 2H), 3.08 (t, J=8.1 Hz, 2H), 2.70 (t, J=8.1 Hz, 2H), 2.35 (s, 6H), 1.89 (m, 2H), 1.56 (br, 2H), 1.29 (br, 16H), 0.91 (t, J=6.6 Hz, 3H); ¹³C (101 MHz CDCl₃) δ 154.19, 137.54, 123.80, 122.68, 120.36, 114.68, 102.53, 99.97, 67.49, 61.49, 45.42, 31.91, 29.65(3C), 29.47, 29.34 (2C), 29.30, 24.85, 24.44, 22.69, 14.39. LRMS 373.4, HRMS calculated 373.3213. found 373.3213 (M+1).

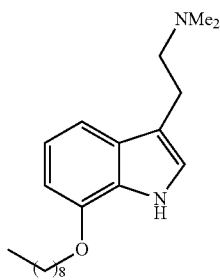

KD54

¹H NMR (400 MHz, CDCl₃) δ 8.12 (s, 1H), 7.12 (d, J=8.0 Hz, 1H), 6.98-6.90 (m, 2H), 6.56 (d, J=7.6 Hz, 1H), 4.04 (t, J=6.5 Hz, 2H), 2.87 (t, J=8.0 Hz, 2H), 2.59 (t, J=8.0 Hz, 2H), 2.29 (s, 6H), 1.83-1.72 (m, 2H), 1.42 (br, 2H), 1.21 (br, 10H), 0.82 (t, J=6.9 Hz, 3H); ¹³C NMR (101 MHz, CDCl₃) δ 145.88, 128.67, 126.93, 120.90, 119.48, 114.27, 111.40, 102.84, 67.81, 60.30, 48.54, 45.10, 31.91, 29.57, 29.43, 29.28, 26.16, 23.59, 22.71, 14.06. LRMS (ESI) 331.2, HRMS calculated 331.2744. found 331.2742 (M+1).

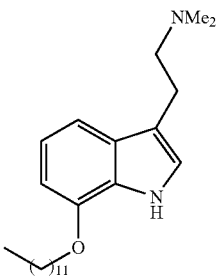

KD55

¹H NMR (400 MHz, CDCl₃) δ 8.17 (br, 1H), 7.20 (d, J=5.6 Hz, 1H), 7.04-6.97 (m, 2H), 6.62 (d, J=7.4 Hz, 1H), 4.11 (t, J=6.4 Hz, 2H), 2.93 (t, J=6.8 Hz, 2H), 2.64 (t, J=6.8 Hz, 2H), 2.35 (s, 6H), 1.87-1.81 (m, 2H), 1.48 (br, 2H), 1.26 (br, 16H), 0.88 (t, J=6.8 Hz, 3H); ¹³C NMR (101 MHz, CDCl₃) δ 144.20, 128.64, 126.91, 120.66, 119.34, 114.23, 110.92, 103.86, 67.81, 59.78, 48.53, 44.92, 32.02, 29.56 (2C), 29.33 (2C), 29.23, 26.12, 23.54, 22.72, 14.29 (1C missing). LRMS (ESI) 373.4, HRMS calculated 373.3213. found 373.3212 (M+1).

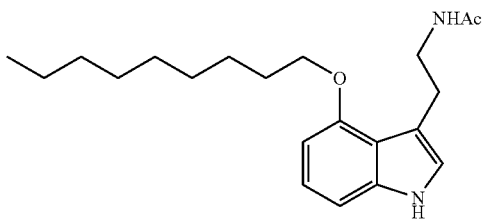

KD56

N-acetyl-4-nonylindole ¹H (400 MHz CDCl₃) δ 8.20 (br, 1H), 7.10 (t, J=8.0 Hz, 1H), 6.99 (d, J=8.1 Hz, 1H), 6.90 (s, 1H), 6.51 (d, 1H, J=8.0 Hz), 5.96 (br, 1H), 4.12 (t, J=6.6 Hz, 2H), 3.60 (m, 2H), 3.10 (t, J=6.4 Hz, 2H), 1.89 (s, 3H), 1.52 (br, 2H), 1.31 (br, 12H), 0.91 (t, J=7.6 Hz, 3H); (101 MHz CDCl₃) δ 170.07, 153.78, 138.22, 122.90, 121.21, 117.26, 113.50, 104.56, 100.12, 67.78, 41.29, 31.86, 29.57 (2C), 29.42, 29.28(2C), 26.26, 23.31, 22.68, 14.11. LRMS (ESI) 367.2, HRMS calculated 367.2356. found 367.2355 (M+1).

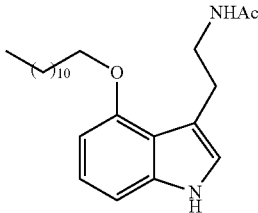

KD57

¹H NMR (400 MHz, CDCl₃) δ 8.02 (br, 1H), 7.08 (t, J=8.0 Hz, 1H), 6.97 (d, J=8.0 Hz, 1H), 6.90 (s, 1H), 6.49 (d, J=8.0 Hz, 1H), 5.90 (br, 1H), 4.09 (t, J=6.5 Hz, 2H), 3.62-3.54 (t, J=6.3 Hz, 2H), 3.08 (t, J=6.3 Hz, 2H), 1.87 (br, 5H), 1.54-1.47 (m, 2H), 1.43-1.35 (m, 2H), 1.26 (br, 14H), 0.88 (t, J=6.8 Hz, 3H); ¹³C NMR (101 MHz, CDCl₃) δ 170.03, 153.64, 138.13, 122.92, 121.25, 117.48, 113.72, 104.53, 100.21, 68.06, 41.09, 32.23, 29.66 (3C), 29.63, 29.42 (2), 29.34, 26.26, 23.26, 22.64, 14.17. LRMS (ESI) 409.4, HRMS calculated 409.2826 found 409.2823 (M+1).

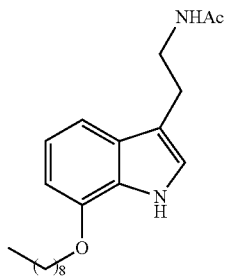
KD58

$^1$H NMR (400 MHz, CDCl$_3$) δ 8.20 (s, 1H), 7.11 (d, J=8.6 Hz, 1H), 7.01-6.92 (m, 2H), 6.58 (d, J=7.6 Hz, 1H), 5.44 (br, 1H), 4.05 (t, J=6.5 Hz, 2H), 3.54-3.49 (m, 2H), 2.88 (t, J=6.6 Hz, 2H), 1.84 (s, 3H), 1.83-1.72 (m, 2H), 1.48-1.36 (m, 2H), 1.22 (br, 10H), 0.82 (t, J=6.8 Hz, 3H); $^{13}$C NMR (101 MHz, CDCl$_3$) δ 170.02, 145.86, 128.68, 126.92, 121.45, 119.80, 113.49, 111.15, 102.84, 68.04, 39.99, 31.88, 29.57, 29.43, 29.36, 29.28, 26.16, 25.39, 23.39, 22.67, 14.09. LRMS (ESI) 367.2, HRMS calculated 367.2356. found 367.2355 (M+1).

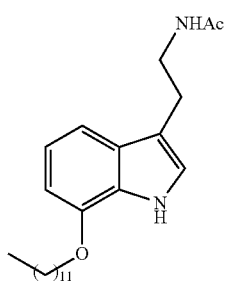
KD59

$^1$H NMR (400 MHz, CDCl$_3$) δ 8.21 (br, 1H), 7.11 (d, J=8.0 Hz, 1H), 7.00-6.91 (m, 2H), 6.58 (d, J=7.5 Hz, 1H), 5.45 (br, 1H), 4.05 (t, J=6.5 Hz, 2H), 3.54-3.49 (m, 2H), 2.88 (t, J=6.4 Hz, 2H), 1.84 (s, 3H), 1.83-1.72 (m, 2H), 1.43 (br, 2H), 1.30 (br, 2H), 1.20 (br, 14H), 0.81 (t, J=6.9 Hz, 3H); $^{13}$C NMR (101 MHz, CDCl$_3$) δ 170.27, 145.64, 128.68, 126.92, 121.25, 119.48, 113.17, 111.15, 102.85, 68.05, 39.98, 31.91, 29.67, 29.63, 29.62, 29.43, 29.35, 29.35, 26.46, 25.26, 23.59, 22.69, 14.06. LRMS (ESI) 409.2, HRMS calculated 409.2823. found 409.2825 (M+1).

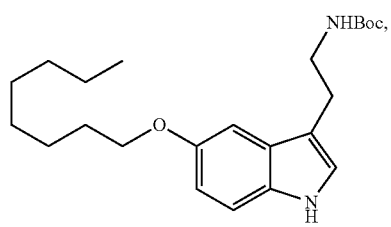
KD17

IC$_{50}$: NA
Molecular Weight: 388.54

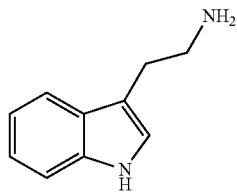
KD26

IC$_{50}$: >100 µM
Molecular Weight: 160.22

Example 22

Compound Characterization

Once tumors are established (at least 3-5 mm), mice (10 mice/group) will be given the liposomal drug twice weekly (i.v. injections of drug or control). The treatment will be carried out for at least 3-4 weeks. When the maximum size of local tumors is ~1-1.5 cm$^3$ in mean value mice will be euthanized by CO$_2$ inhalation. Animals will be monitored daily for adverse effects and evidence of toxicity, e.g. weight loss and reduced daily activity. Mice that have lost 20% of their original weight, exhibit labored breathing, hunched posture, or are incapacitated by tumor burden will be euthanized. The size of the breast cancer tumor xenografts will be measured before and after treatment every week by direct measurement using an electronic caliper. Imaging of luciferase models will occur weekly by measuring bioluminescence using a cryogenically cooled IVIS imaging system coupled with data acquisition controlled by a computer running LivingImage software (Xenogen, Alameda, Calif.). Statistical analysis will be performed. The expression of regulators of angiogenesis (e.g. VEGF, HIF-1α, CD31), the expression of elements of endoplasmic stress (phospho-eIF2α), stress pathways (e.g. MAPK) and induction of apoptopsis (PARP, caspase 9 and caspase 3 cleavage) will be assessed by western blot analysis. We previously optimized conditions for western blotting of samples from in vivo experiments (Akar et al., 2008; Ozpolat et al., 2008). Apoptosis will also be assessed by Annexin V, by examining cell cycle analysis (sub-G1). Evaluation of autophagy will achieved by detection of acidic vesicular organelles, and LC3-II (e.g. FIG. 5), and Beclin-1, expression (Akar et al., 2008). Proliferation will be assessed by the Ki-67 proliferation marker. Models: Nude mice (nu/nu) will be obtained from Jackson laboratories. Three models will be used: an MCF-7 (ER+) orthotopic model (Kim and Price, 2005) will be prepared by priming mice with 17β-Estradiol applied subcutaneously (1.7 mg estradiol/pellet) under the left shoulder to promote tumor growth. In this model the mammary fat pad under the nipple of each mouse is inoculated (0.1 mL, 7×10$^6$ breast cancer cells in PBS) by subcutaneous injection using a sterile 28-g needle. An MDA-MB-231 orthotopic model (Akar et al., 2010) or luciferase-expressing MDA-MB-231 orthotopic model (Akar et al., 2010) will be prepared in a similar manner by injecting 1 or 2×106 tumor cells, respectively into the mammary fat pad.

IC50 Concentrations of Compounds were Determined by Cell Viability Assay (aka proliferation assay, in this case MTS assay was used. MTS, MTT, XTT all similar assays often used as cell viability/toxicity assay). Cell viability in response to compounds such as 5NT and KD06 was studied with a tetrazolium/formazan based assay (MTS, Celltiter 96 aqueous one solution cell proliferation assay, Promega, WI) [Akar U, Chaves-Reyez A, Barria g Tari A, Sanguino A, Kondo Y, Kondo S, Arun B, Lopez-Berestein G, Ozpolat B: *Silencing of Bcl-2 expression by small interfering RNA induces autophagic cell death in MCF-7 breast cancer cells. Autophagy* 2008, 4:669-679, Ozpolat 2007 MCR]. Cells were seeded in 96 wells plates at a density of 1.5 to 3.0×10$^3$ cells per well in 100 µl of medium. Next day the medium was removed and cells were treated with the drug in 100 µl of medium for 72 hours. Plates were read at 490 nm wavelength in an Elisa plate reader (Kinetic Microplate Reader, Molecular Devices Corporation, Sunnyvale, Calif.).

Example 23

Autophosphorylation of eEF-2K

The following five autophosphorylation sites were identified, Thr-348, Thr-353, Ser-445, Ser-474 and Ser-500. Mutation of each site to either Ala or Asp suggested that only Thr-348 is required for activity of eEF-2K against a peptide substrate in the presence of Ca$^{2+}$/CaM. Stoichiometric analysis indicates the incorporation of ~3.5 mol phosphate/mol enzyme over 3 hours, with the rapid intramolecular incorporation of ~1 mol phosphate within the first 10 min—this initial phosphate most likely being incorporated at Thr-348.

Cellular homeostasis demands a controlled balance between protein synthesis and protein degradation. Eukaryotes regulate their rate of protein synthesis through a variety of pathways; several of which include phosphorylation of translation initiation and elongation factors (Hershey, J. W. B. Annual Review of Biochemistry 1991: 60, 717-755; Morley, S. J., and Thomas, G. Pharmacology & Therapeutics 1991: 50, 291-319; Proud, C. G. Curr Top Cell Regul 1992: 32, 243-369; Rhoads, R. E. Journal of Biological Chemistry 1999: 274, 30337-30340). An important component of this regulatory process is the eukaryotic elongation factor 2 kinase (eEF-2K). eEF-2K functions to generally impede the elongation phase of translation, thereby disrupting proteins synthesis (Nairn, A. C., et al., Proc Natl Acad Sci USA 1985: 82, 7939-7943; Nairn, A. C., and Palfrey, H. C. Journal of Biological Chemistry 1987: 262, 17299-17303; Ryazanov, A. G. FEBS Letters 1987: 214, 331-334; Ryazanov, A. G., et al. Biochimie 1988: 70, 619-626; Carlberg, U., et al. European Journal of Biochemistry 1990: 191, 639-645). Additionally, it may also induce the translation of specific transcripts (Weatherill, D. B., et al. Journal of Neurochemistry 2011: 117, 841-855). eEF-2K inhibits translation by phosphorylating, and thereby blocking, the ability of elongation factor 2 (eEF-2) to bind the ribosome (Nairn, A. C., et al., Proc Natl Acad Sci USA 1985: 82, 7939-7943; Nairn, A. C., and Palfrey, H. C. Journal of Biological Chemistry 1987: 262, 17299-17303; Ryazanov, A. G. FEBS Letters 1987: 214, 331-334; Ryazanov, A. G., et al. Biochimie 1988: 70, 619-626; Carlberg, U., et al. European Journal of Biochemistry 1990: 191, 639-645). eEF-2 is responsible for the ribosomal translocation of the nascent peptide chain from the A-site to the P-site during translation (Moldave, K. Annual Review of Biochemistry 1985: 54, 1109-1149; Moazed, D., and Noller, H. F. Nature 1989: 342, 142-148; Proud, C. G. Mol Biol Rep 1994: 19, 161-170).

eEF-2K is classified as a Ca$^{2+}$/CaM-dependent protein kinase (CaMK-III) (Nairn, A. C., et al., Proc Natl Acad Sci USA 1985: 82, 7939-7943; Ryazanov, A. G., et al. Biochimie 1988: 70, 619-626; Mitsui, K., et al. Journal of Biological Chemistry 1993: 268, 13422-13433; Redpath, N. T., and Proud, C. G. European Journal of Biochemistry 1993: 212, 511-520) because it requires Ca$^{2+}$ and calmodulin (CaM) for autophosphorylation. When the cell is in the resting state, basal levels of intracellular calcium (50-100 nM) appear to be insufficient for CaM to exert an effect on the Ca$^{2+}$/CaM-dependent protein kinase (Chin, D., and Means, A. R. Trends in Cell Biology 2000: 10, 322-328; Swulius, M., and Waxham, M. Cellular and Molecular Life Sciences 2008: 65, 2637-2657). However, during signaling events, influx of calcium into the cytoplasm raises the free intracellular Ca$^{2+}$ concentration to ~10-100 µM which is adequate for the activation of calmodulin (Chin, D., and Means, A. R. Trends in Cell Biology 2000: 10, 322-328; Swulius, M., and Waxham, M. Cellular and Molecular Life Sciences 2008: 65, 2637-2657). Autophosphorylation of eEF-2K in the presence of Ca$^{2+}$/CaM activates the kinase (Mitsui, K., et al. Journal of Biological Chemistry 1993: 268, 13422-13433; Redpath, N. T., and Proud, C. G. European Journal of Biochemistry 1993: 212, 511-520).

A compelling factor behind deciphering the mechanism of activation and regulation of eEF-2K is its recent implication in enhancing tumor survival (Bagaglio, D. M., and Hait, W. N. Cell Growth Differ 1994: 5, 1403-1408; Farmer, T. G., et al. Br J Cancer 1998: 79, 59-64; Arora, S., et al., Cancer Res 2003: 63, 6894-6899; Hait, W. N., et al., Autophagy 2006: 2, 294-296; Wu, H., et al. Cancer Research 2006: 66, 3015-3023). Results reveal that glioblastoma cells employ the kinase to regulate autophagy—a pro-survival pathway stimulated in response to nutrient deficiency and cell stress (Hait, W. N., et al., Autophagy 2006: 2, 294-296; Wu, H., et al. Cancer Research 2006: 66, 3015-3023; Wu, H., et al. Cancer Research 2009: 69, 2453-2460). Cancer research on squamous carcinoma cells and metastatic breast cancer cells has indicated that treatment of the malignant cells with chemotherapeutic agents appears to up-regulate the activity of the kinase—an event that has been associated with the induction of autophagy (Ren, H., et al., Cancer Res 2005: 65, 5841-5847; Dalby, K. N., et al. Autophagy 2010: 6, 322-329). Triggering of this adaptive mechanism consequently endows the cells with resistance against anti-tumorous agents, and as a result reduces therapeutic potency (Wu, H., et al. Cancer Research 2009: 69, 2453-2460, Dalby, K. N., et al. Autophagy 2010: 6, 322-329). Additionally, we have found evidence that eEF-2K promotes proliferation, migration and invasion of breast cancer cells (Tekedereli, I., et al, (2011 Submitted) Calmodulin-Dependent Protein Kinase III (Elongation Factor-2 Kinase) Regulates Proliferation and Invasiveness of Breast Cancer Cells). These findings suggest that eEF-2K may be a target for anti-cancer therapy.

This study reports five novel autophosphorylation sites in eEF-2K, which include Thr-348, Thr-353, Ser-445, Ser-474 and Ser-500. Of these, only Thr-348 is found to be essential for kinase activity against a peptide substrate.

Peptide synthesis—For the kinetic analysis of eEF-2K, the peptide substrate, Acetyl-RKKYKFNEDTERRRFL-Amide (SEQ ID NO:6) (2,227.8 Da), was synthesized and purified at the UT Molecular Biology Core Facilities as described earlier (Abramczyk, O., et al. (2011) Purification and characterization of tagless recombinant human elongation factor 2 kinase (eEF-2K) expressed in *Escherichia coli*, Protein Expression and Purification In Press, Uncorrected Proof).

General kinetic assays—eEF-2 kinase activity was assayed at 30° C. in Buffer D (25 mM HEPES (pH 7.5), 2 mM DTT, 0.15 µM BSA, 100 µM EDTA, 100 µM EGTA, 250 µM CaCl$_2$, 2 µM calmodulin and 10 mM MgCl$_2$), containing 150 µM (Acetyl-RKKYKFNEDTERRRFL-Amide) (SEQ ID NO:6) peptide substrate (Pep-S), 2 nM eEF-2K enzyme and 0.5 mM

[γ-$^{32}$P]ATP (100-1000 cpm/pmol) in a final reaction volume of 100 µL. The reaction mixture was incubated at 30° C. for 10 mM before the reaction was initiated by addition of 0.5 mM [γ-$^{32}$P]ATP. At set time points, 10 µL aliquots were taken and spotted onto P81 cellulose filters (Whatman, 2×2 cm). The filter papers were then washed thrice in 50 mM phosphoric acid (15 mM each wash), once in acetone (15 mM) and finally dried. The amount of labeled peptide associated with each paper was determined by measuring the cpm on a Packard 1500 scintillation counter.

(Autophosphorylation assay—Autophosphorylation of eEF-2K was carried out in Buffer E (25 mM HEPES (pH 7.5), 2 mM DTT, 0.6 µM BSA, 6 µM CaM, 150 µM CaCl$_2$ and 10 mM MgCl$_2$) containing 200 nM eEF-2K enzyme and 0.5 mM [γ-$^{32}$P]ATP (100-1000 cpm/pmol) in a final volume of 200 µL. The reaction mixture was incubated at 30° C. for 10 mM before the reaction was initiated by addition of 0.5 mM [γ-$^{32}$P]ATP. Aliquots (2 pmol) of eEF-2K were removed at intervals over a 3 h time period and the reaction quenched by addition of SDS-PAGE sample loading buffer (125 mM tris-HCl (pH 6.75), 20% glycerol (v/v), 10% 2-mercaptoethanol (v/v), 4% SDS and 0.02% bromophenol blue) followed by heating for 10 mM at 95° C. The samples were resolved by SDS-PAGE and stained with Coomassie Brilliant Blue. Gels were exposed for 1 h in a Phosphorimager cassette which was then scanned in a Typhoon Phosphorimager and then analyzed using ImageQuant™ TL software. To determine the stoichiometry of the autophosphorylation, the gels were dried, the pieces containing eEF-2K excised, and the associated radioactivity measured with a Packard 1500 liquid scintillation analyzer. The mechanism of autophosphorylation was analyzed using Buffer F (25 mM HEPES (pH 7.5), 2 mM DTT, 0.6 µM BSA, 0.6 µM CaM, 1.5 mM CaCl$_2$ and 10 mM MgCl$_2$) containing 0.5 mM [γ-$^{32}$P]ATP and varying concentrations of the purified enzyme (0-400 nM). The reaction was carried out under conditions in which linear incorporation of $^{32}$P was achieved (10 min incubation) and quenched by addition of hot SDS-PAGE sample loading buffer. The extent of phosphate incorporation for each sample was determined as described above, and then plotted as a function of enzyme concentration.

Phosphopeptide analysis—Phosphorylation sites on the purified enzyme were detected by mass spectrometry analysis of the in-gel tryptic and chymotryptic digests. The eEF-2K sample (5 µM) purified from E. coli was resolved using SDS-PAGE (Bio-Rad Ready Gel Tris-HCl Gel 10% precast polyacrylamide gel), stained with Coomassie Brilliant Blue and destained. The band corresponding to eEF-2K was carefully excised and diced into small pieces which were dehydrated twice with 100 µL acetonitrile (ACN) for 5-10 mM. Gel pieces were destained further with 100 µL of destaining solution (50% methanol and 5% glacial acetic acid) for 1 h, following which the sample was again dehydrated twice with 100 µL ACN for 5-10 mM. The gel was dried in a speed vacuum (5-10 mM) and the enzyme then reduced with 100 µL 10 mM DTT at 60° C. for 1 h. The excess solution was removed and the sample treated with 100 µL ACN for 5-10 min. Alkylation was then performed for 1 h in the dark by the addition of 100 µL 55 mM iodoacetamide. The excess solution was again removed and the sample treated this time with 50 mM ammonium bicarbonate (pH 8.5) for 5-10 mM, dehydrated with 100 µL ACN (5-10 min) and dried in a speed vacuum (5-10 mM). The gel pieces were treated with Trypsin (Promega) or Chymotrypsin (Sigma) in 50 mM ammonium bicarbonate (pH 8.5) to give a final protease-enzyme ratio of ~1:5. Digestion was carried out at 37° C. for 16 h, after which the sample was treated with 5 µL of a solution containing 60% ACN and 5% formic acid, and sonicated for 5 min. Excess solution was removed and retained. ACN (10 µL) was added twice and the excess solution each time was pooled with the solution from the previous step. The combined digested peptide sample was dried in a speed vacuum (5-10 mM) and stored at −20° C. (The protocol followed was suggested by the Mass Spectrometry Facility, Department of Chemistry and Biochemistry, UT Austin). To detect potential autophosphorylation sites, 5 µM of the purified enzyme was allowed to autophosphorylate in the presence of CaM, Ca$^{2+}$ and Mg$_2$ATP for 3 h as outlined above. The sample was then resolved by SDS-PAGE and the autophosphorylated eEF-2K subjected to tryptic and chymotryptic in-gel digestion as described. Tryptic and chymotryptic eEF-2K peptide digests were solubilized in mobile phase A (MPA: 0.1% formic acid and 0.01% trifluoroacetic acid) and adjusted to pH <3 with addition of 10% trifluoroacetic acid. The peptides (20 pmol) were then loaded onto a reversed phase trap column (Symmetry C18, 180 µm×20 mm, Waters Corporation) mounted on a nanoAcquity UPLC system (Waters Corporation) and washed for 10 min with 10 µL/min MPA. A reversed phase nano-LC analytical column (Atlantis dC18, 75 µm×150 mm, Waters Corportation) was then incorporated into the flow path. Peptides were eluted with a linear 30 min 2-30% mobile phase B (MPB: acetonitrile, 0.1% formic acid and 0.01% trifluoroacetic acid) gradient followed by a linear 10 min 30-60% MPB gradient. Eluted peptides were infused directly into a Q-TOF Premier mass spectrometer (Waters Corporation) using a nanospray ion source. Mass spectra were acquired using a nanospray voltage of 3.5 kV, sampling cone voltage of 40 V, cone gas (nitrogen) flow of 20 L/h, a source temperature of 100° C., and a collision gas (nitrogen) pressure of 5.1e$^{-3}$. All mass spectra were collected for 1.95 s over m/z 50-2000 with an interscan delay of 0.1 s. The mass spectrometer was programmed to perform an experiment sequence consisting of an MS analysis at a collision energy of 5.0 V, followed by MS/MS analysis on the 3 most intense ions observed in the MS spectrum. For each precursor ion, MS/MS spectra were collected at four collision energies: 18, 27, 35 and 42 V. Dynamic exclusion was enabled for all experiments for a duration of 78.9 s with a rejection mass window of m/z 2.3. The ProteinLynx 4.1 software suite (Waters Corporation) was used to de-isotope the MS and MS/MS spectra, and the MS/MS spectra at all four collision energies for each peptide were averaged and combined. Processed MS/MS spectra were then searched locally against the Swiss-Prot all-species database (downloaded 02/24/2010, ftp://ftp.uniprot.org/pub/databases/uniprot/current_release/knowledgebase/complete/) using the Mascot 2.2 algorithm (Matrix Science). The local version of the Swiss-Prot all-species database was modified to include the sequence of the recombinant tryptic eEF-2K protein digest analyzed in this work. Peptides with up to three possible missed cleavages were specified as a search parameter. Protein molecular weight and pI constraints were not used in the database searches. Dynamic chemical modifications corresponding to M-oxidation, C-carbamidomethylation and S,T,Y-phosphorylation were included as search parameters. A peptide mass accuracy of 150 ppm was used for MS spectra and a peptide fragment mass accuracy of 0.3 Da was used for MS/MS spectra. Peptide summary reports were generated for all protein identifications using Mascot. Therefore, protein identifications resulted solely from peptide sequence information (MS/MS) without consideration of peptide mass fingerprints (MS). Peptide ion scores equal to or greater than 45-49 (varies for each database search) represent an identification with 95% confidence (<5% chance that the peptide ID is a random event).

Analysis of the autophosphorylation site mutants—Buffer D was used to measure the kinetic activity of the autophosphorylation-site mutants in a reaction containing 2 nM eEF-2K enzyme and 0.5 mM [γ-$^{32}$P]ATP (100-1000 cpm/pmol) in a final volume of 100 µL. Kinase activity in each case was determined by calculating the rate of phosphorylation of the peptide (µM·s$^{-1}$) in a similar manner to the general kinetic assay described above. The assays were performed in triplicate.

The rate of phosphate incorporation was found to be proportional to the concentrations of eEF-2K over the entire range of concentrations examined (Appendix FIG. 1D). As eEF-2K shows no propensity to self-associate over this concentration range, a mechanism corresponding to more than one eEF-2K molecule in the rate-limiting transition state may be excluded. Thus, following binding of Ca$^{2+}$/CaM and Mg$_2$ATP, eEF-2K is presumed to autophosphorylate in an intramolecular manner (within the same polypeptide) rather than within an eEF-2K dimer, with regards to the initial rapid incorporation of the first mole of phosphate. However, the possibility of the subsequent incorporation of phosphate occurring in an intermolecular manner cannot be ruled out.

Autophosphorylation sites on eEF-2K—To determine the possible autophosphorylation sites on eEF-2K, the recombinant enzyme was allowed to autophosphorylate in the presence of CaM, Ca$^{2+}$ and Mg$_2$ATP for 3 h. The sample was resolved by SDS-PAGE and then subjected to in-gel digestion with trypsin or chymotrypsin as described under 'Experimental Procedures'. Tryptic and chymotryptic digests were then analyzed by tandem mass spectrometry and MS/MS spectra from the analysis were searched against the modified Swiss-Prot all-species database using Mascot. Peptide identifications with Mascot scores equal to or above 45 (tryptic digest) or 49 (chymotryptic digest) represent an identification with ≥95% confidence and were considered for protein identification and phosphorylation site determination. Combined data from the analysis of both digests gave coverage of ~86% (624/725) of the eEF-2K sequence, with ~94% (78/83) of the threonine and serine residues covered (Appendix FIG. 2B). Mass spectrometric analysis of the autophosphorylated sample, the results of which have been summarized in Appendix Table 1, revealed five sites of autophosphorylation in recombinant human eEF-2K-Thr-348, Thr-353, Ser-445, Ser-474 and Ser-500. MS data also indicated other residues (Thr-64 and Ser-491) as being phosphorylated, but these peptides did not have significant Mascot scores and hence could not be confidently claimed as autophosphorylation sites.

The autophosphorylation of the Thr-348 site appears to be critical for activity of the kinase. Mutation of this site to alanine results in a loss of ~95% of kinase activity. Negative regulation of eEF-2K activity occurs through an inhibitory phosphorylation (Ser-78, Ser-359, Ser-366 and Ser-396). Regulation through the mTOR pathway involves the phosphorylation of Ser-366 by p70 S6 kinase, and the phosphorylation of Ser-359 and Ser-78 by at least two additional unknown kinases (Wang, X., et al. EMBO J 2001: 20, 4370-4379; Knebel, A., et al. Biochem. J. 2002: 367, 525-532; Browne, G. J., and Proud, C. G. Mol. Cell. Biol. 2004: 24, 2986-2997). It has been postulated that the Ser-78 phosphorylation acts to hinder the binding of CaM to eEF-2K (Browne, G. J., and Proud, C. G. Mol. Cell. Biol. 2004: 24, 2986-2997). The cdc2-cyclin B complex has been shown to modulate eEF-2K activity via Ser-359 in a manner that is dependent on the cell cycle as well as amino acid availability, and is perhaps controlled by mTOR (Smith, E. M., and Proud, C. G. (2008) cdc2-cyclin B regulates eEF2 kinase activity in a cell cycle- and amino acid-dependent manner, EMBO J 27, 1005-1016). Regulation through the MAPK cascade occurs via the phosphorylation of Ser-366 by p90$^{RSK1}$ in an ERK-dependent fashion (Wang, X., et al. EMBO J 2001: 20, 4370-4379). In addition, the stress-activated protein kinases p38α and p38δ inhibit eEF2K via phosphorylation on Ser-396 (Knebel, A., et al. Biochem. J. 2002: 367, 525-532). p38δ is also known to phosphorylate eEF-2K on Ser-359 (Knebel, A., et al. EMBO J 2001: 20, 4360-4369); (AMPK, PKA, Energy Stress, Elevated cAMP, S398, S500)—involved in positive regulation of eEF-2K activity through an activating phosphorylation (Ser-398 and Ser-500). Phosphorylation of Ser-398 by the energy-supply regulator AMPK is known to activate eEF-2K (Browne, G. J., et al. Journal of Biological Chemistry 2004: 279, 12220-12231). The cAMP-dependent PKA has also been shown to activate eEF-2K via a phosphorylation on Ser-500, and in the process imparts Ca$^{2+}$/CaM-independent activity to the kinase (Redpath, N. T., and Proud, C. G. Biochem J 1993: 293 (Pt 1), 31-34; Diggle, T. A., et al. Biochem. J. 2001: 353, 621-626; Diggle, T. A., et al., Biochem. J. 1998: 336, 525-529); (Elevated [Ca2+]I, Ca2+/CaM, T248, T252, S445, S474, eEF-2 Binding Domain)—involved in autophosphorylation of eEF-2K (Thr-348, Thr-353, Ser-445, Ser-474 and Ser-500). Of the 5 autophosphorylation sites, only Thr-348 appears to be essential for activity. Ser-500 is an autophosphorylation site and is also known to be phosphorylated by PKA, and could be the key residue responsible for autophosphorylation-induced Ca$^{2+}$-independence (Mitsui, K., et al. Journal of Biological Chemistry 1993: 268, 13422-13433; Redpath, N. T., and Proud, C. G. European Journal of Biochemistry 1993: 212, 511-520). phosphorylation at Ser-377 by MAPKAP-K2.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula:

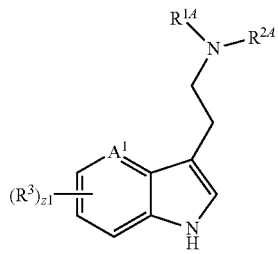

wherein
R$^{1A}$ is independently hydrogen, halogen, —CX$^{1A}_3$, —C(O)R$^{7A}$, —C(O)—OR$^{7A}$, —C(O)NR$^{7A}$R$^{8A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{2A}$ is independently hydrogen, halogen, —CX$^{2A}_3$, —C(O)R$^{9A}$, —C(O)—OR$^{9A}$, —C(O)NR$^{9A}$R$^{10A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

wherein R$^{1A}$ and R$^{2A}$ are optionally joined to form a substituted or unsubstituted heterocycloalkyl or substituted or unsubstituted heteroaryl;

R$^3$ is independently halogen, —CX$^3_3$, —CN, —SO$_2$Cl, —SO$_n$R$^{14}$, —SO$_k$NR$^{11}$R$^{12}$, —NHNH$_2$, —ONR$^{11}$R$^{12}$, —NHC=(O)NHNH$_2$, —NHC=(O)NR$^{11}$R$^{12}$, —N(O)$_m$, —NR$^{11}$R$^{12}$, —C(O)R$^{13}$, —C(O)—OR$^{13}$, —O—C(O)—R$^{13}$, —C(O)NR$^{11}$R$^{12}$, —NR$^{11}$C(O)R$^{13}$, —OR$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{7A}$, R$^{8A}$, R$^{9A}$, R$^{10A}$, R$^{11}$, R$^{12}$, and R$^{13}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{14}$ is substituted or unsubstituted C$_8$-C$_{16}$ alkyl;
A$^1$ is independently =CR$^3$—;
k and m are independently 1 or 2;
n is independently an integer from 0 to 4;
z1 is independently 0;
X$^{1A}$, X$^{2A}$, and X$^3$ are independently —Cl, —Br, —I, or —F.

2. The compound of claim 1, wherein
R$^{1A}$ is independently —C(O)R$^{7A}$ or —C(O)—OR$^{7A}$;
R$^{7A}$ is independently hydrogen, substituted or unsubstituted C$_1$-C$_{20}$ alkyl, substituted or unsubstituted 2 to 20 membered heteroalkyl, substituted or unsubstituted C$_3$-C$_8$ cycloalkyl, substituted or unsubstituted 3 to 8 membered heterocycloalkyl, substituted or unsubstituted C$_6$-C$_{10}$ aryl, or substituted or unsubstituted 5 to 10 membered heteroaryl.

3. The compound of claim 1, wherein
R$^{2A}$ is independently —C(O)R$^{9A}$ or —C(O)—OR$^{9A}$;
R$^{9A}$ is independently hydrogen, substituted or unsubstituted C$_1$-C$_{20}$ alkyl, substituted or unsubstituted 2 to 20 membered heteroalkyl, substituted or unsubstituted C$_3$-C$_8$ cycloalkyl, substituted or unsubstituted 3 to 8 membered heterocycloalkyl, substituted or unsubstituted C$_6$-C$_{10}$ aryl, or substituted or unsubstituted 5 to 10 membered heteroaryl.

4. The compound of claim 1, wherein the compound is:

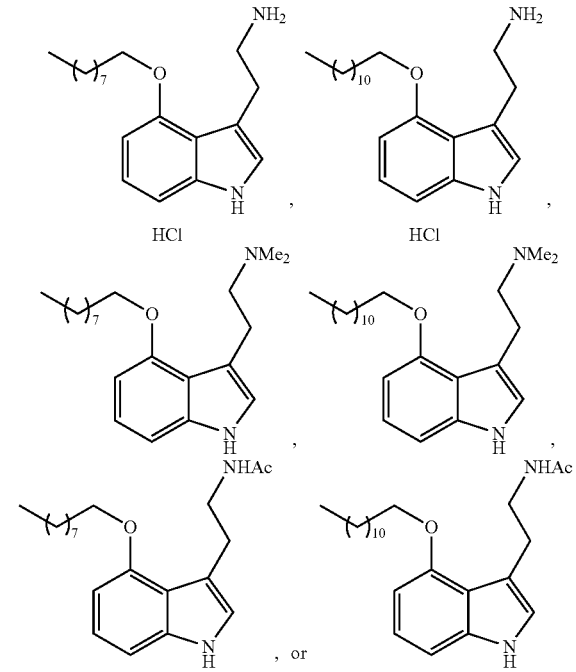

5. A pharmaceutical composition comprising a pharmaceutically acceptable excipient and a compound of claim 1.

6. A pharmaceutical composition comprising a pharmaceutically acceptable excipient, a liposome, and a compound of claim 1.

7. The compound of claim 1, wherein R$^{1A}$ and R$^{2A}$ are hydrogen.

8. The compound of claim 1, wherein R$^3$ is —OR$^{14}$.

9. The compound of claim 8, wherein R$^{14}$ is substituted or unsubstituted C$_8$-C$_{14}$ alkyl.

10. The compound of claim 8, wherein R$^{14}$ is unsubstituted C$_8$-C$_{14}$ alkyl.

11. The compound of claim 8, wherein R$^{14}$ is substituted or unsubstituted C$_8$-C$_{12}$ alkyl.

12. The compound of claim 8, wherein R$^{14}$ is unsubstituted C$_8$-C$_{12}$ alkyl.

13. The compound of claim 1, wherein R$^{13}$ or R$^{14}$ are independently unsubstituted C$_{12}$-C$_{16}$ alkyl.

14. The compound of claim 1, wherein R$^{13}$ and R$^{14}$ are independently substituted or unsubstituted C$_8$-C$_{14}$ alkyl.

15. The compound of claim 1, wherein R$^{13}$ and R$^{14}$ are independently substituted or unsubstituted C$_{12}$-C$_{16}$ alkyl.

16. The compound of claim 1, wherein R$^{14}$ is unsubstituted C$_8$-C$_{16}$ alkyl.

17. The compound of claim 1, wherein R$^{14}$ is substituted or unsubstituted C$_8$-C$_{14}$ alkyl.

18. The compound of claim 1, wherein R$^{14}$ is unsubstituted C$_8$-C$_{14}$ alkyl.

19. The compound of claim 1, wherein $R^{14}$ is substituted or unsubstituted $C_8$-$C_{12}$ alkyl.

20. The compound of claim 1, wherein $R^{14}$ is unsubstituted $C_8$-$C_{12}$ alkyl.

21. The compound of claim 1, wherein $R^{14}$ is substituted or unsubstituted $C_{12}$-$C_{16}$ alkyl.

22. The compound of claim 1, wherein $R^{14}$ is substituted or unsubstituted $C_{13}$-$C_{16}$ alkyl.

23. The compound of claim 1, wherein $R^{1A}$ and $R^{2A}$ are independently hydrogen or substituted or unsubstituted alkyl.

24. The compound of claim 1, wherein $R^{1A}$ and $R^{2A}$ are independently hydrogen or substituted or unsubstituted $C_1$-$C_{12}$ alkyl.

25. The compound of claim 1, wherein $R^{1A}$ and $R^{2A}$ are independently hydrogen or substituted or unsubstituted $C_1$-$C_5$ alkyl.

26. The compound of claim 1, wherein $R^{1A}$ and $R^{2A}$ are independently hydrogen, unsubstituted methyl, unsubstituted ethyl, or unsubstituted propyl.

27. A method of treating a disease in a patient in need of such treatment, said method comprising administering a therapeutically effective amount of a compound of claim 1, wherein said disease is breast cancer.

* * * * *